(12) United States Patent
Chen et al.

(10) Patent No.: US 11,939,396 B2
(45) Date of Patent: Mar. 26, 2024

(54) ANTI-TRYPTASE ANTIBODIES, COMPOSITIONS THEREOF, AND USES THEREOF

(71) Applicant: Genentech, Inc., South San Francisco, CA (US)

(72) Inventors: Xiaocheng Chen, Foster City, CA (US); Mark Dennis, San Carlos, CA (US); Janet Jackman, Half Moon Bay, CA (US); James T. Koerber, San Francisco, CA (US); Mason Lu, Houston, TX (US); Henry R. Maun, San Francisco, CA (US); Kathila Rajapaksa, San Francisco, CA (US); Saroja Ramanujan, San Mateo, CA (US); Tracy Staton, Stanford, CA (US); Lawren Wu, Foster City, CA (US); Tangsheng Yi, Belmont, CA (US)

(73) Assignee: Genentech, Inc., South San Francisco, CA (US)

( * ) Notice: Subject to any disclaimer, the term of this patent is extended or adjusted under 35 U.S.C. 154(b) by 210 days.

(21) Appl. No.: 16/916,822

(22) Filed: Jun. 30, 2020

(65) Prior Publication Data
US 2020/0325248 A1    Oct. 15, 2020

Related U.S. Application Data

(62) Division of application No. 15/893,238, filed on Feb. 9, 2018, now Pat. No. 10,738,131.

(60) Provisional application No. 62/457,722, filed on Feb. 10, 2017.

(51) Int. Cl.
| C07K 16/40 | (2006.01) |
| A61K 39/395 | (2006.01) |
| C07K 16/24 | (2006.01) |
| A61K 39/00 | (2006.01) |
| A61K 45/06 | (2006.01) |
| A61K 47/10 | (2017.01) |
| A61K 47/18 | (2017.01) |
| A61K 47/22 | (2006.01) |
| A61K 47/26 | (2006.01) |

(52) U.S. Cl.
CPC .......... *C07K 16/40* (2013.01); *A61K 39/3955* (2013.01); *A61K 39/39591* (2013.01); *C07K 16/244* (2013.01); *C12Y 304/21059* (2013.01); *A61K 2039/505* (2013.01); *A61K 45/06* (2013.01); *A61K 47/10* (2013.01); *A61K 47/183* (2013.01); *A61K 47/22* (2013.01); *A61K 47/26* (2013.01); *C07K 2317/24* (2013.01); *C07K 2317/31* (2013.01); *C07K 2317/34* (2013.01); *C07K 2317/40* (2013.01); *C07K 2317/55* (2013.01); *C07K 2317/56* (2013.01); *C07K 2317/565* (2013.01); *C07K 2317/567* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| 5,595,756 A * | 1/1997 | Bally ................. A61K 9/1272 |
| | | 264/4.1 |
| 5,744,319 A * | 4/1998 | Niles .................... C07K 1/22 |
| | | 530/389.1 |
| 5,861,264 A | 1/1999 | Elrod et al. |

FOREIGN PATENT DOCUMENTS

| EP | 0379295 A2 * | 1/1990 |
| EP | 0379295 A2 | 7/1990 |
| EP | 0419292 A1 | 3/1991 |
| EP | 2913062 A1 | 9/2015 |
| JP | 2004-500876 A | 1/2004 |
| WO | WO-97/17373 A1 | 5/1997 |
| WO | WO-99/60139 A1 | 11/1999 |
| WO | WO-01/98470 A2 | 12/2001 |
| WO | WO-2006/010492 A1 | 2/2006 |

OTHER PUBLICATIONS

Vajdos et al. (J Mol Biol. Jul. 5, 2002;320(2):415-28) (Year: 2002).*
Brown et al. (J Immunol. May 1996;156(9):3285-91) (Year: 1996).*
Skolnick et al (Trends Biotechnol. Jan. 2000;18(1):34-9) (Year: 2000).*
Burgess et al. (J. Cell Biol. 111:2129-2138, 1990) (Year: 1990).*
Miosge (Proc Natl Acad Sci U S A. Sep. 15, 2015;112(37):E5189-98) (Year: 2015).*
Bork (Genome Research, 2000,10:398-400) (Year: 2000).*
Aagaard et al (Advanced Drug Delivery Reviews 59 (2007) 75-86) (Year: 2007).*
Warzocha et al (Leukemia and Lymphoma (1997) vol. 24. pp. 267-281) (Year: 1997).*
McKeague et al (J Nucleic Acids. 2012;2012:748913. Epub Oct. 24, 2012) (Year: 2012).*
Guido et al (Curr Med Chem. 2008;15(1):37-46) (Year: 2008).*
Clark et al (J. Med. Chem., 2014, 57 (12), pp. 5023-5038) (Year: 2014).*

(Continued)

*Primary Examiner* — Brian Gangle
*Assistant Examiner* — Andrea K McCollum
(74) *Attorney, Agent, or Firm* — Clark & Elbing LLP; Thomas J. Takara

(57) ABSTRACT

The invention provides compositions including anti-tryptase antibodies and pharmaceutical compositions thereof, as well as methods of using the same.

33 Claims, 32 Drawing Sheets
Specification includes a Sequence Listing.

(56) References Cited

OTHER PUBLICATIONS

Steinman et al (Nat Med. Jan. 6, 2012;18(1):59-65) (Year: 2012).*
Blumberg et al (Nat Med.; 18(1): 35-41) (Year: 2015).*
Sporn et al, "Chemoprevention of Cancer," Carcinogenesis, vol. 21 (2000), 525-530 (Year: 2000).*
Auerbach et al (Cancer and Metastasis Reviews, 2000, 19: 167-172) (Year: 2000).*
Gura T (Science, 1997, 278(5340): 1041-1042) (Year: 1997).*
Jain RK (Scientific American, Jul. 1994,58-65) (Year: 1994).*
HogenEsch et al (J Control Release. Dec. 10, 2012; 164(2): 183-186.) (Year: 2012).*
Ma (Modern Drug Discovery 2004, 7(6)) (Year: 2004).*
Pinto et al (Journal of Cell Communication and Signaling (2018) 12:615-624) (Year: 2018).*
Hershey (J Allergy Clin Immunol. Apr. 2003;111(4):677-90) (Year: 2003).*
Pelaia et al (Front Physiol. Dec. 17, 2019;10:1514) (Year: 2019).*
Warncke (J Immunol (2012) 188 (9): 4405-4411) (Year: 2012).*
1. Fukuoka et al (The Journal of Immunology, vol. 176, No. 5, Mar. 1, 2006 (Mar. 1, 2006), pp. 3165-3172) (Year: 2006).*
Aagaard et al., "RNAi therapeutics: principles, prospects and challenges," Adv Drug Deliv Rev. 59(2-3):75-86 (2007).
Bowie et al., "Deciphering the message in protein sequences: tolerance to amino acid substitutions," Science. 247(4948):1306-10 (1990).
Brown et al., "Tolerance to single, but not multiple, amino acid replacements in antibody VH CDR2: a means of minimizing B cell wastage from somatic hypermutation?" J Immunol. 156(9):3285-91 (1996).
Burgess et al., "Possible dissociation of the heparin-binding and mitogenic activities of heparin-binding (acidic fibroblast) growth factor-1 from its receptor-binding activities by site-directed mutagenesis of a single lysine residue," J Cell Biol. 111(5 Pt 1):2129-38 (1990).
Caughey, "Mast cell tryptases and chymases in inflammation and host defense," Available in PMC Mar. 27, 2008, published in final edited form as: Immunol Rev. 217:141-54 (2007) (22 pages).
Clark et al., "Discovery and development of Janus kinase (JAK) inhibitors for inflammatory diseases," J Med Chem. 57(12):5023-38 (2014).
Cooper et al., "Variable domain-identical antibodies exhibit IgG subclass-related differences in affinity and kinetic constants as determined by surface plasmon resonance," Mol Immunol. 31(8):577-84 (1994).
Daugherty et al., "Formulation and delivery issues for monoclonal antibody therapeutics," Adv Drug Deliv Rev. 58(5-6):686-706 (2006).
Feng et al., "Current Therapeutic Antibody Production and Process Optimization," BioProcess J. 4(5):1-8 (2005).
Frenzel et al., "Expression of recombinant antibodies," Front Immunol. 4:217 (2013) (20 pages).
Fukuoka et al., "The B12 anti-tryptase monoclonal antibody disrupts the tetrameric structure of heparin-stabilized beta-tryptase to form monomers that are inactive at neutral pH and active at acidic pH," J Immunol. 176(5):3165-72 (2006).
Guido et al., "Virtual screening and its integration with modern drug design technologies," Curr Med Chem. 15(1):37-46 (2008).
Guo et al., "Tryptase is a candidate autoantigen in rheumatoid arthritis," Immunology. 142(1):67-77 (2014).
Ji et al., "Methionine, tryptophan, and histidine oxidation in a model protein, PTH: mechanisms and stabilization," J Pharm Sci. 98(12):4485-500 (2009).
Lazar et al., "Transforming growth factor alpha: mutation of aspartic acid 47 and leucine 48 results in different biological activities," Mol. Cell. Biol. 8(3):1247-52 (1988).
Maselli et al., "Profile of lebrikizumab and its potential in the treatment of asthma," J Asthma Allergy. 8:87-92 (2015).
McKeague et al., "Challenges and opportunities for small molecule aptamer development," J Nucleic Acids. 2012:748913 (2012) (21 pages).
Overed-Sayer et al., "Are mast cells instrumental for fibrotic diseases?," Front Pharmacol. 4:174 (2014) (10 pages).
Ren et al., "Human tryptase fibrinogenolysis is optimal at acidic pH and generates anticoagulant fragments in the presence of the anti-tryptase monoclonal antibody B12," J Immunol. 159(7):3540-8 (1997) (10 pages).
Schwartz et al., "Development of a new, more sensitive immunoassay for human tryptase: use in systemic anaphylaxis," J Clin Immunol. 14(3):190-204 (1994).
Schwartz et al., "Immunologic and physicochemical evidence for conformational changes occurring on conversion of human mast cell tryptase from active tetramer to inactive monomer. Production of monoclonal antibodies recognizing active tryptase," J Immunol. 144(6):2304-11 (1990).
Vajdos et al., "Comprehensive Functional Maps of the Antigen-Binding Site of an anti-ErbB2 Antibody Obtained With Shotgun Scanning Mutagenesis," J Mol Biol. 320(2):415-28 (2002).
Walls et al., "Production and characterization of monoclonal antibodies specific for human mast cell tryptase," Clin Exp Allergy. 20(5):581-9 (1990).
Wang et al., "Antibody structure, instability, and formulation," J Pharm Sci. 96(1):1-26 (2007).
Wang et al., "Efficacy and Safety of Anti-Interleukin-5 Therapy in Patients with Asthma: A Systematic Review and Meta-Analysis," PLoS One. 11(11):e0166833 (2016) (20 pages).
Warzocha et al., "Antisense strategy: biological utility and prospects in the treatment of hematological malignancies," Leuk Lymphoma. 24(3-4):267-81 (1997).
Wu et al., "Targeting IgE production in mice and humans," Curr Opin Immunol. 31:8-15 (2014).
Examination Report for Gulf Cooperation Council Patent Application No. 2018-34738, dated Sep. 5, 2019 (5 pages).
International Preliminary Report on Patentability for International Patent Application No. PCT/US2018/017680, dated Aug. 13, 2019 (16 pages).
International Search Report for PCT Application No. PCT/US2018/017680, dated Jul. 17, 2018 (10 pages).
Invitation to Pay Additional Fees for International Patent Application No. PCT/US2018/017680, dated Apr. 26, 2018 (23 pages).
Non-Final Rejection for U.S. Appl. No. 16/544,421, dated Oct. 11, 2019 (31 pages).
Notice of Rejection for Iranian Patent Application No. 139850140003004008, dated Jul. 7, 2020 (2 pages).
Office Action for Russian Patent Application No. 2019127870, dated Dec. 19, 2019 (4 pages).
Office Action for U.S. Appl. No. 15/893,238, dated Nov. 27, 2019 (28 pages).
Office Action for Vietnamese Patent Application No. 1-2019-04967, dated Oct. 8, 2019 (2 pages).
Search Report for Iranian Patent Application No. 139850140003004008, dated Jul. 21, 2020 (10 pages).
Second Examination Report for Patent Office of the Cooperation Council for the Arab States of the Gulf Patent Application No. 2018-34738, dated Dec. 10, 2020 (5 pages).
Hunt et al., "Immunofluorescent Staining for Mast Cells in Idiopathic Pulmonary Fibrosis: Quantification and Evidence for Extracellular Release of Mast Cell Tryptase," Mayo Clin Proc. 67(10):941-8 (1992).
Communication pursuant to Article 94(3) EPC for European Patent Application No. 18707205.3, dated Nov. 13, 2020 (5 pages).
Notice of Reasons for Rejection for Japanese Patent Application No. 2019-541323, dated Mar. 9, 2021 (6 pages).
Search Report for Korean Patent Application No. 10-2019-7026305, dated Feb. 17, 2021 (25 pages).
Written Opinion for Singaporean Patent Application No. 11201907364W, dated Nov. 21, 2020 (8 pages).
Coffman et al., "Nonhuman primate models of asthma" J Exp Med. 201(12):1875-1879 (2005).
Labrijn et al., "Species-specific determinants in the IgG CH3 domain enable Fab-arm exchange by affecting the noncovalent CH3-CH3 interaction strength" J Immunol. 187:3238-3246 (2011) (10 pages).

(56) References Cited

OTHER PUBLICATIONS

Kotlyar et al., "Non-pulmonary allergic diseases and inflammatory bowel disease: A qualitative review," World J Gastroenterol. 20(32):11023-32 (2014).

* cited by examiner

FIG.1

Light chain variable region

```
              CDR L1 - Kabat / CDR L1 - Contact
Kabat number
31A.V11    D I Q M T Q S P S S L S A S V G D R V T I T C S A S . . S S V T Y M Y W Y Q Q K P G
E104.V2    D I Q M T Q S P S S L S A S V G D R V T I T C Q S I K S V Y N N R L G W Y Q Q K P G CDR L2 - Contact / CDR L2 - Kabat
Kabat number
31A.V11    K S P K P W I Y R T S D L A S G V P S R F S G S G S G T D F T L T I S S L Q P E D F
E104.V2    K A P K L L I Y E T S I L T S G V P S R F S G S G S G T D F T L T I S S L Q P E D F CDR L3 - Contact / CDR L3 - Kabat
Kabat number
31A.V11    A T Y Y C Q H Y H S Y P . . L T F G Q G T K V E I K     SEQ ID NO: 10
E104.V2    A T Y Y C A G G F D R S G D T T F G Q G T K V E I K     SEQ ID NO: 37
```

Heavy chain variable region

```
              CDR H1 - Contact / CDR H1 - Kabat
Kabat number
31A.V11    E V Q L V E S G G G L V Q P G G S L R L S C A A S G F T F S D Y G M V W V R Q A P G
E104.V2    E V Q L V E S G P G L V K P S E T L S L T C T V S R F S L I G Y A I T W I R Q P P G CDR H2 - Contact / CDR H2 - Kabat
Kabat number
31A.V11    K G L E W V A F I S S G S S T V Y Y A D T M K G R F T I S R D N S K N T L Y L Q M N
E104.V2    K G L E W I G G I S . S A A T T F Y S S W A K S R V T I S R D T S K N Q V S L K L S CDR H3 - Contact / CDR H3 - Kabat
Kabat number
31A.V11    S L R A E D T A V Y Y C T R R N Y D D W Y F . . . . D V W G Q G T L V T V S S     SEQ ID NO: 9
E104.V2    S V T A A D T A V Y Y C A R D P R G Y G A A L D R L D L W G Q G T L V T V S S     SEQ ID NO: 36
```

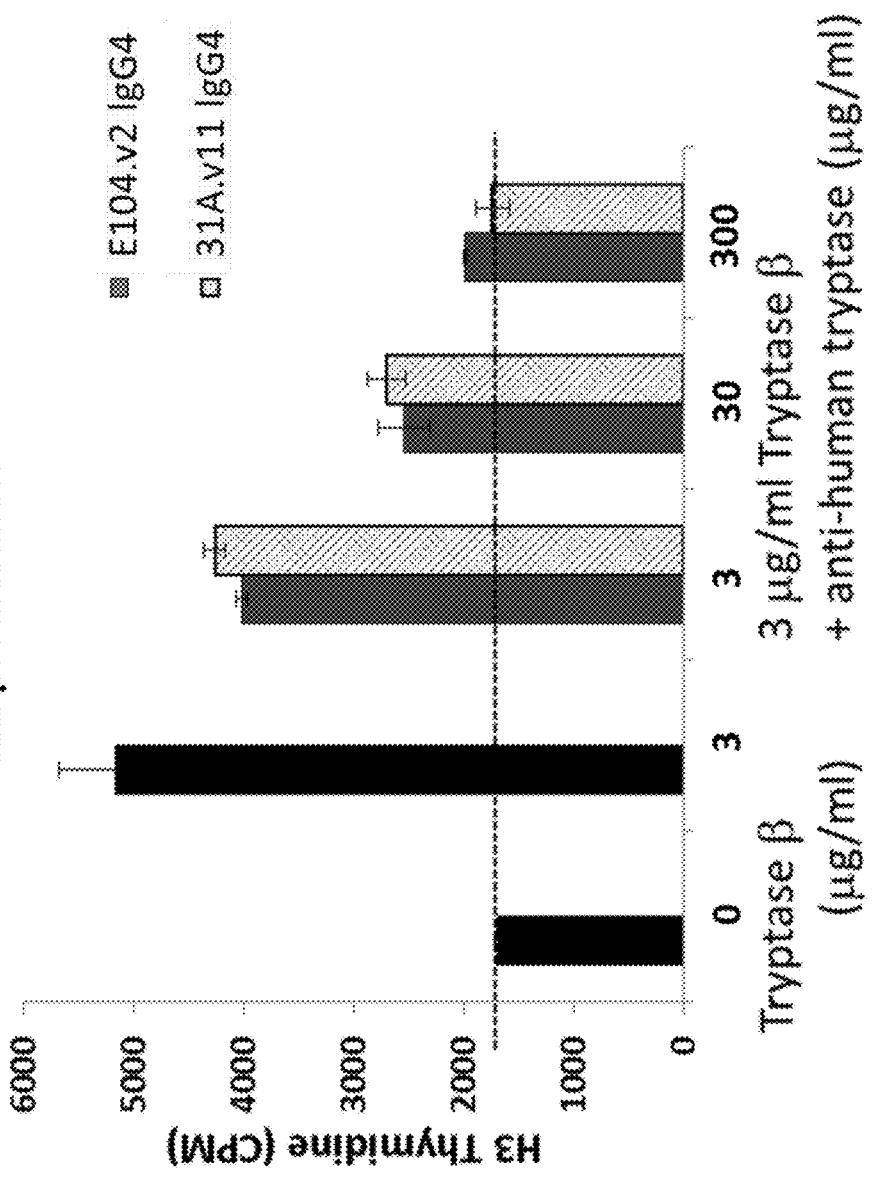

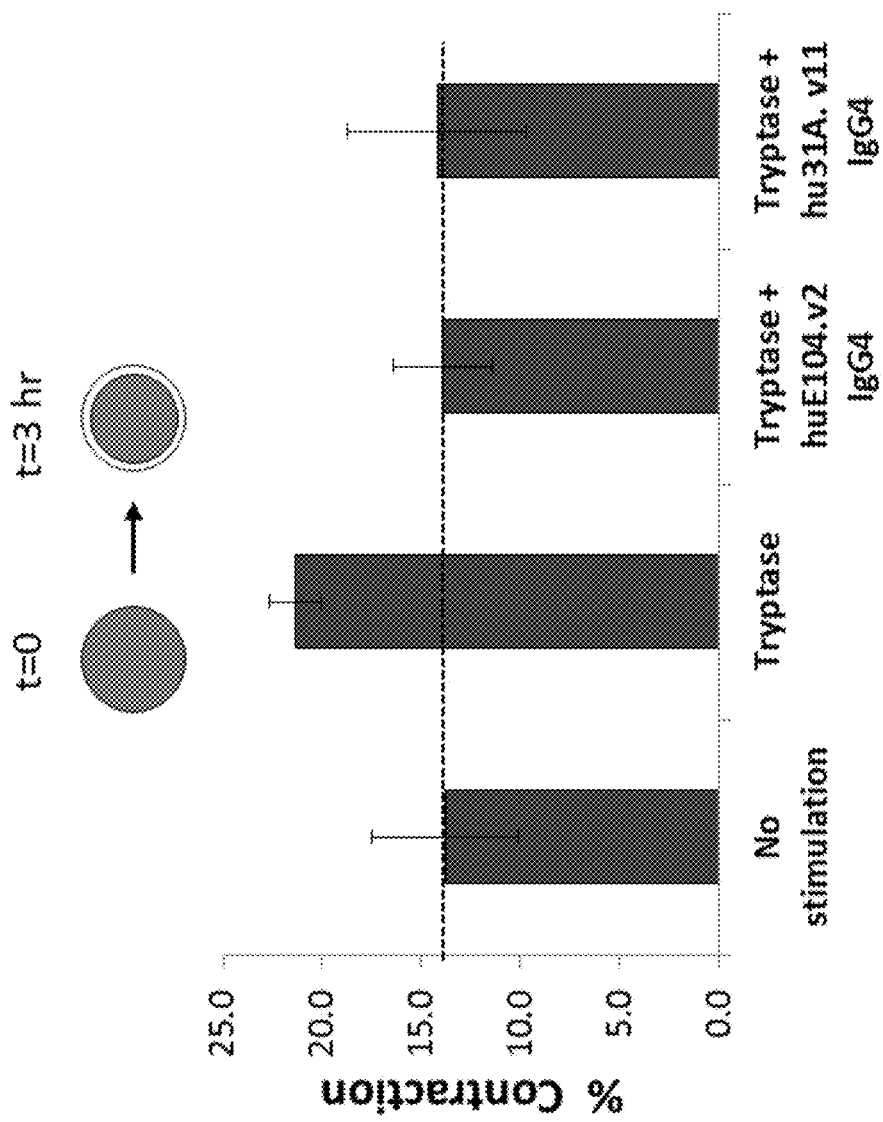

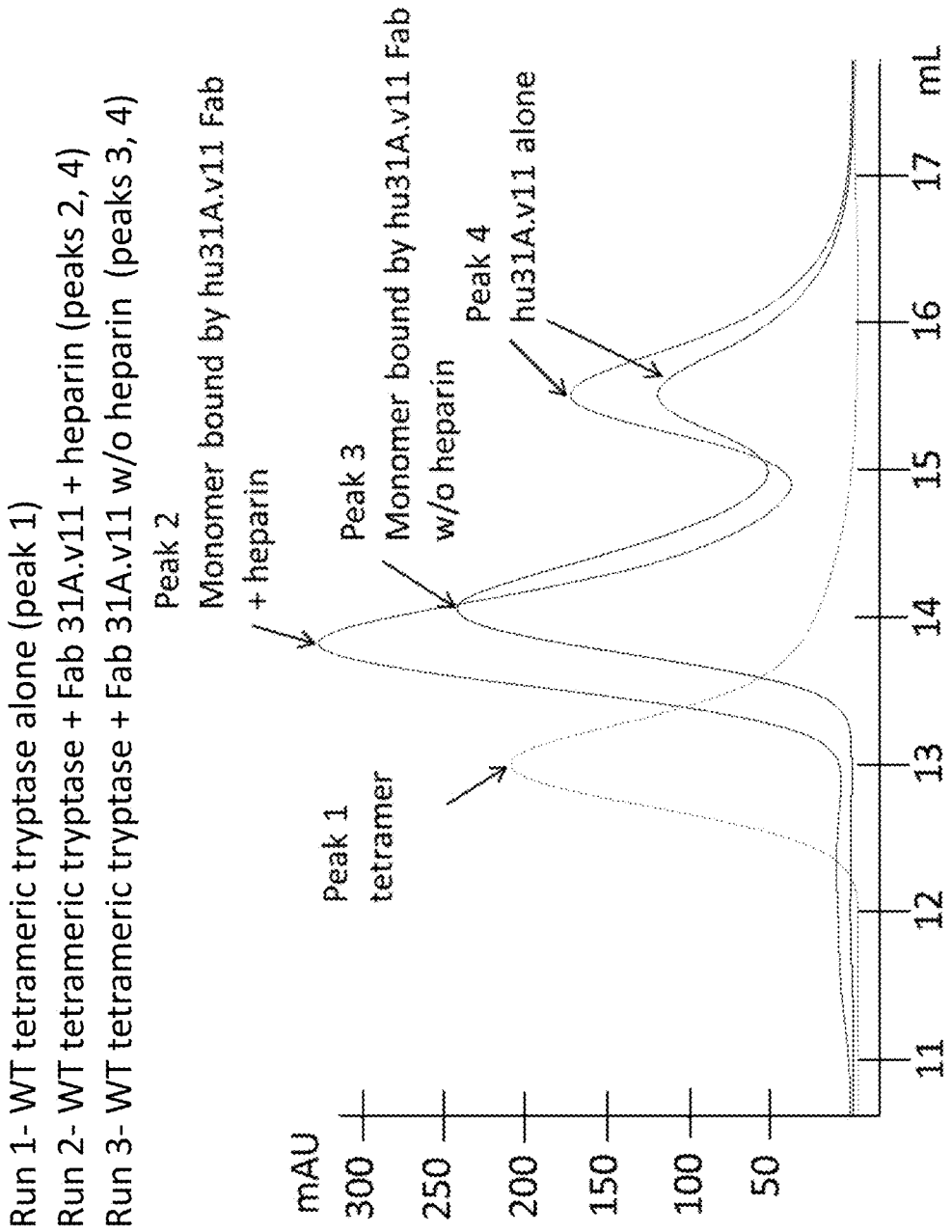

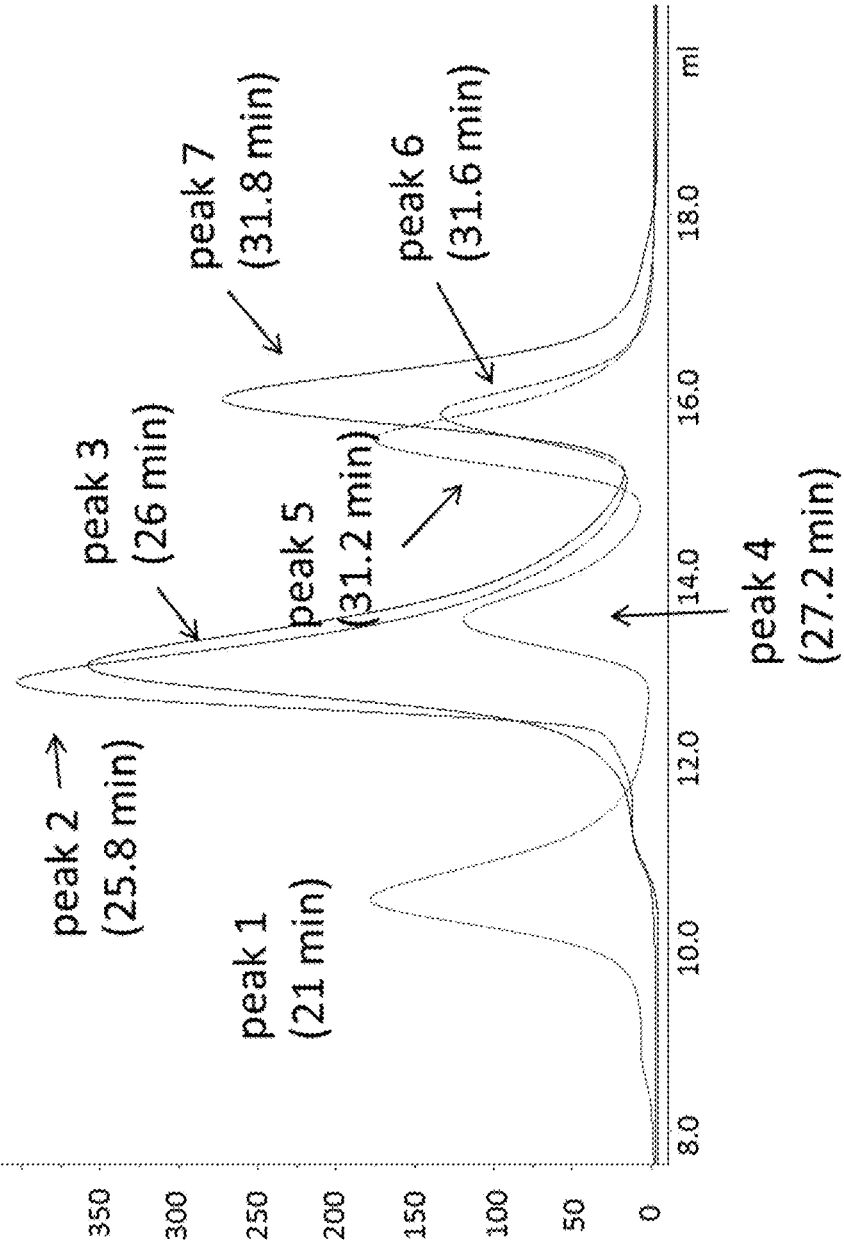

FIG. 5A
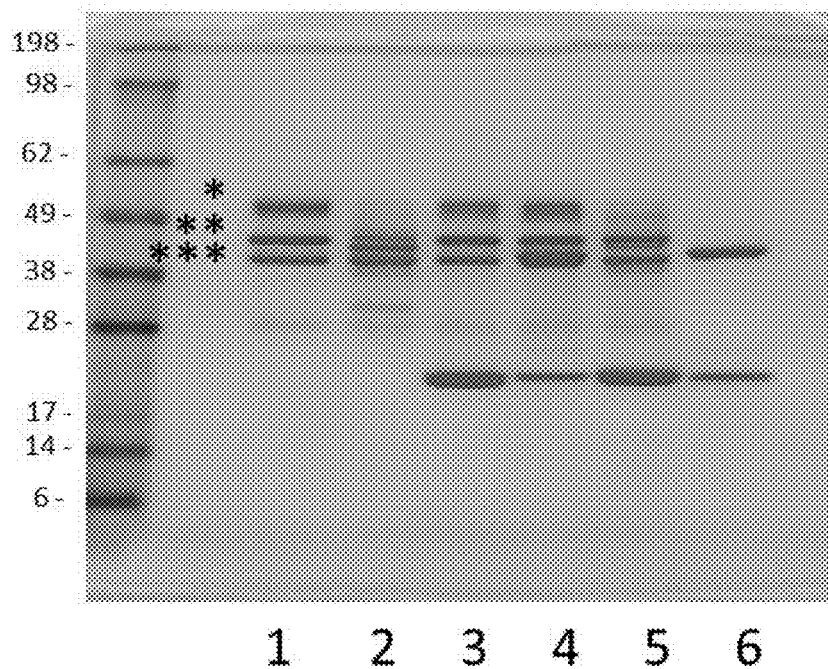
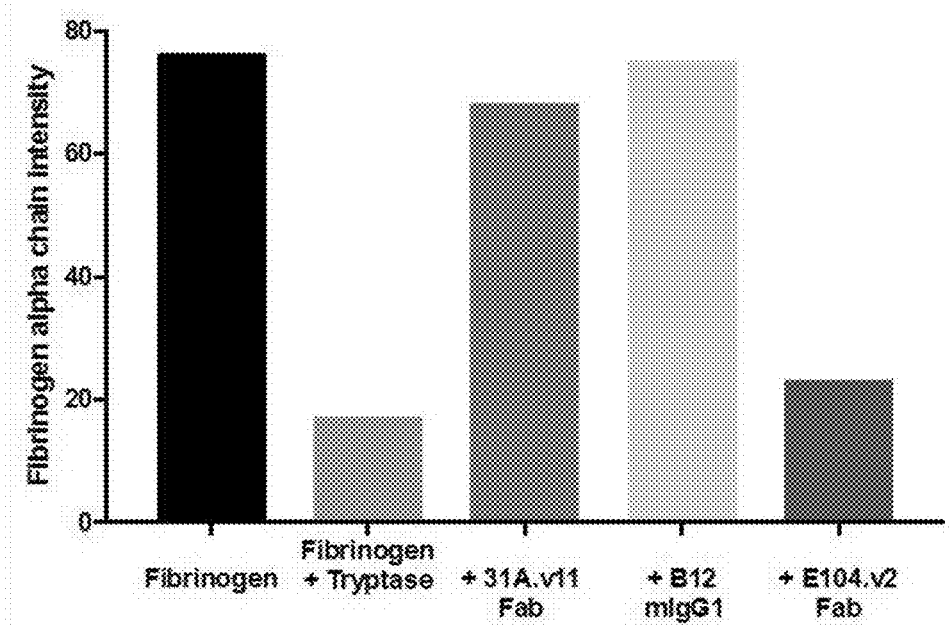

FIG. 5B
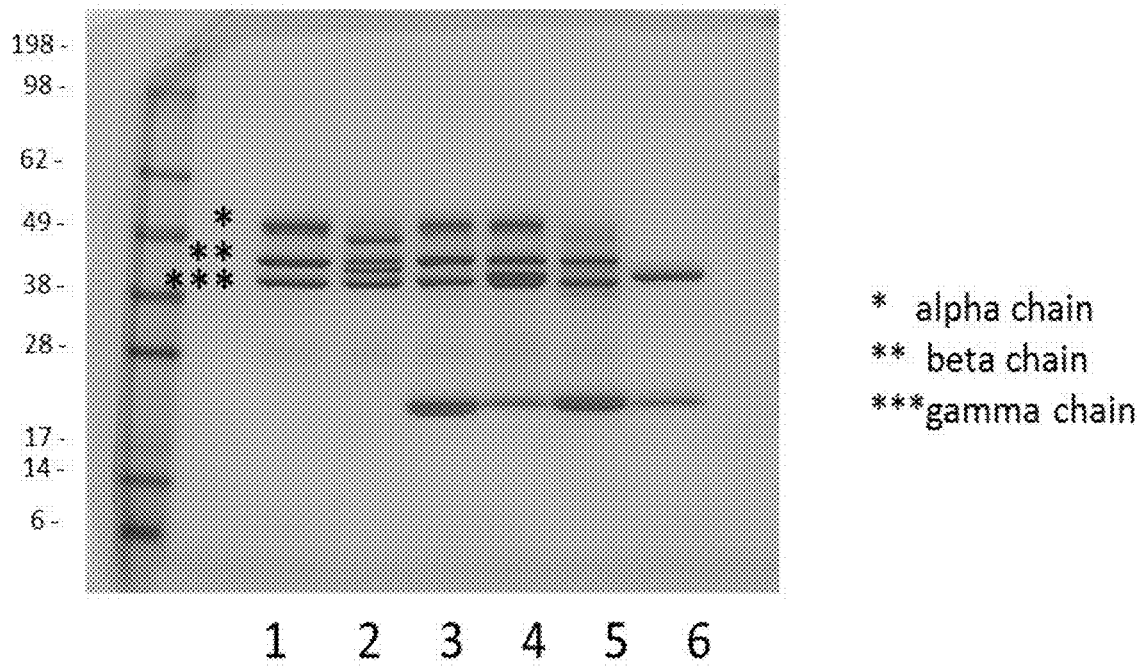
* alpha chain
** beta chain
***gamma chain
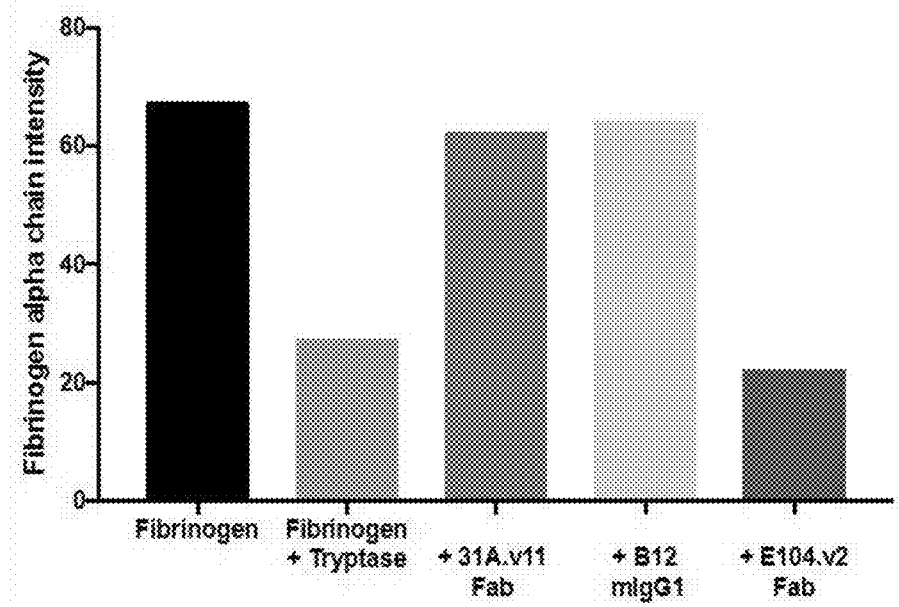

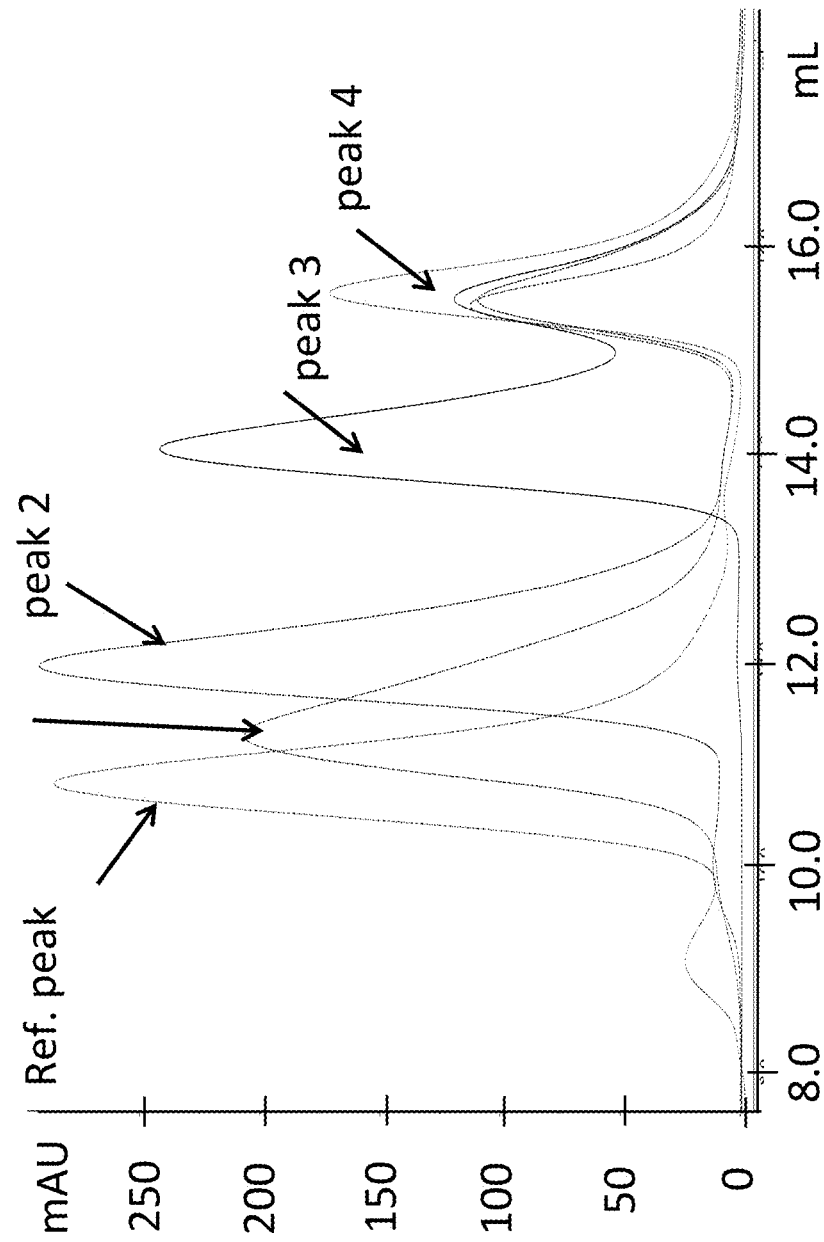

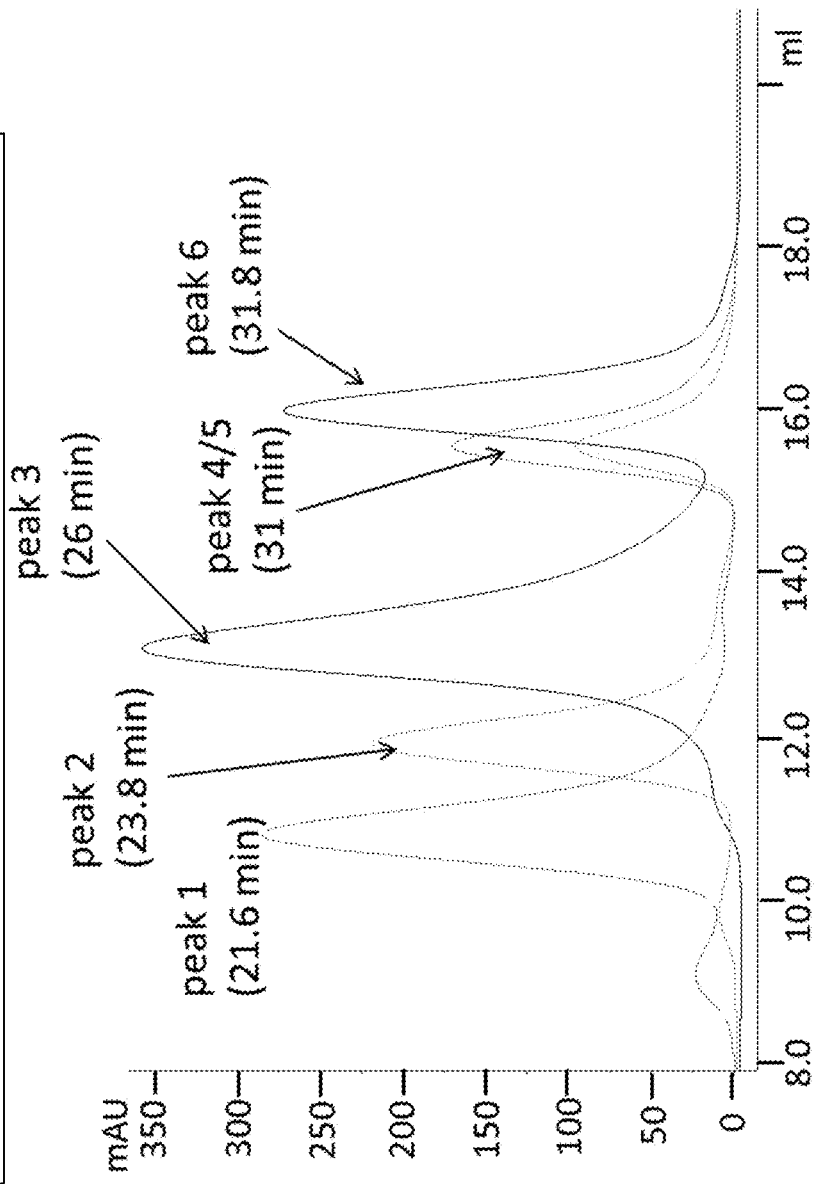

FIG. 7

Mature human tryptase beta 1 amino acid sequence:

IVGGQEAPRSKWPWQVSLRVHGPYWMH

FCGGSLIHPQWVLTAAHCVGPDVKD

LAALRVQLREQHLYYQDQLLPVSRIIV

VHPQFYTAQIGADIALLELEEPVNV

SSHVHTVTLPPASETFPPGMPCWVT

GWGDVDNDERLPPPFPLKQVKVPIME

NHICDAKYHLGAYTGDDVRIVRDDML

CAGNTRRDSCQGDSGGPLVCKVNGT

WLQAGVVSWGEGCAQPNRPGIYTRV

TYYLDWIHHYVPKKP    SEQ ID NO: 97

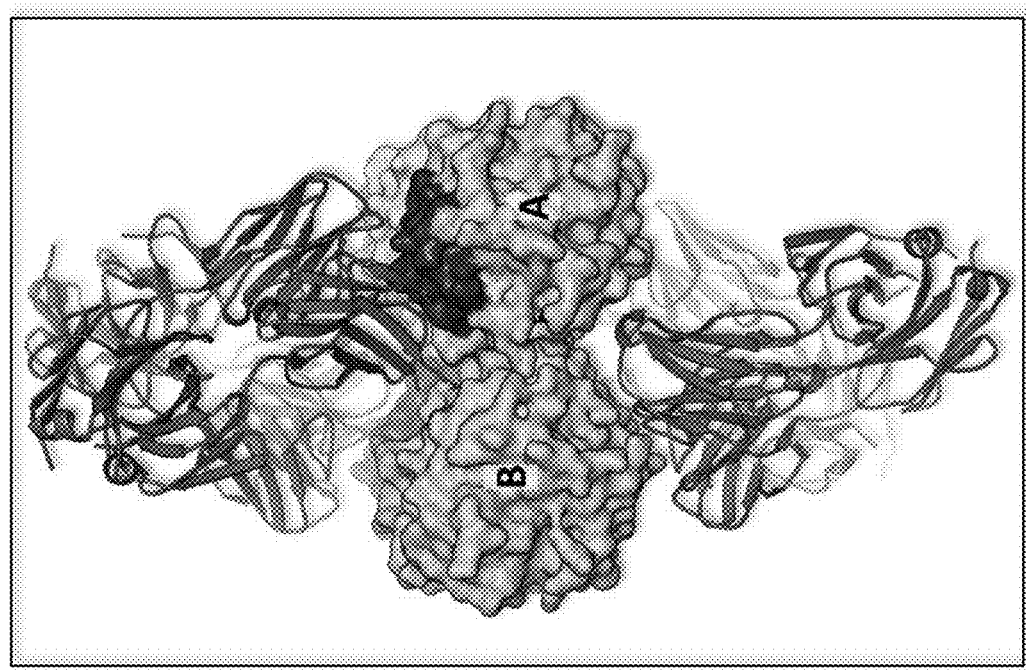
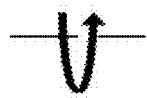
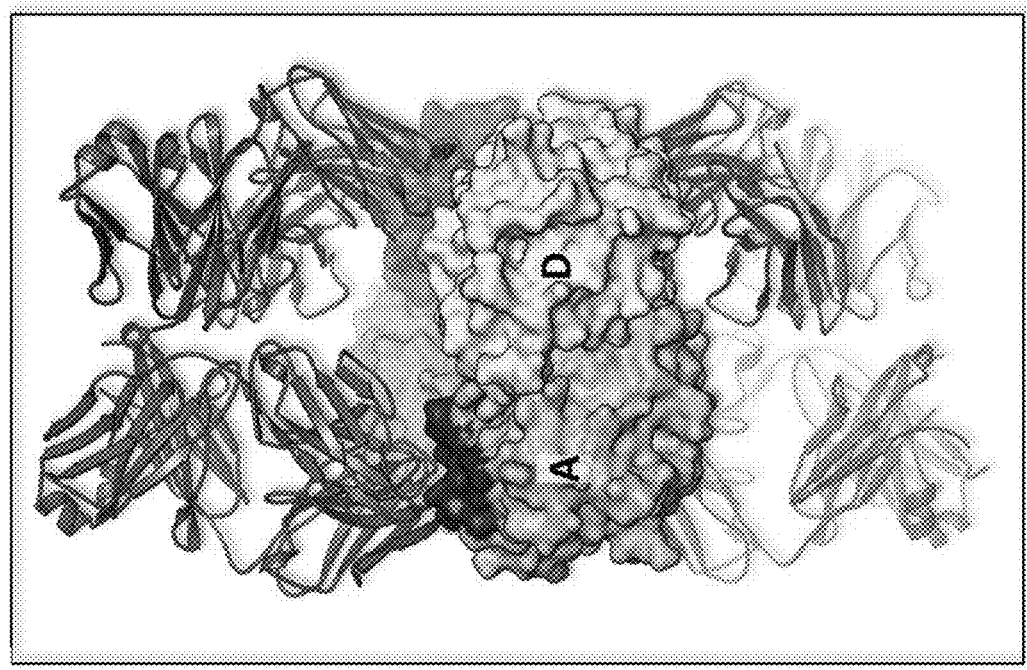
FIG. 12A

US 11,939,396 B2

ANTI-TRYPTASE ANTIBODIES, COMPOSITIONS THEREOF, AND USES THEREOF

CROSS-REFERENCE TO RELATED APPLICATIONS

This application is a divisional application of U.S. application Ser. No. 15/893,238, filed on Feb. 9, 2018, which claims benefit to U.S. Provisional Application No. 62/457,722, filed on Feb. 10, 2017, the contents of which are incorporated herein by reference in their entirety

SEQUENCE LISTING

The instant application contains a Sequence Listing which has been submitted electronically in ASCII format and is hereby incorporated by reference in its entirety. Said ASCII copy, created on Jun. 26, 2020, is named 50474-112004_Sequence_Listing_6.26.20_ST25 and is 108,979 bytes in size.

FIELD OF THE INVENTION

The invention relates to anti-tryptase antibodies, pharmaceutical compositions, and methods of using the same.

BACKGROUND

Human tryptase beta is a trypsin-like serine protease that is abundant in mast cells and, to a lesser extent, in basophils. Human tryptase beta (of which there are three subtypes, tryptase beta 1, tryptase beta 2, and tryptase beta 3) produced by the TPSAB1 and TPSB2 loci is the predominant active tryptase produced by human mast cells. These two loci produce four tryptase isoforms; TPSAB1 produces tryptase alpha and tryptase beta 1, while TPSB2 produces tryptase beta 2 and tryptase beta 3. Tryptase alpha, as well as other isoforms such as tryptase gamma, tryptase delta, and tryptase epsilon are largely inactive.

The proteolytically processed, active tryptase beta is stored in the secretory granules of mast cells as a tetramer in complex with heparin. Mast cell degranulation, which can be caused by IgE-dependent stimuli (e.g., allergens), or non-IgE-dependent stimuli (e.g., substance P or active tryptase), leads to release of tryptase beta along with other granule enzymes and histamine. Previous studies have observed increased mast cell numbers in bronchial smooth muscle and epithelium of asthma patients, as well as increased levels of tryptase beta in broncoalveolar lavage fluid. In addition, tryptase contributes to airway bronchoconstriction and hyperresponsiveness, and has also been suggested to play a role in fibrosis and extracellular matrix turnover, which are hallmarks of the airway remodeling process.

Tryptase has been suggested to be involved in various diseases and disorders, including asthma and other pulmonary, inflammatory, autoimmune, and fibrotic disorders, for which there remains a need for improved therapeutics, including therapeutic anti-tryptase antagonists, and methods of treatment. There have been attempts to develop small molecule tryptase inhibitors (see, e.g., Cairns, J. A., 2005, *Pulmonary Pharmacology & Therapeutics* 18:55-66); however, to our knowledge, no biologic tryptase antagonistic therapeutics, especially anti-tryptase antagonistic antibodies, have been reported.

SUMMARY OF THE INVENTION

The present invention relates to anti-tryptase antibodies and pharmaceutical compositions thereof, as well as methods of using the same.

In one aspect, the invention features an isolated antibody that binds to human tryptase beta 1, or an antigen-binding fragment thereof, wherein the antibody comprises the following six hypervariable regions (HVRs): (a) an HVR-H1 comprising the amino acid sequence of DYGMV (SEQ ID NO: 7); (b) an HVR-H2 comprising the amino acid sequence of FISSGSSTVYYADTMKG (SEQ ID NO: 2); (c) an HVR-H3 comprising the amino acid sequence of RNYDD-WYFDV (SEQ ID NO: 8); (d) an HVR-L1 comprising the amino acid sequence of SASSSVTYMY (SEQ ID NO: 4); (e) an HVR-L2 comprising the amino acid sequence of RTSDLAS (SEQ ID NO: 5); and (f) an HVR-L3 comprising the amino acid sequence of QHYHSYPLT (SEQ ID NO: 6). In some embodiments, the antibody is defined by the six HVRs comprising the amino acid sequence of SEQ ID NO: 7, 2, 8, 4, 5, and 6. In some embodiments, the antibody further comprises S43, P46, and W47 in the light chain variable (VL) domain framework region L2 (FR-L2) (Kabat numbering). In some embodiments, the antibody comprises (a) a heavy chain variable (VH) domain comprising an amino sequence having at least 90%, at least 95%, or at least 99% sequence identity to the amino acid sequence of SEQ ID NO: 9; (b) a light chain variable (VL) domain comprising an amino acid sequence having at least 90%, at least 95%, or at least 99% identity to the amino acid sequence of SEQ ID NO: 10; or (c) a VH domain as in (a) and a VL domain as in (b). In some embodiments, the antibody further comprises the following VH domain framework regions (FRs): (a) an FR-H1 comprising the amino acid sequence of EVQLVESGGGLVQPGGSLRLSCAASGFTFS (SEQ ID NO: 11); (b) an FR-H2 comprising the amino acid sequence of WVRQAPGKGLEWVA (SEQ ID NO: 12); (c) an FR-H3 comprising the amino acid sequence of RFTISRDNSKNT-LYLQMNSLRAEDTAVYYCTR (SEQ ID NO: 13); and (d) an FR-H4 comprising the amino acid sequence of WGQGTLVTVSS (SEQ ID NO: 14). In some embodiments, the VH domain comprises the amino acid sequence of SEQ ID NO: 9. In some embodiments, the antibody further comprises the following VL domain FRs: (a) an FR-L1 comprising the amino acid sequence of DIQMTQSPSSL-SASVGDRVTITC (SEQ ID NO: 15); (b) an FR-L2 comprising the amino acid sequence of WYQQKPGKSPKP-WIY (SEQ ID NO: 16); (c) an FR-L3 comprising the amino acid sequence of GVPSRFSGSGSGTDFTLTISSLQPED-FATYYC (SEQ ID NO: 17); and (d) an FR-L4 comprising the amino acid sequence of FGQGTKVEIK (SEQ ID NO: 18). In some embodiments, the VL domain comprises the amino acid sequence of SEQ ID NO: 10. In some embodiments, the antibody comprises (a) a heavy chain comprising the amino acid sequence of SEQ ID NO: 76 and (b) a light chain comprising the amino acid sequence of SEQ ID NO: 77. In other embodiments, the antibody comprises (a) a heavy chain comprising the amino acid sequence of SEQ ID NO: 78 and (b) a light chain comprising the amino acid sequence of SEQ ID NO: 79.

In another aspect, the invention features an isolated antibody that binds to human tryptase beta 1, or an antigen-binding fragment thereof, wherein the antibody comprises (a) a VH domain comprising an amino acid sequence having at least 90%, at least 95%, or at least 99% sequence identity to the amino acid sequence of SEQ ID NO: 9 and (b) a VL domain comprising an amino acid sequence having at least 90%, at least 95%, or at least 99% sequence identity to the amino acid sequence of SEQ ID NO: 10. In some embodiments, the antibody comprises a VH domain comprising the amino acid sequence of SEQ ID NO: 9 and a VL domain comprising the amino acid sequence of SEQ ID NO: 10. In some embodiments, the antibody comprises (a) a heavy chain comprising the amino acid sequence of SEQ ID NO: 76 and (b) a light chain comprising the amino acid sequence of SEQ ID NO: 77. In other embodiments, the antibody comprises (a) a heavy chain comprising the amino acid sequence of SEQ ID NO: 78 and (b) a light chain comprising the amino acid sequence of SEQ ID NO: 79.

In another aspect, the invention features an isolated antibody comprising (a) a heavy chain comprising the amino acid sequence of SEQ ID NO: 76 and (b) a light chain comprising the amino acid sequence of SEQ ID NO: 77.

In another aspect, the invention features an isolated antibody comprising (a) a heavy chain comprising the amino acid sequence of SEQ ID NO: 78 and (b) a light chain comprising the amino acid sequence of SEQ ID NO: 79.

In another aspect, the invention features an isolated antibody that binds to human tryptase beta 1, or an antigen-binding fragment thereof, wherein the antibody comprises the following six HVRs: (a) an HVR-H1 comprising the amino acid sequence of DYGMV (SEQ ID NO: 7); (b) an HVR-H2 comprising the amino acid sequence of FISSGSSTVYYADTMKG (SEQ ID NO: 2); (c) an HVR-H3 comprising the amino acid sequence of RDNYDWYFDV (SEQ ID NO: 29); (d) an HVR-L1 comprising the amino acid sequence of SASSSVTYMY (SEQ ID NO: 4); (e) an HVR-L2 comprising the amino acid sequence of RTSDLAS (SEQ ID NO: 5); and (f) an HVR-L3 comprising the amino acid sequence of QHYHSYPLT (SEQ ID NO: 6). In some embodiments, the antibody further comprises the following VH domain FRs: (a) an FR-H1 comprising the amino acid sequence of EVKLVESGGGSVQPGGSRKLSCAASGFTFS (SEQ ID NO: 21); (b) an FR-H2 comprising the amino acid sequence of WVRQAPGKGLEWVA (SEQ ID NO: 22); (c) an FR-H3 comprising the amino acid sequence of RFTISRDNPKNTLFLQMSSLRSEDTAMYYCAR (SEQ ID NO: 23); and (d) an FR-H4 comprising the amino acid sequence of WGTGTTVTVSS (SEQ ID NO: 24). In some embodiments, the VH domain comprises the amino acid sequence of SEQ ID NO: 19. In some embodiments, the antibody further comprises the following VL domain FRs: (a) an FR-L1 comprising the amino acid sequence of QIVLTQSPAIMSASPGEKVTISC (SEQ ID NO: 25); (b) an FR-L2 comprising the amino acid sequence of WYQQKPGSSPKPWIY (SEQ ID NO: 26); (c) an FR-L3 comprising the amino acid sequence of GVPARFSGSGSGTSYSLTISSMEAEDAATYYC (SEQ ID NO: 27); and (d) an FR-L4 comprising the amino acid sequence of FGAGTKLELK (SEQ ID NO: 28). In some embodiments, the VL domain comprises the amino acid sequence of SEQ ID NO: 20.

In another aspect, the invention features an isolated antibody that binds to human tryptase beta 1, or an antigen-binding fragment thereof, wherein the antibody comprises (a) a VH domain comprising an amino sequence having at least 90%, at least 95% sequence, or at least 99% identity to the amino acid sequence of SEQ ID NO: 19; (b) a VL domain comprising the amino acid sequence of SEQ ID NO: 20; or (c) a VH domain as in (a) and a VL domain as in (b). In some embodiments, the antibody further comprises the following VH domain FRs: (a) an FR-H1 comprising the amino acid sequence of EVKLVESGGGSVQPGGSRKLSCAASGFTFS (SEQ ID NO: 21); (b) an FR-H2 comprising the amino acid sequence of WVRQAPGKGLEWVA (SEQ ID NO: 22); (c) an FR-H3 comprising the amino acid sequence of RFTISRDNPKNTLFLQMSSLRSEDTAMYYCAR (SEQ ID NO: 23); and (d) an FR-H4 comprising the amino acid sequence of WGTGTTVTVSS (SEQ ID NO: 24). In some embodiments, the VH domain comprises the amino acid sequence of SEQ ID NO: 19. In some embodiments, the antibody further comprises the following VL domain FRs: (a) an FR-L1 comprising the amino acid sequence of QIVLTQSPAIMSASPGEKVTISC (SEQ ID NO: 25); (b) an FR-L2 comprising the amino acid sequence of WYQQKPGSSPKPWIY (SEQ ID NO: 26); (c) an FR-L3 comprising the amino acid sequence of GVPARFSGSGSGTSYSLTISSMEAEDAATYYC (SEQ ID NO: 27); and (d) an FR-L4 comprising the amino acid sequence of FGAGTKLELK (SEQ ID NO: 28). In some embodiments, the VL domain comprises the amino acid sequence of SEQ ID NO: 20.

In another aspect, the invention features an isolated antibody that binds to human tryptase beta 1, or an antigen-binding fragment thereof, comprising (a) a VH domain comprising an amino acid sequence having at least 99% sequence identity to the amino acid sequence of SEQ ID NO: 19 and (b) a VL domain comprising an amino acid sequence having at least 99% sequence identity to the amino acid sequence of SEQ ID NO: 20.

In some embodiments of any of the preceding aspects, the antibody binds to an epitope on human tryptase beta 1 comprising at least one, at least two, at least three, or all four residues selected from the group consisting of His51, Val80, Lys81, and Asp82 of SEQ ID NO: 71. In some embodiments, the antibody binds to an epitope on human tryptase beta 1 comprising at least one, at least two, at least three, or all four residues selected from the group consisting of His51, Val80, Lys81, and Asp82 of SEQ ID NO: 71. In some embodiments, the antibody binds to an epitope on human tryptase beta 1 comprising His51 and at least one, at least two, or all three residues selected from the group consisting of Val80, Lys81, and Asp82 of SEQ ID NO: 71. In some embodiments, the epitope on human tryptase beta 1 further comprises one or more amino acid residues selected from the group consisting of Gln67, Leu83, Ala84, Ala85, Arg87, Pro103, Val104, Ser105, Arg106, Glu128, Glu129, and Pro130 of SEQ ID NO: 71. In some embodiments, the epitope on human tryptase beta 1 comprises at least two, at least three, at least four, at least five, at least six, at least seven, at least eight, at least nine, at least ten, at least eleven, or all twelve amino acid residues selected from the group consisting of Gln67, Leu83, Ala84, Ala85, Arg87, Pro103, Val104, Ser105, Arg106, Glu128, Glu129, and Pro130 of SEQ ID NO: 71. In some embodiments, the epitope on human tryptase beta 1 comprises His51, Gln67, Val80, Lys81, Asp82, Leu83, Ala84, Ala85, Arg87, Pro103, Va104, Ser105, Arg106, Glu128, Glu129, and Pro130 of SEQ ID NO:71. In some embodiments, the epitope is relative to a human tryptase beta 1 monomer or tetramer. In some embodiments, the epitope is determined by an X-ray crystallography model. In some embodiments, the antibody is capable of dissociating both the small interface of tetrameric human tryptase beta 1 and the large interface of tetrameric human tryptase beta 1.

In another aspect, the invention features an isolated antibody that binds to human tryptase beta 1, or an antigen-binding fragment thereof, wherein the antibody comprises the following six HVRs: (a) an HVR-H1 comprising the amino acid sequence of GYAIT (SEQ ID NO: 30); (b) an HVR-H2 comprising the amino acid sequence of GISSAAT- TFYSSWAKS (SEQ ID NO: 31); (c) an HVR-H3 comprising the amino acid sequence of DPRGYGAALDRLDL (SEQ ID NO: 32); (d) an HVR-L1 comprising the amino acid sequence of QSIKSVYNNRLG (SEQ ID NO: 33); (e) an HVR-L2 comprising the amino acid sequence of ETSILTS (SEQ ID NO: 34); and (f) an HVR-L3 comprising the amino acid sequence of AGGFDRSGDTT (SEQ ID NO: 35). In some embodiments, the antibody is defined by the six HVRs comprising the amino acid sequence of SEQ ID NO: 30, 31, 32, 33, 34, and 35. In some embodiments, the antibody further comprises Arg71 and Va78 in VH domain FR-H3 (Kabat numbering). In some embodiments, the antibody further comprises the following VH domain FRs: (a) an FR-H1 comprising the amino acid sequence of EVQLVESGPGLVKPSETLSLTCTVSRFSLI (SEQ ID NO: 38); (b) an FR-H2 comprising the amino acid sequence of WIRQPPGKGLEWIG (SEQ ID NO: 42); (c) an FR-H3 comprising the amino acid sequence of RVTISRDTSKNQVSLKLSSVTAADTAVYYCAR (SEQ ID NO: 43); and (d) an FR-H4 comprising the amino acid sequence of WGQGTLVTVSS (SEQ ID NO: 41). In some embodiments, the VH domain comprises the amino acid sequence of SEQ ID NO: 36. In some embodiments, the antibody comprises the following VL domain FRs: (a) an FR-L1 comprising the amino acid sequence of DIQMTQSPSSLSASVGDRVTITC (SEQ ID NO: 64); (b) an FR-L2 comprising the amino acid sequence of WYQQKPGKAPKLLIY (SEQ ID NO: 65); (c) an FR-L3 comprising the amino acid sequence of GVPSRFSGSGSGTDFTLTISSLQPEDFATYYC (SEQ ID NO: 66); and (d) an FR-L4 comprising the amino acid sequence of FGQGTKVEIK (SEQ ID NO: 63). In some embodiments, the VL domain comprises the amino acid sequence of SEQ ID NO: 37. In some embodiments, the antibody comprises (a) a heavy chain comprising the amino acid sequence of SEQ ID NO: 80 and (b) a light chain comprising the amino acid sequence of SEQ ID NO: 81. In other embodiments, the antibody comprises (a) a heavy chain comprising the amino acid sequence of SEQ ID NO: 82 and (b) a light chain comprising the amino acid sequence of SEQ ID NO: 83.

In another aspect, the invention features an isolated antibody that binds to human tryptase beta 1, or an antigen-binding fragment thereof, wherein the antibody comprises (a) a VH domain comprising an amino sequence having at least 90%, at least 95%, or at least 99% sequence identity to the amino acid sequence of any one of SEQ ID NOs: 36, 47, 48, 49, 50, 51, and 52; (b) a VL domain comprising an amino acid sequence having at least 90%, at least 95%, or at least 99% identity to the amino acid sequence of any one of SEQ ID NO: 37, 53, 58, or 59; or (c) a VH domain as in (a) and a VL domain as in (b). In some embodiments, the antibody further comprises the following VH domain FRs: (a) an FR-H1 comprising the amino acid sequence of EVQLVESGPGLVKPSETLSLTCTVSRFSLI (SEQ ID NO: 38); (b) an FR-H2 comprising the amino acid sequence of WIRQPPGKGLEWIG (SEQ ID NO: 42); (c) an FR-H3 comprising the amino acid sequence of RVTISRDTSKNQVSLKLSSVTAADTAVYYCAR (SEQ ID NO: 43); and (d) an FR-H4 comprising the amino acid sequence of WGQGTLVTVSS (SEQ ID NO: 41). In some embodiments, the VH domain comprises the amino acid sequence of SEQ ID NO: 36. In some embodiments, the antibody comprises the following VL domain FRs: (a) an FR-L1 comprising the amino acid sequence of DIQMTQSPSSLSASVGDRVTITC (SEQ ID NO: 64); (b) an FR-L2 comprising the amino acid sequence of WYQQKPGKAPKLLIY (SEQ ID NO: 65); (c) an FR-L3 comprising the amino acid sequence of GVPSRFSGSGSGTDFTLTISSLQPEDFATYYC (SEQ ID NO: 66); and (d) an FR-L4 comprising the amino acid sequence of FGQGTKVEIK (SEQ ID NO: 63). In some embodiments, the VL domain comprises the amino acid sequence of SEQ ID NO: 37. In some embodiments, the antibody comprises (a) a heavy chain comprising the amino acid sequence of SEQ ID NO: 80 and (b) a light chain comprising the amino acid sequence of SEQ ID NO: 81. In other embodiments, the antibody comprises (a) a heavy chain comprising the amino acid sequence of SEQ ID NO: 82 and (b) a light chain comprising the amino acid sequence of SEQ ID NO: 83.

In another aspect, the invention features an isolated antibody comprising (a) a heavy chain comprising the amino acid sequence of SEQ ID NO: 80 and (b) a light chain comprising the amino acid sequence of SEQ ID NO: 81.

In another aspect, the invention features an isolated antibody comprising (a) a heavy chain comprising the amino acid sequence of SEQ ID NO: 82 and (b) a light chain comprising the amino acid sequence of SEQ ID NO: 83.

In another aspect, the invention features an isolated antibody that binds to human tryptase, or an antigen-binding fragment thereof, wherein the antibody comprises (a) a VH domain comprising an amino acid sequence having at least 90%, at least 95%, or at least 99% sequence identity to the amino acid sequence of SEQ ID NO: 52 and (b) a VL domain comprising an amino acid sequence having at least 90%, at least 95%, or at least 99% sequence identity to the amino acid sequence of SEQ ID NO: 53.

In some embodiments of any of the preceding aspects, the antibody binds to an epitope on human tryptase beta 1 comprising at least one, at least two, or all three residues selected from the group consisting of Gln100, Leu101, and Leu102 of SEQ ID NO: 71. In some embodiments, the epitope on human tryptase beta 1 further comprises one or more amino acid residues selected from the group consisting of Trp55, Gln67, Asp82, Leu83, Ala84, Arg87, Pro103, Val104, Ser105, Arg106, Glu126, Leu127, Glu128, and Glu129 of SEQ ID NO: 71. In some embodiments, the epitope on human tryptase beta 1 comprises at least two, at least three, at least four, at least five, at least six, at least seven, at least eight, at least nine, at least ten, at least eleven, at least twelve, at least thirteen, or all fourteen amino acid residues selected from the group consisting of Trp55, Gln67, Asp82, Leu83, Ala84, Arg87, Pro103, Val104, Ser105, Arg106, Glu126, Leu127, Glu128, and Glu129 of SEQ ID NO: 71. In some embodiments, the epitope comprises Gln35, Trp55, Gln67, Asp82, Leu83, Ala84, Arg87, Gln100, Leu101, Leu102, Pro103, Val104, Ser105, Arg106, Glu126, Leu127, Glu128, Glu129, and Arg216 of SEQ ID NO: 71. In some embodiments, the epitope is relative to a human tryptase beta 1 monomer or tetramer. In some embodiments, the epitope is relative to a human tryptase beta 1 tetramer, and the epitope on human tryptase beta 1 further comprises one or both of Gln35 and Arg216 of SEQ ID NO: 71. In some embodiments, the epitope is determined by an X-ray crystallography model. In some embodiments, the antibody is capable of dissociating the small interface and/or the large interface of human tryptase beta 1.

In some embodiments of any of the preceding aspects, the antibody further binds cynomolgus monkey (cyno) tryptase. In some embodiments, the antibody further binds human tryptase alpha. In some embodiments, the antibody further binds human tryptase beta 2 or human tryptase beta 3. In some embodiments, the antibody binds human tryptase beta 2 and human tryptase beta 3.

In some embodiments of any of the preceding aspects, the antibody binds the tryptase with a $K_D$ of about 1 nM or less. In some embodiments, the $K_D$ is measured by a surface plasmon resonance (SPR) assay. In some embodiments, the antibody binds the tryptase with a $K_D$ of between about 120 pM and about 0.5 nM. In some embodiments, the antibody binds the tryptase with a $K_D$ of between about 120 pM and about 300 pM. In some embodiments, the antibody binds the tryptase with a $K_D$ of between about 120 pM and about 200 pM. In some embodiments, the antibody binds the tryptase with a $K_D$ of about 180 pM. In some embodiments, the antibody binds tryptase with a $K_D$ of about 400 pM. In some embodiments, the SPR assay is performed at 25° C. In some embodiments, the $K_D$ is measured using a BIACORE® SPR assay, for example, as described in Example 1, Section (A)(vii). In some embodiments, the SPR assay can use a BIAcore® T200 or an equivalent device. In some embodiments, BIAcore® Series S CM5 sensor chips (or equivalent sensor chips) are immobilized with monoclonal mouse anti-human IgG (Fc) antibody and anti-tryptase antibodies are subsequently captured on the flow cell. Serial 3-fold dilutions of the His-tagged human tryptase beta 1 monomer (SEQ ID NO: 128) are injected at a flow rate of 30 µl/min. Each sample is analyzed with 3 min association and 10 min dissociation. The assay is performed at 25° C. After each injection, the chip is regenerated using 3 M $MgCl_2$. Binding response is corrected by subtracting the response units (RU) from a flow cell capturing an irrelevant IgG at similar density. A 1:1 Languir model of simultaneous fitting of $k_{on}$ and $k_{off}$ is used for kinetics analysis.

In some embodiments of any of the preceding aspects, the antibody is capable of inhibiting the enzymatic activity of human tryptase beta 1. In some embodiments, the antibody inhibits the activity of tryptase with an IC50 of about 2.5 nM or lower as determined by a human tryptase beta enzymatic assay using a synthetic peptide S-2288 as a substrate. In some embodiments, the antibody inhibits the activity of tryptase with an IC50 of between about 550 pM and about 2.5 nM. In some embodiments, the antibody inhibits the activity of tryptase with an IC50 of between about 500 pM and about 2 nM. In some embodiments, the antibody inhibits the activity of tryptase with an IC50 of between about 550 nM and 1.5 nM. In some embodiments, the antibody inhibits the activity of tryptase with an IC50 of between about 500 pM and about 700 pM. In some embodiments, the inhibitory activity of the antibody is determined as described in Example 1(A)(viii)(a)). In some embodiments, the final concentration of heparin in the human tryptase beta enzymatic assay using the synthetic peptide S-2288 is 66 pg/ml.

In some embodiments, recombinant human tryptase beta 1 tetramer active enzyme is diluted to 0.75 nM in TNH Buffer (200 mM Tris, 150 mM NaCl, 0.1 mg/mL heparin, 0.01% TRITON™ X-100, pH 8.0), and combined 1:1 with anti-tryptase antibodies (diluted in PBS) in 384-well plates. Plates are incubated for 1 h at ambient temperature with gentle agitation. Colorimetric substrate S-2288 (Chromogenix, Part No. 82-0852-39), or an equivalent substrate, is diluted to 1200 µM in TNH Buffer and added to the plate. In some embodiments, the final in-well concentrations are 400 µM S-2288, 0.25 nM recombinant human tryptase beta 1 tetramer, 66 pg/mL heparin, and from 0.10 to 222 nM anti-tryptase antibody. Plates are incubated for 40 min at ambient temperature with gentle agitation and then read at $A_{405}$. The IC50 of the anti-tryptase antibodies is determined from a four-parameter fit of their respective curves.

In some embodiments of any of the preceding aspects, the antibody is capable of inhibiting the enzymatic activity of human tryptase beta 1 at pH 6. In particular, the inhibitory activity of the antibody may be determined at pH 6.

In some embodiments, the antibody is capable inhibiting tryptase-mediated stimulation of bronchial smooth muscle cell proliferation and/or collagen-based contraction. In some embodiments, the antibody is capable of inhibiting mast cell histamine release. In some embodiments, the antibody is capable of inhibiting IgE-triggered histamine release and/or tryptase-triggered histamine release. In some embodiments, the antibody is capable of inhibiting cyno tryptase D1 as assessed by an active tryptase ELISA assay. In some embodiments, the antibody is capable of inhibiting tryptase activity in cynomolgus monkey broncheoloar lavage (BAL) or nasosorption samples. In some embodiments, the antibody is capable of dissociating tetrameric human tryptase beta 1. In some embodiments, the antibody is capable of dissociating tetrameric human tryptase beta 1 when in a monovalent format. In some embodiments, the monovalent format is a Fab format. In some embodiments, the antibody is capable of dissociating tetrameric human tryptase beta 1 in the presence of heparin. In some embodiments, the antibody is capable of dissociating tetrameric tryptase beta in the presence of 66 µg/ml heparin.

In another aspect, the invention features an antibody that binds to the same epitope as any one of the preceding antibodies. In some embodiments, whether the antibody binds to the same epitope or competes for binding to human tryptase beta 1 is determined by an epitope binning assay. In some embodiments, the epitope binning assay is an OCTET® epitope binning assay such as described in Example 3, Section C. In some embodiments, human tryptase beta 1 monomer protein is biotinylated at Lys residue by reacting with NHS-PEG4-biotin. Biotinylated monomer is diluted to 5 pg/ml in kinetics buffer (ForteBio, Inc.) and immobilized onto streptavidin sensor tips (ForteBio, Inc.). After the immobilization step, human tryptase beta 1-immobilized sensors are saturated with the first antibody, diluted at 10-20 pg/ml, followed by binding with second antibody diluted at 2.5 pg/ml. In some embodiments, the epitope binning assay is performed at 30° C.

In another aspect, the invention features an antibody that competes for binding to human tryptase beta 1 with, or cross-blocks or is cross-blocked by any one of the preceding antibodies.

In some embodiments of any of the preceding aspects, the antibody is monoclonal, human, humanized, or chimeric. In some embodiments, the antibody is humanized.

In some embodiments of any of the preceding aspects, the antibody is an antibody fragment that binds tryptase. In some embodiments, the antibody fragment is selected from the group consisting of Fab, Fab'-SH, Fv, scFv, and (Fab')$_2$ fragments.

In some embodiments of any of the preceding aspects, the antibody is a full-length antibody. In some embodiments, the antibody is an IgG antibody. In some embodiments, the IgG antibody is an IgG1 antibody. In some embodiments, the IgG antibody is an IgG4 antibody. In some embodiments, the IgG4 antibody comprises a mutation in the hinge region. In some embodiments, the mutation is a substitution mutation. In some embodiments, the substitution mutation is at amino acid residue S228 (EU numbering). In some embodiments, the IgG4 antibody comprises an S228P mutation (EU numbering).

In some embodiments of any of the preceding aspects, the antibody is a monospecific antibody.

In some embodiments of any of the preceding aspects, the antibody is a multispecific antibody. In some embodiments, the antibody is a bispecific antibody. In some embodiments, the antibody comprises a first binding domain that binds to tryptase and a second binding domain that binds to a second biological molecule, wherein the second biological molecule is selected from the group consisting of interleukin-13 (IL-13), interleukin-4 (IL-4), interleukin-5 (IL-5), interleukin-17 (IL-17), IgE, and interleukin-33 (IL-33). In some embodiments, the second biological molecule is IL-13. In some embodiments, the second biological molecule is IL-33. In some embodiments, the second biological molecule is IgE.

In another aspect, the invention features an isolated nucleic acid encoding any of the antibodies described herein or a set of isolated nucleic acids together encoding the antibody.

In another aspect, the invention features an isolated nucleic acid encoding an antibody comprising a VH domain comprising the amino acid sequence of SEQ ID NO: 9 and/or a VL domain comprising the amino acid sequence of SEQ ID NO: 10, or a set of isolated nucleic acids together encoding the antibody, wherein the nucleic acid comprises a sequence that is at least 85%, at least 90%, at least 95%, or at least 99% identical to the sequence of SEQ ID NO: 104 and/or SEQ ID NO: 105. In some embodiments, the antibody comprises (a) a heavy chain comprising the amino acid sequence of SEQ ID NO: 76 and/or (b) a light chain comprising the amino acid sequence of SEQ ID NO: 77, and wherein the nucleic acid or set comprises a sequence that is at least 85%, at least 90%, at least 95%, or at least 99% identical to the sequence of SEQ ID NO: 106 and/or SEQ ID NO: 107. In some embodiments, the antibody comprises (a) a heavy chain comprising the amino acid sequence of SEQ ID NO: 78 and/or (b) a light chain comprising the amino acid sequence of SEQ ID NO: 79, and wherein the nucleic acid or set comprises a sequence that is at least 85%, at least 90%, at least 95%, or at least 99% identical to the sequence of SEQ ID NO: 108 and/or SEQ ID NO: 107. In some embodiments, the nucleic acid or set comprises the sequence of SEQ ID NO: 108 and/or SEQ ID NO: 107.

In another aspect, the invention features an isolated nucleic acid encoding the antibody comprising a VH domain comprising the amino acid sequence of SEQ ID NO: 36 and/or a VL domain comprising the amino acid sequence of SEQ ID NO: 37, or a set of isolated nucleic acids together encoding the antibody, wherein the nucleic acid comprises a sequence that is at least 85%, at least 90%, at least 95%, or at least 99% identical to the sequence of SEQ ID NO: 109 and/or SEQ ID NO: 110. In some embodiments, the antibody comprises (a) a heavy chain comprising the amino acid sequence of SEQ ID NO: 80 and/or (b) a light chain comprising the amino acid sequence of SEQ ID NO: 81, and wherein the nucleic acid or set comprises a sequence that is at least 85%, at least 90%, at least 95%, or at least 99% identical to the sequence of SEQ ID NO: 111 and/or SEQ ID NO: 112. In some embodiments, the antibody comprises (a) a heavy chain comprising the amino acid sequence of SEQ ID NO: 82 and/or (b) a light chain comprising the amino acid sequence of SEQ ID NO: 83, and wherein the nucleic acid or set comprises a sequence that is at least 85%, at least 90%, at least 95%, or at least 99% identical to the sequence of SEQ ID NO: 113 and/or SEQ ID NO: 112. In some embodiments, the nucleic acid or set comprises the sequence of SEQ ID NO: 113 and/or SEQ ID NO: 112.

In another aspect, the invention features a vector (e.g., an expression vector) or set of vectors comprising any of the isolated nucleic acids or set of isolated nucleic acids described herein. In another aspect, the invention features host cells comprising the preceding nucleic acids and/or vectors and/or sets of nucleic acids and/or sets of vectors. In some embodiments, the host cell is a mammalian cell. In some embodiments, the mammalian cell is a Chinese hamster ovary (CHO) cell. In some embodiments, the host cell is a prokaryotic cell. In some embodiments, the prokaryotic cell is E. coli.

In another aspect, the invention features a method of producing any of the antibodies described herein, the method comprising culturing a host cell that comprises any of the preceding vectors (e.g., expression vectors) or set of vectors in a culture medium under suitable conditions that allow production of the antibody. In some embodiments, the method further comprises recovering the antibody from the host cell or the culture medium.

In another aspect, the invention features composition (e.g., a pharmaceutical composition) comprising any one of the preceding antibodies. In some embodiments, the composition further comprises a pharmaceutically acceptable carrier, excipient, or diluent.

In another aspect, the invention features a pharmaceutical composition comprising an isolated monoclonal antibody that binds to human tryptase beta 1, or an antigen-binding fragment thereof, and a pharmaceutically acceptable carrier, excipient, or diluent, wherein the antibody binds to monomeric tryptase beta 1 with a $K_D$ of about 0.1 nM to about 1 nM, and/or wherein the antibody is capable of inhibiting the enzymatic activity of the tryptase with a half-maximal inhibitory concentration (IC50) of about 0.1 nM to about 5 nM as determined by an in vitro tryptase enzymatic assay using S-2288 as a substrate.

In some embodiments of the preceding aspect, the antibody binds the tryptase with a $K_D$ between about 0.5 nM to about 1 nM. In some embodiments, the antibody binds the tryptase with a $K_D$ between about 0.1 nM to about 0.5 nM. In some embodiments, the antibody binds the tryptase with a $K_D$ of about 0.4 nM. In some embodiments, the antibody binds the tryptase with a $K_D$ of about 0.2 nM. In some embodiments, the $K_D$ is measured by a surface plasmon resonance (SPR) assay. In some embodiments, the SPR assay is performed at 25° C. In some embodiments, the $K_D$ is measured using a BIACORE® SPR assay, for example, as described in Example 1, Section (A)(vii). In some embodiments, the SPR assay can use a BIAcore® T200 or an equivalent device. In some embodiments, BIAcore® Series S CM5 sensor chips (or equivalent sensor chips) are immobilized with monoclonal mouse anti-human IgG (Fc) antibody and anti-tryptase antibodies are subsequently captured on the flow cell. Serial 3-fold dilutions of the His-tagged human tryptase beta 1 monomer (SEQ ID NO: 128) are injected at a flow rate of 30 μl/min. Each sample is analyzed with 3 min association and 10 min dissociation. The assay is performed at 25° C. After each injection, the chip is regenerated using 3 M MgCl$_2$. Binding response is corrected by subtracting the response units (RU) from a flow cell capturing an irrelevant IgG at similar density. A 1:1 Languir model of simultaneous fitting of k$_{on}$ and k$_{off}$ is used for kinetics analysis.

In some embodiments of the preceding aspect, the antibody is capable of inhibiting the activity of the tryptase with an IC50 of about 0.5 nM to about 5 nM. In some embodiments, the antibody is capable of inhibiting the activity of the tryptase with an IC50 of about 0.1 nM to about 2 nM. In some embodiments, the antibody is capable of inhibiting the activity of human tryptase with an IC50 of about 4 nM. In some embodiments, the antibody is capable of inhibiting the activity of the tryptase with an IC50 of about 0.6 nM. In some embodiments, the antibody is capable of inhibiting the tryptase activity at pH 6 in an in vitro tryptase enzymatic assay using S-2288 as a substrate. In some embodiments, the inhibitory activity of the antibody is determined as described in the Examples (e.g., Example 1, Section (A)(viii)(a)). In some embodiments, recombinant human tryptase beta 1 tetramer active enzyme is diluted to 0.75 nM in TNH Buffer (200 mM Tris, 150 mM NaCl, 0.1 mg/mL heparin, 0.01% TRITON™ X-100, pH 8.0), and combined 1:1 with anti-tryptase antibodies (diluted in PBS) in 384-well plates. Plates are incubated for 1 h at ambient temperature with gentle agitation. Colorimetric substrate S-2288 (Chromogenix, Part No. 82-0852-39), or an equivalent substrate, is diluted to 1200 pM in TNH Buffer and added to the plate. In some embodiments, the final in-well concentrations are 400 pM S-2288, 0.25 nM recombinant human tryptase beta 1 tetramer, 66 pg/mL heparin, and from 0.10 to 222 nM anti-tryptase antibody. Plates are incubated for 40 min at ambient temperature with gentle agitation and then read at A$_{405}$. The IC50 of the anti-tryptase antibodies is determined from a four-parameter fit of their respective curves. In some embodiments, the final concentration of heparin in the human tryptase beta enzymatic assay using the synthetic peptide S-2288 is 66 pg/ml.

In some embodiments of the preceding aspect, the antibody is capable inhibiting tryptase-mediated stimulation of bronchial smooth muscle cell proliferation and/or collagen-based contraction. In some embodiments, the antibody is capable of inhibiting mast cell histamine release. In some embodiments, the antibody is capable of inhibiting IgE-triggered histamine release and/or tryptase-triggered histamine release. In some embodiments, the antibody is capable of inhibiting tryptase activity in cynomolgus monkey broncheolar lavage (BAL) or nasosorption samples. In some embodiments, the antibody is capable of dissociating tetrameric human tryptase beta 1. In some embodiments, the antibody is capable of dissociating tetrameric human tryptase beta 1 when in a monovalent format. In some embodiments, the monovalent format is a Fab format. In some embodiments, the antibody is capable of dissociating tetrameric human tryptase beta 1 in the presence of heparin. In some embodiments, the antibody is capable of dissociating tetrameric tryptase beta in the presence of 66 pg/ml heparin.

In some embodiments of the preceding aspect, the antibody comprises the following six hypervariable regions (HVRs): (a) an HVR-H1 comprising the amino acid sequence of DYGMV (SEQ ID NO: 7); (b) an HVR-H2 comprising the amino acid sequence of FISSGSSTVYY-ADTMKG (SEQ ID NO: 2); (c) an HVR-H3 comprising the amino acid sequence of RNYDDWYFDV (SEQ ID NO: 8); (d) an HVR-L1 comprising the amino acid sequence of SASSSVTYMY (SEQ ID NO: 4); (e) an HVR-L2 comprising the amino acid sequence of RTSDLAS (SEQ ID NO: 5); and (f) an HVR-L3 comprising the amino acid sequence of QHYHSYPLT (SEQ ID NO: 6). In some embodiments, the antibody comprises (a) a heavy chain variable (VH) domain comprising an amino sequence having at least 90%, at least 95%, or at least 99% sequence identity to the amino acid sequence of SEQ ID NO: 9; (b) a light chain variable (VL) domain comprising an amino acid sequence having at least 90%, at least 95%, or at least 99% identity to the amino acid sequence of SEQ ID NO: 10; or (c) a VH domain as in (a) and a VL domain as in (b). In some embodiments, the antibody further comprises the following VH domain FRs: (a) an FR-H1 comprising the amino acid sequence of EVQLVESGGGLVQPGGSLRLSCAASGFTFS (SEQ ID NO: 11); (b) an FR-H2 comprising the amino acid sequence of WVRQAPGKGLEWVA (SEQ ID NO: 12); (c) an FR-H3 comprising the amino acid sequence of RFTISRDNSKNT-LYLQMNSLRAEDTAVYYCTR (SEQ ID NO: 13); and (d) an FR-H4 comprising the amino acid sequence of WGQGTLVTVSS (SEQ ID NO: 14). In some embodiments, the VH domain of the antibody comprises the amino acid sequence of SEQ ID NO: 9. In some embodiments, the antibody further comprises the following VL domain FRs: (a) an FR-L1 comprising the amino acid sequence of DIQMTQSPSSLSASVGDRVTITC (SEQ ID NO: 15); (b) an FR-L2 comprising the amino acid sequence of WYQQKPGKSPKPWIY (SEQ ID NO: 16); (c) an FR-L3 comprising the amino acid sequence of GVPSRFSGSGSGTDFTLTISSLQPEDFATYYC (SEQ ID NO: 17); and (d) an FR-L4 comprising the amino acid sequence of FGQGTKVEIK (SEQ ID NO: 18). In some embodiments, the VL domain of the antibody comprises the amino acid sequence of SEQ ID NO: 10. In some embodiments, the antibody comprises (a) a heavy chain comprising the amino acid sequence of SEQ ID NO: 76 and (b) a light chain comprising the amino acid sequence of SEQ ID NO: 77. In some embodiments, the antibody comprises (a) a heavy chain comprising the amino acid sequence of SEQ ID NO: 78 and (b) a light chain comprising the amino acid sequence of SEQ ID NO: 79. In some embodiments, the antibody binds to an epitope on human tryptase beta 1 comprising at least one, at least two, at least three, or all four residues selected from the group consisting of His51, Val80, Lys81, and Asp82 of SEQ ID NO: 71. In some embodiments, the antibody binds to an epitope on human tryptase beta 1 comprising His51 and at least one, at least two, or all three residues selected from the group consisting of Val 80, Lys81, and Asp82 of SEQ ID NO: 71. In some embodiments, the epitope on human tryptase beta 1 further comprises one or more amino acid residues selected from the group consisting of Gln67, Leu83, Ala84, Ala85, Arg87, Pro103, Va104, Ser105, Arg106, Glu128, Glu129, and Pro130 of SEQ ID NO: 71. In some embodiments, the epitope on human tryptase beta 1 comprises at least two, at least three, at least four, at least five, at least six, at least seven, at least eight, at least nine, at least ten, at least eleven, or all twelve amino acid residues selected from the group consisting of Gln67, Leu83, Ala84, Ala85, Arg87, Pro103, Val104, Ser105, Arg106, Glu128, Glu129, and Pro130 of SEQ ID NO: 71. In some embodiments, the epitope on human tryptase beta 1 comprises His51, Gln67, Val80, Lys81, Asp82, Leu83, Ala84, Ala85, Arg87, Pro103, Val104, Ser105, Arg106, Glu128, Glu129, and Pro130 of SEQ ID NO:71. In some embodiments, the epitope is relative to a human tryptase beta 1 monomer or tetramer. In some embodiments, the epitope is determined by an X-ray crystallography model. In some embodiments, the antibody is capable of dissociating both the small interface of tetrameric human tryptase beta 1 and the large interface of tetrameric human tryptase beta 1.

In other embodiments of the preceding aspect, the antibody comprises the following six HVRs: (a) an HVR-H1 comprising the amino acid sequence of GYAIT (SEQ ID NO: 30); (b) an HVR-H2 comprising the amino acid sequence of GISSAATTFYSSWAKS (SEQ ID NO: 31); (c) an HVR-H3 comprising the amino acid sequence of DPRGYGAALDRLDL (SEQ ID NO: 32); (d) an HVR-L1 comprising the amino acid sequence of QSIKSVYNNRLG (SEQ ID NO: 33); (e) an HVR-L2 comprising the amino acid sequence of ETSILTS (SEQ ID NO: 34); and (f) an HVR-L3 comprising the amino acid sequence of AGGFDRSGDTT (SEQ ID NO: 35). In some embodiments, the antibody comprises (a) a VH domain comprising an amino sequence having at least 90%, at least 95%, or at least 99% sequence identity to the amino acid sequence of any one of SEQ ID NOs: 36, 47, 48, 49, 50, 51, and 52; (b) a VL domain comprising an amino acid sequence having at least 90%, at least 95%, or at least 99% identity to the amino acid sequence of any one of SEQ ID NO: 37, 53, 58, or 59; or (c) a VH domain as in (a) and a VL domain as in (b). In some embodiments, the antibody further comprises the following VH domain FRs: (a) an FR-H1 comprising the amino acid sequence of EVQLVESGPGLVKPSETLSLTCTVSRFSLI (SEQ ID NO: 38); (b) an FR-H2 comprising the amino acid sequence of WIRQPPGKGLEWIG (SEQ ID NO: 42); (c) an FR-H3 comprising the amino acid sequence of RVTISRDTSKNQVSLKLSSVTAADTAVYYCAR (SEQ ID NO: 43); and (d) an FR-H4 comprising the amino acid sequence of WGQGTLVTVSS (SEQ ID NO: 41). In some embodiments, the VH domain of the antibody comprises the amino acid sequence of SEQ ID NO: 36. In some embodiments, the antibody further comprises the following VL domain FRs: (a) an FR-L1 comprising the amino acid sequence of DIQMTQSPSSLSASVGDRVTITC (SEQ ID NO: 64); (b) an FR-L2 comprising the amino acid sequence of WYQQKPGKAPKLLIY (SEQ ID NO: 65); (c) an FR-L3 comprising the amino acid sequence of GVPSRFSGSGSGTDFTLTISSLQPEDFATYYC (SEQ ID NO: 66); and (d) an FR-L4 comprising the amino acid sequence of FGQGTKVEIK (SEQ ID NO: 63). In some embodiments, the VL domain of the antibody comprises the amino acid sequence of SEQ ID NO: 37. In some embodiments, the antibody comprises (a) a heavy chain comprising the amino acid sequence of SEQ ID NO: 80 and (b) a light chain comprising the amino acid sequence of SEQ ID NO: 81. In some embodiments, the antibody comprises (a) a heavy chain comprising the amino acid sequence of SEQ ID NO: 82 and (b) a light chain comprising the amino acid sequence of SEQ ID NO: 83. In some embodiments, the antibody binds to an epitope on human tryptase beta 1 comprising at least one, at least two, or all three residues selected from the group consisting of Gln100, Leu101, and Leu102 of SEQ ID NO: 71. In some embodiments, the epitope on human tryptase beta 1 further comprises one or more amino acid residues selected from the group consisting of Trp55, Gln67, Asp82, Leu83, Ala84, Arg87, Pro103, Val104, Ser105, Arg106, Glu126, Leu127, Glu128, and Glu129 of SEQ ID NO: 71. In some embodiments, the epitope on human tryptase beta 1 comprises at least two, at least three, at least four, at least five, at least six, at least seven, at least eight, at least nine, at least ten, at least eleven, at least twelve, at least thirteen, or all fourteen amino acid residues selected from the group consisting of Trp55, Gln67, Asp82, Leu83, Ala84, Arg87, Pro103, Val104, Ser105, Arg106, Glu126, Leu127, Glu128, and Glu129 of SEQ ID NO: 71. In some embodiments, the epitope comprises Gln35, Trp55, Gln67, Asp82, Leu83, Ala84, Arg87, Gln100, Leu101, Leu102, Pro103, Va104, Ser105, Arg106, Glu126, Leu127, Glu128, Glu129, and Arg216 of SEQ ID NO: 71. In some embodiments, the epitope is relative to a human tryptase beta 1 monomer or tetramer. In some embodiments, the epitope is relative to a human tryptase beta 1 tetramer, and the epitope on human tryptase beta 1 further comprises one or both of Gln35 and Arg216 of SEQ ID NO: 71. In some embodiments, the epitope is determined by an X-ray crystallography model. In some embodiments, the antibody is capable of dissociating the small interface and/or the large interface of human tryptase beta 1.

In another aspect, the invention features a composition (e.g., a pharmaceutical composition) comprising an isolated monoclonal antibody that binds to human tryptase beta 1, or an antigen-binding fragment thereof, and a pharmaceutically acceptable carrier, excipient, or diluent, wherein the antibody binds to an epitope on human tryptase beta 1 comprising at least one, at least two, at least three, or all four residues selected from the group consisting of His51, Val80, Lys81, and Asp82 of SEQ ID NO: 71. In some embodiments, the antibody binds to an epitope on human tryptase beta 1 comprising His51 and at least one, at least two, or all three residues selected from the group consisting of Val80, Lys81, and Asp82 of SEQ ID NO: 71. In some embodiments, the epitope on human tryptase beta 1 further comprises one or more amino acid residues selected from the group consisting of Gln67, Leu83, Ala84, Ala85, Arg87, Pro103, Val104, Ser105, Arg106, Glu128, Glu129, and Pro130 of SEQ ID NO: 71. In some embodiments, the epitope on human tryptase beta 1 comprises at least two, at least three, at least four, at least five, at least six, at least seven, at least eight, at least nine, at least ten, at least eleven, or all twelve amino acid residues selected from the group consisting of Gln67, Leu83, Ala84, Ala85, Arg87, Pro103, Val104, Ser105, Arg106, Glu128, Glu129, and Pro130 of SEQ ID NO: 71. In some embodiments, the epitope on human tryptase beta 1 comprises His51, Gln67, Val80, Lys81, Asp82, Leu83, Ala84, Ala85, Arg87, Pro103, Va104, Ser105, Arg106, Glu128, Glu129, and Pro130 of SEQ ID NO:71. In some embodiments, the epitope is relative to a human tryptase beta 1 monomer or tetramer. In some embodiments, the epitope is determined by an X-ray crystallography model. In some embodiments, the antibody is capable of dissociating both the small interface of tetrameric human tryptase beta 1 and the large interface of tetrameric human tryptase beta 1. In some embodiments, the antibody comprises the following six hypervariable regions (HVRs): (a) an HVR-H1 comprising the amino acid sequence of DYGMV (SEQ ID NO: 7); (b) an HVR-H2 comprising the amino acid sequence of FISSGSSTVYYADTMKG (SEQ ID NO: 2); (c) an HVR-H3 comprising the amino acid sequence of RNYDDWYFDV (SEQ ID NO: 8); (d) an HVR-L1 comprising the amino acid sequence of SASSSVTYMY (SEQ ID NO: 4); (e) an HVR-L2 comprising the amino acid sequence of RTSDLAS (SEQ ID NO: 5); and (f) an HVR-L3 comprising the amino acid sequence of QHYHSYPLT (SEQ ID NO: 6). In some embodiments, the antibody comprises (a) a heavy chain variable (VH) domain comprising an amino sequence having at least 90%, at least 95%, or at least 99% sequence identity to the amino acid sequence of SEQ ID NO: 9; (b) a light chain variable (VL)

domain comprising an amino acid sequence having at least 90%, at least 95%, or at least 99% identity to the amino acid sequence of SEQ ID NO: 10; or (c) a VH domain as in (a) and a VL domain as in (b). In some embodiments, the antibody further comprises the following VH domain FRs: (a) an FR-H1 comprising the amino acid sequence of EVQLVESGGGLVQPGGSLRLSCAASGFTFS (SEQ ID NO: 11); (b) an FR-H2 comprising the amino acid sequence of WVRQAPGKGLEWVA (SEQ ID NO: 12); (c) an FR-H3 comprising the amino acid sequence of RFTISRDNSKNT-LYLQMNSLRAEDTAVYYCTR (SEQ ID NO: 13); and (d) an FR-H4 comprising the amino acid sequence of WGQGTLVTVSS (SEQ ID NO: 14). In some embodiments, the VH domain of the antibody comprises the amino acid sequence of SEQ ID NO: 9. In some embodiments, the antibody further comprises the following VL domain FRs: (a) an FR-L1 comprising the amino acid sequence of DIQMTQSPSSLSASVGDRVTITC (SEQ ID NO: 15); (b) an FR-L2 comprising the amino acid sequence of WYQQKPGKSPKPWIY (SEQ ID NO: 16); (c) an FR-L3 comprising the amino acid sequence of GVPSRFSGSGSGTDFTLTISSLQPEDFATYYC (SEQ ID NO: 17); and (d) an FR-L4 comprising the amino acid sequence of FGQGTKVEIK (SEQ ID NO: 18). In some embodiments, the VL domain of the antibody comprises the amino acid sequence of SEQ ID NO: 10. In some embodiments, the antibody comprises (a) a heavy chain comprising the amino acid sequence of SEQ ID NO: 76 and (b) a light chain comprising the amino acid sequence of SEQ ID NO: 77. In some embodiments, the antibody comprises (a) a heavy chain comprising the amino acid sequence of SEQ ID NO: 78 and (b) a light chain comprising the amino acid sequence of SEQ ID NO: 79.

In another aspect, the invention features a composition (e.g., a pharmaceutical composition) comprising an isolated monoclonal antibody that binds to human tryptase beta 1, or an antigen-binding fragment thereof, and a pharmaceutically acceptable carrier, excipient, or diluent, wherein the antibody binds to an epitope on human tryptase beta 1 comprising at least one, at least two, or all three residues selected from the group consisting of Gln100, Leu101, and Leu102 of SEQ ID NO: 71. In some embodiments, the epitope on human tryptase beta 1 further comprises one or more amino acid residues selected from the group consisting of Trp55, Gln67, Asp82, Leu83, Ala84, Arg87, Pro103, Val104, Ser105, Arg106, Glu126, Leu127, Glu128, and Glu129 of SEQ ID NO: 71. In some embodiments, the epitope on human tryptase beta 1 comprises at least two, at least three, at least four, at least five, at least six, at least seven, at least eight, at least nine, at least ten, at least eleven, at least twelve, at least thirteen, or all fourteen amino acid residues selected from the group consisting of Trp55, Gln67, Asp82, Leu83, Ala84, Arg87, Pro103, Val104, Ser105, Arg106, Glu126, Leu127, Glu128, and Glu129 of SEQ ID NO: 71. In some embodiments, the epitope comprises Gln35, Trp55, Gln67, Asp82, Leu83, Ala84, Arg87, Gln100, Leu101, Leu102, Pro103, Val104, Ser105, Arg106, Glu126, Leu127, Glu128, Glu129, and Arg216 of SEQ ID NO: 71. In some embodiments, the epitope is relative to a human tryptase beta 1 monomer or tetramer. In some embodiments, the epitope is relative to a human tryptase beta 1 tetramer, and the epitope on human tryptase beta 1 further comprises one or both of Gln35 and Arg216 of SEQ ID NO: 71. In some embodiments, the epitope is determined by an X-ray crystallography model. In some embodiments, the antibody is capable of dissociating the small interface and/or the large interface of human tryptase beta 1. In some embodiments, the antibody comprises the following six HVRs: (a) an HVR-H1 comprising the amino acid sequence of GYAIT (SEQ ID NO: 30); (b) an HVR-H2 comprising the amino acid sequence of GISSAATTFYSSWAKS (SEQ ID NO: 31); (c) an HVR-H3 comprising the amino acid sequence of DPRGYGAALDRLDL (SEQ ID NO: 32); (d) an HVR-L1 comprising the amino acid sequence of QSIKSVYNNRLG (SEQ ID NO: 33); (e) an HVR-L2 comprising the amino acid sequence of ETSILTS (SEQ ID NO: 34); and (f) an HVR-L3 comprising the amino acid sequence of AGGFDRSGDTT (SEQ ID NO: 35). In some embodiments, the antibody comprises (a) a VH domain comprising an amino sequence having at least 90%, at least 95%, or at least 99% sequence identity to the amino acid sequence of any one of SEQ ID NOs: 36, 47, 48, 49, 50, 51, and 52; (b) a VL domain comprising an amino acid sequence having at least 90%, at least 95%, or at least 99% identity to the amino acid sequence of any one of SEQ ID NO: 37, 53, 58, or 59; or (c) a VH domain as in (a) and a VL domain as in (b). In some embodiments, the antibody further comprises the following VH domain FRs: (a) an FR-H1 comprising the amino acid sequence of EVQLVESGPGLVKPSETLSLTCTVSRFSLI (SEQ ID NO: 38); (b) an FR-H2 comprising the amino acid sequence of WIRQPPGKGLEWIG (SEQ ID NO: 42); (c) an FR-H3 comprising the amino acid sequence of RVTIS-RDTSKNQVSLKLSSVTAADTAVYYCAR (SEQ ID NO: 43); and (d) an FR-H4 comprising the amino acid sequence of WGQGTLVTVSS (SEQ ID NO: 41). In some embodiments, the VH domain of the antibody comprises the amino acid sequence of SEQ ID NO: 36. In some embodiments, the antibody further comprises the following VL domain FRs: (a) an FR-L1 comprising the amino acid sequence of DIQMTQSPSSLSASVGDRVTITC (SEQ ID NO: 64); (b) an FR-L2 comprising the amino acid sequence of WYQQKPGKAPKLLIY (SEQ ID NO: 65); (c) an FR-L3 comprising the amino acid sequence of GVPSRFSGSGSGTDFTLTISSLQPEDFATYYC (SEQ ID NO: 66); and (d) an FR-L4 comprising the amino acid sequence of FGQGTKVEIK (SEQ ID NO: 63). In some embodiments, the VL domain of the antibody comprises the amino acid sequence of SEQ ID NO: 37. In some embodiments, the antibody comprises (a) a heavy chain comprising the amino acid sequence of SEQ ID NO: 80 and (b) a light chain comprising the amino acid sequence of SEQ ID NO: 81. In some embodiments, the antibody comprises (a) a heavy chain comprising the amino acid sequence of SEQ ID NO: 82 and (b) a light chain comprising the amino acid sequence of SEQ ID NO: 83.

In some embodiments, the antibody is capable of further binding to human tryptase alpha, tryptase beta 2, tryptase beta 3 and/or cyno tryptase D1.

In any of the preceding compositions (e.g., pharmaceutical compositions), the antibody may be monoclonal, human, humanized, or chimeric. In some embodiments, the antibody is humanized.

In any of the preceding compositions (e.g., pharmaceutical compositions), the composition may be for use in a human.

Any of the preceding compositions (e.g., pharmaceutical compositions) may be lyophilized. In other embodiments, any of the preceding compositions (e.g., pharmaceutical compositions) may be a liquid.

In any of the preceding compositions (e.g., pharmaceutical compositions), the excipient may be an antioxidant. In some embodiments, the composition comprises one or more antioxidants selected from the group consisting of N-acetyl-tryptophan, tryptophan, methionine, cysteine, glutathione, thiosorbitol, ascorbic acid, monothioglycerol, cyclodextrins, Trolox (6-hydroxy-2,5,7,8-tetramethylchroman-2-carboxylic acid), pyridoxine, mannitol, and a metal chelator. In some embodiments, the composition comprises N-acetyltryptophan or methionine. In some embodiments, the composition comprises N-acetyltryptophan and methionine.

In another aspect, the invention features a composition (e.g., a pharmaceutical composition) comprising: (i) an isolated antibody that binds to human tryptase beta 1, or an antigen-binding fragment thereof, wherein the antibody comprises the following six hypervariable regions (HVRs): (a) an HVR-H1 comprising the amino acid sequence of DYGMV (SEQ ID NO: 7); (b) an HVR-H2 comprising the amino acid sequence of FISSGSSTVYYADTMKG (SEQ ID NO: 2); (c) an HVR-H3 comprising the amino acid sequence of RNYDDWYFDV (SEQ ID NO: 8); (d) an HVR-L1 comprising the amino acid sequence of SASSSVTYMY (SEQ ID NO: 4); (e) an HVR-L2 comprising the amino acid sequence of RTSDLAS (SEQ ID NO: 5); and (f) an HVR-L3 comprising the amino acid sequence of QHYHSYPLT (SEQ ID NO: 6), wherein the oxidation of tryptophan at position 6 of HVR-H3 (SEQ ID NO: 8) is no more than 30%. In some embodiments, the oxidation of tryptophan at position 6 of HVR-H3 (SEQ ID NO: 8) is no more than 28%, 25%, 20%, 15%, 10%, or 6%. In some embodiments, the oxidation of tryptophan at position 6 of HVR-H3 (SEQ ID NO: 8) is determined following an AAPH stress test. In some embodiments, the oxidation of tryptophan at position 6 of HVR-H3 (SEQ ID NO: 8) is determined within one year from the initial production of the composition.

Any of the preceding compositions (e.g., pharmaceutical compositions) may comprise N-acetyltryptophan at a concentration of about 0.1 mM to about 5 mM. In some embodiments, the concentration of N-acetyltryptophan is about 0.1 mM to about 1 mM. In some embodiments, the concentration of N-acetyltryptophan is about 0.3 mM. In some embodiments, the composition comprises methionine at a concentration of about 1 mM to about 20 mM. In some embodiments, the concentration of methionine is about 1 mM to about 10 mM. In some embodiments, the concentration of methionine is about 5 mM.

In another aspect, the invention features a composition (e.g., a pharmaceutical composition) comprising: (i) an isolated antibody that binds to human tryptase, or an antigen-binding fragment thereof, wherein the antibody comprises the following six hypervariable regions (HVRs): (a) an HVR-H1 comprising the amino acid sequence of DYGMV (SEQ ID NO: 7); (b) an HVR-H2 comprising the amino acid sequence of FISSGSSTVYYADTMKG (SEQ ID NO: 2); (c) an HVR-H3 comprising the amino acid sequence of RNYDDWYFDV (SEQ ID NO: 8); (d) an HVR-L1 comprising the amino acid sequence of SASSSVTYMY (SEQ ID NO: 4); (e) an HVR-L2 comprising the amino acid sequence of RTSDLAS (SEQ ID NO: 5); and (f) an HVR-L3 comprising the amino acid sequence of QHYHSYPLT (SEQ ID NO: 6); (ii) N-acetyltryptophan at a concentration of about 0.1 mm to about 1 mM; and (iii) methionine at a concentration of about 1 mM to about 10 mM.

In any of the preceding compositions (e.g., pharmaceutical compositions), the antibody concentration may be about 1 mg/ml to about 250 mg/ml. In some embodiments, the antibody concentration is about 150 mg/ml.

Any of the preceding compositions (e.g., pharmaceutical compositions) may further include one or more additional excipients selected from the group consisting of a stabilizer, a buffer, a surfactant, and a tonicity agent. In some embodiments, the composition further comprises a buffer. In some embodiments, the buffer is arginine succinate and/or histidine succinate. In some embodiments, the buffer comprises arginine succinate and histidine succinate. In some embodiments, the concentration of arginine succinate is about 50 mM to about 500 mM. In some embodiments, the concentration of arginine succinate is about 100 mM to about 300 mM. In some embodiments, the concentration of arginine succinate is about 200 mM. In some embodiments, the concentration of histidine succinate is about 1 mM to about 50 mM. In some embodiments, the concentration of histidine succinate is about 15 mM to about 25 mM. In some embodiments, the concentration of histidine succinate is about 20 mM. In some embodiments, the composition further comprises a surfactant. In some embodiments, the surfactant is poloxamer 188 or polysorbate 20. In some embodiments, the surfactant is poloxamer 188. In some embodiments, the concentration of poloxamer 188 is about 0.005% to about 0.1%. In some embodiments, the concentration of poloxamer 188 is about 0.005% to about 0.05%. In some embodiments, the concentration of poloxamer 188 is about 0.02%. In some embodiments, the pH of the composition is about 4.5 to about 7.0. In some embodiments, the pH of the composition is about 4.5 to about 6.5. In some embodiments, the pH of the composition is about 5.5. In some embodiments, the composition is in a light-proof container. In some embodiments, the composition is in a pre-filled syringe.

Any of the preceding compositions (e.g., pharmaceutical compositions) may further include an IL-13 axis binding antagonist, an IL-5 axis binding antagonist, an IL-33 axis binding antagonist, an M1 prime antagonist, an IgE antagonist, a TRPA1 antagonist, a CRTH2 antagonist, a broncodilator or asthma symptom controller medication, an immunomodulator, a corticosteroid, a Th2 pathway inhibitor, a tyrosine kinase inhibitor, or a phosphodiesterase inhibitor. In some embodiments, the IL-13 axis binding antagonist is an anti-IL-13 antibody. In some embodiments, the anti-IL-13 antibody is lebrikizumab. In some embodiments, the IL-5 axis binding antagonist is an IL-5 binding antagonist or an IL-5 receptor binding antagonist. In some embodiments, the IL-33 axis binding antagonist is an IL-33 binding antagonist or an ST2 binding antagonist. In some embodiments, the IL-33 binding antagonist is an anti-IL-33 antibody. In some embodiments, the M1 prime antagonist is quilizumab. In some instances, the IgE antagonist is omalizumab (XOLAIR®).

Any of the preceding compositions (e.g., pharmaceutical compositions) may be formulated for administration to a human. In certain embodiments, the pharmaceutical compositions comprise antibodies that do not comprise non-human constant region sequences. In certain embodiments, the pharmaceutical compositions comprise antibodies that do not comprise non-human framework and non-human constant region sequences. In certain embodiments, the pharmaceutical compositions comprise antibodies that are human antibodies, humanized antibodies, or chimeric antibodies.

In some aspects, any one of the preceding antibodies can be used as a medicament.

In some aspects, any of the preceding antibodies can be used in treating a disorder. In some embodiments, the disorder is selected from the group consisting of a pulmonary disorder, an autoimmune disorder, an inflammatory disorder, a fibrotic disorder, a granulocytic (neutrophilic or eosinophilic) disorder, a monocytic disorder, a lymphocytic disorder, or a disorder associated with increased numbers or distribution of normal or aberrant tissue resident cells (such as mast cells, macrophages, or lymphocytes) or stromal cells (such as fibroblasts, myofibroblasts, smooth muscle cells, epithelia, or endothelia). In some embodiments, the disorder is a pulmonary disorder. In some embodiments, the pulmonary disorder is selected from the group consisting of asthma, airway hyperresponsiveness, and chronic obstructive pulmonary disease (COPD). In some embodiments, the pulmonary disorder is asthma. In some embodiments, the asthma is Th2-high asthma or Th2-low asthma. In some embodiments, the autoimmune disorder is selected from the group consisting of rheumatoid arthritis, psoriasis, eosinophilic esophagitis, inflammatory bowel disease (IBD), and Crohn's disease. In some embodiments, the inflammatory disorder is chronic idiopathic urticaria (CIU, also known as chronic spontaneous urticaria, CSU), anaphylaxis, anaphylactic shock, atopic dermatitis, or allergic rhinitis. In some embodiments, the fibrotic disorder is idiopathic pulmonary fibrosis (IPF). In some embodiments, the disorder is a disorder associated with increased numbers or distribution of normal or aberrant tissue resident cells (such as mast cells, macrophages, or lymphocytes) or stromal cells (such as fibroblasts, myofibroblasts, smooth muscle cells, epithelia, or endothelia). In some embodiments, the disorder is mastocytosis. In some embodiments, the antibody is for use in combination with an additional therapeutic agent. In some embodiments, the additional therapeutic agent is an IL-13 axis binding antagonist, an IL-5 axis binding antagonist, an IL-33 axis binding antagonist, an M1 prime antagonist, an IgE antagonist, a TRPA1 antagonist, a CRTH2 antagonist, a broncodilator or asthma symptom controller medication, an immunomodulator, a corticosteroid, a Th2 pathway inhibitor, a tyrosine kinase inhibitor, or a phosphodiesterase inhibitor. In some embodiments, the IL-13 axis binding antagonist is an anti-IL-13 antibody. In some embodiments, the anti-IL-13 antibody is lebrikizumab. In some embodiments, the IL-5 axis binding antagonist is an IL-5 binding antagonist or an IL-5 receptor binding antagonist. In some embodiments, the IL-33 axis binding antagonist is an IL-33 binding antagonist or an ST2 binding antagonist. In some embodiments, the IL-33 binding antagonist is an anti-IL-33 antibody. In some embodiments, the M1 prime antagonist is quilizumab. In some embodiments, the antibody is for administration subcutaneously, intravenously, intramuscularly, topically, orally, transdermally, intraperitoneally, intraorbitally, by implantation, by inhalation, intrathecally, intraventricularly, or intranasally. In some embodiments, the antibody is for administration subcutaneously. In some embodiments, the antibody is for use in a human subject.

In some aspects, any one of the preceding compositions (e.g., pharmaceutical compositions) can be used as a medicament.

In some aspects, any of the preceding compositions (e.g., pharmaceutical compositions) can be used in treating a disorder. In some embodiments, the disorder is selected from the group consisting of a pulmonary disorder, an autoimmune disorder, an inflammatory disorder, a fibrotic disorder, a granulocytic (neutrophilic or eosinophilic) disorder, a monocytic disorder, a lymphocytic disorder, or a disorder associated with increased numbers or distribution of normal or aberrant tissue resident cells (such as mast cells, macrophages, or lymphocytes) or stromal cells (such as fibroblasts, myofibroblasts, smooth muscle cells, epithelia, or endothelia). In some embodiments, the disorder is a pulmonary disorder. In some embodiments, the pulmonary disorder is selected from the group consisting of asthma, airway hyperresponsiveness, and chronic obstructive pulmonary disease (COPD). In some embodiments, the pulmonary disorder is asthma. In some embodiments, the asthma is Th2-high asthma or Th2-low asthma. In some embodiments, the autoimmune disorder is selected from the group consisting of rheumatoid arthritis, psoriasis, eosinophilic esophagitis, inflammatory bowel disease (IBD), and Crohn's disease. In some embodiments, the inflammatory disorder is chronic idiopathic urticaria (CIU or CSU), anaphylaxis, anaphylactic shock, atopic dermatitis, or allergic rhinitis. In some embodiments, the fibrotic disorder is idiopathic pulmonary fibrosis (IPF). In some embodiments, the disorder is a disorder associated with increased numbers or distribution of normal or aberrant tissue resident cells (such as mast cells, macrophages, or lymphocytes) or stromal cells (such as fibroblasts, myofibroblasts, smooth muscle cells, epithelia, or endothelia). In some embodiments, the disorder is mastocytosis. In some embodiments, the composition (e.g., pharmaceutical composition) is for use in combination with an additional therapeutic agent. In some embodiments, the additional therapeutic agent is an IL-13 axis binding antagonist, an IL-5 axis binding antagonist, an IL-33 axis binding antagonist, an M1 prime antagonist, an IgE antagonist, a TRPA1 antagonist, a CRTH2 antagonist, a broncodilator or asthma symptom controller medication, an immunomodulator, a corticosteroid, a Th2 pathway inhibitor, a tyrosine kinase inhibitor, or a phosphodiesterase inhibitor. In some embodiments, the IL-13 axis binding antagonist is an anti-IL-13 antibody. In some embodiments, the anti-IL-13 antibody is lebrikizumab. In some embodiments, the IL-5 axis binding antagonist is an IL-5 binding antagonist or an IL-5 receptor binding antagonist. In some embodiments, the IL-33 axis binding antagonist is an IL-33 binding antagonist or an ST2 binding antagonist. In some embodiments, the IL-33 binding antagonist is an anti-IL-33 antibody. In some embodiments, the M1 prime antagonist is quilizumab. In some embodiments, the composition (e.g., pharmaceutical composition) is for administration subcutaneously, intravenously, intramuscularly, topically, orally, transdermally, intraperitoneally, intraorbitally, by implantation, by inhalation, intrathecally, intraventricularly, or intranasally. In some embodiments, the composition (e.g., pharmaceutical composition) is for administration subcutaneously. In some embodiments, the composition (e.g., pharmaceutical composition) is for use in a human subject.

In some aspects, any one of the preceding antibodies can be used in the manufacture of a medicament for treating a disorder. In some embodiments, the disorder is selected from the group consisting of a pulmonary disorder, an autoimmune disorder, an inflammatory disorder, a fibrotic disorder, a granulocytic (neutrophilic or eosinophilic) disorder, a monocytic disorder, a lymphocytic disorder, or a disorder associated with increased numbers or distribution of normal or aberrant tissue resident cells (such as mast cells, macrophages, or lymphocytes) or stromal cells (such as fibroblasts, myofibroblasts, smooth muscle cells, epithelia, or endothelia). In some embodiments, the disorder is a pulmonary disorder. In some embodiments, the pulmonary disorder is selected from the group consisting of asthma, airway hyperresponsiveness, and chronic obstructive pulmonary disease (COPD). In some embodiments, the pulmonary disorder is asthma. In some embodiments, the asthma is Th2-high asthma or Th2-low asthma. In some embodiments, the autoimmune disorder is selected from the group consisting of rheumatoid arthritis, psoriasis, eosinophilic esophagitis, inflammatory bowel disease (IBD), and Crohn's disease. In some embodiments, the inflammatory disorder is chronic idiopathic urticaria (CIU or CSU), anaphylaxis, anaphylactic shock, atopic dermatitis, or allergic rhinitis. In some embodiments, the fibrotic disorder is idiopathic pulmonary fibrosis (IPF). In some embodiments, the disorder is a disorder associated with increased numbers or distribution of normal or aberrant tissue resident cells (such as mast cells, macrophages, or lymphocytes) or stromal cells (such as fibroblasts, myofibroblasts, smooth muscle cells, epithelia, or endothelia). In some embodiments, the disorder is mastocytosis. In some embodiments, the medicament is formulated for use in combination with an additional therapeutic agent. In some embodiments, the additional therapeutic agent is an IL-13 axis binding antagonist, an IL-5 axis binding antagonist, an IL-33 axis binding antagonist, an M1 prime antagonist, an IgE antagonist, a TRPA1 antagonist, a CRTH2 antagonist, a broncodilator or asthma symptom controller medication, an immunomodulator, a corticosteroid, a Th2 pathway inhibitor, a tyrosine kinase inhibitor, or a phosphodiesterase inhibitor. In some embodiments, the IL-13 axis binding antagonist is an anti-IL-13 antibody. In some embodiments, the anti-IL-13 antibody is lebrikizumab. In some embodiments, the IL-5 axis binding antagonist is an IL-5 binding antagonist or an IL-5 receptor binding antagonist. In some embodiments, the IL-33 axis binding antagonist is an IL-33 binding antagonist or an ST2 binding antagonist. In some embodiments, the IL-33 binding antagonist is an anti-IL-33 antibody. In some embodiments, the M1 prime antagonist is quilizumab. In some embodiments, the medicament is formulated for administration subcutaneously, intravenously, intramuscularly, topically, orally, transdermally, intraperitoneally, intraorbitally, by implantation, by inhalation, intrathecally, intraventricularly, or intranasally. In some embodiments, the medicament is formulated for administration subcutaneously. In some embodiments, the medicament is formulated for use in a human subject.

In some aspects, any one of the preceding compositions (e.g., pharmaceutical compositions) can be used in the manufacture of a medicament for treating a disorder. In some embodiments, the disorder is selected from the group consisting of a pulmonary disorder, an autoimmune disorder, an inflammatory disorder, a fibrotic disorder, a granulocytic (neutrophilic or eosinophilic) disorder, a monocytic disorder, a lymphocytic disorder, or a disorder associated with increased numbers or distribution of normal or aberrant tissue resident cells (such as mast cells, macrophages, or lymphocytes) or stromal cells (such as fibroblasts, myofibroblasts, smooth muscle cells, epithelia, or endothelia). In some embodiments, the disorder is a pulmonary disorder. In some embodiments, the pulmonary disorder is selected from the group consisting of asthma, airway hyperresponsiveness, and chronic obstructive pulmonary disease (COPD). In some embodiments, the pulmonary disorder is asthma. In some embodiments, the asthma is Th2-high asthma or Th2-low asthma. In some embodiments, the autoimmune disorder is selected from the group consisting of rheumatoid arthritis, psoriasis, eosinophilic esophagitis, inflammatory bowel disease (IBD), and Crohn's disease. In some embodiments, the inflammatory disorder is chronic idiopathic urticaria (CIU or CSU), anaphylaxis, anaphylactic shock, atopic dermatitis, or allergic rhinitis. In some embodiments, the fibrotic disorder is idiopathic pulmonary fibrosis (IPF). In some embodiments the disorder is a disorder associated with increased numbers or distribution of normal or aberrant tissue resident cells (such as mast cells, macrophages, or lymphocytes) or stromal cells (such as fibroblasts, myofibroblasts, smooth muscle cells, epithelia, or endothelia). In some embodiments, the disorder is mastocytosis. In some embodiments, the medicament is formulated for use in combination with an additional therapeutic agent. In some embodiments, the additional therapeutic agent is an IL-13 axis binding antagonist, an IL-5 axis binding antagonist, an IL-33 axis binding antagonist, an M1 prime antagonist, an IgE antagonist, a TRPA1 antagonist, a CRTH2 antagonist, a broncodilator or asthma symptom controller medication, an immunomodulator, a corticosteroid, a Th2 pathway inhibitor, a tyrosine kinase inhibitor, or a phosphodiesterase inhibitor. In some embodiments, the IL-13 axis binding antagonist is an anti-IL-13 antibody. In some embodiments, the anti-IL-13 antibody is lebrikizumab. In some embodiments, the IL-5 axis binding antagonist is an IL-5 binding antagonist or an IL-5 receptor binding antagonist. In some embodiments, the IL-33 axis binding antagonist is an IL-33 binding antagonist or an ST2 binding antagonist. In some embodiments, the IL-33 binding antagonist is an anti-IL-33 antibody. In some embodiments, the M1 prime antagonist is quilizumab. In some embodiments, the medicament is formulated for administration subcutaneously, intravenously, intramuscularly, topically, orally, transdermally, intraperitoneally, intraorbitally, by implantation, by inhalation, intrathecally, intraventricularly, or intranasally. In some embodiments, the medicament is formulated for administration subcutaneously. In some embodiments, the medicament is formulated for use in a human subject.

In another aspect, the invention features a method of treating a disorder in a subject in need thereof, the method comprising administering to the subject a therapeutically effective amount of any one of the preceding antibodies. In some embodiments, the disorder is selected from the group consisting of a pulmonary disorder, an autoimmune disorder, an inflammatory disorder, a fibrotic disorder, a granulocytic (neutrophilic or eosinophilic) disorder, a monocytic disorder, a lymphocytic disorder, or a disorder associated with increased numbers or distribution of normal or aberrant tissue resident cells (such as mast cells, macrophages, or lymphocytes) or stromal cells (such as fibroblasts, myofibroblasts, smooth muscle cells, epithelia, or endothelia). In some embodiments, the disorder is a pulmonary disorder. In some embodiments, the pulmonary disorder is selected from the group consisting of asthma, airway hyperresponsiveness, and chronic obstructive pulmonary disease (COPD). In some embodiments, the pulmonary disorder is asthma. In some embodiments, the asthma is Th2-high asthma or Th2-low asthma. In some embodiments, the autoimmune disorder is selected from the group consisting of rheumatoid arthritis, psoriasis, eosinophilic esophagitis, inflammatory bowel disease (IBD), and Crohn's disease. In some embodiments, the inflammatory disorder is chronic idiopathic urticaria (CIU or CSU), anaphylaxis, anaphylactic shock, atopic dermatitis, or allergic rhinitis. In some embodiments, the fibrotic disorder is idiopathic pulmonary fibrosis (IPF). In some embodiments, the disorder is a disorder associated with increased numbers or distribution of normal or aberrant tissue resident cells (such as mast cells, macrophages, or lymphocytes) or stromal cells (such as fibroblasts, myofibroblasts, smooth muscle cells, epithelia, or endothelia). In some embodiments, the disorder is mastocytosis. In some embodiments, the method further comprises administering an additional therapeutic agent to the subject. In some embodiments, the additional therapeutic agent is an IL-13 axis binding antagonist, an IL-5 axis binding antagonist, an IL-33 axis binding antagonist, an M1 prime antagonist, an IgE antagonist, a TRPA1 antagonist, a CRTH2 antagonist, a broncodilator or asthma symptom controller medication, an immunomodulator, a corticosteroid, a Th2 pathway inhibitor, a tyrosine kinase inhibitor, or a phosphodiesterase inhibitor. In some embodiments, the IL-13 axis binding antagonist is an anti-IL-13 antibody. In some embodiments, the anti-IL-13 antibody is lebrikizumab. In some embodiments, the IL-5 axis binding antagonist is an IL-5 binding antagonist or an IL-5 receptor binding antagonist. In some embodiments, the IL-33 axis binding antagonist is an IL-33 binding antagonist or an ST2 binding antagonist. In some embodiments, the IL-33 binding antagonist is an anti-IL-33 antibody. In some embodiments, the M1 prime antagonist is quilizumab. In some embodiments, the IgE antagonist is omalizumab (Xolair®). In some embodiments, the antibody is administered subcutaneously, intravenously, intramuscularly, topically, orally, transdermally, intraperitoneally, intraorbitally, by implantation, by inhalation, intrathecally, intraventricularly, or intranasally. In some embodiments, the subject is a human.

In another aspect, the invention features a method of treating a disorder in a subject in need thereof, the method comprising administering to the subject a therapeutically effective amount of any one of the preceding compositions (e.g., pharmaceutical compositions). In some embodiments, the disorder is selected from the group consisting of a pulmonary disorder, an autoimmune disorder, an inflammatory disorder, a fibrotic disorder, a granulocytic (neutrophilic or eosinophilic) disorder, a monocytic disorder, a lymphocytic disorder, or a disorder associated with increased numbers or distribution of normal or aberrant tissue resident cells (such as mast cells, macrophages, or lymphocytes) or stromal cells (such as fibroblasts, myofibroblasts, smooth muscle cells, epithelia, or endothelia). In some embodiments, the disorder is a pulmonary disorder. In some embodiments, the pulmonary disorder is selected from the group consisting of asthma, airway hyperresponsiveness, and chronic obstructive pulmonary disease (COPD). In some embodiments, the pulmonary disorder is asthma. In some embodiments, the asthma is Th2-high asthma or Th2-low asthma. In some embodiments, the autoimmune disorder is selected from the group consisting of rheumatoid arthritis, psoriasis, eosinophilic esophagitis, inflammatory bowel disease (IBD), and Crohn's disease. In some embodiments, the inflammatory disorder is chronic idiopathic urticaria (CIU or CSU), anaphylaxis, anaphylactic shock, atopic dermatitis, or allergic rhinitis. In some embodiments, the fibrotic disorder is idiopathic pulmonary fibrosis (IPF). In some embodiments the disorder is a disorder associated with increased numbers or distribution of normal or aberrant tissue resident cells (such as mast cells, macrophages, or lymphocytes) or stromal cells (such as fibroblasts, myofibroblasts, smooth muscle cells, epithelia, or endothelia). In some embodiments, the disorder is mastocytosis. In some embodiments, the method further comprises administering an additional therapeutic agent to the subject. In some embodiments, the additional therapeutic agent is an IL-13 axis binding antagonist, an IL-5 axis binding antagonist, an IL-33 axis binding antagonist, an M1 prime antagonist, an IgE antagonist, a TRPA1 antagonist, a CRTH2 antagonist, a broncodilator or asthma symptom controller medication, an immunomodulator, a corticosteroid, a Th2 pathway inhibitor, a tyrosine kinase inhibitor, or a phosphodiesterase inhibitor. In some embodiments, the IL-13 axis binding antagonist is an anti-IL-13 antibody. In some embodiments, the anti-IL-13 antibody is lebrikizumab. In some embodiments, the IL-5 axis binding antagonist is an IL-5 binding antagonist or an IL-5 receptor binding antagonist. In some embodiments, the IL-33 axis binding antagonist is an IL-33 binding antagonist or an ST2 binding antagonist. In some embodiments, the IL-33 binding antagonist is an anti-IL-33 antibody. In some embodiments, the M1 prime antagonist is omalizumab (Xolair). In some embodiments, the composition is administered subcutaneously, intravenously, intramuscularly, topically, orally, transdermally, intraperitoneally, intraorbitally, by implantation, by inhalation, intrathecally, intraventricularly, or intranasally. In some embodiments, the subject is a human.

BRIEF DESCRIPTION OF THE DRAWINGS

FIG. 1 is a sequence alignment of the VH and VL domains of hu31A.v11 and huE104.v2 showing the complementarity determining regions (CDRs) according to the Kabat, Chothia and Contact designations. The hypervariable regions (HVRs) are underlined.

FIGS. 2B and 2C are graphs showing the results of human primary airway smooth muscle cell (SMC) proliferation (FIG. 2B) and contraction (FIG. 2C) assays. Addition of tryptase beta stimulated human primary airway SMC proliferation, which was inhibited in a dose-dependent manner by addition of the anti-tryptase antibody hu31A.v1 IgG4 or huE104.v2 IgG4 (FIG. 2B). Addition of tryptase also stimulated human primary airway SMC contraction, which was also inhibited by addition of hu31A.v11 IgG4 and huE104.v2 IgG4 (FIG. 2C).

FIG. 3A is a graph showing the results of dissociation of human tryptase beta 1 tetramer by hu31A.v1 Fab analyzed by size exclusion chromatography (SEC). Three runs were analyzed by SEC: run 1 contained WT tetrameric tryptase alone, which resulted in peak 1 with a retention time Tr=26 min, a retention volume Vr=13 ml; run 2 contained WT tetrameric tryptase+Fab hu31A.v11+heparin, which resulted in peak 2 (Tr=27.6 min, Vr=13.8 ml) and peak 4 (Tr=31 min, Vr=15.5 ml); run 3 contained WT tetrameric tryptase+Fab hu31A.v1 without heparin, which resulted in peak 3 (Tr=28.1 min, Vr=14 ml) and peak 4 (Tr=31 min, Vr=15.5 ml).

FIG. 3B is a graph showing the results of dissociation of human tryptase beta 1 tetramer by huE104.v2 Fab. Three runs were analyzed by SEC: run 1 contained His-tagged monomeric tryptase+Fab huE104.v2, which resulted in peak 2 (Tr=25.8 min) and peak 6 (31.6 min); run 2 contained WT tetrameric tryptase+Fab huE104.v2, which resulted in peak 3 (Tr=26 min) and peak 7 (Tr=31.8 min); and run 3 contained WT tetrameric tryptase+Fab huE104.v2+heparin, which resulted in peak 1 (Tr=21 min), peak 4 (Tr=27.2 min) and peak 5 (Tr=31.2 min).

FIGS. 5A and 5B show images of Coomassie blue-stained sodium dodecyl sulfate-polyacrylamide gel electrophoresis (SDS-PAGE) gels (top panels), showing that human tryptase beta 1 cleaved fibrinogen into peptide fragments at both pH 6 (FIG. 5A) and 7.5 (FIG. 58). The anti-tryptase antibody hu31A.v11 Fab blocked fibrinogen cleavage at both pH 6 and pH 7.5, while huE102.v2 Fab did not, under the experimental conditions of high concentration of heparin. Lane 1, fibrinogen only, showing the alpha, beta, and gamma chains of uncleaved fibrinogen; lane 2, fibrinogen and tryptase beta; lane 3, fibrinogen, tryptase beta, and hu31A.v1 Fab; lane 4, fibrinogen, tryptase beta, and B12 IgG; lane 5, fibrinogen, tryptase beta 1, and huE104.v2 Fab; and lane 6 shows B12 mIgG1 alone. The decrease in intensity of the alpha chain indicates tryptase proteolytic activity, which was analyzed and quantified in the bottom panels.

FIG. 6A is a graph showing the results of dissociation of WT or mutant tetramer by hu31A.v11 Fab. Four runs were analyzed by SEC: run 1 contained WT tetramer+huE104.v1 Fab, which resulted in the reference peak (Tr=21.6 min); run 2 contained tetramer Y75C variant+hu31A.v11 Fab, which resulted in peak 1 (Tr=25.6 min) and peak 4 (Tr=31.6 min); run 3 contained tetramer I99C variant+hu31A.v11 Fab, which resulted in peak 2 (Tr=23.9 min) and peak 4 (Tr=31.6 min); and rune 4 contained WT tetramer+hu31A.v1 Fab, which resulted in peak 3 (Tr=28.1 min) and peak 4 (Tr=31.6 min).

FIG. 6C is a graph showing the results of dissociation of WT or mutant tetramer by huE104.v2 Fab. Three runs were analyzed by SEC: run 1 contained tetramer Y75C variant+huE104.v2 Fab, which resulted in peak 1 (Tr=21.6 min) and peak 4 (Tr=31 min); run 2 contained tetramer I99C variant+huE104.v2 Fab, which resulted in peak 2 and peak 5 (Tr=31 min); and run 3 contained WT tetramer+huE104.v2 Fab, which resulted in peak 3 (Tr=26 min) and peak 6 (Tr=31.8 min). The results show that huE104.v2 Fab formed complexes with tryptase mutants Y75C and I99C and only dissociated the I99C large interface-locked tetramer into covalently linked dimers. Peaks 4, 5 and 6 all contain excess Fab as determined by SDS-PAGD (data not shown).

FIG. 7 shows the amino acid sequence of mature human tryptase beta 1 along with the gene sequential numbering and the chymotrypsinogen numbering ("chymo-numb") system typically used for mammalian serine trypsin.

FIG. 12A is a rendering of the crystal structure of WT tryptase tetramer in complex with four huE104.v1 Fabs. Tryptase protomers are indicated according to the letter labeling or the protomers (see Pereira et al. *Nature* 392:306-311, 1998).

DETAILED DESCRIPTION OF EMBODIMENTS OF THE INVENTION

I. Definitions

Figure 2A:
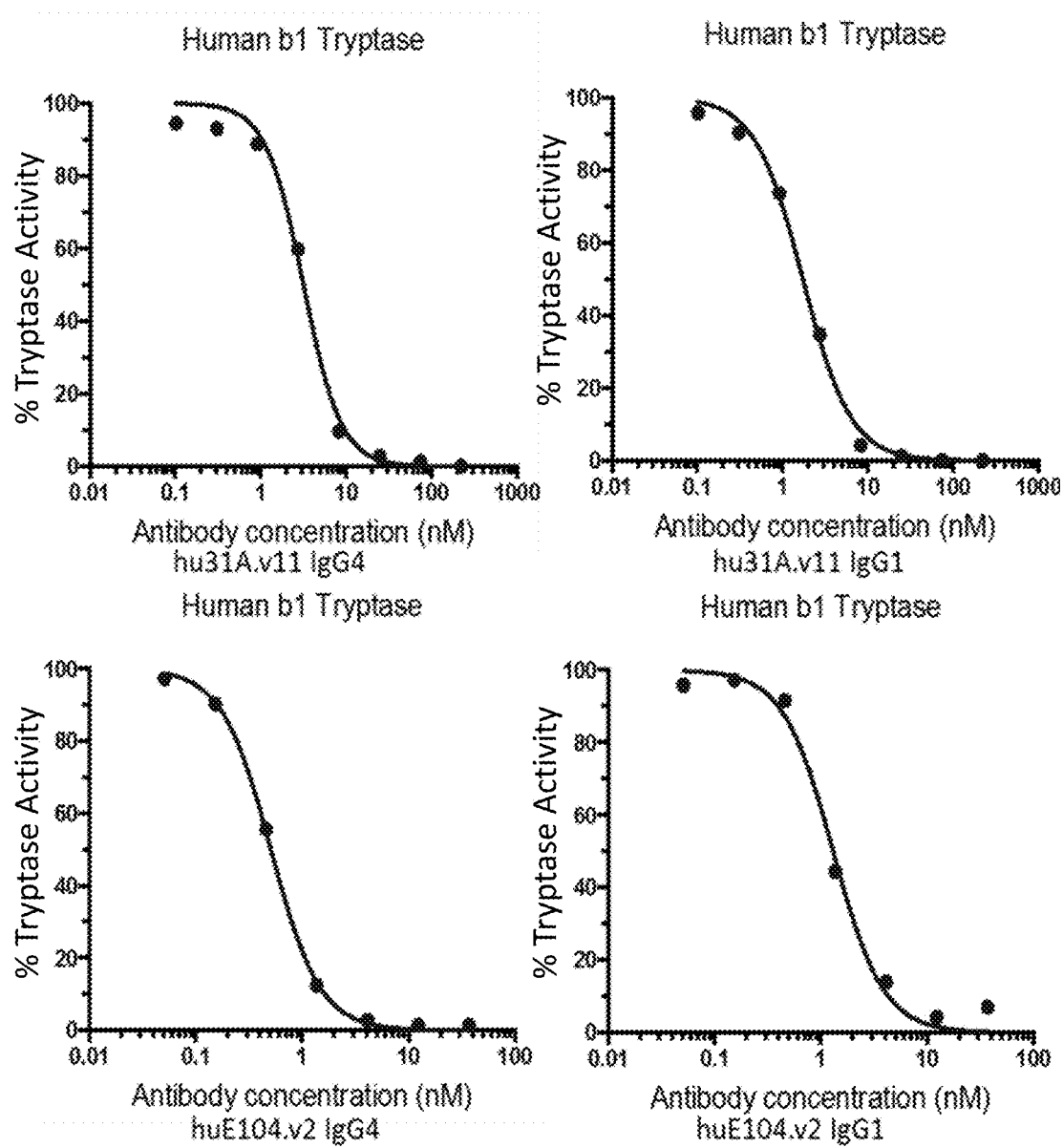
FIG. 2A is a series of graphs showing the results of an inhibition analysis of hu31A.v11 and huE104.v2 IgG as determined by a human tryptase enzymatic assay. Both antibodies completely inhibited tryptase enzymatic activity.

The term "about" as used herein refers to the usual error range for the respective value readily known to the skilled person in this technical field. Reference to "about" a value or parameter herein includes (and describes) embodiments that are directed to that value or parameter per se.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Specific illustrative and exemplary embodiments for measuring binding affinity are described in the following.

The term "$K_D$ is measured by a surface plasmon resonance assay," when used in the context of the claims, means that the $K_D$ is measured according the method described in Example 1(A)(vii), which measures kinetic parameters for binding of anti-tryptase antibodies to human tryptase beta 1 monomer, e.g., His6-tagged tryptase monomer as shown in SEQ ID NO: 128, which does not spontaneously form a tryptase tetramer. The assay can use a BIAcore® T200 or an equivalent device. Briefly, BIAcore® Series S CM5 sensor chips (or equivalent sensor chips) are immobilized with monoclonal mouse anti-human IgG (Fc) antibody and anti-tryptase antibodies are subsequently captured on the flow cell. Serial 3-fold dilutions of the human tryptase beta 1 monomer are injected at a flow rate of 30 μl/min. Each sample is analyzed with 3 min association and 10 min dissociation. The assay is performed at 25° C. After each injection, the chip is regenerated using 3 M $MgCl_2$. Binding response is corrected by subtracting the response units (RU) from a flow cell capturing an irrelevant IgG at similar density. A 1:1 Languir model of simultaneous fitting of $k_{on}$ and $k_{off}$ is used for kinetics analysis.

An "affinity-matured" antibody is one with one or more alterations in one or more HVRs and/or framework regions which result in an improvement in the affinity of the antibody for antigen, compared to a parent antibody which does not possess those alteration(s). Preferred affinity-matured antibodies will have nanomolar or even picomolar affinities for the target antigen. Affinity-matured antibodies are produced by procedures known in the art. For example, Marks et al. *Bio/Technology* 10:779-783, 1992 describes affinity maturation by VH and VL domain shuffling. Random mutagenesis of HVR and/or framework residues is described by: Barbas et al. *Proc. Nat. Acad. Sci. USA* 91:3809-3813, 1994; Schier et al. *Gene* 169:147-155, 1995; Yelton et al. *J. Immunol.* 155:1994-2004, 1995; Jackson et al. *J. Immunol.* 154(7):3310-3319, 1995; and Hawkins et al. *J. Mol. Biol.* 226:889-896, 1992.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

As used herein, "tryptase" refers to any native tryptase from any vertebrate source, including mammals such as primates (e.g., humans) and rodents (e.g., mice and rats), unless otherwise indicated. Tryptase is also known in the art as mast cell tryptase, mast cell protease II, skin tryptase, lung tryptase, pituitary tryptase, mast cell neutral proteinase, and mast cell serine proteinase II. The term "tryptase" encompasses tryptase alpha (encoded in humans by TPSAB1), tryptase beta (encoded in humans by TPSAB1 and TPSB2; see below), tryptase delta (encoded in humans by TPSD1), tryptase gamma (encoded in humans by TPSG1), and tryptase epsilon (encoded in humans by PRSS22). Tryptase alpha, beta, and gamma proteins are soluble, whereas tryptase epsilon proteins are membrane anchored. Tryptase beta and gamma are active serine proteases, although they have different specificities. Tryptase alpha and delta proteins are largely inactive proteases as they have residues in critical position that differ from typical active serine proteases. An exemplary tryptase alpha full length protein sequence can be found under NCBI GenBank Accession No. ACZ98910.1 (SEQ ID NO: 118). Exemplary tryptase gamma full length protein sequences can be found under Uniprot Accession No. Q9NRR2 or GenBank Accession Nos. Q9NRR2.3, AAF03695.1, NP_036599.3 or AAF76457.1. Exemplary tryptase delta full length protein sequences can be found under Uniprot Accession No. Q9BZJ3 or GenBank Accession No. NP_036349.1. Several tryptase genes are clustered on human chromosome 16p13.3. The term encompasses "full-length," unprocessed tryptase as well as any form of tryptase that results from processing in the cell. Tryptase beta is the main tryptase expressed in mast cells, while tryptase alpha is the main tryptase expressed in basophils. Tryptase alpha and tryptase beta typically include a leader sequence of approximately 30 amino acids and a catalytic sequence of approximately 245 amino acids (see, e.g., Schwartz, *Immunol. Allergy Clin. N. Am.* 26:451-463, 2006).

As used herein, "tryptase beta" refers to any native tryptase beta from any vertebrate source, including mammals such as primates (e.g., humans) and rodents (e.g., mice and rats), unless otherwise indicated. Tryptase beta is a serine protease that is a major constituent of mast cell secretory granules. As used herein, the term encompasses tryptase beta 1 (encoded by the TPSAB1 gene, which also encodes tryptase alpha 1), tryptase beta 2 (encoded by the TPSB2 gene), and tryptase beta 3 (also encoded by the TPSB2 gene). An exemplary human tryptase beta 1 sequence is shown in SEQ ID NO: 71 (see also GenBank Accession No. NP_003285.2). An exemplary human tryptase beta 2 sequence is shown in SEQ ID NO: 72 (see also GenBank Accession No. AAD13876.1). An exemplary human tryptase beta 3 sequence is shown in SEQ ID NO: 73 (see also GenBank Accession No. NP_077078.5). The term tryptase beta encompasses "full-length," unprocessed tryptase beta as well as tryptase beta that results from post-translational modifications, including proteolytic processing. Full-length, pro-tryptase beta is thought to be processed in two proteolytic steps. First, autocatalytic intermolecular cleavage at R-occurs, particularly at acidic pH and in the presence of a polyanion (e.g., heparin or dextran sulfate). Next, the remaining pro' dipeptide is removed (likely by dipeptidyl peptidase I). For full-length human tryptase beta 1, with reference to SEQ ID NO: 71 below, the underlined amino acid residues correspond to the native leader sequence, and the bolded and gray-shaded amino acid residues correspond to the pro-domain, which are cleaved to form the mature protein (see, e.g., Sakai et al. *J. Clin. Invest.* 97:988-995, 1996)

useful as a diagnostic and/or therapeutic agent in targeting tryptase. In one embodiment, the extent of binding of an anti-tryptase antibody to an unrelated, non-tryptase protein is less than about 10% of the binding of the antibody to tryptase as measured, e.g., by a radioimmunoassay (RIA). In certain embodiments, an antibody that binds to tryptase has a dissociation constant ($K_D$) of ≤1 μM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M). In certain embodiments, an anti-tryptase antibody binds to an epitope of tryptase that is conserved among tryptase from different species.

An "antibody that binds to the same epitope" as a reference antibody refers to an antibody that contacts an overlapping set of amino acid residues of the antigen as compared to the reference antibody or blocks binding of the reference antibody to its antigen in a competition assay by 50% or more, 60% or more, 70% or more, 80% or more, or 90% or more. In some embodiments, the set of amino acid residues contacted by the antibody may be completely overlapping or partially overlapping with the set of amino acid residues contacted by the reference antibody. In some embodiments, an antibody that binds to the same epitope as a reference antibody blocks binding of the reference antibody to its antigen in a competition assay by 50% or more, 60% or more, 70% or more, 80% or more, or 90% or more, and conversely, the reference antibody blocks binding of the antibody to its antigen in a competition assay by 50% or more, 60% or more, 70% or more, 80% or more, or 90% or more. An exemplary competition assay is provided herein.

The term "is determined by an epitope binning assay," in the context of the claims, means that an antibody is determined to bind to the same epitope and/or compete for binding with a reference anti-tryptase antibody (e.g.,

```
                                                         (SEQ ID NO: 71)
MLNLLLLALPVLASRAYAAPAPGQALQRVGIVGGQEAPRSKWPWQVSLRVHGPYWMHFCG

GSLIHPQWVLTAAHCVGPDVKDLAALRVQLREQHLYYQDQLLPVSRIIVHPQFYTAQIGA

DIALLELEEPVNVSSHVHTVTLPPASETFPPGMPCWVTGWGDVDNDERLPPPFPLKQVKV

PIMENHICDAKYHLGAYTGDDVRIVRDDMLCAGNTRRDSCQGDSGGPLVCKVNGTWLQAG

VVSWGEGCAQPNRPGIYTRVTYYLDWIHHYVPKKP.
```

Mature, enzymatically active tryptase beta is typically a homotetramer or heterotetramer, although active monomer has been reported (see, e.g., Fukuoka et al. *J. Immunol.* 176:3165, 2006). The subunits of the tryptase beta tetramer are held together by hydrophobic and polar interactions between subunits and stabilized by polyanions (particularly heparin and dextran sulfate). The term tryptase can refer to tryptase tetramer or tryptase monomer. Exemplary sequences for mature human tryptase beta 1, beta 2, and beta 3 are shown in SEQ ID NO: 97, SEQ ID NO: 116, and SEQ ID NO: 117, respectively. The active site of each subunit faces into a central pore of the tetramer, which measures approximately 50×30 angstroms (see, e.g., Pereira et al. *Nature* 392:306-311, 1998). The size of the central pore typically restricts access of the active sites by inhibitors. Exemplary substrates of tryptase beta include, but are not limited to, PAR2, C3, fibrinogen, fibronectin, and kininogen.

The terms "anti-tryptase antibody," an "antibody that binds to tryptase," and "antibody that specifically binds tryptase" refer to an antibody that is capable of binding tryptase with sufficient affinity such that the antibody is hu31A.v11 or huE104.v2) using the OCTET® epitope binning assay such as described in Example 3, Section C. Briefly, human tryptase beta 1 monomer protein is biotinylated at Lys residue by reacting with NHS-PEG4-biotin. Biotinylated monomer is diluted to 5 μg/ml in kinetics buffer (ForteBio, Inc.) and immobilized onto streptavidin sensor tips (ForteBio, Inc.). After the immobilization step, human tryptase beta 1-immobilized sensors are saturated with the first antibody, diluted at 10-20 μg/ml, followed by binding with second antibody diluted at 2.5 μg/ml. The run temperature for such epitope binding assays is 30° C. A binding signal by second antibody implies that the two antibodies can bind antigen simultaneously at distinct, non-overlapping epitopes, whereas no binding signal implies that they share a common epitope. In some instances, a partial signal by the second antibody is observed (i.e., the signal is less than the signal observed if the first antibody was not added, but greater than background), which implies the epitopes are partially overlapping.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870, Example 2; Zapata et al. *Protein Eng.* 8(10):1057-1062, 1995); single-chain antibody molecules; and multispecific antibodies formed from antibody fragments.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain ($C_H1$). Pepsin treatment of an antibody yields a single large F(ab')2 fragment which roughly corresponds to two disulfide linked Fab fragments having divalent antigen-binding activity and is still capable of cross-linking antigen. Fab' fragments differ from Fab fragments by having an additional few residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al. *Sequences of Proteins of Immunological Interest*, 5th Ed. Public Health Service, National Institutes of Health, Bethesda, MD, 1991.

"Fv" consists of a dimer of one heavy- and one light-chain variable region domain in tight, noncovalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three Hs specific for an antigen) has the ability to recognize and bind antigen, although often at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and VL domains which enables the sFv to form the desired structure for antigen binding. For a review of sFv, see Pluckthun in *The Pharmacology of Monoclonal Antibodies, vol.* 113, Rosenburg and Moore eds., Springer-Verlag, New York, pp. 269-315, 1994.

The term "diabodies" refers to small antibody fragments prepared by constructing sFv fragments (see preceding paragraph) with short linkers (about 5-10 residues) between the VH and VL domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the VH and VL domains of the two antibodies are present on different polypeptide chains. Diabodies are described more fully in, for example, EP 404,097; WO 93/11161; and Hollinger et al. *Proc. Natl. Acad. Sci. USA* 90:6444-6448, 1993.

By "binding domain" is meant a part of a compound or a molecule that specifically binds to a target epitope, antigen, ligand, or receptor. Binding domains include but are not limited to antibodies (e.g., monoclonal, polyclonal, recombinant, humanized, and chimeric antibodies), antibody fragments or portions thereof (e.g., Fab fragments, Fab'2, scFv antibodies, SMIP, domain antibodies, diabodies, minibodies, scFv-Fc, affibodies, nanobodies, and VH and/or VL domains of antibodies), receptors, ligands, aptamers, and other molecules having an identified binding partner.

A "blocking" antibody or an "antagonist" antibody is one which inhibits or reduces biological activity of the antigen it binds. Certain blocking antibodies or antagonist antibodies substantially or completely inhibit the biological activity of the antigen. In some embodiments, the activity may be a tryptase enzymatic activity, e.g., protease activity. In other instances, the activity may be tryptase-mediated stimulation of bronchial smooth muscle cell proliferation and/or collagen-based contraction. In other instances, the activity may be mast cell histamine release (e.g., IgE-triggered histamine release and/or tryptase-triggered histamine release). An antibody of the invention can inhibit a biological activity of tryptase at least about 1%, about 5%, about 10%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, about 99%, or about 100%.

The term "as determined by a human tryptase beta enzymatic assay using a synthetic peptide S-2288 as a substrate," in the context of the claims, means that inhibitory activity is measured according to the assay described in Example 1(A)(viii)(a). Briefly, recombinant human tryptase beta 1 tetramer active enzyme is diluted to 0.75 nM in TNH Buffer (200 mM Tris, 150 mM NaCl, 0.1 mg/mL heparin, 0.01% TRITON™ X-100, pH 8.0), and combined 1:1 with anti-tryptase antibodies (diluted in PBS) in 384-well plates. Plates are incubated for 1 h at ambient temperature with gentle agitation. Colorimetric substrate S-2288 (Chromogenix, Part No. 82-0852-39), or an equivalent substrate, is diluted to 1200 µM in TNH Buffer and added to the plate. Final in-well concentrations are 400 µM-2288, 0.25 nM recombinant human tryptase beta 1 tetramer, 66 µg/mL heparin, and from 0.10 to 222 nM anti-tryptase antibody. Plates are incubated for 40 min at ambient temperature with gentle agitation and then read at $A_{405}$. The IC50 of the anti-tryptase antibodies is determined from a four-parameter fit of their respective curves.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and µ, respectively.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC);

phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch et al. Annu. Rev. Immunol. 9:457-492, 1991. To assess ADCC activity of a molecule of interest, an in vitro ADCC assay, such as that described in U.S. Pat. No. 5,500,362 or 5,821,337 can be performed. Useful effector cells for such assays include peripheral blood mononuclear cells (PBMC) and Natural Killer (NK) cells. Alternatively, or additionally, ADCC activity of the molecule of interest can be assessed in vivo, e.g., in an animal model such as that disclosed in Clynes et al. Proc. Natl. Acad. Sci. USA 95:652-656,1998.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRI receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review M. in Daëron, Annu. Rev. Immunol. 15:203-234,1997). FcRs are reviewed, for example, in Ravetch et al. Annu. Rev. Immunol. 9:457-492, 1991; Capel et al. Immunomethods 4:25-34,1994; and de Haas et al. J. Lab. Clin. Med. 126:330-41, 1995. Other FcRs, including those to be identified in the future, are encompassed by the term "FcR" herein. The term also includes the neonatal receptor, FcRn, which is responsible for the transfer of maternal IgGs to the fetus (see, e.g., Guyer et al. J. Immunol. 117:587, 1976; and Kim et al. J. Immunol. 24:249, 1994).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells, and neutrophils; with PBMCs and NK cells being preferred. The effector cells can be isolated from a native source, e.g., from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al. J. Immuno. Methods 202:163, 1996, can be performed.

An "epitope" is the portion of the antigen to which the antibody selectively binds. For a polypeptide antigen, a linear epitope can be a peptide portion of about 4-15 (e.g., 4, 5, 6, 7, 8, 9, 10, 11, 12, amino acid residues. A non-linear, conformational epitope may comprise residues of a polypeptide sequence brought to close vicinity in the three-dimensional (3D) structure of the protein. In some embodiments, the epitope comprises amino acids that are within 4 angstroms (Å) of any atom of an antibody. In some embodiments, the epitope comprises amino acids of a tryptase protomer that are within 4 Å of any atom of a partner Fab. In certain embodiments, the epitope comprises amino acids that are within 3.5 Å, 3 Å, 2.5 Å, or 2 Å of any atom of an antibody. The amino acid residues of an antibody that contact an antigen (i.e., paratope) can be determined, for example, by determining the crystal structure of the antibody in complex with the antigen or by performing hydrogen/deuterium exchange.

The term "the epitope is determined by an X-ray crystallography model," when used in the context of the claims, means that an atom of a tryptase amino acid residue (e.g., human tryptase beta 1 residue) is determined to be within 4 Å of any atom of an anti-tryptase antibody (e.g., any anti-tryptase antibody described herein, e.g., hu31A.v11 or huE104.v2) in an X-ray crystallography model, for example, as described in Example 3. In some embodiments, the X-ray crystallography model has a resolution of about 3.5 Å or less, about 3 Å or less, about 2.5 Å or less, about 2.15 Å or less, or about 2 Å or less.

The terms "full-length antibody," "intact antibody," and "whole antibody" are used herein interchangeably to refer to an antibody having a structure substantially similar to a native antibody structure or having heavy chains that contain an Fc region as defined herein.

A "human antibody" is one which possesses an amino acid sequence which corresponds to that of an antibody produced by a human and/or has been made using any of the techniques for making human antibodies. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al. Sequences of Proteins of Immunological Interest, Fifth Edition, NIH Publication 91-3242, Bethesda MD, vols. 1-3, 1991. In one embodiment, for the VL, the subgroup is subgroup kappa III or kappa IV as in Kabat et al. supra. In one embodiment, for the VH, the subgroup is subgroup III as in Kabat et al. supra.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al. *Nature* 321:522-525, 1986; Riechmann et al. *Nature* 332:323-329, 1988; and Presta, *Curr. Op. Struct. Biol.* 2:593-596, 1992.

An "immunoconjugate" is an antibody conjugated to one or more heterologous molecule(s), including but not limited to a cytotoxic agent.

The term "isolated" when used to describe the various antibodies disclosed herein, means an antibody that has been identified and separated and/or recovered from a cell or cell culture from which it was expressed. Contaminant components of its natural environment are materials that would typically interfere with diagnostic or therapeutic uses for the polypeptide, and can include enzymes, hormones, and other proteinaceous or non-proteinaceous solutes. In some embodiments, an antibody is purified to greater than 95% or 99% purity as determined by, for example, electrophoretic (e.g., sodium dodecyl sulfate polyacrylamide gel electrophoresis (SDS-PAGE), isoelectric focusing (IEF), capillary electrophoresis) or chromatographic (e.g., ion exchange or reverse phase HPLC) methods. For a review of methods for assessment of antibody purity, see, for example, Flatman et al. *J. Chromatogr. B* 848:79-87, 2007. In preferred embodiments, the antibody will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated antibody includes antibodies in situ within recombinant cells, because at least one component of the polypeptide natural environment will not be present. Ordinarily, however, isolated polypeptide will be prepared by at least one purification step.

The term "monoclonal antibody" as used herein refers to an antibody obtained from a population of substantially homogeneous antibodies, i.e., the individual antibodies comprising the population are identical and/or bind the same epitope on an antigen, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein. In certain embodiments, the term "monoclonal antibody" encompasses bispecific antibodies.

The term "bivalent antibody" refers to an antibody that has two binding sites for the antigen. A bivalent antibody can be, without limitation, in the IgG format or in the F(ab')$_2$ format.

The term "multispecific antibody" is used in the broadest sense and covers an antibody that binds to two or more determinants or epitopes on one antigen or two or more determinants or epitopes on more than one antigen. Such multispecific antibodies include, but are not limited to, full-length antibodies, antibodies having two or more VL and VH domains, antibody fragments such as Fab, Fv, dsFv, scFv, diabodies, bispecific diabodies and triabodies, antibody fragments that have been linked covalently or non-covalently. "Polyepitopic specificity" refers to the ability to specifically bind to two or more different epitopes on the same or different target(s). In certain embodiments, the multispecific antibody is a bispecific antibody. "Dual specificity" or "bispecificity" refers to the ability to specifically bind to two different epitopes on the same or different target(s). However, in contrast to bispecific antibodies, dual-specific antibodies have two antigen-binding arms that are identical in amino acid sequence and each Fab arm is capable of recognizing two antigens. Dual-specificity allows the antibodies to interact with high affinity with two different antigens as a single Fab or IgG molecule. According to one embodiment, the multispecific antibody binds to each epitope with an affinity of 5 pM to 0.001 pM, 3 pM to 0.001 pM, 1 pM to 0.001 pM, 0.5 pM to 0.001 pM or 0.1 pM to 0.001 pM. "Monospecific" refers to the ability to bind only one epitope.

A "naked antibody" refers to an antibody that is not conjugated to a heterologous moiety (e.g., a cytotoxic moiety) or radiolabel. The naked antibody may be present in a pharmaceutical composition.

With regard to the binding of a antibody to a target molecule, the term "binds" or "binding" or "specific binding" or "specifically binds" or is "specific for" a particular polypeptide or an epitope on a particular polypeptide target means binding that is measurably different from a non-specific interaction. Specific binding can be measured, for example, by determining binding of a molecule compared to binding of a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a $K_D$ for the target of $10^{-4}$ M or lower, alternatively $10^{-5}$ M or lower, alternatively $10^{-6}$ M or lower, alternatively $10^{-7}$ M or lower, alternatively $10^{-8}$ M or lower, alternatively $10^{-9}$ M or lower, alternatively $10^{-10}$ M or lower, alternatively $10^{-11}$ M or lower, alternatively $10^{-12}$ M or lower or a $K_D$ in the range of $10^{-4}$ M to $10^{-6}$ M or $10^{-6}$ M to $10^{-10}$ M or $10^{-7}$ M to $10^{-9}$ M. As will be appreciated by the skilled artisan, affinity and $K_D$ values are inversely related. A high affinity for an antigen is measured by a low $K_D$ value. In one embodiment, the term "specific binding" refers to binding where a molecule binds to a particular polypeptide or epitope on a particular polypeptide without substantially binding to any other polypeptide or polypeptide epitope.

By "paratope" is meant the part of an antibody which binds the epitope of an antigen. The paratope is typically a region of about 15-22 amino acid residues of the antibody's Fv region and may contain amino acids from the antibody's $V_H$ and $V_L$ chains.

The term "variable" refers to the fact that certain segments of the variable domains differ extensively in sequence among antibodies. The variable or "V" domain mediates antigen binding and defines specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The term "hypervariable region" or "HVR" when used herein refers to the amino acid residues of an antibody which are responsible for antigen-binding. The hypervariable region generally comprises amino acid residues from e.g., around about residues 24-34 (L1), 50-56 (L2) and 89-97 (L3) in the VL, and around about residues 26-35 (H1), 49-65 (H2) and 95-102 (H3) in the VH (in one embodiment, H1 is around about residues 31-35); Kabat et al. supra) and/or those residues from a "hypervariable loop" (e.g., residues 26-32 (L1), 50-52 (L2), and 91-96 (L3) in the VL, and 26-32 (H1), 53-55 (H2), and 96-101 (H3) in the VH; Chothia et al. *J. Mol. Biol.* 196:901-917, 1987. The variable domains of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al. supra). Accordingly, the HVR and FR sequences generally appear in the following sequence in VH (or VL): FR1-H1(L1)-FR2-H2(L2)-FR3-H3(L3)-FR4. The constant domains are not involved directly in binding an antibody to an antigen, but exhibit various effector functions, such as participation of the antibody in antibody dependent cellular cytotoxicity (ADCC).

The term "variable domain residue numbering as in Kabat" or "amino acid position numbering as in Kabat," and variations thereof, refers to the numbering system used for heavy chain variable domains or light chain variable domains of the compilation of antibodies in Kabat et al. supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g., residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g., Kabat et al. supra). The "EU numbering system" or "EU index" is generally used when referring to a residue in an immunoglobulin heavy chain constant region (e.g., the EU index reported in Kabat et al. supra). The "EU index as in Kabat" refers to the residue numbering of the human IgG1 EU antibody. Unless stated otherwise herein, references to residue numbers in the variable domain of antibodies means residue numbering by the Kabat numbering system. Unless stated otherwise herein, references to residue numbers in the constant domain of antibodies means residue numbering by the EU numbering system (e.g., see U.S. Provisional Application No. 60/640,323, Figures for EU numbering).

A "disorder" or "disease" is any condition that would benefit from treatment with the antibody (e.g., any anti-tryptase antibody described herein). This includes chronic and acute disorders or diseases including those pathological conditions which predispose the mammal to the disorder in question. In some embodiments, the disorder is a pulmonary disorder, an autoimmune disorder, an inflammatory disorder, a fibrotic disorder, a granulocytic (neutrophilic or eosinophilic) disorder, a monocytic disorder, a lymphocytic disorder, or a disorder associated with increased numbers or distribution of normal or aberrant tissue resident cells (such as mast cells, macrophages, or lymphocytes) or stromal cells (such as fibroblasts, myofibroblasts, smooth muscle cells, epithelia, or endothelia). In some embodiments, the disorder is a pulmonary disorder. In some examples, a disorder may be a tryptase-associated disorder or a tryptase-mediated disorder.

The terms "tryptase-associated disorder" and "tryptase-mediated disorder," as used herein, refers to any disorder or condition mediated by, or associated with, tryptase. In some embodiments, tryptase-associated disorders are associated with excess tryptase levels or activity in which atypical symptoms may manifest due to the levels or activity of tryptase locally and/or systemically in the body.

In some embodiments, the pulmonary disorder is asthma. In some embodiments, the asthma is persistent chronic severe asthma with acute events of worsening symptoms (exacerbations or flares) that can be life threatening. In some embodiments, the asthma is atopic (also known as allergic) asthma, non-allergic asthma (e.g., often triggered by infection with a respiratory virus (e.g., Influenza, parainfluenza, rhinovirus, human metapneumovirus, and respiratory syncytial virus) or inhaled irritant (air pollutants, smog, diesel particles, volatile chemicals and gases indoors or outdoors, or even by cold dry air).

In some embodiments, the asthma is intermittent or exercise-induced, asthma due to acute or chronic primary or second-hand exposure to "smoke" (typically cigarettes, cigars, pipes), inhaling or "vaping" (tobacco, marijuana or other such substances), or asthma triggered by recent ingestion of aspirin or related NSAIDS. In some embodiments, the asthma is mild, or corticosteroid naïve asthma, newly diagnosed and untreated asthma, or not previously requiring chronic use of inhaled topical or systemic steroids to control the symptoms (cough, wheeze, shortness of breath/breathlessness, or chest pain). In some embodiments, the asthma is chronic, corticosteroid resistant asthma, corticosteroid refractory asthma, asthma uncontrolled on corticosteroids or other chronic asthma controller medications.

In some embodiments, the asthma is moderate to severe asthma. In certain embodiments, the asthma is Th2-high asthma. In some embodiments, the asthma is severe asthma. In some embodiments, the asthma is atopic asthma, allergic asthma, non-allergic asthma (e.g., due to infection and/or respiratory syncytial virus (RSV)), exercise-induced asthma, aspirin sensitive/exacerbated asthma, mild asthma, moderate to severe asthma, corticosteroid naïve asthma, chronic asthma, corticosteroid resistant asthma, corticosteroid refractory asthma, newly diagnosed and untreated asthma, asthma due to smoking, asthma uncontrolled on corticosteroids. In some embodiments, the asthma is T helper lymphocyte type 2 (Th2) or type 2 (Th2) high, or Type 2 (T2)-driven asthma. In some embodiments, the asthma is eosinophilic asthma. In some embodiments, the asthma is allergic asthma. In some embodiments, the individual has been determined to be Eosinophilic Inflammation Positive (EIP). See WO 2015/061441. In some embodiments, the asthma is periostin-high asthma (e.g., having periostin level at least about any of 20 ng/mL, 25 ng/mL, or 50 ng/mL serum). In some embodiments, the asthma is eosinophil-high asthma (e.g., at least about any of 150, 200, 250, 300, 350, 400 eosinophil counts/ml blood). In certain embodiments, the asthma is Th2-low asthma or nonTh2-driven asthma. In some embodiments, the individual has been determined to be Eosinophilic Inflammation Negative (EIN). See WO 2015/061441. In some embodiments, the asthma is periostin-low asthma (e.g., having periostin level less than about 20 ng/mL serum). In some embodiments, the asthma is eosinophil-low asthma (e.g., less than about 150 eosinophil counts/µl blood or less than about 100 eosinophil counts/µl blood).

The term "Th2-high asthma," as used herein, refers to asthma that exhibits high levels of one or more Th2 cell-related cytokines, for example, IL13, IL4, IL9, IL5, or that exhibits Th2 cytokine-associated inflammation. In certain embodiments, the term Th2-high asthma may be used interchangeably with eosinophil-high asthma. In certain embodiments, the Th2-high asthma is Th2 driven asthma. In some embodiments, the asthma patient has been determined to be Eosinophilic Inflammation Positive (EIP). See, e.g., International Patent Application Publication No. WO 2015/061441, which is incorporated by reference herein in its entirety. In certain embodiments, the individual has been determined to have elevated levels of at least one of the eosinophilic signature genes as compared to a control or reference level. See WO2015/061441. In certain embodiments, the Th2-high asthma is periostin-high asthma. In some embodiments, the individual has high serum periostin. In certain embodiments, the individual is eighteen years or older. In certain embodiments, the individual has been determined to have an elevated level of serum periostin as compared to a control or reference level. In certain embodiments, the control or reference level is the median level of periostin in a population. In certain embodiments, the individual has been determined to have 20 ng/ml or higher serum periostin. In certain embodiments, the individual has been determined to have 25 ng/ml or higher serum periostin. In certain embodiments, the individual has been determined to have 50 ng/ml or higher serum periostin. In certain embodiments, the control or reference level of serum periostin is 20 ng/ml, 25 ng/ml, or 50 ng/ml. In certain embodiments, the asthma is eosinophil-high asthma. In certain embodiments, the individual has been determined to have an elevated eosinophil count as compared to a control or reference level. In certain embodiments, the control or reference level is the median level of a population. In certain embodiments, the individual has been determined to have 150 or higher eosinophil count/µl blood. In certain embodiments, the individual has been determined to have 200 or higher eosinophil count/µl blood. In certain embodiments, the individual has been determined to have 250 or higher eosinophil count/µl blood. In certain embodiments, the individual has been determined to have 300 or higher eosinophil count/µl blood. In certain embodiments, the individual has been determined to have 350 or higher eosinophil count/µl blood. In certain embodiments, the individual has been determined to have 400 or higher eosinophil count/µl blood. In certain embodiments, the individual has been determined to have 450 or higher eosinophil count/µl blood. In certain embodiments, the individual has been determined to have 500 or higher eosinophil count/µl blood. In certain preferred embodiments, the individual has been determined to have 300 or higher eosinophil count/µl blood. In certain embodiments, the eosinophils are peripheral blood eosinophils. In certain embodiments, the eosinophils are sputum eosinophils. In certain embodiments, the individual exhibits elevated level of FeNO (fractional exhaled nitric acid) and/or elevated level of IgE. For example, in some instances, the individual exhibits a FeNO level above about 250 parts per billion (ppb), above about 275 ppb, above about 300 ppb, above about 325 ppb, above about 325 ppb, or above about 350 ppb. In some instances, the individual has an IgE level that is above 50 IU/ml.

The term "Th2-low asthma" or "non-Th2-high asthma" as used herein, refers to asthma that exhibits low levels of one or more Th2 cell-related cytokines, for example, IL13, IL4, IL9, IL5, or exhibits non-Th2 cytokine-associated inflammation. In certain embodiments, the term Th2-low asthma may be used interchangeably with eosinophil-low asthma. In some embodiments, the asthma patient has been determined to be Eosinophilic Inflammation Negative (EIN). See, e.g., WO 2015/061441. In certain embodiments, the Th2-low asthma is Th17-driven asthma. In certain embodiments, the Th2-low asthma is periostin-low asthma. In certain embodiments, the individual is eighteen years or older. In certain embodiments, the individual has been determined to have a reduced level of serum periostin as compared to a control or reference level. In certain embodiments, the control or reference level is the median level of periostin in a population. In certain embodiments, the individual has been determined to have less than 20 ng/ml serum periostin. In certain embodiments, the asthma is eosinophil-low asthma. In certain embodiments, the individual has been determined to have a reduced esosinophil count as compared to a control or reference level. In certain embodiments, the control or reference level is the medium level of a population. In certain embodiments, the individual has been determined to have less than 150 eosinophil count/µl blood. In certain embodiments, the individual has been determined to have less than 100 eosinophil count/µl blood. In certain preferred embodiments, the individual has been determined to have less than 300 eosinophil count/µl blood.

In some embodiments, the autoimmune disorder, inflammatory disorder, fibrotic disorder, granulocytic (neutrophilic or eosinophilic) disorder, monocytic disorder, or lymphocytic disorder is esophagitis (e.g., eosinophilic esophagitis), allergic rhinitis, non-allergic rhinitis, rhinosinusitis with polyps, nasal polyposis, bronchitis, chronic pneumonia, allergic bronchopulmonary aspergillosis, airway inflammation, allergic rhinitis, bronchiectasis, and/or chronic bronchitis.

In some embodiments, the autoimmune disorder, inflammatory disorder, fibrotic disorder, granulocytic (neutrophilic or eosinophilic) disorder, monocytic disorder, or lymphocytic disorder, is arthritis. In some embodiments, the arthritis is rheumatoid arthritis. In some embodiments, the arthritis is osteoarthritis, rheumatoid arthritis, juvenile arthritis, juvenile rheumatoid arthritis, early arthritis, polyarticular rheumatoid arthritis, systemic-onset rheumatoid arthritis, enteropathic arthritis, reactive arthritis, psoriatic arthritis, and/or arthritis as a result of injury.

In some embodiments, the autoimmune disorder, inflammatory disorder, fibrotic disorder, granulocytic (neutrophilic or eosinophilic) disorder, monocytic disorder, or lymphocytic disorder is a gastrointestinal inflammatory condition.

In some embodiments, the gastrointestinal inflammatory condition is IBD (inflammatory bowel disease), ulcerative colitis (UC), Crohn's disease (CD), colitis (e.g., colitis caused by environmental insults (e.g., caused by or associated with a therapeutic regimen, such as chemotherapy, radiation therapy, etc.)), infectious colitis, ischemic colitis, collagenous or lymphocytic colitis, necrotizing enterocolitis, colitis in conditions such as chronic granulomatous disease or celiac disease, food allergies, gastritis, gastroenteritis, infectious gastritis or enterocolitis (e.g., *Helicobacter pylori*-infected chronic active gastritis), esophagitis, and other forms of gastrointestinal inflammation caused by an infectious agent, or indeterminate colitis.

In some embodiments, the autoimmune disorder, inflammatory disorder, fibrotic disorder, granulocytic (neutrophilic or eosinophilic) disorder, monocytic disorder, or lymphocytic disorder is a gastrointestinal inflammatory condition. In some embodiments, the gastrointestinal inflammatory condition is IBD (inflammatory bowel disease). In some embodiments the inflammatory bowel disease is ulcerative colitis (UC) or Crohn's disease (CD). In some embodiments, the gastrointestinal inflammatory condition is colitis (e.g., colitis caused by environmental insults (e.g., caused by or associated with a therapeutic regimen, such as chemotherapy, radiation therapy, etc.), infectious colitis, ischemic colitis, collagenous or lymphocytic colitis, necrotizing enterocolitis, colitis in conditions such as chronic granulomatous disease or celiac disease, food allergies, gastritis, gastroenteritis, infectious gastritis or enterocolitis (e.g., *Helicobacter pylori*-infected chronic active gastritis), and other forms of gastrointestinal inflammation caused by an infectious agent, or indeterminate colitis. In some embodiments, the gastrointestinal inflammatory condition is ulcerative colitis (UC) or Crohn's disease (CD). In some embodiments, the gastrointestinal inflammatory condition is ulcerative colitis (UC). In some embodiments, the ulcerative colitis is mild to moderate distal colitis. In some embodiments, the ulcerative colitis is mild to moderate extensive colitis. In some embodiments, the ulcerative colitis is severe colitis. In some embodiments, the gastrointestinal inflammatory condition is Crohn's disease (CD). In some embodiments, the Crohn's disease is in acute disease stage. In some embodiments, the Crohn's disease is in induced clinical remission stage. In some embodiments, the Crohn's disease is in maintain response/remission stage. In some embodiments, the Crohn's disease is mild to moderate disease. In some embodiments, the Crohn's disease is moderate to severe disease. In some embodiments, the Crohn's disease is severe/fulminant disease. In some embodiments, the Crohn's disease is ileal, ileocolonic, or colonic disease.

In some embodiments, the autoimmune disorder, inflammatory disorder, fibrotic disorder, granulocytic (neutrophilic or eosinophilic) disorder, monocytic disorder, or lymphocytic disorder, or disorder associated with increased numbers or distribution of normal or aberrant tissue resident cells (such as mast cells, macrophages, or lymphocytes) or stromal cells (such as fibroblasts, myofibroblasts, smooth muscle cells, epithelia, or endothelia) is lupus or Systemic Lupus Erythematosus (SLE), or one or more organ-specific manifestations of lupus (e.g., lupus nephritis (LN) affecting the kidney, or extra-renal lupus (ERL) affecting the blood and/or lymphoid organs (lymph nodes, spleen, thymus, and associated lymphatic vessels), and/or joints and/or other organs, but not necessarily the kidney).

In some embodiments, the autoimmune disorder, inflammatory disorder, or fibrotic disorder is related to sepsis and/or trauma, HIV infection, or idiopathic (of unknown etiology) such as ANCA-associated vaculitides (AAV), granulomatosis with polyangiitis (formerly known as Wegener's granulomatosis), Behcet's disease, cardiovascular disease, eosinophilic bronchitis, Reiter's Syndrome, SEA Syndrome (Seronegativity, Enthesopathy, Arthropathy Syndrome), ankylosing spondylitis, dermatomyositis, scleroderma, e.g., systemic scleroderma also called systemic sclerosis, vasculitis (e.g., Giant Cell Arteritis (GCA), also called temporal arteritis, cranial arteritis or Horton disease), myositis, polymyositis, dermatomyositis, polyarteritis nodosa, arteritis, polymyalgia rheumatica, sarcoidosis, primary biliary sclerosis, sclerosing cholangitis, Sjogren's syndrome, psoriasis, plaque psoriasis, guttate psoriasis, inverse psoriasis, pustular psoriasis, erythrodermic psoriasis, dermatitis, atopic dermatitis, pemphigus, e.g., pemphigus vulgaris, atherosclerosis, lupus, Still's disease, myasthenia gravis, celiac disease, multiple sclerosis (MS) of the relapsing-remitting (RRMS) or primary progressive (PPMS) or secondary progressive (SPMS) subtypes, Guillain-Barre disease, Type I diabetes mellitus (T1DM) or insulin-dependent (IDDM) or juvenile onset DM type, thyroiditis (e.g., Graves' disease), coeliac disease, Churg-Strauss syndrome, myalgia syndrome, hypereosinophilic syndrome, oedematous reactions including episodic angioedema, helminth infections, onchocercal dermatitis, eosinophilic esophagitis, eosinophilic enteritis, eosinophilic colitis, obstructive sleep apnea, endomyocardial fibrosis, Addison's disease, Raynaud's disease or phenomenon, autoimmune hepatitis, graft versus host disease (GVHD), or organ transplant rejection.

In some embodiments, the disorder is an inflammatory disorder of the skin. In some embodiments, the disorder is atopic dermatitis or onchocercal dermatitis. In some embodiments, the disorder is chronic idiopathic urticaria (CIU or CSU).

In some embodiments, the autoimmune disorder, inflammatory disorder, fibrotic disorder, neutrophilic disorder, or eosinophilic disorder is a fibrotic disorder. In some embodiments, the fibrotic disorders include lung fibrosis, liver fibrosis (e.g., fibrosis associated with cirrhosis (e.g., alcohol-induced cirrhosis, viral-induced cirrhosis, post-hepatitis C cirrhosis, and primary biliary cirrhosis), schistosomiasis, cholangitis (e.g., sclerosing cholangitis), and autoimmune-induced hepatitis), kidney fibrosis (e.g., tubulointerstitial fibrosis, scleroderma, diabetic nephritis, and glomerular nephritis), dermal fibrosis (e.g., scleroderma, hypertrophic and keloid scarring, nephrogenic fibrosing dermatopathy, and burns), myelofibrosis, neurofibromatosis, fibroma, intestinal fibrosis, and fibrotic adhesions resulting from surgical procedures), heart fibrosis (e.g., fibrosis associated with myocardial infarction), vascular fibrosis (e.g., fibrosis associated with postangioplasty arterial restenosis and atherosclerosis), eye fibrosis (e.g., fibrosis associated with post-cataract surgery, proliferative vitreoretinopathy, and retro-orbital fibrosis), and bone marrow fibrosis (e.g., idiopathic myelofibrosis and drug-induced myelofibrosis). The fibrosis can be organ-specific or systemic (e.g., systemic sclerosis and fibrosis associated with GVHD). In some embodiments, the fibrotic disorder is pulmonary fibrosis. In some embodiments, the pulmonary fibrosis is fibrosing interstitial pneumonia. In some embodiments, the pulmonary fibrosis is idiopathic pulmonary fibrosis (IPF), also known as cryptogenic fibrosing alveolitis. In some embodiments, the IPF is gender, age and physiology (GAP)-stage I. In some embodiments, the IPF is GAP-stage II. In some embodiments, the IPF is GAP-stage III. In some embodiments, the pulmonary fibrosis is sporadic IPF. In some embodiments, the pulmonary fibrosis is familial pulmonary fibrosis. In some embodiments, the pulmonary fibrosis is combined pulmonary fibrosis and emphysema. In some embodiments, the pulmonary fibrosis is associated with one or more of the following: usual interstitial pneumonia; idiopathic interstitial pneumonia; desquamative interstitial pneumonia; respiratory bronchiolitis-interstitial lung disease; acute interstitial pneumonia; nonspecific interstitial pneumonia; sarcoidosis; cryptogenic organizing pneumonia; eosinophilic pneumonia; infection; exposure to occupational or environmental agents; cigarette smoking; interstitial lung disease induced by drugs or radiation; rheumatic disease-associated interstitial lung disease; lymphoid interstitial pneumonia; pleuropulmonary fibroelastosis; pulmonary Langerhans cell histiocytosis; systemic sclerosis-interstitial lung disease; Hermansky-Pudlak syndrome; and telomeropathy.

In some embodiments, the pulmonary disorder, autoimmune disorder, inflammatory disorder, fibrotic disorder, neutrophilic disorder, or eosinophilic disorder is chronic obstructive pulmonary disease (COPD). In some embodiments, the COPD is Global Initiative for Chronic Obstructive Lung Disease (GOLD) category A. In some embodiments, the COPD is GOLD category B. In some embodiments, the COPD is GOLD category C. In some embodiments, the COPD is GOLD category D. In some embodiments, the COPD is chronic bronchitis. In some embodiments, the COPD is emphysema. In some embodiments, the emphysema is proximal acinar, panacinar, or distal acinar emphysema. In some embodiments, the emphysema is cigarette-induced emphysema. In some embodiments, the COPD is associated with exposure to particulate dusts, chemical fumes, and/or air pollution. In some embodiments, the COPD is associated with impaired lung development. In some embodiments, the COPD is chronic obstructive asthma. In some embodiments, the COPD is associated with alpha-1 antitrypsin deficiency. In some embodiments, the COPD is associated with serine protease inhibitor clade E, member 2 (SERPINE2) disruption. In some embodiments, the COPD is COPD with persistent systemic inflammation. In some embodiments, the COPD is eosinophilic or T-helper type 2 ($T_H2$) high COPD. In some embodiments, the COPD is COPD with persistent bacterial colonization. In some embodiments, the COPD is COPD with frequent exacerbations. In some embodiments, the autoimmune disorder, inflammatory disorder, fibrotic disorder, neutrophilic disorder, or eosinophilic disorder is asthma-COPD overlap syndrome (ACOS). In some embodiments, the ACOS is eosinophil-predominant, neutrophil-predominant, mixed-pattern, or no inflammation (paucigranulocytic) ACOS. In some embodiments, the autoimmune disorder, inflammatory disorder, fibrotic disorder, a neutrophilic disorder, or an eosinophilic disorder is COPD-obstructive sleep apnea (OSA) overlap syndrome.

The above lists are not all-inclusive, and it will be understood by the skilled artisan that a disease or disorder may fall within various categories.

The term "package insert" is used to refer to instructions customarily included in commercial packages of therapeutic products, that contain information about the indications, usage, dosage, administration, combination therapy, contraindications and/or warnings concerning the use of such therapeutic products.

The terms "pharmaceutical formulation" and "pharmaceutical composition" are used interchangeably herein, and refer to a preparation which is in such form as to permit the biological activity of an active ingredient contained therein to be effective, and which contains no additional components which are unacceptably toxic to a subject to which the formulation would be administered. Such formulations are sterile. In a preferred embodiment, the pharmaceutical composition or pharmaceutical formulation is administered to a human subject.

A "sterile" pharmaceutical formulation is aseptic or free or essentially free from all living microorganisms and their spores.

A "stable" pharmaceutical formulation is one in which the protein (e.g., an antibody, such as an anti-tryptase antibody) therein essentially retains its physical stability and/or chemical stability and/or biological activity upon storage. Preferably, the formulation essentially retains its physical and chemical stability, as well as its biological activity upon storage. The storage period is generally selected based on the intended shelf-life of the formulation. Various analytical techniques for measuring protein stability are available in the art and are reviewed in *Peptide and Protein Drug Delivery,* 247-301, Vincent Lee Ed., Marcel Dekker, Inc., New York, N.Y., Pubs. (1991) and Jones, A. *Adv. Drug Delivery Rev.* 10: 29-90 (1993), for example. Stability can be measured at a selected amount of light exposure and/or temperature for a selected time period. Stability can be evaluated qualitatively and/or quantitatively in a variety of different ways, including evaluation of aggregate formation (for example, using size exclusion chromatography, by measuring turbidity, and/or by visual inspection); evaluation of ROS formation (for example, by using a light stress assay or an AAPH stress assay); oxidation of specific amino acid residues of the protein (for example, a Trp residue and/or a Met residue of a monoclonal antibody); by assessing charge heterogeneity using cation exchange chromatography, image capillary isoelectric focusing (icIEF) or capillary zone electrophoresis; amino-terminal or carboxy-terminal sequence analysis; mass spectrometric analysis; SDS-PAGE analysis to compare reduced and intact antibody; peptide map (for example, tryptic or LYS-C) analysis; evaluating biological activity or target binding function of the protein (e.g., antigen binding function of an antibody); and the like. Instability may involve any one or more of: aggregation, deamidation (e.g., Asn deamidation), oxidation (e.g., Met oxidation and/or Trp oxidation), isomerization (e.g., Asp isomerization), clipping/hydrolysis/fragmentation (e.g., hinge region fragmentation), succinimide formation, unpaired cysteine(s), N-terminal extension, C-terminal processing, glycosylation differences, and the like.

An antibody (e.g., an anti-tryptase antibody) "retains its physical stability" in a pharmaceutical formulation if it shows no signs or very little of aggregation, precipitation, fragmentation, and/or denaturation upon visual examination of color and/or clarity, or as measured by UV light scattering or by size exclusion chromatography.

An antibody (e.g., an anti-tryptase antibody) "retains its chemical stability" in a pharmaceutical formulation, if the chemical stability at a given time is such that the antibody is considered to still retain its biological activity as defined below. Chemical stability can be assessed by detecting and quantifying chemically altered forms of the antibody. Chemical alteration may involve protein oxidation which can be evaluated using tryptic peptide mapping, reverse-phase high-performance liquid chromatography (HPLC) and liquid chromatography-mass spectrometry (LC/MS), for example. Other types of chemical alteration include charge alteration of the antibody which can be evaluated by ion-exchange chromatography or icIEF, for example.

An antibody (e.g., an anti-tryptase antibody) "retains its biological activity" in a pharmaceutical formulation, if the biological activity of the antibody at a given time is within about 20% (such as within about 10%) of the biological activity exhibited at the time the pharmaceutical formulation was prepared (within the errors of the assay), as determined for example in an antigen binding assay or an in vitro inhibitory assay for a monoclonal antibody (e.g., an anti-tryptase monoclonal antibody). In some embodiments, the biological activity of an antibody at a given time is within about 25%, about 30%, about 35%, about 40%, about 45%, about 50% of the biological activity exhibited at the time the pharmaceutical formulation was prepared.

As used herein, "biological activity" of an antibody (e.g., an anti-tryptase antibody) refers to the ability of the antibody to bind its target, for example the ability of a monoclonal antibody to bind to an antigen. It can further include a biological response which can be measured in vitro or in vivo. Such activity may be antagonistic or agonistic.

A protein (e.g., an antibody, such as an anti-tryptase antibody) which is "susceptible to oxidation" is one comprising one or more residue(s) that has been found to be prone to oxidation such as, but not limited to, methionine (Met), cysteine (Cys), histidine (His), tryptophan (Trp), and tyrosine (Tyr). For example, a tryptophan amino acid in the Fab portion of a monoclonal antibody or a methionine amino acid in the Fc portion of a monoclonal antibody may be susceptible to oxidation.

The term "percent oxidation" refers to the percentage of antibodies in a formulation (e.g., a pharmaceutical composition) that are oxidized at a particular amino acid residue, for example, a Trp residue (e.g., Trp100 in HVR-H3 of hu31A.v11) or a Met residue. Percent oxidation can be determined by, e.g., mass spectrometry (MS) analysis of one or more tryptic peptides, in which one or more particular oxidation-prone amino acid residues reside. In certain embodiments, the percentage oxidation of Trp100 in HVR-H3 of hu31A.v11 is determined by the mass of oxidized tryptic peptide in which Trp 100 resides, over the mass of the overall (oxidized and non-oxidized) tryptic peptide, as determined by MS analysis. Percent oxidation may be determined, for example, within 9 months, 12 months, 18 months, or two years from the initial production of an antibody or pharmaceutical composition thereof.

The term "is determined following an AAPH stress test," as used herein, means that the percent oxidation at a particular amino acid residue (for example, at Trp100 in HVR-H3 of hu31A.v11) is determined by mass spectrometry analysis of tryptic peptides following formulating the antibody at 150 mg/ml in 5 mM AAPH for 25 h at 40° C., for example, as described in Example 5. The stressed antibody is digested with trypsin and the digested peptides were subjected to ultra high performance liquid chromatography-high resolution mass spectrometry (UHPLC-HRMS) to determine the percentage of oxidation.

As used herein, "buffer" refers to a buffered solution that resists changes in pH by the action of its acid-base conjugate components. The buffer of this invention preferably has a pH in the range from about 4.5 to about 8.0 (e.g., about 4.5, about 5, about 5.5, about 6, about 6.5, about 7, about 7.5, or about 8), e.g., about pH 5.5. For example, histidine acetate is an example of a buffer that will control the pH in this range. Another suitable buffer is arginine succinate and/or histidine succinate.

A "preservative" is a compound which can be optionally included in the formulation to essentially reduce bacterial action therein, thus facilitating the production of a multi-use formulation, for example. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl, and benzyl alcohol; alkyl parabens such as methyl or propyl paraben; catechol; resorcinol; cyclohexanol; 3-pentanol, and m-cresol. In one embodiment, the preservative herein is benzyl alcohol.

As used herein, a "surfactant" refers to a surface-active agent, preferably a nonionic surfactant. Examples of surfactants herein include polysorbate (for example, polysorbate 20 and polysorbate 80); poloxamer (e.g., poloxamer 188); TRITON®; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristamidopropyl-, palmidopropyl-, or isostearamidopropyl-dimethylamine; sodium methyl cocoyl-, or disodium methyl oleyl-taurate; and the MONAQUAT™ series (Mona Industries, Inc., Paterson, N.J.); polyethyl glycol, polypropyl glycol, and copolymers of ethylene and propylene glycol (e.g., PLURONIC® type block copolymers, e.g., PLURONIC® F-68); and the like. In one embodiment, the surfactant herein is polysorbate 20. In yet another embodiment, the surfactant herein is poloxamer 188.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" *Biochemical Society Transactions*, 14, pp. 375-382, 615th Meeting Belfast (1986) and Stella et al. "Prodrugs: A Chemical Approach to Targeted Drug Delivery," *Directed Drug Delivery*, Borchardt et al. (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

A "subject" is a vertebrate, preferably a mammal, more preferably a human. Mammals include, but are not limited to, farm animals (such as cows, and sheep), sport animals, pets (such as cats, dogs and horses), primates (e.g., humans and non-human primates such as monkeys (e.g., cynomolgus monkeys)), and rodents (e.g., mice and rats).

As used herein, "administering" is meant a method of giving a dosage of a compound (e.g., an anti-tryptase antibody of the invention or an additional therapeutic agent) or a composition (e.g., a pharmaceutical composition, e.g., a pharmaceutical composition including an anti-tryptase antibody of the invention, optionally also including an additional therapeutic agent, which may include an excipient such as an antioxidant (e.g., N-acetyltryptophan and/or methionine)) to a subject. The compositions utilized in the methods described herein can be administered, for example, intravitreally, intramuscularly, intravenously, intradermally, percutaneously, intraarterially, intraperitoneally, intralesionally, intracranially, intraarticularly, intraprostatically, intrapleurally, intratracheally, intrathecally, intranasally, intravaginally, intrarectally, topically, intratumorally, peritoneally, subcutaneously, subconjunctivally, intravesicularly, mucosally, intrapericardially, intraumbilically, intraocularly, intraorbitally, orally, topically, transdermally, periocularly, conjunctivally, subtenonly, intracamerally, subretinally, retrobulbarly, intracanalicularly, by inhalation, by injection, by implantation, by infusion, by continuous infusion, by localized perfusion bathing target cells directly, by catheter, by lavage, in cremes, or in lipid compositions. The compositions utilized in the methods described herein can also be administered systemically or locally. The method of administration can vary depending on various factors (e.g., the compound or composition being administered and the severity of the condition, disease, or disorder being treated).

An "effective amount" or "therapeutically effective amount" of an agent, e.g., an anti-tryptase antibody or a pharmaceutical formulation (e.g., a pharmaceutical formulation that includes an anti-tryptase antibody, which may include an excipient such as an antioxidant (e.g., N-acetyltryptophan and/or methionine)), refers to an amount effective, at dosages and for periods of time necessary, to achieve the desired therapeutic or prophylactic result. The therapeutically effective amount of the antibody or antibody fragment (e.g., an anti-tryptase antibody), or composition thereof, may ameliorate or treat the disorder or disease, or prevent, reduce, ameliorate, or treat symptoms associated with the disorder or disease.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease. A patient may be successfully "treated" for asthma if, for example, after receiving an asthma therapy, the patient shows observable and/or measurable reduction in or absence of one or more of the following: recurrent wheezing, coughing, trouble breathing, chest tightness, symptoms that occur or worsen at night, symptoms that are triggered by cold air, exercise or exposure to allergens.

The term "interleukin-5 (IL-5)," as used herein, refers to any native IL-5 from any vertebrate source, including mammals such as primates (e.g., humans) and rodents (e.g., mice and rats), unless otherwise indicated. The term encompasses "full-length," unprocessed IL-5, mature IL-5, as well as any form of IL-5 that results from post-translational modifications. The term also encompasses naturally occurring variants of IL-5, such as splice variants or allelic variants. The amino acid sequence of an exemplary IL-5 can be found, for example, under UniProtKB accession number P05113.

The term "IL-5 axis binding antagonist" refers to a molecule that decreases, blocks, inhibits, abrogates or interferes with signal transduction resulting from the interaction of IL-5 with one or more of its binding partners, such as IL-5 receptor, alpha (IL5RA). Exemplary IL-5 axis binding antagonists that can be used in the methods of the invention include, for example, IL-5 binding antagonists (e.g., anti-IL-5 antibodies (e.g., mepolizumab, benralizumab, and reslizumab) and IL-5 receptor binding antagonists (e.g., anti-IL-5R antibodies)).

As used herein, "interleukin-13 (IL-13)" refers to any native IL-13 from any vertebrate source, including mammals such as primates (e.g., humans) and rodents (e.g., mice and rats), unless otherwise indicated. IL-13 is a cytokine secreted by many cell types, including T helper type 2 (Th2) cells. The term encompasses "full-length," unprocessed IL-13, mature IL-13, as well as any form of IL-13 that results from post-translational modifications. The amino acid sequence of an exemplary human IL-13 can be found, for example, under UniProtKB accession number P35225.

The term "IL-13 axis binding antagonist" refers to a molecule that decreases, blocks, inhibits, abrogates or interferes with signal transduction resulting from the interaction of IL-13 with one or more of its binding partners, such as IL-4 receptor alpha (IL4Rα), IL-13 receptor alpha1 (IL13RA1) and IL-13 receptor alpha2 (IL13RA2). IL-13 axis binding antagonists include IL-13 binding antagonists (e.g., anti-IL-13 antibodies, for example, lebrikizumab, 228B/C-1, 228A-4, 227-26, and 227-43 (see, for example, U.S. Pat. Nos. 7,674,459; 8,067,199; 8,088,618; 8,318,160; and 8,734,797) and IL-13 receptor binding antagonists (e.g., an anti-IL4Rα antibody, an anti-IL13RA1 antibody, or an anti-IL13RA2 antibody).

As used herein, "interleukin-17 (IL-17)" refers to any native IL-17 from any vertebrate source, including mammals such as primates (e.g., humans) and rodents (e.g., mice and rats), unless otherwise indicated, and includes family members IL-17A, IL-17B, IL-17C, IL-17D, IL-17E, and IL-17F. The term encompasses "full-length," unprocessed IL-17, mature IL-17, as well as any form of IL-17 that results from post-translational modifications. The amino acid sequence of an exemplary human IL-17A can be found, for example, under UniProtKB accession number Q16552. The amino acid sequence of an exemplary human IL-17B can be found, for example, under UniProtKB accession number Q9UHF5. The amino acid sequence of an exemplary human IL-17C can be found, for example, under UniProtKB accession number Q9P0M4. The amino acid sequence of an exemplary human IL-17D can be found, for example, under UniProtKB accession number Q8TAD2. The amino acid sequence of an exemplary human IL-17E can be found, for example, under UniProtKB accession number Q9H293. The amino acid sequence of an exemplary human IL-17F can be found, for example, under UniProtKB accession number Q96PD4.

The term "IL-17 axis binding antagonist" refers to a molecule that decreases, blocks, inhibits, abrogates or interferes with signal transduction resulting from the interaction of IL-17 with one or more of its binding partners, such as interleukin-17 receptor (IL-17R) family member proteins interleukin 17 receptor A (IL17RA), interleukin 17 receptor B (IL17RB), interleukin 17 receptor C (IL17RC), interleukin 17 receptor D (IL17RD), interleukin 17 receptor E (IL17RE), and interleukin 17 receptor E-like (IL7REL). Exemplary IL-17 axis binding antagonists include, for example, IL-17 binding antagonists (e.g., anti-IL-17 antibodies (e.g., secukinumab (AIN417), ixekizumab (LY2439821), bimekizumab, and NI-1401) and IL-17 receptor binding antagonists (e.g., anti-IL-17R antibodies (e.g., brodalumab (AMG-827))). See, e.g., WO 2006/013107, WO 2007/070750, WO 2012/156219, and U.S. Pat. No. 8,715,669.

The term "interleukin-33 (IL-33)," as used herein, refers to any native IL-33 from any vertebrate source, including mammals such as primates (e.g., humans and cynomolgus monkeys) and rodents (e.g., mice and rats), unless otherwise indicated. IL-33 is also referred to in the art as nuclear factor of high endothelial venules (NF-HEV; see, e.g., Baekkevold et al. *Am. J. Pathol.* 163(1): 69-79, 2003), DVS27, C9orf26, and interleukin-1 family member 11 (IL-1F11). The term encompasses "full-length," unprocessed IL-33, mature IL-33, as well as any form of IL-33 that results from post-translational modifications. Human full-length, unprocessed IL-33 contains 270 amino acids (a.a.) and may also be referred to as IL-33$_{1-270}$. Processed forms of human IL-33 include, for example, IL-33$_{95-270}$, IL-33$_{99-270}$, IL-33$_{109-270}$, IL-33$_{112-270}$, IL-33$_{1-178}$, and IL-33$_{179-270}$ (Lefrangais et al. *Proc. Natl. Acad. Sci.* 109(5):1673-1678, 2012 and Martin, *Semin. Immunol.* 25: 449-457, 2013). In some embodiments, processed forms of human IL-33, e.g., IL-33$_{95-270}$, IL-33$_{99-270}$, IL-33$_{109-270}$, or other forms processed by proteases such as calpain, proteinase 3, neutrophil elastase, and cathepsin G may have increased biological activity compared to full-length IL-33. The term also encompasses naturally occurring variants of IL-33, for example, splice variants (e.g., the constitutively active splice variant spIL-33 which lacks exon 3, Hong et al. *J. Biol. Chem.* 286(22):20078-20086, 2011) or allelic variants. IL-33 may be present within a cell (e.g., within the nucleus) or as a secreted cytokine form. Full-length IL-33 protein contains a helix-turn-helix DNA-binding motif including nuclear localization sequence (a.a. 1-75 of human IL-33), which includes a chromatin binding motif (a.a. 40-58 of human IL-33). Forms of IL-33 that are processed and secreted lack these N-terminal motifs. The amino acid sequence of an exemplary human IL-33 can be found, for example, under UniProtKB accession number O95760.

The terms "interleukin 1 receptor-like 1 (IL1RL1)" and "ST2," used interchangeably herein, refer to any native ST2 from any vertebrate source, including mammals such as primates (e.g., humans) and rodents (e.g., mice and rats), unless otherwise indicated. ST2 is also referred to in the art as DER4, T1, and FIT-1. The term encompasses "full-length," unprocessed ST2, mature ST2, as well as any form of ST2 that results from post-translational modifications. At least four isoforms of ST2 are known in the art, including soluble (sST2, also known as IL1RL1-a) and transmembrane (ST2L, also known as IL1RL1-b), which arise from differential mRNA expression from a dual promoter system, and ST2V and ST2LV, which arise from alternative splicing, as described below. The domain structure of ST2L includes three extracellular immunoglobulin-like C2 domains, a transmembrane domain, and a cytoplasmic Toll/Interleukin-1 receptor (TIR) domain. sST2 lacks the transmembrane and cytoplasmic domains contained within ST2L and includes a unique 9 amino acid (a.a.) C-terminal sequence (see, e.g., Kakkar et al. *Nat. Rev. Drug Disc.* 7: 827-840, 2008). sST2 can function as a decoy receptor to inhibit soluble IL-33. The term also encompasses naturally occurring variants of ST2, e.g., splice variants (e.g., ST2V, which lacks the third immunoglobulin motif and has a unique hydrophobic tail, and ST2LV, which lacks the transmembrane domain of ST2L) or allelic variants (e.g., variants that are protective against asthma risk or that confer asthma risk as described herein). The amino acid sequence of an exemplary human ST2 can be found, for example, under UniProtKB accession number Q01638. ST2 is a part of the IL-33 receptor along with the co-receptor protein IL-1RAcP. Binding of IL-33 to ST2 and the co-receptor interleukin-1 receptor accessory protein (IL-1RAcP) forms a 1:1:1 ternary signaling complex to promote downstream signal transduction (see, e.g., Lingel et al. *Structure* 17(10): 1398-1410, 2009, and Liu et al. *Proc. Natl. Acad. Sci.* 110(37): 14918-14924, 2013).

By "IL-33 axis" is meant a nucleic acid (e.g., a gene or mRNA transcribed from the gene) or polypeptide that is involved in IL-33 signal transduction. For example, the IL-33 axis may include the ligand IL-33, a receptor (e.g., ST2 and/or IL-1RAcP), adaptor molecules (e.g., MyD88), or proteins that associate with receptor molecules and/or adaptor molecules (e.g., kinases, such as interleukin-1 receptor-associated kinase 1 (IRAK1) and interleukin-1 receptor-associated kinase 4 (IRAK4), or E3 ubiquitin ligases, such as TNF receptor associated factor 6 (TRAF6)).

An "IL-33 axis binding antagonist" refers to a molecule that inhibits the interaction of an IL-33 axis binding partner with one or more of its binding partners. As used herein, an IL-33 axis binding antagonist includes IL-33 binding antagonists, ST2 binding antagonists, and IL1RAcP binding antagonists. Exemplary IL-33 axis binding antagonists include anti-IL-33 antibodies and antigen-binding fragments thereof (e.g., anti-IL-33 antibodies such as ANB-020 (AnaptysBio, Inc.) or any of the antibodies described in EP1725261, U.S. Pat. No. 8,187,596, WO2011031600, WO2014164959, WO2015099175 or WO2015106080, which are each incorporated herein by reference in their entirety); polypeptides that bind IL-33 and/or its receptor (ST2 and/or IL-1RAcP) and block ligand-receptor interaction (e.g., ST2-Fc proteins, such as those described in WO 2014/152195, which is herein incorporated by reference in its entirety; immunoadhesins, peptibodies, and soluble ST2, or derivatives thereof); anti-IL-33 receptor antibodies (e.g., anti-ST2 antibodies, for example, AMG-282 (Amgen) or STLM15 (Janssen) or any of the anti-ST2 antibodies described in WO 2013/173761 and WO 2013/165894, which are each incorporated herein by reference in their entirety; or ST2-Fc proteins, such as those described in WO 2013/173761; WO 2013/165894; or WO 2014/152195, which are each incorporated herein by reference in their entirety); and IL-33 receptor antagonists, such as small molecule inhibitors, aptamers that bind IL-33, and nucleic acids that hybridize under stringent conditions to IL-33 axis nucleic acid sequences (e.g., short interfering RNAs (siRNA) or clustered regularly interspaced short palindromic repeat RNAs (CRISPR-RNA or crRNA), including single guide RNAs (sgRNAs) having a crRNA and tracrRNA sequence as described in Mali et al. (Science. 339: 823-26, 2013), which is incorporated herein by reference in its entirety).

The terms "anti-IL-33 antibody," an "antibody that binds to IL-33," and "antibody that specifically binds IL-33" refer to an antibody that is capable of binding IL-33 with sufficient affinity such that the antibody is useful as a diagnostic and/or therapeutic agent in targeting IL-33. In one embodiment, the extent of binding of an anti-IL-33 antibody to an unrelated, non-IL-33 protein is less than about 10% of the binding of the antibody to IL-33 as measured, e.g., by a radioimmunoassay (RIA). In certain embodiments, an antibody that binds to IL-33 has a dissociation constant ($K_D$) of $\leq 1$ µM, $\leq 100$ nM, $\leq 10$ nM, $\leq 1$ nM, $\leq 0.1$ nM, $\leq 0.01$ nM, or $\leq 0.001$ nM (e.g., $10^{-8}$ M or less, e.g., from $10^{-8}$ M to $10^{-13}$ M, e.g., from $10^{-9}$ M to $10^{-13}$ M). In certain embodiments, an anti-IL-33 antibody binds to an epitope of IL-33 that is conserved among IL-33 from different species.

The term "ST2 binding antagonist" refers to a molecule that inhibits the interaction of an ST2 with IL-33, IL1RAcP, and/or a second ST2 molecule. The ST2 binding antagonist may be a protein, such as an "ST2-Fc protein" that includes an IL-33-binding domain (e.g., all or a portion of an ST2 or IL1RAcP protein) and a multimerizing domain (e.g., an Fc portion of an immunoglobulin, e.g., an Fc domain of an IgG selected from the isotypes IgG1, IgG2, IgG3, and IgG4, as well as any allotype within each isotype group), which are attached to one another either directly or indirectly through a linker (e.g., a serine-glycine (SG) linker, glycine-glycine (GG) linker, or variant thereof (e.g., a SGG, a GGS, an SGS, or a GSG linker)), and includes, but is not limited to, ST2-Fc proteins and variants thereof described in WO 2013/173761, WO 2013/165894, and WO 2014/152195, which are each incorporated herein by reference in their entirety. In some embodiments, a ST2 binding antagonist may be an anti-ST2 antibody, for example, AMG-282 (Amgen) or STLM15 (Janssen) or any of the anti-ST2 antibodies described in WO 2013/173761 and WO 2013/165894.

An "isolated nucleic acid" refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Percent (%) amino acid sequence identity" with respect to the polypeptide sequences identified herein is defined as the percentage of amino acid residues in a candidate sequence that are identical with the amino acid residues in the polypeptide being compared, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, or Megalign (DNASTAR) software. Those skilled in the art can determine appropriate parameters for measuring alignment, including any algorithms needed to achieve maximal alignment over the full-length of the sequences being compared. For purposes herein, however, % amino acid sequence identity values are generated using the sequence comparison computer program ALIGN-2. The ALIGN-2 sequence comparison computer program was authored by Genentech, Inc. and the source code has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, California The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The amino acid sequences described herein are contiguous amino acid sequences unless otherwise specified.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors" or "expression vectors"). In general, expression vectors of utility in recombinant DNA techniques are often in the form of plasmids. In the present specification, "plasmid" and "vector" may be used interchangeably.

II. Compositions and Methods

In one aspect, the invention is based, in part, on novel antibodies that bind to tryptase. In another aspect, the invention is based, in part, on the discovery that particular residues (e.g., HVR residues, such as HVR-H3 W100, which refers to W100 of the VH domain of the anti-tryptase antibody hu31A.v11) of anti-tryptase antibodies may be susceptible to oxidation. The invention provides pharmaceutical compositions that include antioxidants (e.g., N-acetyltryptophan and/or methionine) to reduce or prevent oxidation of antibodies described herein (e.g., anti-tryptase antibodies). Other suitable antioxidant excipients include, without limitation, free tryptophan, cyclodextrins, Trolox (6-hydroxy-2,5,7,8-tetramethylchroman-2-carboxylic acid), pyridoxine, polyols (e.g., mannitol), and metal chelators (e.g., EDTA). See, e.g., Ji et al., *Biotechnology* 98:4485-4500, 2009. Antibodies and pharmaceutical compositions of the invention are useful, e.g., for the diagnosis and/or treatment of disorders (e.g., a pulmonary disorder, an autoimmune disorder, an inflammatory disorder, a fibrotic disorder, a granulocytic (neutrophilic or eosinophilic) disorder, a monocytic disorder, a lymphocytic disorder, a disorder associated with increased numbers or distribution of normal or aberrant tissue resident cells (such as mast cells, macrophages, or lymphocytes) or stromal cells (such as fibroblasts, myofibroblasts, smooth muscle cells, epithelia, or endothelia, or a tryptase-associated disorder or a tryptase-mediated disorder. In another aspect, the invention provides lyophilized pharmaceutical compositions to reduce or eliminate oxidation of antibodies described herein (e.g., anti-tryptase antibodies).

A. Exemplary Anti-Tryptase Antibodies

The invention provides isolated antibodies that bind to tryptase. In certain embodiments, an anti-tryptase antibody of the invention binds to tryptase with a $K_D$ of about 100 nM or lower (e.g., 100 nM or lower, 10 nM or lower, 1 nM or lower, 100 pM or lower, 10 pM or lower, 1 pM or lower, or 0.1 pM or lower). In some embodiments, the antibody binds tryptase with a $K_D$ of 10 nM or lower (e.g., 10 nM or lower, 1 nm or lower, 100 pM or lower, 10 pM or lower, 1 pM or lower, or 0.1 pM or lower). In some embodiments, the antibody binds tryptase with a $K_D$ of 1 nM or lower (e.g., 1 nm or lower, 100 pM or lower, 10 pM or lower, 1 pM or lower, or 0.1 pM or lower). In some embodiments, the antibody binds tryptase with a $K_D$ of 0.5 nM or lower (e.g., 0.5 nm or lower, 400 pM or lower, 300 pM or lower, 200 pM or lower, 100 pM or lower, 50 pM or lower, 25 pM or lower, 10 pM or lower, 1 pM or lower, or 0.1 pM or lower). In some embodiments, the antibody binds tryptase with a $K_D$ between about 0.1 nM to about 0.5 nM (e.g., about 0.1 nM, about 0.2 nM, about 0.3 nM, about 0.4 nM, or about 0.5 nM). In some embodiments, the antibody binds tryptase with a $K_D$ between about 1 pM to about 500 pM, about 1 pM to about 400 pM, about 1 pM to about 300 pM, about 1 pM to about 200 pM, about 1 pM to about 100 pM, about 1 pM to about 50 pM, about 25 pM to about 500 pM, about 25 pM to about 400 pM, about 25 pM to about 300 pM, about 25 pM to about 100 pM, about 50 pM to about 500 pM, about 50 pM to about 450 pM, about 50 pM to about 425 pM, about 50 pM to about 400 pM, about 50 pM to about 375 pM, about 50 pM to about 350 pM, about 50 pM to about 325 pM, about 50 pM to about 300 pM, about 50 pM to about 275 pM, about 50 pM to about 250 pM, about 50 pM to about 200 pM, about 50 pM to about 180 pM, about 50 pM to about 175 pM, about 50 pM to about 150 pM, about 50 pM to about 125 pM, about 50 pM to about 100 pM, about 50 pM to about 75 pM, about 100 pM to about 500 pM, about 100 pM to about 475 pM, about 100 pM to about 450 pM, about 100 pM to about 425 pM, about 100 pM to about 400 pM, about 100 pM to about 375 pM, about 100 pM to about 350 pM, about 100 pM to about 325 pM, about 100 pM to about 300 pM, about 100 pM to about 275 pM, about 100 pM to about 250 pM, about 100 pM to about 225 pM, about 100 pM to about 200 pM, about 100 pM to about 180 pM, about 100 pM to about 175 pM, about 100 pM to about 150 pM, about 100 pM to about 125 pM, about 150 pM to about 500 pM, about 150 pM to about 475 pM, about 150 pM to about 450 pM, about 150 pM to about 425 pM, about 150 pM to about 400 pM, about 150 pM to about 375 pM, about 150 pM to about 350 pM, about 150 pM to about 325 pM, about 150 pM to about 300 pM, about 150 pM to about 275 pM, about 150 pM to about 250 pM, about 150 pM to about 225 pM, about 150 pM to about 200 pM, about 175 pM to about 500 pM, about 175 pM to about 475 pM, about 175 pM to about 450 pM, about 175 pM to about 425 pM, about 175 pM to about 400 pM, about 175 pM to about 375 pM, about 175 pM to about 350 pM, about 175 pM to about 325 pM, about 175 pM to about 300 pM, or about 180 pM to about 400 pM. In some embodiments, the antibody binds tryptase with a $K_D$ of about 0.4 nM. In some embodiments, the antibody binds tryptase with a $K_D$ of about 0.2 nM. In some embodiments, the antibody binds tryptase with a $K_D$ of about 0.18 nM. In some embodiments, the tryptase is human tryptase, for example, human tryptase beta (e.g., human tryptase beta 1, human tryptase beta 2, and/or human tryptase beta 3). In some embodiments, the $K_D$ is determined in a BIACORE® SPR assay. In certain embodiments, the tryptase is human tryptase alpha. In certain embodiments, the antibody is a human or humanized antibody.

In another example, in some embodiments, an anti-tryptase antibody of the invention (including any of the preceding anti-tryptase antibodies) is capable of inhibiting an activity of tryptase. In some embodiments, an anti-tryptase antibody of the invention is capable of inhibiting a proteolytic activity of tryptase, for example, as determined in an in vitro tryptase enzymatic assay. In some embodiments, an artificial substrate, for example, the synthetic peptide S-2288 can be used as a substrate in an in vitro tryptase enzymatic assay. In some embodiments, an anti-tryptase antibody of the invention is capable of inhibiting the activity of human tryptase with a half-maximal inhibitory concentration (IC50) of about 100 nM or lower (e.g., 100 nM or lower, 10 nM or lower, 5 nM or lower, 2.5 nM or lower, 1 nM or lower, 100 pM or lower, 10 pM or lower, 1 pM or lower, or 0.1 pM or lower) as determined by an in vitro tryptase enzymatic assay, for example, using S-2288 as a substrate. In some embodiments, the antibody is capable of inhibiting the activity of human tryptase with an IC50 of about 10 nM or lower (e.g., 10 nM or lower, 5 nM or lower, 2.5 nM or lower, 1 nM or lower, 100 pM or lower, 10 pM or lower, 1 pM or lower, or 0.1 pM or lower) as determined by an in vitro tryptase enzymatic assay, for example, using S-2288 as a substrate. In some embodiments, the antibody is capable of inhibiting the activity of human tryptase with an IC50 of about 2.5 nM or lower (e.g., 2.5 nM or lower, 1 nM or lower, 100 pM or lower, 10 pM or lower, 1 pM or lower, or 0.1 pM or lower) as determined by an in vitro tryptase enzymatic assay, for example, using S-2288 as a substrate. In some embodiments, the antibody is capable of inhibiting the activity of human tryptase with an IC50 of about 0.1 nM to about 2 nM (e.g., about 0.1 nM, about 0.2 nM, about 0.3 nM, about 0.4 nM, about 0.5 nM, about 0.6 nM, about 0.7 nM, about 0.8 nM, about 0.9 nM, about 1.0 nM, about 1.1 nM, about 1.2 nM, about 1.3 nM, about 1.4 nM, about 1.5 nM, about 1.6 nM, about 1.7 nM, about 1.8 nM, about 1.9 nM, or about 2.0 nM). In some embodiments, the antibody is capable of inhibiting the activity of human tryptase with an IC50 of about 0.5 nM to about 2.5 nM (e.g., about 0.5 nM, about 0.6 nM, about 0.7 nM, about 0.8 nM, about 0.9 nM, about 1.0 nM, about 1.1 nM, about 1.2 nM, about 1.3 nM, about 1.4 nM, about 1.5 nM, about 1.6 nM, about 1.7 nM, about 1.8 nM, about 1.9 nM, about 2.0 nM, about 2.1 nM, about 2.2 nM, about 2.3 nM, about 2.4 nM, or about 2.5 nM). In some embodiments, the antibody is capable of inhibiting the activity of human tryptase with an IC50 of about 1 pM to about 2.5 nM, about 25 pM to about 2.5 nM, about 50 pM to about 2.5 nM, about 75 pM to about 2.5 nM, about 100 pM to about 2.5 nM, about 125 pM to about 2.5 nM, about 150 pM to about 2.5 nM, about 175 pM to about 2.5 nM, about 200 pM to about 2.5 nM, about 225 pM to about 2.5 nM, about 250 pM to about 2.5 nM, about 300 pM to about 2.5 nM, about 325 pM to about 2.5 nM, about 325 pM to about 2.5 nM, about 350 pM to about 2.5 nM, about 375 pM to about 2.5 nM, about 400 pM to about 2.5 nM, about 425 pM to about 2.5 nM, about 450 pM to about 2.5 nM, about 500 pM to about 2.5 nM, about 450 pM to about 2.5 nM, about 500 pM to about 2.5 nM, about 550 pM to about 2.5 nM, about 600 pM to about 2.5 nM, about 650 pM to about 2.5 nM, about 700 pM to about 2.5 nM, about 750 pM to about 2.5 nM, about 800 pM to about 2.5 nM, about 850 pM to about 2.5 nM, about 900 pM to about 2.5 nM, about 950 pM to about 2.5 nM, about 1 nM to about 2.5 nM, about 1.1 nM to about 2.5 nM, about 1.2 nM to about 2.5 nM, about 1.3 nM to about 2.5 nM, about 1.4 nM to about 2.5 nM, about 1.5 nM to about 2.5 nM, about 1.6 nM to about 2.5 nM, about 1.7 nM to about 2.5 nM, about 1.8 nM to about 2.5 nM, about 1.9 nM to about 2.5 nM, about 2.0 nM to about 2.5 nM, about 2.1 nM to about 2.5 nM, about 2.2 nM to about 2.5 nM, about 2.3 nM to about 2.5 nM, about 500 pM to about 1.9 pM, about 750 pM to about 1.9 pM, about 1 nM to about 1.9 pM, about 1.25 nM to about 1.9 pM, about 1.5 nM to about 1.9 pM, about 1 nM to about 1.85 nM, about 1.25 nM to about 1.85 nM, about 1.25 nM to about 1.85 nM, about 1.5 nM to about 1.85 nM, about 1 nM to about 1.8 nM, about 1.25 nM to about 1.8 nM, about 1.5 nM to about 1.8 nM, or about 1.6 nM to about 1.8 nM. In some embodiments, the antibody is capable of inhibiting the activity of human tryptase with an IC50 of about 1.8 nM. In other embodiments, the antibody is capable of inhibiting the activity of human tryptase with an IC50 of about 0.5 nM to about 1 nM (e.g., about 0.5 nM, about 0.6 nM, about 0.7 nM, about 0.8 nM, about 0.9 nM, or about 1.0 nM). In some embodiments, the antibody is capable of inhibiting the activity of human tryptase with an IC50 of about 1 pM to about 1 nM, about 25 pM to about 1 nM, about 50 pM to about 1 nM, about 75 pM to about 1 nM, about 100 pM to about 1 nM, about 125 pM to about 1 nM, about 150 pM to about 1 nM, about 175 pM to about 1 nM, about 200 pM to about 1 nM, about 225 pM to about 1 nM, about 250 pM to about 1 nM, about 300 pM to about 1 nM, about 325 pM to about 1 nM, about 350 pM to about 1 nM, about 375 pM to about 1 nM, about 400 pM to about 1 nM, about 425 pM to about 1 nM, about 450 pM to about 1 nM, about 500 pM to about 1 nM, about 450 pM to about 1 nM, about 500 pM to about 1 nM, about 550 pM to about 1 nM, about 600 pM to about 1 nM, about 650 pM to about 1 nM, about 700 pM to about 1 nM, about 750 pM, about 250 pM to about 800 pM, about 300 pM to about 800 pM, about 325 pM to about 800 pM, about 325 pM to about 800 pM, about 350 pM to about 800 pM, about 375 pM to about 800 pM, about 400 pM to about 800 pM, about 425 pM to about 800 pM, about 450 pM to about 800 pM, about 500 pM to about 800 pM, about 450 pM to about 800 pM, about 500 pM to about 800 pM, about 550 pM to about 800 pM, about 600 pM to about 800 pM, about 650 pM to about 800 pM, about 700 pM to about 800 pM, about 750 pM to about 800 pM, about 1 pM to about 600 pM, about 25 pM to about 600 pM, about 50 pM to about 600 pM, about 75 pM to about 600 pM, about 100 pM to about 600 pM, about 125 pM to about 600 pM, about 150 pM to about 600 pM, about 175 pM to about 600 pM, about 200 pM to about 600 pM, about 225 pM to about 600 pM, about 250 pM to about 600 pM, about 300 pM to about 600 pM, about 325 pM to about 600 pM, about 325 pM to about 600 pM, about 350 pM to about 600 pM, about 375 pM to about 600 pM, about 400 pM to about 600 pM, about 425 pM to about 600 pM, about 450 pM to about 600 pM, about 500 pM to about 600 pM, about 450 pM to about 600 pM, about 500 pM to about 600 pM, about 600 pM, or about 550 pM to about 600 pM. In some embodiments, the antibody is capable of inhibiting the activity of human tryptase with an IC50 of about 0.6 nM. In some embodiments, the tryptase is human tryptase, for example, human tryptase beta (e.g., human tryptase beta 1, human tryptase beta 2, and/or human tryptase beta 3). In some instances, the inhibitory activity of the antibody is determined described herein, for example, in the Examples (e.g., Example 1, particularly Section (A)(viii)(a)), or by other approaches known in the art. In certain embodiments, the antibody is a human or a humanized antibody. In some embodiments, the antibody is capable of inhibiting the activity of human tryptase as a monovalent antibody or antigen-binding antibody fragment thereof (e.g., an Fab). In other embodiments, the antibody is capable of inhibiting the activity of human tryptase as a bivalent antibody (e.g., an IgG antibody (e.g., an IgG1 or IgG4 antibody) or an F(ab')2).

In some instances, any of the anti-tryptase antibodies described herein can inhibit tryptase-stimulated contraction of human primary airway smooth muscle cells. In other instances, any of the anti-tryptase antibodies described herein can inhibit tryptase-stimulated contraction of human primary airway smooth muscle cells. In yet other instances, any of the anti-tryptase antibodies described herein can inhibit tryptase or IgE-stimulated mast cell degranulation and/or histamine release. In further instances, any of the anti-tryptase antibodies described herein can reduce the amount of active tryptase (e.g., in a sample such as bronchoalveolar lavage fluid or a nasosorption sample), for example, upon administration to a subject. For example, any of the anti-tryptase antibodies described herein can reduce the amount of active tryptase by about 1%, about 5%, about 10%, about 15%, about 20%, about 25%, about 30%, about 35%, about 40%, about 45%, about 50%, about 55%, about 60%, about 75%, about 80%, about 90%, about 95%, about 96%, about 97%, about 98%, about 99%, or more. The reduction may be relative to a reference amount of active tryptase, for example, the amount of active tryptase in a sample prior to administration of the anti-tryptase antibody.

In some instances, the antibody (e.g., the anti-tryptase antibody) may include at least one, two, three, four, five, or six hypervariable regions (HVRs) selected from: (a) an HVR-H1 comprising the amino acid sequence of $X_1X_2GMX_3$ (SEQ ID NO: 1), wherein $X_1$ is Asp or Ser, $X_2$ is Tyr or Phe, and X₃ is Val or His; (b) an HVR-H2 comprising the amino acid sequence of FISSGSSTVYY-ADTMKG (SEQ ID NO: 2); (c) an HVR-H₃ comprising the amino acid sequence of RX₁X₂X₃DWYFDV (SEQ ID NO: 3), wherein X₁ is Asn or Asp, X₂ is Tyr or Asn, and X₃ is Asp or Tyr; (d) an HVR-L1 comprising the amino acid sequence of SASSSVTYMY (SEQ ID NO: 4); (e) an HVR-L2 comprising the amino acid sequence of RTSDLAS (SEQ ID NO: 5); and (f) an HVR-L3 comprising the amino acid sequence of QHYHSYPLT (SEQ ID NO: 6), or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 1-6.

For instance, in some embodiments, the antibody (e.g., the anti-tryptase antibody) may include at least one, two, three, four, five, or six hypervariable regions (HVRs) selected from: (a) an HVR-H1 comprising the amino acid sequence of DYGMV (SEQ ID NO: 7); (b) an HVR-H2 comprising the amino acid sequence of FISSGSSTVYY-ADTMKG (SEQ ID NO: 2); (c) an HVR-H3 comprising the amino acid sequence of RNYDDWYFDV (SEQ ID NO: 8); (d) an HVR-L1 comprising the amino acid sequence of SASSSVTYMY (SEQ ID NO: 4); (e) an HVR-L2 comprising the amino acid sequence of RTSDLAS (SEQ ID NO: 5); and (f) an HVR-L3 comprising the amino acid sequence of QHYHSYPLT (SEQ ID NO: 6), or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 2 or 4-8.

In one particular example, in some embodiments, the antibody (e.g., the anti-tryptase antibody) may include (a) an HVR-H1 comprising the amino acid sequence of DYGMV (SEQ ID NO: 7); (b) an HVR-H2 comprising the amino acid sequence of FISSGSSTVYYADTMKG (SEQ ID NO: 2); (c) an HVR-H3 comprising the amino acid sequence of RNY-DDWYFDV (SEQ ID NO: 8); (d) an HVR-L1 comprising the amino acid sequence of SASSSVTYMY (SEQ ID NO: 4); (e) an HVR-L2 comprising the amino acid sequence of RTSDLAS (SEQ ID NO: 5); and (f) an HVR-L3 comprising the amino acid sequence of QHYHSYPLT (SEQ ID NO: 6). In some embodiments, the antibody (e.g., the anti-tryptase antibody) includes (a) a heavy chain variable (VH) domain comprising an amino sequence having at least 90% sequence identity to (e.g., at least 91%, 92%, 93%, 94%, 95%, 96%, 97%, 98%, or 99% sequence identity), or the sequence of, the amino acid sequence of SEQ ID NO: 9; (b) a light chain variable (VL) domain comprising an amino acid sequence having at least 90% identity to (e.g., at least 91%, 92%, 93%, 94%, 95%, 96%, 97%, 98%, or 99% sequence identity), or the sequence of, the amino acid sequence of SEQ ID NO: 10; or (c) a VH domain as in (a) and a VL domain as in (b). In some embodiments, the antibody (e.g., the anti-tryptase antibody) includes one, two, three, or four of the following heavy chain framework regions (FRs): (a) an FR-H1 comprising the amino acid sequence of EVQLVESGG-GLVQPGGSLRLSCAASGFTFS (SEQ ID NO: 11); (b) an FR-H2 comprising the amino acid sequence of WVRQAPGKGLEWVA (SEQ ID NO: 12); (c) an FR-H3 comprising the amino acid sequence of RFTISRDNSKNT-LYLQMNSLRAEDTAVYYCTR (SEQ ID NO: 13); and (d) an FR-H4 comprising the amino acid sequence of WGQGTLVTVSS (SEQ ID NO: 14). In some embodiments, the antibody (e.g., the anti-tryptase antibody) includes one, two, three, or four of the following light chain FRs: (a) an FR-L1 comprising the amino acid sequence of DIQMTQSPSSLSASVGDRVTITC (SEQ ID NO: 15); (b) an FR-L2 comprising the amino acid sequence of WYQQKPGKSPKPWIY (SEQ ID NO: 16); (c) an FR-L3 comprising the amino acid sequence of GVPSRFSGSGSGTDFTLTISSLQPEDFATYYC (SEQ ID NO: 17); and (d) an FR-L4 comprising the amino acid sequence of FGQGTKVEIK (SEQ ID NO: 18). In some embodiments, the antibody (e.g., the anti-tryptase antibody) includes a VH domain comprising the amino acid sequence of SEQ ID NO: 9 and a VL domain comprising the amino acid sequence of SEQ ID NO: 10, such as the antibody hu31A.v11.

In another particular example, in some embodiments, the antibody (e.g., the anti-tryptase antibody) may include (a) an HVR-H1 comprising the amino acid sequence of DYGMV (SEQ ID NO: 7); (b) an HVR-H2 comprising the amino acid sequence of FISSGSSTVYYADTMKG (SEQ ID NO: 2); (c) an HVR-H3 comprising the amino acid sequence of RDNY-DWYFDV (SEQ ID NO: 29); (d) an HVR-L1 comprising the amino acid sequence of SASSSVTYMY (SEQ ID NO: 4); (e) an HVR-L2 comprising the amino acid sequence of RTSDLAS (SEQ ID NO: 5); and (f) an HVR-L3 comprising the amino acid sequence of QHYHSYPLT (SEQ ID NO: 6). In some embodiments, the antibody (e.g., the anti-tryptase antibody) includes (a) a heavy chain variable (VH) domain comprising an amino sequence having at least 90% sequence identity to (e.g., at least 91%, 92%, 93%, 94%, 95%, 96%, 97%, 98%, or 99% sequence identity), or the sequence of, the amino acid sequence of SEQ ID NO: 19; (b) a light chain variable (VL) domain comprising an amino acid sequence having at least 90% identity to (e.g., at least 91%, 92%, 93%, 94%, 95%, 96%, 97%, 98%, or 99% sequence identity), or the sequence of, the amino acid sequence of SEQ ID NO: 20; or (c) a VH domain as in (a) and a VL domain as in (b). In some embodiments, the antibody (e.g., the anti-tryptase antibody) includes one, two, three, or four of the following heavy chain framework regions (FRs): (a) an FR-H1 comprising the amino acid sequence of EVKLVES-GGGSVQPGGSRKLSCAASGFTFS (SEQ ID NO: 21); (b) an FR-H2 comprising the amino acid sequence of WVRQAPGKGLEWVA (SEQ ID NO: 22); (c) an FR-H3 comprising the amino acid sequence of RFTIS-RDNPKNTLFLQMSSLRSEDTAMYYCAR (SEQ ID NO: 23); and (d) an FR-H4 comprising the amino acid sequence of WGTGTTVTVSS (SEQ ID NO: 24). In some embodiments, the antibody (e.g., the anti-tryptase antibody) includes one, two, three, or four of the following light chain FRs: (a) an FR-L1 comprising the amino acid sequence of QIVLTQSPAIMSASPGEKVTISC (SEQ ID NO: 25); (b) an FR-L2 comprising the amino acid sequence of WYQQKPGSSPKPWIY (SEQ ID NO: 26); (c) an FR-L3 comprising the amino acid sequence of GVPARFSGSGSGTSYSLTISSMEAEDAATYYC (SEQ ID NO: 27); and (d) an FR-L4 comprising the amino acid sequence of FGAGTKLELK (SEQ ID NO: 28). In some embodiments, the antibody (e.g., the anti-tryptase antibody) includes a VH domain comprising the amino acid sequence of SEQ ID NO: 19 and a VL domain comprising the amino acid sequence of SEQ ID NO: 20, such as the antibody 31a.

In some instances, the antibody (e.g., the anti-tryptase antibody) includes (a) a heavy chain variable (VH) domain comprising an amino sequence having at least 90% sequence identity to (e.g., at least 91%, 92%, 93%, 94%, 95%, 96%, 97%, 98%, or 99% sequence identity), or the sequence of, the amino acid sequence of any one of SEQ ID NOs: 9, 101, 102, 103, and 104; (b) a light chain variable ($V_L$) domain comprising an amino acid sequence having at least 90% identity to (e.g., at least 91%, 92%, 93%, 94%, 95%, 96%, 97%, 98%, or 99% sequence identity), or the sequence of, the amino acid sequence of any one of SEQ ID NOs: 10, 105, and 106; or (c) a VH domain as in (a) and a VL domain as in (b). For example, in some instances, the antibody comprises a VH domain comprising the amino acid sequence of SEQ ID NO: 98 and a VL domain comprising the amino acid sequence of SEQ ID NO: 102. In other instances, the antibody comprises a VH domain comprising the amino acid sequence of SEQ ID NO: 98 and a VL domain comprising the amino acid sequence of SEQ ID NO: 10. In other instances, the antibody comprises a VH domain comprising the amino acid sequence of SEQ ID NO: 98 and a VL domain comprising the amino acid sequence of SEQ ID NO: 103. In other instances, the antibody comprises a VH domain comprising the amino acid sequence of SEQ ID NO: 99 and a VL domain comprising the amino acid sequence of SEQ ID NO: 102. In other instances, the antibody comprises a VH domain comprising the amino acid sequence of SEQ ID NO: 99 and a VL domain comprising the amino acid sequence of SEQ ID NO: 10. In other instances, the antibody comprises a VH domain comprising the amino acid sequence of SEQ ID NO: 99 and a VL domain comprising the amino acid sequence of SEQ ID NO: 103. In other instances, the antibody comprises a VH domain comprising the amino acid sequence of SEQ ID NO: 100 and a VL domain comprising the amino acid sequence of SEQ ID NO: 102. In other instances, the antibody comprises a VH domain comprising the amino acid sequence of SEQ ID NO: 100 and a VL domain comprising the amino acid sequence of SEQ ID NO: 10. In other instances, the antibody comprises a VH domain comprising the amino acid sequence of SEQ ID NO: 100 and a VL domain comprising the amino acid sequence of SEQ ID NO: 103. In other instances, the antibody comprises a VH domain comprising the amino acid sequence of SEQ ID NO: 9 and a VL domain comprising the amino acid sequence of SEQ ID NO: 102. In other instances, the antibody comprises a VH domain comprising the amino acid sequence of SEQ ID NO: 9 and a VL domain comprising the amino acid sequence of SEQ ID NO: 10. In other instances, the antibody comprises a VH domain comprising the amino acid sequence of SEQ ID NO: 9 and a VL domain comprising the amino acid sequence of SEQ ID NO: 103. In other instances, the antibody comprises a VH domain comprising the amino acid sequence of SEQ ID NO: 101 and a VL domain comprising the amino acid sequence of SEQ ID NO: 102. In other instances, the antibody comprises a VH domain comprising the amino acid sequence of SEQ ID NO: 101 and a VL domain comprising the amino acid sequence of SEQ ID NO: 10. In other instances, the antibody comprises a VH domain comprising the amino acid sequence of SEQ ID NO: 101 and a VL domain comprising the amino acid sequence of SEQ ID NO: 103.

In some instances, any of the preceding antibodies binds to an epitope on human tryptase beta 1 comprising at least one, at least two, at least three, or all four residues selected from the group consisting of His51, Val80, Lys81, and Asp82 of SEQ ID NO: 71. In some embodiments, the antibody binds to an epitope on human tryptase beta 1 comprising at least one, at least two, at least three, or all four residues selected from the group consisting of His51, Val80, Lys81, and Asp82 of SEQ ID NO: 71. In some embodiments, the antibody binds to an epitope on human tryptase beta 1 comprising His51 and at least one, at least two, or all three residues selected from the group consisting of Val 80, Lys81, and Asp82 of SEQ ID NO: 71. In some embodiments, the epitope on human tryptase beta 1 further comprises one or more amino acid residues selected from the group consisting of Gln67, Leu83, Ala84, Ala85, Arg87, Pro103, Val104, Ser105, Arg106, Glu128, Glu129, and Pro130 of SEQ ID NO: 71. In some embodiments, the epitope on human tryptase beta 1 comprises at least two, at least three, at least four, at least five, at least six, at least seven, at least eight, at least nine, at least ten, at least eleven, or all twelve amino acid residues selected from the group consisting of Gln67, Leu83, Ala84, Ala85, Arg87, Pro103, Val104, Ser105, Arg106, Glu128, Glu129, and Pro130 of SEQ ID NO: 71. In some embodiments, the epitope on human tryptase beta 1 comprises His51, Gln67, Val80, Lys81, Asp82, Leu83, Ala84, Ala85, Arg87, Pro103, Val104, Ser105, Arg106, Glu128, Glu129, and Pro130 of SEQ ID NO:71. In some embodiments, the epitope is relative to a human tryptase beta 1 monomer or tetramer. In some embodiments, the epitope is determined by an X-ray crystallography model. In some embodiments, the antibody is capable of dissociating both the small interface of tetrameric human tryptase beta 1 and the large interface of tetrameric human tryptase beta 1.

In some instances, any of the preceding anti-tryptase antibodies includes a paratope that binds tryptase (e.g., human tryptase beta 1) that includes one or more amino acid residues (e.g., 1, 2, 3, 4, 5, 6, 7, 8, 9, 10, 11, 12, 13, 14, 15, 16, 17, 18, or 19 amino acid residues) selected from the group consisting of light chain variable region amino acid residues Va30; Thr31; Tyr32; Tyr34; Arg50; Tyr90; His92; Ser93; and Tyr94 and the heavy chain variable region amino acid residues Phe50; Ser52; Gly53; Ser54; Ser55; Thr56; Tyr58; Arg95; Tyr97; and Asp98.

For example, in some instances, the anti-tryptase antibody includes a paratope that binds tryptase (e.g., human tryptase beta 1) that includes light chain variable region amino acid residues Va30, Thr31, Tyr32, Tyr34, Arg50, Tyr90, His92, Ser93, and Tyr94 or the heavy chain variable region amino acid residues Phe50, Ser52, Gly53, Ser54, Ser55, Thr56, Tyr58, Arg95, Tyr97, and Asp98. In some instances, the anti-tryptase antibody includes a paratope that binds tryptase (e.g., human tryptase beta 1) that includes light chain variable region amino acid residues Val30, Thr31, Tyr32, Tyr34, Arg50, Tyr90, His92, Ser93, and Tyr94 and the heavy chain variable region amino acid residues Phe50, Ser52, Gly53, Ser54, Ser55, Thr56, Tyr58, Arg95, Tyr97, and Asp98.

In some instances, the antibody (e.g., the anti-tryptase antibody) may include at least one, two, three, four, five, or six hypervariable regions (HVRs) selected from: (a) an HVR-H1 comprising the amino acid sequence of GYAIT (SEQ ID NO: 30); (b) an HVR-H2 comprising the amino acid sequence of GISSAATTFYSSWAKS (SEQ ID NO: 31); (c) an HVR-H3 comprising the amino acid sequence of DPRGYGAALDRLDL (SEQ ID NO: 32); (d) an HVR-L1 comprising the amino acid sequence of QSIKSVYNNRLG (SEQ ID NO: 33); (e) an HVR-L2 comprising the amino acid sequence of ETSILTS (SEQ ID NO: 34); and (f) an HVR-L3 comprising the amino acid sequence of AGGFDRSGDTT (SEQ ID NO: 35), or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 30-35.

In some instances, the antibody (e.g., the anti-tryptase antibody) includes (a) a heavy chain variable (VH) domain comprising an amino sequence having at least 90% sequence identity to (e.g., at least 91%, 92%, 93%, 94%, 95%, 96%, 97%, 98%, or 99% sequence identity), or the sequence of, the amino acid sequence of any one of SEQ ID NOs: 36, 47, 48, 49, 50, 51, and 52; (b) a light chain variable (VL) domain comprising an amino acid sequence having at least 90% identity to (e.g., at least 91%, 92%, 93%, 94%, 95%, 96%, 97%, 98%, or 99% sequence identity), or the sequence of, the amino acid sequence of any one of SEQ ID NO: 37, 53, 58, or 59; or (c) a VH domain as in (a) and a VL domain as in (b).

In some instances, any of the preceding antibodies (e.g., anti-tryptase antibodies) may include one, two, three, or four of the following heavy chain framework regions (FRs): (a) an FR-H1 comprising an amino sequence having at least 90% sequence identity to (e.g., at least 91%, 92%, 93%, 94%, 95%, 96%, 97%, 98%, or 99% sequence identity), or the sequence of, the amino acid sequence of EVQLVES-GPGLVKPSETLSLTCTVSRFSLI (SEQ ID NO: 38); (b) an FR-H2 comprising an amino sequence having at least 90% sequence identity to (e.g., at least 91%, 92%, 93%, 94%, 95%, 96%, 97%, 98%, or 99% sequence identity), or the sequence of, the amino acid sequence of WX$_1$RQPPGKGLEWIG (SEQ ID NO: 39), wherein X$_1$ is Ile or Val; (c) an FR-H3 comprising an amino sequence having at least 90% sequence identity to (e.g., at least 91%, 92%, 93%, 94%, 95%, 96%, 97%, 98%, or 99% sequence identity), or the sequence of, the amino acid sequence of RX$_1$TISX$_2$DTSKNQX$_3$SLKLSSVTAADTAVYX$_4$CAR (SEQ ID NO: 40), wherein X$_1$ is Val or Ser, X$_2$ is Arg or Val, X$_3$ is Val or Phe, and X$_4$ is Tyr or Phe; and (d) an FR-H4 comprising an amino sequence having at least 90% sequence identity to (e.g., at least 91%, 92%, 93%, 94%, 95%, 96%, 97%, 98%, or 99% sequence identity), or the sequence of, the amino acid sequence of WGQGTLVTVSS (SEQ ID NO: 41).

For example, in some instances, any of the preceding antibodies (e.g., anti-tryptase antibodies) may include one, two, three, or four of the following heavy chain FRs: (a) an FR-H1 comprising the amino acid sequence of EVQLVES-GPGLVKPSETLSLTCTVSRFSLI (SEQ ID NO: 38); (b) an FR-H2 comprising the amino acid sequence of WIRQPPGKGLEWIG (SEQ ID NO: 42); (c) an FR-H3 comprising the amino acid sequence of RVTIS-RDTSKNQVSLKLSSVTAADTAVYYCAR (SEQ ID NO: 43); and (d) an FR-H4 comprising the amino acid sequence of WGQGTLVTVSS (SEQ ID NO: 41).

In another example, in some instances, any of the preceding antibodies (e.g., anti-tryptase antibodies) may include one, two, three, or four of the following heavy chain FRs: (a) an FR-H1 comprising the amino acid sequence of EVQLVESGGGLVQPGGSLRLSCAVSRFSLI (SEQ ID NO: 44); (b) an FR-H2 comprising the amino acid sequence of WVRQAPGKGLEWIG (SEQ ID NO: 45); (c) an FR-H3 comprising the amino acid sequence of RSTIS-RDTSKNTVYLQMNSLRAEDTAVYFCAR (SEQ ID NO: 46); and (d) an FR-H4 comprising the amino acid sequence of WGQGTLVTVSS (SEQ ID NO: 41).

In another example, in some instances, any of the preceding antibodies (e.g., anti-tryptase antibodies) may include one, two, three, or four of the following heavy chain FRs: (a) an FR-H1 comprising the amino acid sequence of EVQLVESGGGLVQPGGSLRLSCAVSRFSLI (SEQ ID NO: 44); (b) an FR-H2 comprising the amino acid sequence of WVRQAPGKGLEWIG (SEQ ID NO: 45); (c) an FR-H3 comprising the amino acid sequence of RSTIS-RDTSKNTVYLQMNSLRAEDTAVYFCAR (SEQ ID NO: 46); and (d) an FR-H4 comprising the amino acid sequence of WGQGTLVTVSS (SEQ ID NO: 41).

In some instances, any of the preceding antibodies (e.g., anti-tryptase antibodies) may include one, two, three, or four of the following light chain FRs: (a) an FR-L1 comprising an amino sequence having at least 90% sequence identity to (e.g., at least 91%, 92%, 93%, 94%, 95%, 96%, 97%, 98%, or 99% sequence identity), or the sequence of, the amino acid sequence of DX$_1$QX$_2$TQSPSSLSASVGDRVTITC (SEQ ID NO: 60), wherein X$_1$ is Ile or Ala, and X$_2$ is Met or Leu; (b) an FR-L2 comprising an amino sequence having at least 90% sequence identity to (e.g., at least 91%, 92%, 93%, 94%, 95%, 96%, 97%, 98%, or 99% sequence identity), or the sequence of, the amino acid sequence of WYQQKPGKX$_1$PKLLIY (SEQ ID NO: 61), wherein X$_1$ is Ala or Pro; (c) an FR-L3 comprising an amino sequence having at least 90% sequence identity to (e.g., at least 91%, 92%, 93%, 94%, 95%, 96%, 97%, 98%, or 99% sequence identity), or the sequence of, the amino acid sequence of VPSRFSGSGSX$_1$TDFTLTISSLQPEDFATYX$_2$C (SEQ ID NO: 62), wherein X$_1$ is Gly or Glu, and X$_2$ is Tyr or Phe; and (d) an FR-L4 comprising an amino sequence having at least 90% sequence identity to (e.g., at least 91%, 92%, 93%, 94%, 95%, 96%, 97%, 98%, or 99% sequence identity), or the sequence of, the amino acid sequence of FGQGTKVEIK (SEQ ID NO: 63).

For example, in particular instances, any of the preceding antibodies (e.g., anti-tryptase antibodies) may include one, two, three, or four of the following light chain FRs: (a) an FR-L1 comprising the amino acid sequence of DIQMTQSPSSLSASVGDRVTITC (SEQ ID NO: 64); (b) an FR-L2 comprising the amino acid sequence of WYQQKPGKAPKLLIY (SEQ ID NO: 65); (c) an FR-L3 comprising the amino acid sequence of GVPSRFSGSGSGTDFTLTISSLQPEDFATYYC (SEQ ID NO: 66); and (d) an FR-L4 comprising the amino acid sequence of FGQGTKVEIK (SEQ ID NO: 63).

In some embodiments, any of the preceding antibodies (e.g., anti-tryptase antibodies) may include one, two, three, or four of the following light chain FRs: (a) an FR-L1 comprising the amino acid sequence of AAVLTQT-PASVSAAVGGTVSISC (SEQ ID NO: 67); (b) an FR-L2 comprising the amino acid sequence of WYQQKPGQPPKLLIY (SEQ ID NO: 68); (c) an FR-L3 comprising the amino acid sequence of GVPSRFKGSGSETQFTLTISDVQX$_1$DDAATYFC (SEQ ID NO: 69), wherein X$_1$ is Cys or Ala; and (d) an FR-L4 comprising the amino acid sequence of FGQGTKVEIK FGGGTEVVVK (SEQ ID NO: 70).

In some instances, the antibody (e.g., the anti-tryptase antibody) includes (a) a heavy chain variable (VH) domain comprising an amino sequence having at least 90% sequence identity to (e.g., at least 91%, 92%, 93%, 94%, 95%, 96%, 97%, 98%, or 99% sequence identity), or the sequence of, the amino acid sequence of any one of SEQ ID NOs: 36, 47, 48, 49, 50, 51, and 52; (b) a light chain variable (VL) domain comprising an amino acid sequence having at least 90% identity to (e.g., at least 91%, 92%, 93%, 94%, 95%, 96%, 97%, 98%, or 99% sequence identity), or the sequence of, the amino acid sequence of any one of SEQ ID NO: 37, 53, 58, and 59; or (c) a VH domain as in (a) and a VL domain as in (b). For example, in some instances, the antibody comprises a VH domain comprising the amino acid sequence of SEQ ID NO: 36 and a VL domain comprising the amino acid sequence of SEQ ID NO: 37. In some instances, the antibody comprises a VH domain comprising the amino acid sequence of SEQ ID NO: 47 and a VL domain comprising the amino acid sequence of SEQ ID NO: 37. In some instances, the antibody comprises a VH domain comprising the amino acid sequence of SEQ ID NO: 48 and a VL domain comprising the amino acid sequence of SEQ ID NO: 37. In some instances, the antibody comprises a VH domain comprising the amino acid sequence of SEQ ID NO: 49 and a VL domain comprising the amino acid sequence of SEQ ID NO: 37. In some instances, the antibody comprises a VH domain comprising the amino acid sequence of SEQ ID NO: 50 and a VL domain comprising the amino acid sequence of SEQ ID NO: 37. In some instances, the antibody comprises a VH domain comprising the amino acid sequence of SEQ ID NO: 50 and a VL domain comprising the amino acid sequence of SEQ ID NO: 37. In some instances, the antibody comprises a VH domain comprising the amino acid sequence of SEQ ID NO: 51 and a VL domain comprising the amino acid sequence of SEQ ID NO: 37. In some instances, the antibody comprises a VH domain comprising the amino acid sequence of SEQ ID NO: 52 and a VL domain comprising the amino acid sequence of SEQ ID NO: 37. In some instances, the antibody comprises a VH domain comprising the amino acid sequence of SEQ ID NO: 36 and a VL domain comprising the amino acid sequence of SEQ ID NO: 53. In some instances, the antibody comprises a VH domain comprising the amino acid sequence of SEQ ID NO: 47 and a VL domain comprising the amino acid sequence of SEQ ID NO: 53. In some instances, the antibody comprises a VH domain comprising the amino acid sequence of SEQ ID NO: 48 and a VL domain comprising the amino acid sequence of SEQ ID NO: 53. In some instances, the antibody comprises a VH domain comprising the amino acid sequence of SEQ ID NO: 49 and a VL domain comprising the amino acid sequence of SEQ ID NO: 53. In some instances, the antibody comprises a VH domain comprising the amino acid sequence of SEQ ID NO: 50 and a VL domain comprising the amino acid sequence of SEQ ID NO: 53. In some instances, the antibody comprises a VH domain comprising the amino acid sequence of SEQ ID NO: 51 and a VL domain comprising the amino acid sequence of SEQ ID NO: 53. In some instances, the antibody comprises a VH domain comprising the amino acid sequence of SEQ ID NO: 52 and a VL domain comprising the amino acid sequence of SEQ ID NO: 53. In some instances, the antibody comprises a VH domain comprising the amino acid sequence of SEQ ID NO: 36 and a VL domain comprising the amino acid sequence of SEQ ID NO: 58. In some instances, the antibody comprises a VH domain comprising the amino acid sequence of SEQ ID NO: 47 and a VL domain comprising the amino acid sequence of SEQ ID NO: 58. In some instances, the antibody comprises a VH domain comprising the amino acid sequence of SEQ ID NO: 48 and a VL domain comprising the amino acid sequence of SEQ ID NO: 58. In some instances, the antibody comprises a VH domain comprising the amino acid sequence of SEQ ID NO: 49 and a VL domain comprising the amino acid sequence of SEQ ID NO: 58. In some instances, the antibody comprises a VH domain comprising the amino acid sequence of SEQ ID NO: 50 and a VL domain comprising the amino acid sequence of SEQ ID NO: 58. In some instances, the antibody comprises a VH domain comprising the amino acid sequence of SEQ ID NO: 51 and a VL domain comprising the amino acid sequence of SEQ ID NO: 58. In some instances, the antibody comprises a VH domain comprising the amino acid sequence of SEQ ID NO: 36 and a VL domain comprising the amino acid sequence of SEQ ID NO: 59. In some instances, the antibody comprises a VH domain comprising the amino acid sequence of SEQ ID NO: 47 and a VL domain comprising the amino acid sequence of SEQ ID NO: 59. In some instances, the antibody comprises a VH domain comprising the amino acid sequence of SEQ ID NO: 48 and a VL domain comprising the amino acid sequence of SEQ ID NO: 59. In some instances, the antibody comprises a VH domain comprising the amino acid sequence of SEQ ID NO: 49 and a VL domain comprising the amino acid sequence of SEQ ID NO: 59. In some instances, the antibody comprises a VH domain comprising the amino acid sequence of SEQ ID NO: 50 and a VL domain comprising the amino acid sequence of SEQ ID NO: 59. In some instances, the antibody comprises a VH domain comprising the amino acid sequence of SEQ ID NO: 51 and a VL domain comprising the amino acid sequence of SEQ ID NO: 59.

In another particular example, in some embodiments, the anti-tryptase antibody may include (a) an HVR-H1 comprising the amino acid sequence of GYAIT (SEQ ID NO: 30); (b) an HVR-H2 comprising the amino acid sequence of GISSAATTFYSSWAKS (SEQ ID NO: 31); (c) an HVR-H3 comprising the amino acid sequence of DPR-GYGAALDRLDL (SEQ ID NO: 32); (d) an HVR-L1 comprising the amino acid sequence of QSIKSVYNNRLG (SEQ ID NO: 33); (e) an HVR-L2 comprising the amino acid sequence of ETSILTS (SEQ ID NO: 34); and (f) an HVR-L3 comprising the amino acid sequence of AGGFDRSGDTT (SEQ ID NO: 35). In some embodiments, the anti-tryptase antibody includes (a) a heavy chain variable (VH) domain comprising an amino sequence having at least 90% sequence identity to (e.g., at least 91%, 92%, 93%, 94%, 95%, 96%, 97%, 98%, or 99% sequence identity), or the sequence of, the amino acid sequence of SEQ ID NO: 36; (b) a light chain variable (VL) domain comprising an amino acid sequence having at least 90% identity to (e.g., at least 91%, 92%, 93%, 94%, 95%, 96%, 97%, 98%, or 99% sequence identity), or the sequence of, the amino acid sequence of SEQ ID NO: 37; or (c) a VH domain as in (a) and a VL domain as in (b). In some embodiments, the anti-tryptase antibody includes one, two, three, or four of the following heavy chain framework regions (FRs): (a) an FR-H1 comprising the amino acid sequence of EVQLVES-GPGLVKPSETLSLTCTVSRFSLI (SEQ ID NO: 38); (b) an FR-H2 comprising the amino acid sequence of WIRQPPGKGLEWIG (SEQ ID NO: 42); (c) an FR-H3 comprising the amino acid sequence of RVTIS-RDTSKNQVSLKLSSVTAADTAVYYCAR (SEQ ID NO: 43); and (d) an FR-H4 comprising the amino acid sequence of WGQGTLVTVSS (SEQ ID NO: 41). In some embodiments, the anti-tryptase antibody includes one, two, three, or four of the following light chain FRs: (a) an FR-L1 comprising the amino acid sequence of DIQMTQSPSSL-SASVGDRVTITC (SEQ ID NO: 64); (b) an FR-L2 comprising the amino acid sequence of WYQQKPGKAPKLLIY (SEQ ID NO: 65); (c) an FR-L3 comprising the amino acid sequence of GVPSRFSGSGSGTDFTLTISSLQPEDFA-TYYC (SEQ ID NO: 66); and (d) an FR-L4 comprising the amino acid sequence of FGQGTKVEIK (SEQ ID NO: 63). In some embodiments, the anti-tryptase antibody includes a VH domain comprising the amino acid sequence of SEQ ID NO: 36 and a VL domain comprising the amino acid sequence of SEQ ID NO: 37, such as the anti-tryptase antibody huE04.v2.

In another particular example, in some embodiments, the antibody (e.g., the anti-tryptase antibody) may include (a) an HVR-H1 comprising the amino acid sequence of GYAIT (SEQ ID NO: 30); (b) an HVR-H2 comprising the amino acid sequence of GISSAATTFYSSWAKS (SEQ ID NO:

31); (c) an HVR-H3 comprising the amino acid sequence of DPRGYGAALDRLDL (SEQ ID NO: 32); (d) an HVR-L1 comprising the amino acid sequence of QSIKSVYNNRLG (SEQ ID NO: 33); (e) an HVR-L2 comprising the amino acid sequence of ETSILTS (SEQ ID NO: 34); and (f) an HVR-L3 comprising the amino acid sequence of AGGFDRSGDTT (SEQ ID NO: 35). In some embodiments, the antibody (e.g., the anti-tryptase antibody) includes (a) a heavy chain variable (VH) domain comprising an amino sequence having at least 90% sequence identity to (e.g., at least 91%, 92%, 93%, 94%, 95%, 96%, 97%, 98%, or 99% sequence identity), or the sequence of, the amino acid sequence of SEQ ID NO: 52; (b) a light chain variable (VL) domain comprising an amino acid sequence having at least 90% identity to (e.g., at least 91%, 92%, 93%, 94%, 95%, 96%, 97%, 98%, or 99% sequence identity), or the sequence of, the amino acid sequence of SEQ ID NO: 53; or (c) a VH domain as in (a) and a VL domain as in (b). In some embodiments, the antibody (e.g., the anti-tryptase antibody) includes one, two, three, or four of the following heavy chain framework regions (FRs): (a) an FR-H1 comprising the amino acid sequence of QXSLEESGG-GLFKPTDTLTLTCTVSRFSLI (SEQ ID NO: 54); (b) an FR-H2 comprising the amino acid sequence of WVRQSPENGLEWIG (SEQ ID NO: 55); (c) an FR-H3 comprising the amino acid sequence of RSTITRN-TNENTVTLKMTSLTAADTATYFCAR (SEQ ID NO: 56); and (d) an FR-H4 comprising the amino acid sequence of WGQGTLVTVSS (SEQ ID NO: 57). In some embodiments, the antibody (e.g., the anti-tryptase antibody) includes one, two, three, or four of the following light chain FRs: (a) an FR-L1 comprising the amino acid sequence of AAVLTQT-PASVSAAVGGTVSISC (SEQ ID NO: 67); (b) an FR-L2 comprising the amino acid sequence of WYQQKPGQPPKLLIY (SEQ ID NO: 68); (c) an FR-L3 comprising the amino acid sequence of GVPSRFKGSGSETQFTLTISDVQX$_1$DDAATYFC (SEQ ID NO: 69), wherein X$_1$ is Cys or Ala; and (d) an FR-L4 comprising the amino acid sequence of FGQGTKVEIKFGGGTEVVVK (SEQ ID NO: 70). In some embodiments, the antibody (e.g., the anti-tryptase antibody) includes a VH domain comprising the amino acid sequence of SEQ ID NO: 52 and a VL domain comprising the amino acid sequence of SEQ ID NO: 53, such as the antibody E104. In some embodiments, the antibody (e.g., the anti-tryptase antibody) includes a VH domain comprising the amino acid sequence of SEQ ID NO: 52 and a VL domain comprising the amino acid sequence of SEQ ID NO: 59.

In some instances, the invention provides an antibody comprising (a) a heavy chain comprising an amino sequence having at least 90% sequence identity to (e.g., at least 91%, 92%, 93%, 94%, 95%, 96%, 97%, 98%, or 99% sequence identity), or the sequence of, the amino acid sequence of the amino acid sequence of SEQ ID NO: 76 and/or (b) a light chain comprising an amino sequence having at least 90% sequence identity to (e.g., at least 91%, 92%, 93%, 94%, 95%, 96%, 97%, 98%, or 99% sequence identity), or the sequence of, the amino acid sequence of the amino acid sequence of SEQ ID NO: 77. In some instances, the antibody comprises a heavy chain comprising the amino acids sequence of SEQ ID NO: 76 and a light chain comprising the amino acid sequence of SEQ ID NO: 77. In some embodiments, the heavy chain further comprises a lysine (K) residue at the C-terminus.

In some instances, the invention provides an antibody comprising (a) a heavy chain comprising an amino sequence having at least 90% sequence identity to (e.g., at least 91%, 92%, 93%, 94%, 95%, 96%, 97%, 98%, or 99% sequence identity), or the sequence of, the amino acid sequence of the amino acid sequence of SEQ ID NO: 78 and/or (b) a light chain comprising an amino sequence having at least 90% sequence identity to (e.g., at least 91%, 92%, 93%, 94%, 95%, 96%, 97%, 98%, or 99% sequence identity), or the sequence of, the amino acid sequence of the amino acid sequence of SEQ ID NO: 79. In some instances, the antibody comprises a heavy chain comprising the amino acids sequence of SEQ ID NO: 78 and a light chain comprising the amino acid sequence of SEQ ID NO: 79. In some embodiments, the heavy chain further comprises a lysine (K) residue at the C-terminus.

In some instances, the invention provides an antibody comprising (a) a heavy chain comprising an amino sequence having at least 90% sequence identity to (e.g., at least 91%, 92%, 93%, 94%, 95%, 96%, 97%, 98%, or 99% sequence identity), or the sequence of, the amino acid sequence of the amino acid sequence of SEQ ID NO: 80 and/or (b) a light chain comprising an amino sequence having at least 90% sequence identity to (e.g., at least 91%, 92%, 93%, 94%, 95%, 96%, 97%, 98%, or 99% sequence identity), or the sequence of, the amino acid sequence of the amino acid sequence of SEQ ID NO: 81. In some instances, the antibody comprises a heavy chain comprising the amino acids sequence of SEQ ID NO: 80 and a light chain comprising the amino acid sequence of SEQ ID NO: 81. In some embodiments, the heavy chain further comprises a lysine (K) residue at the C-terminus.

In some instances, the invention provides an antibody comprising (a) a heavy chain comprising an amino sequence having at least 90% sequence identity to (e.g., at least 91%, 92%, 93%, 94%, 95%, 96%, 97%, 98%, or 99% sequence identity), or the sequence of, the amino acid sequence of the amino acid sequence of SEQ ID NO: 82 and/or (b) a light chain comprising an amino sequence having at least 90% sequence identity to (e.g., at least 91%, 92%, 93%, 94%, 95%, 96%, 97%, 98%, or 99% sequence identity), or the sequence of, the amino acid sequence of the amino acid sequence of SEQ ID NO: 83. In some instances, the antibody comprises a heavy chain comprising the amino acids sequence of SEQ ID NO: 82 and a light chain comprising the amino acid sequence of SEQ ID NO: 83. In some embodiments, the heavy chain further comprises a lysine (K) residue at the C-terminus.

In some instances, any of the preceding antibodies binds to an epitope on human tryptase beta 1 comprising at least one, at least two, or all three residues selected from the group consisting of Gln100, Leu101, and Leu102 of SEQ ID NO: 71. In some embodiments, the epitope on human tryptase beta 1 further comprises one or more amino acid residues selected from the group consisting of Trp55, Gln67, Asp82, Leu83, Ala84, Arg87, Pro103, Val104, Ser105, Arg106, Glu126, Leu127, Glu128, and Glu129 of SEQ ID NO: 71. In some embodiments, the epitope on human tryptase beta 1 comprises at least two, at least three, at least four, at least five, at least six, at least seven, at least eight, at least nine, at least ten, at least eleven, at least twelve, at least thirteen, or all fourteen amino acid residues selected from the group consisting of Trp55, Gln67, Asp82, Leu83, Ala84, Arg87, Pro103, Val104, Ser105, Arg106, Glu126, Leu127, Glu128, and Glu129 of SEQ ID NO: 71. In some embodiments, the epitope comprises Gln35, Trp55, Gln67, Asp82, Leu83, Ala84, Arg87, Gln100, Leu101, Leu102, Pro103, Val104, Ser105, Arg106, Glu126, Leu127, Glu128, Glu129, and Arg216 of SEQ ID NO: 71. In some embodiments, the epitope is relative to a human tryptase beta 1 monomer or tetramer. In some embodiments, the epitope is relative to a human tryptase beta 1 tetramer, and the epitope on human tryptase beta 1 further comprises one or both of Gln35 and Arg216 of SEQ ID NO: 71. In some embodiments, the epitope is determined by an X-ray crystallography model. In some embodiments, the antibody is capable of dissociating the small interface and/or the large interface of human tryptase beta 1.

In some instances, any of the preceding anti-tryptase antibodies includes a paratope that binds tryptase (e.g., human tryptase beta 1) that includes one or more amino acid residues (e.g., 1, 2, 3, 4, 5, 6, 7, 8, 9, 10, 11, 12, 13, 14, 15, or 16 19 amino acid residues) selected from the group consisting of light chain variable region amino acid residues Tyr29; Asn30; Arg32; and Arg94 and the heavy chain variable region amino acid residues Gly31; Tyr32; Ser52; Ser53; Ala54; Thr56; Phe58; Pro96; Arg97; Gly98; Tyr99; and Arg100e.

For example, in some instances, the anti-tryptase antibody includes a paratope that binds tryptase (e.g., human tryptase beta 1) that includes light chain variable region amino acid residues Tyr29; Asn30; Arg32; and Arg94 or the heavy chain variable region amino acid residues Gly31; Tyr32; Ser52; Ser53; Ala54; Thr56; Phe58; Pro96; Arg97; Gly98; Tyr99; and Arg100e. In some instances, the anti-tryptase antibody includes a paratope that binds tryptase (e.g., human tryptase beta 1) that includes light chain variable region amino acid residues Tyr29; Asn30; Arg32; and Arg94 and the heavy chain variable region amino acid residues Gly31; Tyr32; Ser52; Ser53; Ala54; Thr56; Phe58; Pro96; Arg97; Gly98; Tyr99; and Arg100e.

In some instances, any of the preceding anti-tryptase antibodies binds human tryptase. In some instances, any of the preceding antibodies binds cynomolgus monkey (cyno) tryptase. In some instances, the antibody binds human tryptase alpha or human tryptase beta. In some instances, the antibody binds human tryptase beta 1, human tryptase beta 2, or human tryptase beta 3.

In another aspect, the invention provides anti-tryptase antibodies that bind to an epitope on tryptase (e.g., human tryptase beta 1) that includes one or more amino acid residues (e.g., 1, 2, 3, 4, 5, 6, or 7 amino acid residues) selected from the group consisting of His51, Val80, Lys81, Asp82, Leu83, Ala84, and Ala85, which may be in reference to the amino acid sequence of SEQ ID NO: 71 or a corresponding amino acid of any tryptase protein. For example, in some embodiments, the antibody binds to an epitope on tryptase (e.g., human tryptase beta 1) comprising at least one, at least two, at least three, or all four residues selected from the group consisting of His51, Val80, Lys81, and Asp82 of SEQ ID NO: 71 or a corresponding amino acid of any tryptase protein. In some embodiments, the antibody binds to an epitope on tryptase (e.g., human tryptase beta 1) comprising His51 and at least one, at least two, or all three residues selected from the group consisting of Val 80, Lys81, and Asp82 of SEQ ID NO: 71 or a corresponding amino acid of any tryptase protein. In some embodiments, the epitope on tryptase (e.g., human tryptase beta 1) further comprises one or more amino acid residues selected from the group consisting of Gln67, Leu83, Ala84, Ala85, Arg87, Pro103, Val104, Ser105, Arg106, Glu128, Glu129, and Pro130 of SEQ ID NO: 71 or a corresponding amino acid of any tryptase protein. In some embodiments, the epitope on tryptase (e.g., human tryptase beta 1) comprises at least two, at least three, at least four, at least five, at least six, at least seven, at least eight, at least nine, at least ten, at least eleven, or all twelve amino acid residues selected from the group consisting of Gln67, Leu83, Ala84, Ala85, Arg87, Pro103, Val104, Ser105, Arg106, Glu128, Glu129, and Pro130 of SEQ ID NO: 71 or a corresponding amino acid of any tryptase protein. In some embodiments, the epitope on tryptase (e.g., human tryptase beta 1) comprises His51, Gln67, Val80, Lys81, Asp82, Leu83, Ala84, Ala85, Arg87, Pro103, Va104, Ser105, Arg106, Glu128, Glu129, and Pro130 of SEQ ID NO:71 or a corresponding amino acid of any tryptase protein. In some embodiments, the epitope is relative to a tryptase (e.g., human tryptase beta 1) monomer or tetramer. In some embodiments, the epitope is determined by an X-ray crystallography model. In some embodiments, the antibody is capable of dissociating both the small interface of tetrameric tryptase and the large interface of tetrameric tryptase tryptase (e.g., human tryptase beta 1).

In yet another aspect, the invention provides anti-tryptase antibodies that binds to an epitope on tryptase (e.g., human tryptase beta 1) that includes one or more amino acid residues (e.g., 1, 2, 3, 4, 5, 6, or 7 amino acid residues) elected from the group consisting of Gln100, Leu101, Leu102, Pro103, Val104, Ser105, and Arg106, which may be in reference to the amino acid sequence of SEQ ID NO: 71 or a corresponding amino acid of any tryptase protein. In some embodiments, the epitope on tryptase (e.g., human tryptase beta 1) further comprises one or more amino acid residues selected from the group consisting of Trp55, Gln67, Asp82, Leu83, Ala84, Arg87, Pro103, Va104, Ser105, Arg106, Glu126, Leu127, Glu128, and Glu129 of SEQ ID NO: 71 or a corresponding amino acid of any tryptase protein. In some embodiments, the epitope on tryptase (e.g., human tryptase beta 1) comprises at least two, at least three, at least four, at least five, at least six, at least seven, at least eight, at least nine, at least ten, at least eleven, at least twelve, at least thirteen, or all fourteen amino acid residues selected from the group consisting of Trp55, Gln67, Asp82, Leu83, Ala84, Arg87, Pro103, Val104, Ser105, Arg106, Glu126, Leu127, Glu128, and Glu129 of SEQ ID NO: 71 or a corresponding amino acid of any tryptase protein. In some embodiments, the epitope comprises Gln35, Trp55, Gln67, Asp82, Leu83, Ala84, Arg87, Gln100, Leu101, Leu102, Pro103, Val104, Ser105, Arg106, Glu126, Leu127, Glu128, Glu129, and Arg216 of SEQ ID NO: 71 or a corresponding amino acid of any tryptase protein. In some embodiments, the epitope is relative to a tryptase (e.g., human tryptase beta 1) monomer or tetramer. In some embodiments, the epitope is relative to a tetramer, and the epitope on tryptase (e.g., human tryptase beta 1) further comprises one or both of Gln35 and Arg216 of SEQ ID NO: 71 or a corresponding amino acid of any tryptase protein. In some embodiments, the epitope is determined by an X-ray crystallography model. In some embodiments, the antibody is capable of dissociating the small interface and/or the large interface of tryptase (e.g., human tryptase beta 1).

In some embodiments, any of the preceding antibodies binds to an epitope on tryptase (e.g., human tryptase beta 1) that includes one or more amino acid residues (e.g., 1, 2, 3, 4, 5, 6, 7, 8, 9, 10, or 11 amino acid residues) selected from the group consisting of Gln67, Asp82, Leu83, Ala84, Arg87, Pro103, Val104, Ser105, Arg106, Glu128, and Glu129, which may be in reference to the amino acid sequence of SEQ ID NO: 71 or a corresponding amino acid of any tryptase protein.

For example, in some instances, any of the preceding antibodies binds to an epitope on tryptase (e.g., human tryptase beta 1) that includes Gln67 of SEQ ID NO: 71 or a corresponding amino acid of any tryptase protein. In some instances, the antibody binds to an epitope on tryptase (e.g., human tryptase beta 1) that includes Asp82 of SEQ ID NO: 71 or a corresponding amino acid of any tryptase protein. In some instances, the antibody binds to an epitope on tryptase (e.g., human tryptase beta 1) that includes Leu83 of SEQ ID NO: 71 or a corresponding amino acid of any tryptase protein. In some instances, the antibody binds to an epitope on tryptase (e.g., human tryptase beta 1) that includes Ala84 of SEQ ID NO: 71 or a corresponding amino acid of any tryptase protein. In some instances, the antibody binds to an epitope on tryptase (e.g., human tryptase beta 1) that includes Arg87 of SEQ ID NO: 71 or a corresponding amino acid of any tryptase protein. In some instances, the antibody binds to an epitope on tryptase (e.g., human tryptase beta 1) that includes Pro103 of SEQ ID NO: 71 or a corresponding amino acid of any tryptase protein. In some instances, the antibody binds to an epitope on tryptase (e.g., human tryptase beta 1) comprising Val104 of SEQ ID NO: 71 or a corresponding amino acid of any tryptase protein. In some instances, the antibody binds to an epitope on tryptase (e.g., human tryptase beta 1) that includes Ser105 of SEQ ID NO: 71 or a corresponding amino acid of any tryptase protein. In some instances, the antibody binds to an epitope on tryptase (e.g., human tryptase beta 1) that includes Arg106 of SEQ ID NO: 71 or a corresponding amino acid of any tryptase protein. In some instances, the antibody binds to an epitope on tryptase (e.g., human tryptase beta 1) that includes Glu128 of SEQ ID NO: 71 or a corresponding amino acid of any tryptase protein. In some instances, the antibody binds to an epitope on tryptase (e.g., human tryptase beta 1) that includes Glu129 of SEQ ID NO: 71 or a corresponding amino acid of any tryptase protein.

In some embodiments, any of the preceding antibodies binds to an epitope on tryptase (e.g., human tryptase beta 1) that includes two or more, three or more, four or more, five or more, six or more, seven or more, eight or more, nine or more, ten or more, or all eleven amino acid residues selected from the group consisting of Gln67, Asp82, Leu83, Ala84, Arg87, Pro103, Val104, Ser105, Arg106, Glu128, and Glu129, which may be in reference to the amino acid sequence of SEQ ID NO: 71 or a corresponding amino acid of any tryptase protein.

In some instances, any of the preceding antibodies binds to an epitope on tryptase (e.g., human tryptase beta 1) that further includes one or more additional amino acid residues (e.g., 1, 2, 3, 4, or 5 additional amino acid residues) selected from the group consisting of His51, Val80, Lys81, Ala85, and Pro130, which may be in reference to the amino acid sequence of SEQ ID NO: 71 or a corresponding amino acid of any tryptase protein. For example, in some instances, the antibody binds to an epitope on tryptase (e.g., human tryptase beta 1) that further includes His51 of SEQ ID NO: 71 or a corresponding amino acid of any tryptase protein. In some instances, the antibody binds to an epitope on tryptase (e.g., human tryptase beta 1) that further includes Val80 of SEQ ID NO: 71 or a corresponding amino acid of any tryptase protein. In some embodiments the anti-tryptase antibody binds to an epitope on tryptase (e.g., human tryptase beta 1) that further includes Lys81 of SEQ ID NO: 71 or a corresponding amino acid of any tryptase protein. In some instances, the antibody binds to an epitope on tryptase (e.g., human tryptase beta 1) that further includes Ala85 of SEQ ID NO: 71 or a corresponding amino acid of any tryptase protein. In some instances, the antibody binds to an epitope on tryptase (e.g., human tryptase beta 1) that further includes Pro130 of SEQ ID NO: 71 or a corresponding amino acid of any tryptase protein.

In some instances, the antibody binds to an epitope on tryptase (e.g., human tryptase beta 1) that further includes two or more, three or more, four or more, or five or more additional amino acid residues selected from the group consisting of His51, Val80, Lys81, Ala85, and Pro130, which may be in reference to the amino acid sequence of SEQ ID NO: 71 or a corresponding amino acid of any tryptase protein.

In some instances, the anti-tryptase antibody binds to an epitope on tryptase (e.g., human tryptase beta 1) that includes His51, Gln67, Val80, Lys81, Asp82, Leu83, Ala84, Ala85, Arg87, Pro103, Val104, Ser105, Arg106, Glu128, Glu129, and Pro130 of SEQ ID NO: 71, which may be in reference to the amino acid sequence of SEQ ID NO: 71 or a corresponding amino acid of any tryptase protein. In some instances, the anti-tryptase antibody binds to an epitope on tryptase (e.g., human tryptase beta 1) that consists of His51, Gln67, Val80, Lys81, Asp82, Leu83, Ala84, Ala85, Arg87, Pro103, Val104, Ser105, Arg106, Glu128, Glu129, and Pro130 of SEQ ID NO: 71.

In other instances, any of the preceding anti-tryptase antibodies binds to an epitope on tryptase (e.g., human tryptase beta 1) that further includes one or more (e.g., 1, 2, 3, 4, 5, 6, 7, or 8) additional amino acid residues selected from the group consisting of Gln35, Trp55, Gln100, Leu101, Leu102, Glu126, Leu127, and Arg216, which may be in reference to the amino acid sequence of SEQ ID NO: 71 or a corresponding amino acid of any tryptase protein. For example, in some instances, the antibody binds to an epitope on tryptase (e.g., human tryptase beta 1) that further includes Gln35 of SEQ ID NO: 71 or a corresponding amino acid of any tryptase protein. In some instances, the antibody binds to an epitope on tryptase (e.g., human tryptase beta 1) that further includes Trp55 of SEQ ID NO: 71 or a corresponding amino acid of any tryptase protein. In some instances, the antibody binds to an epitope on tryptase (e.g., human tryptase beta 1) that further includes Gln100 of SEQ ID NO: 71 or a corresponding amino acid of any tryptase protein. In some instances, the antibody binds to an epitope on tryptase (e.g., human tryptase beta 1) that further includes Leu101 of SEQ ID NO: 71 or a corresponding amino acid of any tryptase protein. In some instances, the antibody binds to an epitope on tryptase (e.g., human tryptase beta 1) that further includes Leu102 of SEQ ID NO: 71 or a corresponding amino acid of any tryptase protein. In some instances, the antibody binds to an epitope on tryptase (e.g., human tryptase beta 1) that further includes Glu126 of SEQ ID NO: 71 or a corresponding amino acid of any tryptase protein. In some instances, the antibody binds to an epitope on tryptase (e.g., human tryptase beta 1) that further includes Leu127 of SEQ ID NO: 71 or a corresponding amino acid of any tryptase protein. In some instances, the antibody binds to an epitope on tryptase (e.g., human tryptase beta 1) that further includes Arg216 of SEQ ID NO: 71 or a corresponding amino acid of any tryptase protein. In some instances, the antibody binds to an epitope on tryptase (e.g., human tryptase beta 1) that further includes two or more, three or more, four or more, five or more, six or more, seven or more, or eight or more additional amino acid residues selected from the group consisting of Gln35, Trp55, Gln100, Leu101, Leu102, Glu126, Leu127, and Arg216, which may be in reference to the amino acid sequence of SEQ ID NO: 71 or a corresponding amino acid of any tryptase protein.

In some instances, the anti-tryptase antibody binds to an epitope on tryptase (e.g., human tryptase beta 1) that includes Gln35, Trp55, Gln67, Asp82, Leu83, Ala84, Arg87, Gln100, Leu101, Leu102, Pro103, Val104, Ser105, Arg106, Glu126, Leu127, Glu128, Glu129, and Arg216, which may be in reference to the amino acid sequence of SEQ ID NO: 71 or a corresponding amino acid of any tryptase protein. In some instances, the anti-tryptase antibody binds to an epitope on tryptase (e.g., human tryptase beta 1) that consists of Gln35, Trp55, Gln67, Asp82, Leu83, Ala84, Arg87, Gln100, Leu101, Leu102, Pro103, Val104, Ser105, Arg106, Glu126, Leu127, Glu128, Glu129, and Arg216 of SEQ ID NO: 71.

In another aspect, the invention provides an antibody that competes for binding to tryptase (e.g., human tryptase beta 1) with any of the preceding antibodies.

In another aspect, the invention provides an antibody that binds to the same epitope or an overlapping epitope as any of the preceding antibodies.

In some embodiments, any of the preceding antibodies may have the ability to disrupt tryptase having a tetrameric structure (such as mature tryptase present in, or released from, mast cell secretory granules) to form smaller molecular weight species, e.g., monomers, dimers, and/or trimers.

In a further aspect, an antibody according to any of the above embodiments may incorporate any of the features, singly or in combination, as described in Sections 1-7 below:

1. Antibody Affinity

In certain embodiments, an antibody provided herein has a dissociation constant ($K_D$) of ≤1 μM, ≤100 nM, ≤10 nM, ≤1 nM, ≤0.1 nM, ≤0.01 nM, ≤1 pM, or ≤0.1 pM (e.g., $10^{-6}$ M or less, e.g., from $10^{-6}$ M to $10^{-9}$ M or less, e.g., from $10^{-9}$ M to $10^{-13}$ M or less). In some embodiments, an anti-tryptase antibody of the invention binds to tryptase (e.g., human tryptase, e.g., human tryptase beta) with a $K_D$ of about 100 nM or lower (e.g., 100 nM or lower, 10 nM or lower, 1 nM or lower, 100 pM or lower, 10 pM or lower, 1 pM or lower, or 0.1 pM or lower). In some embodiments, the antibody binds tryptase (e.g., human tryptase, e.g., human tryptase beta) with a $K_D$ of 10 nM or lower (e.g., 10 nM or lower, 1 nm or lower, 100 pM or lower, 10 pM or lower, 1 pM or lower, or 0.1 pM or lower). In some embodiments, the antibody binds tryptase (e.g., human tryptase, e.g., human tryptase beta) with a $K_D$ of 1 nM or lower (e.g., 1 nm or lower, 100 pM or lower, 10 pM or lower, 1 pM or lower, or 0.1 pM or lower). In some embodiments, any of the anti-tryptase antibodies described above or herein binds to tryptase (e.g., human tryptase, e.g., human tryptase beta) with a $K_D$ of about 0.5 nM or lower (e.g., 0.5 nm or lower, 400 pM or lower, 300 pM or lower, 200 pM or lower, 100 pM or lower, 50 pM or lower, 25 pM or lower, 10 pM or lower, 1 pM or lower, or 0.1 pM or lower). In some embodiments, the antibody binds tryptase (e.g., human tryptase, e.g., human tryptase beta) with a $K_D$ between about 0.1 nM to about 0.5 nM (e.g., about 0.1 nM, about 0.2 nM, about 0.3 nM, about 0.4 nM, or about 0.5 nM). In some embodiments, the antibody binds tryptase (e.g., human tryptase, e.g., human tryptase beta) with a $K_D$ of about 0.4 nM. In some embodiments, the antibody binds tryptase (e.g., human tryptase, e.g., human tryptase beta) with a $K_D$ of about 0.18 nM.

In one embodiment, $K_D$ is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al. J. Mol. Biol. 293:865-881, 1999). To establish conditions for the assay, MICROTITER® multi-well plates (Thermo Scientific) are coated overnight with 5 pg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al. Cancer Res. 57:4593-4599, 1997). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN®-20) in PBS. When the plates have dried, 150 μl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, $K_D$ is measured using a BIACORE® surface plasmon resonance assay. For example, an assay using a BIACORE®-2000 or a BIACORE®-3000 (BIAcore, Inc., Piscataway, NJ) is performed at 25° C. with immobilized antigen CM5 chips at ~10 response units (RU). In one embodiment, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 pM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in phosphate buffered saline (PBS) with 0.05% polysorbate 20 (TWEEN®-20) surfactant (PBST) at 25° C. at a flow rate of approximately 25 μl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant ($K_D$) is calculated as the ratio $k_{off}/k_{on}$. See, for example, Chen et al. (J. Mol. Biol. 293: 865-881, 1999). If the on-rate exceeds $10^6$ M$^{-1}$s$^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

In some embodiments, $K_D$ is measured using a BIACORE® SPR assay, for example, as described in Example 1, Section (A)(vii). In some embodiments, the SPR assay can use a BIAcore® T200 or an equivalent device. In some embodiments, BIAcore® Series S CM5 sensor chips (or equivalent sensor chips) are immobilized with monoclonal mouse anti-human IgG (Fc) antibody and anti-tryptase antibodies are subsequently captured on the flow cell. Serial 3-fold dilutions of the His-tagged human tryptase beta 1 monomer (SEQ ID NO: 128) are injected at a flow rate of 30

μl/min. Each sample is analyzed with 3 min association and 10 min dissociation. The assay is performed at 25° C. After each injection, the chip is regenerated using 3 M $MgCl_2$. Binding response is corrected by subtracting the response units (RU) from a flow cell capturing an irrelevant IgG at similar density. A 1:1 Languir model of simultaneous fitting of $k_{on}$ and $k_{off}$ is used for kinetics analysis.

2. Antibody Fragments

In certain embodiments, an antibody provided herein is an antibody fragment. Antibody fragments include, but are not limited to, Fab, Fab', Fab'-SH, $F(ab')_2$, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al. *Nat. Med.* 9:129-134, 2003; and Hollinger et al. *Proc. Natl. Acad. Sci. USA* 90: 6444-6448, 1993. Triabodies and tetrabodies are also described in Hudson et al. *Nat. Med.* 9:129-134, 2003.

Single-domain antibodies are antibody fragments comprising all or a portion of the heavy chain variable domain or all or a portion of the light chain variable domain of an antibody. In certain embodiments, a single-domain antibody is a human single-domain antibody (see, e.g., U.S. Pat. No. 6,248,516 B1).

Antibody fragments can be made by various techniques, including but not limited to proteolytic digestion of an intact antibody as well as production by recombinant host cells (e.g., *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al. *Proc. Natl. Acad. Sci. USA*, 81:6851-6855, 1984). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), for example, to restore or improve antibody specificity or affinity.

Humanized antibodies and methods of making them are reviewed, for example, in Almagro et al. *Front. Biosci.* 13:1619-1633, 2008, and are further described, e.g., in Riechmann et al. *Nature* 332:323-329, 1988; Queen et al. *Proc. Natl. Acad. Sci. USA* 86:10029-10033, 1989; U.S. Pat. Nos. 5,821,337, 7,527,791, 6,982,321, and 7,087,409; Kashmiri et al. Methods 36:25-34, 2005 (describing specificity determining region (SDR) grafting); Padlan, *Mol. Immunol.* 28:489-498, 1991 (describing "resurfacing"); Dall'Acqua et al. *Methods* 36:43-60, 2005 (describing "FR shuffling"); and Osbourn et al. *Methods* 36:61-68, 2005 and Klimka et al. *Br. J. Cancer,* 83:252-260, 2000 (describing the "guided selection" approach to FR shuffling).

Human framework regions that may be used for humanization include but are not limited to: framework regions selected using the "best-fit" method (see, e.g., Sims et al. *J. Immunol.* 151:2296, 1993); framework regions derived from the consensus sequence of human antibodies of a particular subgroup of light or heavy chain variable regions (see, e.g., Carter et al. *Proc. Natl. Acad. Sci. USA,* 89:4285, 1992; and Presta et al. *J. Immunol.,* 151:2623, 1993); human mature (somatically mutated) framework regions or human germline framework regions (see, e.g., Almagro et al. *Front. Biosci.* 13:1619-1633, 2008); and framework regions derived from screening FR libraries (see, e.g., Baca et al. *J. Biol. Chem.* 272:10678-10684, 1997 and Rosok et al. *J. Biol. Chem.* 271:22611-22618, 1996).

4. Human Antibodies

In certain embodiments, an antibody provided herein is a human antibody. Human antibodies can be produced using various techniques known in the art. Human antibodies are described generally in van Dijk et al. *Curr. Opin. Pharmacol.* 5:368-74, 2001 and Lonberg, *Curr. Opin. Immunol.* 20:450-459, 2008.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125, 2005. See also, for example, U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology. Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.* 133:3001, 1984; Brodeur et al. *Monoclonal Antibody Production Techniques and Applications*, pp. 51-63 (Marcel Dekker, Inc., New York, 1987); and Boerner et al. *J. Immunol.* 147: 86, 1991). Human antibodies generated via human B-cell hybridoma technology are also described in Li et al. *Proc. Natl. Acad. Sci. USA,* 103:3557-3562, 2006. Additional methods include those described, for example, in U.S. Pat. No. 7,189,826 (describing production of monoclonal human IgM antibodies from hybridoma cell lines) and Ni, *Xiandai Mianyixue,* 26(4):265-268, 2006 (describing human-human hybridomas). Human hybridoma technology (Trioma technology) is also described in Vollmers et al. *Histology and Histopathology* 20(3):927-937, 2005 and Vollmers et al. *Methods and Findings in Experimental and Clinical Pharmacology* 27(3):185-91, 2005.

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, NJ, 2001) and further described, e.g., in the McCafferty et al. *Nature* 348:552-554, 1990; Clackson et al. *Nature* 352: 624-628, 1991; Marks et al. *J. Mol. Biol.* 222: 581-597, 1992; Marks et al. in *Methods in Molecular Biology* 248:161-175 (Lo, ed., Human Press, Totowa, NJ, 2003); Sidhu et al. *J. Mol. Biol.* 338(2): 299-310, 2004; Lee et al. *J. Mol. Biol.* 340(5): 1073-1093, 2004; Fellouse, *Proc. Natl. Acad. Sci. USA* 101(34):12467-12472, 2004; and Lee et al. *J. Immunol. Methods* 284(1-2): 119-132, 2004.

In certain phage display methods, repertoires of VH and VL genes are separately cloned by polymerase chain reaction (PCR) and recombined randomly in phage libraries, which can then be screened for antigen-binding phage as described in Winter et al. *Ann. Rev. Immunol.*, 12: 433-455, 1994. Phage typically display antibody fragments, either as single-chain Fv (scFv) fragments or as Fab fragments. Libraries from immunized sources provide high-affinity antibodies to the immunogen without the requirement of constructing hybridomas. Alternatively, the naïve repertoire can be cloned (e.g., from human) to provide a single source of antibodies to a wide range of non-self and also self antigens without any immunization as described by Griffiths et al. *EMBO J.* 12: 725-734, 1993. Finally, naïve libraries can also be made synthetically by cloning unrearranged V-gene segments from stem cells, and using PCR primers containing random sequence to encode the highly variable HVR3 regions and to accomplish rearrangement in vitro, as described by Hoogenboom et al. *J. Mol. Biol.*, 227: 381-388, 1992. Patent publications describing human antibody phage libraries include, for example: U.S. Pat. No. 5,750,373, and U.S. Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, for example, a bispecific antibody. Multispecific antibodies are monoclonal antibodies that have binding specificities for at least two different sites. In certain embodiments, bispecific antibodies may bind to two different epitopes of tryptase. In certain embodiments, one of the binding specificities is for tryptase and the other is for any other antigen (e.g., a second biological molecule). In some embodiments, bispecific antibodies may bind to two different epitopes of tryptase. In other embodiments, one of the binding specificities is for tryptase (e.g., human tryptase, e.g., human tryptase beta) and the other is for any other antigen (e.g., a second biological molecule, e.g., IL-13, IL-4, IL-5, IL-17, IL-33, IgE, M1 prime, CRTH2, or TRPA). Accordingly, the bispecific antibody may have binding specificity for tryptase and IL-13; tryptase and IL-4; tryptase and IL-5; tryptase and IL-17, or tryptase ant IL-33. In particular, the bispecific antibody may have binding specificity for tryptase and IL-13 or tryptase and IL-33. Bispecific antibodies can be prepared as full length antibodies or antibody fragments.

For example, in some instances, a bispecific antibody includes a first binding domain that binds tryptase and a second binding domain that binds IL-13. In some embodiments, the first binding domain that binds tryptase may include, for example, at least one, two, three, four, five, or six hypervariable regions (HVRs) selected from: (a) an HVR-H1 comprising the amino acid sequence of $X_1X_2GMX_3$ (SEQ ID NO: 1), wherein $X_1$ is Asp or Ser, $X_2$ is Tyr or Phe, and $X_3$ is Val or His; (b) an HVR-H2 comprising the amino acid sequence of FISSGSSTVYYADTMKG (SEQ ID NO: 2); (c) an HVR-H3 comprising the amino acid sequence of $RX_1X_2X_3DWYFDV$ (SEQ ID NO: 3), wherein $X_1$ is Asn or Asp, $X_2$ is Tyr or Asn, and $X_3$ is Asp or Tyr; (d) an HVR-L1 comprising the amino acid sequence of SASSSVTYMY (SEQ ID NO: 4); (e) an HVR-L2 comprising the amino acid sequence of RTSDLAS (SEQ ID NO: 5); and (f) an HVR-L3 comprising the amino acid sequence of QHYHSYPLT (SEQ ID NO: 6), or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 1-6. In some instances, the second binding domain that binds to IL-13 may, for example, include at least one, two, three, four, five, or six HVRs selected from (a) HVR-H1 comprising the amino acid sequence of AYSVN (SEQ ID NO: 84); (b) HVR-H2 comprising the amino acid sequence of MIWGDGKIVYNSALKS (SEQ ID NO: 85); (c) HVR-H3 comprising the amino acid sequence of DGYYPYAMDN (SEQ ID NO: 86); (d) HVR-L1 comprising the amino acid sequence of RASKSVDSYGNSFMH (SEQ ID NO: 87); (e) HVR-L2 comprising the amino acid sequence of LASNLES (SEQ ID NO: 88); and (f) HVR-L3 comprising the amino acid sequence of QQNNEDPRT (SEQ ID NO: 89), or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 84-89. In some embodiments, the second binding domain comprises one, two, three, four, five, or six HVRs of the anti-IL-13 antibody lebrikizumab.

For example, in some instances, the first binding domain that binds tryptase comprises at least one, two, three, four, five, or six hypervariable regions (HVRs) selected from: (a) an HVR-H1 comprising the amino acid sequence of DYGMV (SEQ ID NO: 7); (b) an HVR-H2 comprising the amino acid sequence of FISSGSSTVYYADTMKG (SEQ ID NO: 2); (c) an HVR-H3 comprising the amino acid sequence of RNYDDWYFDV (SEQ ID NO: 8); (d) an HVR-L1 comprising the amino acid sequence of SASSSVTYMY (SEQ ID NO: 4); (e) an HVR-L2 comprising the amino acid sequence of RTSDLAS (SEQ ID NO: 5); and (f) an HVR-L3 comprising the amino acid sequence of QHYHSYPLT (SEQ ID NO: 6), such as hu31a.v11. In some instances, the second binding domain that binds IL-13 may, for example, comprise at least one, two, three, four, five, or six HVRs selected from (a) HVR-H1 comprising the amino acid sequence of AYSVN (SEQ ID NO: 84); (b) HVR-H2 comprising the amino acid sequence of MIWGDGKIVYN-SALKS (SEQ ID NO: 85); (c) HVR-H3 comprising the amino acid sequence of DGYYPYAMDN (SEQ ID NO: 86); (d) HVR-L1 comprising the amino acid sequence of RASKSVDSYGNSFMH (SEQ ID NO: 87); (e) HVR-L2 comprising the amino acid sequence of LASNLES (SEQ ID NO: 88); and (f) HVR-L3 comprising the amino acid sequence of QQNNEDPRT (SEQ ID NO: 89). In some embodiments, the second binding domain comprises one, two, three, four, five, or six HVRs of the anti-IL-13 antibody lebrikizumab. In some embodiments, the first binding domain comprises the amino acid sequence of the VH and/or VL of hu31a.v11 and the second binding domain comprises the amino acid sequence of the VH and/or VL of the anti-IL-13 antibody lebrikizumab.

Any of the preceding bispecific anti-tryptase/anti-IL-13 antibodies may include a first binding domain that binds tryptase comprising (a) a VH domain comprising an amino acid sequence having at least 80% sequence identity (e.g., 80%, 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 9; (b) a VL domain comprising an amino acid sequence having at least 80% sequence identity (e.g., 80%, 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 10; or (c) a VH domain as in (a) and a $V_L$ domain as in (b). Any of the preceding bispecific anti-tryptase/anti-IL-13 antibodies may include a second binding domain that binds to IL-13 comprising (a) a VH domain comprising an amino acid sequence having at least 80% sequence identity (e.g., 80%, 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 90 or SEQ ID NO: 114; (b) a VL domain comprising an amino acid sequence having at least 80% sequence identity (e.g., 80%, 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 91 or SEQ ID NO: 115; or (c) a VH domain as in (a) and a VL domain as in (b). In some instances, the second binding domain comprises the VH and/or VL domain of lebrikizumab.

In another example, in some instances, a bispecific antibody includes a first binding domain that binds tryptase and a second binding domain that binds IL-33. The second binding domain that binds IL-33 may include any of the anti-IL-33 antibodies described, for example, in U.S. Patent Publication No. 2016/0168242, which is incorporated herein by reference in its entirety. In some embodiments, the first binding domain that binds tryptase may include, for example, at least one, two, three, four, five, or six hypervariable regions (HVRs) selected from: (a) an HVR-H1 comprising the amino acid sequence of $X_1X_2GMX_3$ (SEQ ID NO: 1), wherein $X_1$ is Asp or Ser, $X_2$ is Tyr or Phe, and $X_3$ is Val or His; (b) an HVR-H2 comprising the amino acid sequence of FISSGSSTVYYADTMKG (SEQ ID NO: 2); (c) an HVR-H3 comprising the amino acid sequence of $RX_1X_2X_3DWYFDV$ (SEQ ID NO: 3), wherein $X_1$ is Asn or Asp, $X_2$ is Tyr or Asn, and $X_3$ is Asp or Tyr; (d) an HVR-L1 comprising the amino acid sequence of SASSSVTYMY (SEQ ID NO: 4); (e) an HVR-L2 comprising the amino acid sequence of RTSDLAS (SEQ ID NO: 5); and (f) an HVR-L3 comprising the amino acid sequence of QHYHSYPLT (SEQ ID NO: 6), or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 1-6. In some instances, the second binding domain that binds to IL-33 may, for example, include at least one, two, three, four, five, or six HVRs selected from (a) HVR-H1 comprising the amino acid sequence of SFSMS (SEQ ID NO: 120); (b) HVR-H2 comprising the amino acid sequence of TISGGKTFTDYVDSVKG (SEQ ID NO: 121); (c) HVR-H3 comprising the amino acid sequence of ANYGNWFFEV (SEQ ID NO: 122); (d) HVR-L1 comprising the amino acid sequence of RASESVAKYGLSLLN (SEQ ID NO: 123); (e) HVR-L2 comprising the amino acid sequence of AASNRGS (SEQ ID NO: 124); and (f) HVR-L3 comprising the amino acid sequence of QQSKEVPFT (SEQ ID NO: 125), or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 120-125. In some embodiments, the second binding domain comprises one, two, three, four, five, or six HVRs of the anti-IL-33 antibody 10C12.38.H6.87Y.58I.

For example, in some instances, the first binding domain that binds tryptase comprises at least one, two, three, four, five, or six hypervariable regions (HVRs) selected from: (a) an HVR-H1 comprising the amino acid sequence of DYGMV (SEQ ID NO: 7); (b) an HVR-H2 comprising the amino acid sequence of FISSGSSTVYYADTMKG (SEQ ID NO: 2); (c) an HVR-H3 comprising the amino acid sequence of RNYDDWYFDV (SEQ ID NO: 8); (d) an HVR-L1 comprising the amino acid sequence of SASSSVTYMY (SEQ ID NO: 4); (e) an HVR-L2 comprising the amino acid sequence of RTSDLAS (SEQ ID NO: 5); and (f) an HVR-L3 comprising the amino acid sequence of QHYHSYPLT (SEQ ID NO: 6), such as hu31a.v11. In some instances, the second binding domain that binds IL-33 may, for example, comprise at least one, two, three, four, five, or six HVRs selected from (a) HVR-H1 comprising the amino acid sequence of SFSMS (SEQ ID NO: 120); (b) HVR-H2 comprising the amino acid sequence of TIS-GGKTFTDYVDSVKG (SEQ ID NO: 121); (c) HVR-H3 comprising the amino acid sequence of ANYGNWFFEV (SEQ ID NO: 122); (d) HVR-L1 comprising the amino acid sequence of RASESVAKYGLSLLN (SEQ ID NO: 123); (e) HVR-L2 comprising the amino acid sequence of AASNRGS (SEQ ID NO: 124); and (f) HVR-L3 comprising the amino acid sequence of QQSKEVPFT (SEQ ID NO: 125). In some embodiments, the second binding domain comprises one, two, three, four, five, or six HVRs of the anti-IL-33 antibody 10C12.38.H6.87Y.58I. In some embodiments, the first binding domain comprises the amino acid sequence of the VH and/or VL of hu31a.v11 and the second binding domain comprises the amino acid sequence of the VH and/or VL of the anti-IL-33 antibody 10C12.38.H6.87Y.58I.

Any of the preceding bispecific anti-tryptase/anti-IL-33 antibodies may include a first binding domain that binds tryptase comprising (a) a VH domain comprising an amino acid sequence having at least 80% sequence identity (e.g., 80%, 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 9; (b) a VL domain comprising an amino acid sequence having at least 80% sequence identity (e.g., 80%, 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 10; or (c) a VH domain as in (a) and a VL domain as in (b). Any of the preceding bispecific anti-tryptase/anti-IL-33 antibodies may include a second binding domain that binds to IL-33 comprising (a) a VH domain comprising an amino acid sequence having at least 80% sequence identity (e.g., 80%, 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 126; (b) a VL domain comprising an amino acid sequence having at least 80% sequence identity (e.g., 80%, 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 127; or (c) a VH domain as in (a) and a VL domain as in (b). In some instances, the second binding domain comprises the VH and/or VL domain of 10C12.38.H6.87Y.58I.

Techniques for making multispecific antibodies include, but are not limited to, recombinant co-expression of two immunoglobulin heavy chain-light chain pairs having different specificities (see Milstein et al. *Nature* 305: 537, 1983; WO 93/08829; and Traunecker et al. *EMBO J.* 10: 3655, 1991), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al. *Science*, 229: 81, 1985); using leucine zippers to produce bispecific antibodies (see, e.g., Kostelny et al. *J. Immunol.*, 148(5):1547-1553, 1992); using "diabody" technology for making bispecific antibody fragments (see, e.g., Hollinger et al. *Proc. Natl. Acad. Sci. USA* 90:6444-6448, 1993); and using single-chain Fv (scFv) dimers (see, e.g., Gruber et al. *J. Immunol.* 152:5368, 1994); and preparing trispecific antibodies as described, e.g., in Tutt et al. *J. Immunol.* 147: 60, 1991.

Engineered antibodies with three or more functional antigen binding sites, including "Octopus antibodies," are also included herein (see, e.g., US 2006/0025576A1).

The antibody or fragment herein also includes a "Dual Acting Fab" or "DAF" comprising an antigen binding site that binds to tryptase as well as another, different antigen (see, US 2008/0069820, for example).

Knobs-into-Holes

The use of knobs-into-holes as a method of producing multispecific antibodies is described, e.g., in U.S. Pat. No. 5,731,168, WO2009/089004, US2009/0182127, US2011/0287009, Marvin and Zhu, *Acta Pharmacol. Sin.* (2005) 26(6):649-658, and Kontermann (2005) *Acta Pharmacol. Sin.* 26:1-9. A brief nonlimiting discussion is provided below.

A "protuberance" refers to at least one amino acid side chain which projects from the interface of a first polypeptide and is therefore positionable in a compensatory cavity in the adjacent interface (i.e., the interface of a second polypeptide) so as to stabilize the heteromultimer, and thereby favor heteromultimer formation over homomultimer formation, for example. The protuberance may exist in the original interface or may be introduced synthetically (e.g., by altering nucleic acid encoding the interface). In some embodiments, a nucleic acid encoding the interface of the first polypeptide is altered to encode the protuberance. To achieve this, the nucleic acid encoding at least one "original" amino acid residue in the interface of the first polypeptide is replaced with nucleic acid encoding at least one "import" amino acid residue which has a larger side chain volume than the original amino acid residue. It will be appreciated that there can be more than one original and corresponding import residue. The side chain volumes of the various amino residues are shown, for example, in Table 1 of US 2011/0287009 or Table 1 of U.S. Pat. No. 7,642,228.

In some embodiments, import residues for the formation of a protuberance are naturally occurring amino acid residues selected from arginine (R), phenylalanine (F), tyrosine (Y) and tryptophan (W). In some embodiments, an import residue is tryptophan or tyrosine. In some embodiments, the original residue for the formation of the protuberance has a small side chain volume, such as alanine, asparagine, aspartic acid, glycine, serine, threonine, or valine. See, for example, U.S. Pat. No. 7,642,228.

A "cavity" refers to at least one amino acid side chain which is recessed from the interface of a second polypeptide and therefore accommodates a corresponding protuberance on the adjacent interface of a first polypeptide. The cavity may exist in the original interface or may be introduced synthetically (e.g., by altering nucleic acid encoding the interface). In some embodiments, nucleic acid encoding the interface of the second polypeptide is altered to encode the cavity. To achieve this, the nucleic acid encoding at least one "original" amino acid residue in the interface of the second polypeptide is replaced with DNA encoding at least one "import" amino acid residue which has a smaller side chain volume than the original amino acid residue. It will be appreciated that there can be more than one original and corresponding import residue. In some embodiments, import residues for the formation of a cavity are naturally occurring amino acid residues selected from alanine (A), serine (S), threonine (T), and valine (V). In some embodiments, an import residue is serine, alanine, or threonine. In some embodiments, the original residue for the formation of the cavity has a large side chain volume, such as tyrosine, arginine, phenylalanine, or tryptophan.

The protuberance is "positionable" in the cavity which means that the spatial location of the protuberance and cavity on the interface of a first polypeptide and second polypeptide respectively and the sizes of the protuberance and cavity are such that the protuberance can be located in the cavity without significantly perturbing the normal association of the first and second polypeptides at the interface. Since protuberances such as Tyr, Phe, and Trp do not typically extend perpendicularly from the axis of the interface and have preferred conformations, the alignment of a protuberance with a corresponding cavity may, in some instances, rely on modeling the protuberance/cavity pair based upon a three-dimensional structure such as that obtained by X-ray crystallography or nuclear magnetic resonance (NMR). This can be achieved using widely-accepted techniques in the art.

In some embodiments, a knob mutation in an IgG1 constant region is T366W. In some embodiments, a hole mutation in an IgG1 constant region comprises one or more mutations selected from T366S, L368A, and Y407V. In some embodiments, a hole mutation in an IgG1 constant region comprises T366S, L368A, and Y407V.

In some embodiments, a knob mutation in an IgG4 constant region is T366W. In some embodiments, a hole mutation in an IgG4 constant region comprises one or more mutations selected from T366S, L368A, and Y407V. In some embodiments, a hole mutation in an IgG4 constant region comprises T366S, L368A, and Y407V.

7. Antibody Variants

In certain embodiments, amino acid sequence variants of the antibodies provided herein are contemplated. For example, it may be desirable to improve the binding affinity and/or other biological properties of the antibody, such as inhibitory activity. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, for example, antigen-binding.

a) Substitution, Insertion, and Deletion Variants

In certain embodiments, antibody variants having one or more amino acid substitutions are provided. Sites of interest for substitutional mutagenesis include the HVRs and EFRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for adesired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, for example, using phage display-based affinity maturation techniques such as those described herein. Briefly, one or more HVR residues are mutated and the variant antibodies displayed on phage and screened for a particular biological activity (e.g., binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, Methods Mol. Biol. 207:179-196, 2008), and/or residues that contact antigen, with the resulting variant VH or VL being tested for binding affinity. Affinity maturation by constructing and reselecting from secondary libraries has been described, e.g., in Hoogenboom et al. in Methods in Molecular Biology 178:1-37 (O'Brien et al. ed., Human Press, Totowa, NJ, 2001). In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. HVR-H3 and HVR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham et al. Science 244:1081-1085, 1989. In this method, a residue or group of target residues (e.g., charged residues such as Arg, Asp, His, Lys, and Glu) are identified and replaced by a neutral or negatively charged amino acid (e.g., Ala or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, for example, Wright et al. *TIBTECH* 15:26-32, 1997. The oligosaccharide may include various carbohydrates, for example, mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. 2003/0157108 and 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO 2005/053742; WO 2002/031140; Okazaki et al. *J. Mol. Biol.* 336:1239-1249, 2004; Yamane-Ohnuki et al. *Biotech. Bioeng.* 87: 614, 2004. Examples of cell lines capable of producing defucosylated antibodies include Lec13 CHO cells deficient in protein fucosylation (Ripka et al. *Arch. Biochem. Biophys.* 249:533-545, 1986; US 2003/0157108; and WO 2004/056312 A1, especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614, 2004; Kanda et al. *Biotechnol. Bioeng.* 94(4):680-688, 2006; and WO 2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3, or IgG4 Fc region) comprising an amino acid modification (e.g., a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch et al. *Annu. Rev. Immunol.* 9:457-492, 1991. Non-limiting examples of in vitro assays to assess ADCC activity of a molecule of interest is described in U.S. Pat. No. 5,500,362 (see, e.g., Hellstrom et al. *Proc. Natl. Acad. Sci. USA* 83:7059-7063, 1986 and Hellstrom et al. Proc. Natl. Acad. Sci. USA 82:1499-1502, 1985; U.S. Pat. No. 5,821,337 (see Bruggemann et al. J. Exp. Med. 166:1351-1361, 1987). Alternatively, non-radioactive assays methods may be employed (see, for example, ACTI™ non-radioactive cytotoxicity assay for flow cytometry (CellTechnology, Inc. Mountain View, CA; and CytoTox 96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, for example, in an animal model such as that disclosed in Clynes et al. *Proc. Natl. Acad. Sci. USA* 95:652-656, 1998. C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, e.g., Gazzano-Santoro et al. *J. Immunol. Methods* 202:163, 1996; Cragg et al. Blood 101:1045-1052, 2003; and Cragg et al. *Blood* 103:2738-2743, 2004). FcRn binding and in vivo clearance/half life determinations can also be performed using methods known in the art (see, e.g., Petkova et al. *Intl. Immunol.* 18(12):1759-1769,2006).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312; and Shields et al. *J. Biol. Chem.* 9(2): 6591-6604, 2001).

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), for example, as described in U.S. Pat. No. 6,194,551, WO 99/51642, and Idusogie et al. *J. Immunol.* 164: 4178-4184, 2000.

Antibodies with increased half lives and improved binding to the neonatal Fc receptor (FcRn), which is responsible for the transfer of maternal IgGs to the fetus (Guyer et al. *J. Immunol.* 117:587, 1976 and Kim et al. *J. Immunol.* 24:249, 1994), are described in US2005/0014934. Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan et al. *Nature* 322:738-40, 1988; U.S. Pat. Nos. 5,648,260 and 5,624,821; and WO 94/29351 concerning other examples of Fc region variants.

d) Cysteine Engineered Antibody Variants

In certain embodiments, it may be desirable to create cysteine engineered antibodies, for example, "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, and the like.

In another embodiment, conjugates of an antibody and nonproteinaceous moiety that may be selectively heated by exposure to radiation are provided. In one embodiment, the nonproteinaceous moiety is a carbon nanotube (Kam et al. *Proc. Natl. Acad. Sci. USA* 102: 11600-11605, 2005). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, for example, as described in U.S. Pat. No. 4,816,567. In one embodiment, isolated nucleic acid encoding an anti-tryptase antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the $V_L$ of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, for example, a Chinese Hamster Ovary (CHO) cell, 293 cell, or lymphoid cell (e.g., Y0, NS0, Sp20 cell). In one embodiment, a method of making an anti-tryptase antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-tryptase antibody, nucleic acid encoding an antibody, for example, as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, for example, U.S. Pat. Nos. 5,648,237, 5,789,199, and 5,840,523. See also Charlton, Methods in Molecular Biology, Vol. 248 (B. K. C. Lo, ed., Humana Press, Totowa, NJ, 2003), pp. 245-254, describing expression of antibody fragments in *E. coli*. After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross *Nat. Biotech.* 22:1409-1414, 2004 and Li et al. *Nat. Biotech.* 24:210-215, 2006.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, for example, U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al. *J. Gen Virol.* 36:59, 1977); baby hamster kidney cells (BHK); mouse sertoli cells (TM4 cells as described, e.g., in Mather *Biol. Reprod.* 23:243-251, 1980); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68, 1982; MRC 5 cells; and FS4 cells. Other useful mammalian host cell lines include Chinese hamster ovary (CHO) cells, including DHFR-CHO cells (Urlaub et al. *Proc. Natl. Acad. Sci. USA* 77:4216, 1980); and myeloma cell lines such as Y0, NS0 and Sp2/0. For a review of certain mammalian host cell lines suitable for antibody production, see, e.g., Yazaki et al. *Methods in Molecular Biology, Vol.* 248 (B.K.C. Lo, ed., Humana Press, Totowa, NJ), pp. 255-268, 2003.

C. Assays

Anti-tryptase antibodies provided herein may be identified, screened for, or characterized for their physical/chemical properties and/or biological activities by various assays known in the art.

1. Binding Assays and Other Assays

In one aspect, an anti-tryptase antibody of the invention is tested for its antigen-binding activity, for example, by known methods such as ELISA, Western blot, surface plasmon resonance (SPR), and the like.

In another aspect, competition assays may be used to identify an antibody that competes with an anti-tryptase antibody of the invention for binding to tryptase. In certain embodiments, such a competing antibody binds to the same epitope (e.g., a linear or a conformational epitope) that is bound by an anti-tryptase antibody of the invention. In certain embodiments, such a competing antibody binds to an overlapping epitope (e.g., a linear or a conformational epitope) that is bound by an anti-tryptase antibody of the invention. Detailed exemplary methods for mapping an epitope to which an antibody binds are provided in Morris "Epitope Mapping Protocols," in *Methods in Molecular Biology* Vol. 66 (Humana Press, Totowa, NJ), 1996.

In an exemplary competition assay, immobilized tryptase is incubated in a solution comprising a first labeled antibody that binds to tryptase and a second unlabeled antibody that is being tested for its ability to compete with the first antibody for binding to tryptase. The second antibody may be present in a hybridoma supernatant. As a control, immobilized tryptase is incubated in a solution comprising the first labeled antibody but not the second unlabeled antibody. After incubation under conditions permissive for binding of the first antibody to tryptase, excess unbound antibody is removed, and the amount of label associated with immobilized tryptase is measured. If the amount of label associated with immobilized tryptase is substantially reduced in the test sample relative to the control sample, then that indicates that the second antibody is competing with the first antibody for binding to tryptase. See Harlow et al. *Antibodies: A Laboratory Manual* Ch.14 (Cold Spring Harbor Laboratory, Cold Spring Harbor, NY), 1988.

In another embodiment, the competition of two antibodies for binding to the same epitope is determined by epitope binning. For example, labeled antigen is immobilized on a solid surface, and reacted with a saturating amount of a first antibody. A second competing antibody is then added. Any additional binding by the second antibody as detected by, e.g., OCTET® (ForteBio) or other bio-layer interferometry (BLI) techniques, indicates that the two antibodies bind to distinct, non-overlapping epitopes. No additional binding indicates that the two antibodies bind to the same or overlapping epitope. Several other methods, including ELISA, size exclusion chromatography, crystallography, HDX-MS, mutagenesis, and other SPR methods, can also be employed to demonstrate that two antibodies bind to the same or overlapping epitopes. Similar techniques can be used to determine whether an antibody cross-blocks, or is cross-blocked by, the antibody of the invention.

2. Activity Assays

In one aspect, assays are provided for identifying anti-tryptase antibodies thereof having biological activity. Biological activity may include, for example, binding to tryptase (e.g., tryptase in the bloodstream or in the airway), or a peptide fragment thereof, either in vivo, in vitro, or ex vivo. In other embodiments, biological activity may include blocking or neutralizing tryptase. For example, in some embodiments, biological activity may include blocking or neutralizing tryptase proteolytic activity. Antibodies having such biological activity in vivo and/or in vitro are also provided. In certain embodiments, an antibody of the invention is tested for such biological activity.

For example, in some embodiments, an antibody of the invention is tested for inhibition of tryptase activity in a tryptase enzymatic assay, for example, using a peptide substrate (e.g., synthetic peptide S-2288), for example, as described in the Examples (e.g., Example 1, particularly Section (A)(viii)(a)), or using methods known in the art (see, e.g., Fukuoka et al. *J. Immunol.* 176:3165-3172, 2006). In some embodiments, inhibition of tryptase activity in a tryptase enzymatic assay is performed at or around neutral pH (e.g., around pH 7, e.g., about pH 7, about pH. 7.4, or about pH 8). In other embodiments, inhibition of tryptase activity in a tryptase enzymatic assay is performed at an acidic pH (e.g., about pH 6.0, e.g., about pH 4.0, about pH 5.0, about pH 6.0, or about pH 6.5).

In other embodiments, an antibody of the invention is tested for the ability to disrupt tryptase having a tetrameric structure (such as mature tryptase present in, or released from, mast cell secretory granules) to form monomers, which may be determined using any suitable method known in the art, including gel filtration chromatography (e.g., SUPEROSE®12 gel filtration chromatography). See, e.g., in Fukuoka et al. *J. Immunol.* 176:3165-3172,2006.

In yet other embodiments, an antibody of the invention is tested for the ability to inhibit tryptase-stimulated proliferation and/or contraction of human primary airway smooth muscle cells, as described, for example, in Example 1.

In still other embodiments, an antibody of the invention is tested for the ability to inhibit mast cell degranulation and/or histamine release, for example, stimulated by tryptase and/or IgE. Such assays are described, for example, in Example 1.

In some embodiments, an antibody of the invention is tested for the ability to inhibit active tryptase, for example, in an active tryptase assay (see, e.g., FIG. 15 and Example 6), for example, in a sample (e.g., bronchoalveolar lavage fluid) obtained from a subject following administration of the antibody to the subject (e.g., by intravenous or subcutaneous injection).

In still further embodiments, an antibody of the invention is tested for the ability to modulate (e.g., increase or decrease) total tryptase levels, for example, in a total tryptase assay (see, e.g., FIG. 15 and Example 6), for example, in a sample (e.g., bronchoalveolar lavage fluid) obtained from a subject following administration of the antibody to the subject (e.g., by intravenous or subcutaneous injection).

D. Immunoconjugates

The invention also provides immunoconjugates comprising an anti-tryptase antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498, 298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al. *Cancer Res.* 53:3336-3342, 1993; and Lode et al. *Cancer Res.* 58:2925-2928, 1998); an anthracycline such daunomycin or doxorubicin (see Kratz et al. *Current Med. Chem.* 13:477-523, 2006; Jeffrey et al. *Bloorganic & Med. Chem. Letters* 16:358-362, 2006; Torgov et al. *Bioconj. Chem.* 16:717-721, 2005; Nagy et al. *Proc. Natl. Acad. Sci. USA* 97:829-834, 2000; Dubowchik et al. *Bioorg. & Med. Chem. Letters* 12:1529-1532, 2002; King et al. *J. Med. Chem.* 45:4336-4343, 2002; and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{88}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example technetium-99m (tc99m) or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al. *Science* 238:1098, 1987. Carbon-14-labeled 1-isothiocyanatobenzyl-3-methyldiethylene triaminepentaacetic acid (MX-DTPA) is an exemplary chelating agent for conjugation of radionucleotide to the antibody. See WO 94/11026. The linker may be a "cleavable linker" facilitating release of a cytotoxic drug in the cell. For example, an acid-labile linker, peptidase-sensitive linker, photolabile linker, dimethyl linker or disulfide-containing linker (see, e.g., Chari et al. *Cancer Res.* 52:127-131, 1992; U.S. Pat. No. 5,208,020) may be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, IL, U.S.A).

E. Methods and Compositions for Diagnostics and Detection

In certain embodiments, any of the anti-tryptase antibodies provided herein is useful for detecting the presence of tryptase in a biological sample. The term "detecting" as used herein encompasses quantitative or qualitative detection. In certain embodiments, a biological sample comprises a cell or tissue, including but not limited to mast cells, basophils, epithelial cells, or lung tissue (e.g., bronchial smooth muscle). In certain embodiments, a biological sample comprises blood (e.g., whole blood, serum, or plasma), sputum, bronchoalveolar lavage, or a nasosorption sample.

In one embodiment, an anti-tryptase antibody for use in a method of diagnosis or detection is provided. In a further aspect, a method of detecting the presence of tryptase in a biological sample is provided. In certain embodiments, the method comprises contacting the biological sample with an anti-tryptase antibody as described herein under conditions permissive for binding of the anti-tryptase antibody to tryptase, and detecting whether a complex is formed between the anti-tryptase antibody and tryptase. Such method may be an in vitro or in vivo method. In one embodiment, an anti-tryptase antibody is used to select subjects eligible for therapy with an anti-tryptase antibody, for example, where tryptase is a biomarker for selection of patients.

Exemplary disorders that may be diagnosed using an antibody of the invention include pulmonary disorders (e.g., asthma (e.g., Th2-high asthma or Th2-ow asthma), airway hyperresponsiveness, or COPD), autoimmune disorders (e.g., rheumatoid arthritis, psoriasis, eosinophilic esophagitis, IBD, and Crohn's disease), inflammatory disorders (e.g., chronic idiopathic urticaria (CIU or CSU), atopic dermatitis, or allergic rhinitis), fibrotic disorders (e.g., IPF), granulocytic (neutrophilic or eosinophilic) disorders, monocytic disorders, lymphocytic disorders, disorders associated with increased numbers or distribution of normal or aberrant tissue resident cells (such as mast cells, macrophages, or lymphocytes) or stromal cells (such as fibroblasts, myofibroblasts, smooth muscle cells, epithelia, or endothelia, and tryptase-associated disorders or tryptase-mediated disorders.

For example, in some instances, the antibodies of the invention may be used to diagnose or detect anaphylaxis (e.g., acute systemic anaphylaxis) or mastocytosis (e.g., nonacute systemic mastocytosis), for example, as described in Schwartz et al. *Immunol. Allergy Clin. N. Am.* 26:451-463, 2006). The antibodies of the invention may be used, for example, in an ELISA to detect the levels of total tryptase, pro-tryptase, and/or mature tryptase. In some embodiments, an antibody of the invention may be used as a capture antibody in an ELISA. In other embodiments, an antibody of the invention may be used as a detection antibody in an ELISA. In particular embodiments, a normal reference level of total tryptase in serum or plasma may be about 1-15 ng/mL (e.g., about 1 ng/mL, about 2 ng/mL, about 3 ng/mL, about 4 ng/mL, about 5 ng/mL, about 6 ng/mL, about 7 ng/mL, about 8 ng/mL, about 9 ng/mL, about 10 ng/mL, about 11 ng/mL, about 12 ng/mL, about 13 ng/mL, about 14 ng/mL, or about 15 ng/mL). In some instances, an increase relative to a normal reference level of total tryptase is used as a diagnostic indicator of a tryptase-associated disorder. In some embodiments, a normal reference level of mature tryptase in serum or plasma may be <1 ng/mL. In some embodiments, an increase relative to a normal reference level of mature tryptase may be used as a diagnostic indicator of a tryptase associated disorder.

In certain embodiments, labeled anti-tryptase antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luciferases, e.g., firefly luciferase and bacterial luciferase (U.S. Pat. No. 4,737,456), luciferin, 2,3-dihydrophthalazinediones, horseradish peroxidase (HRP), alkaline phosphatase, p-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-tryptase antibody of the invention are prepared by mixing such antibody having the desired degree of purity with one or more optional pharmaceutically acceptable carriers (see, e.g., *Remington's Pharmaceutical Sciences* 16th edition, Osol, A. Ed., 1980), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYL-ENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO 2006/044908, the latter formulations including a histidine-acetate buffer.

The formulation herein may also contain more than one active ingredient as necessary for the particular indication being treated, preferably those with complementary activities that do not adversely affect each other. For example, it may be desirable to further provide an interleukin-13 (IL-13) binding antagonist, an interleukin-17 (IL-17) axis binding antagonist, an interleukin-5 (IL-5) axis binding antagonist, an IL-33 axis binding antagonist, an M1 prime antagonist, an IgE antagonist, a TRPA1 antagonist, a CRTH2 antagonist, a broncodilator or asthma symptom controller medication, an immunomodulator, a corticosteroid, a Th2 pathway inhibitor, a tyrosine kinase inhibitor, or a phosphodiesterase inhibitor. In some embodiments, the IL-13 axis binding antagonist is an anti-IL-13 antibody, for example, lebrikizumab. In some embodiments, the IL-5 axis binding antagonist is an IL-5 binding antagonist or an IL-5 receptor binding antagonist. In some embodiments, an IL-33 axis binding antagonist is an IL-33 binding antagonist or an ST2 binding antagonist. In some embodiments, the IL-33 binding antagonist is an anti-IL-33 antibody. In some instances, the M1 prime antagonist is quilizumab. In some instances, the IgE antagonist is omalizumab (XOLAIR®). Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed., 1980.

Sustained-release preparations may be prepared. Suitable examples of sustained-release preparations include semipermeable matrices of solid hydrophobic polymers containing the antibody, which matrices are in the form of shaped articles, e.g., films, or microcapsules.

The formulations to be used for in vivo administration are generally sterile. Sterility may be readily accomplished, for example, by filtration through sterile filtration membranes.

The invention provides pharmaceutical compositions that include antioxidants. Such compositions may be used to reduce oxidation of an antibody described herein (e.g., an anti-tryptase antibody, such as hu31A.v11). In some instances, an antioxidant is included to reduce oxidation of a tryptophan residue, for example, a tryptophan residue in a HVR region or a FR region of a variable region. In particular instances, an antioxidant is included to reduce oxidation of an HVR-H3 residue of an anti-tryptase antibody, for example, W100 in hu31A.v1. In some instances, an antioxidant is included in the composition to reduce oxidation of a methionine residue, for example a methionine residue in the Fc region of an antibody (e.g., an anti-tryptase antibody), such as Fc residues M251, M357, and/or M427 (for example, of hu31A.v1).

In some instances, the pharmaceutical composition includes any of the antibodies described herein and an antioxidant. In some instances, the antibody is susceptible to oxidation (e.g., at one or more (e.g., 1, 2, 3, 4, 5, 6, 7, 8, 9, or 10) tryptophan or methionine residues). Any suitable antioxidant may be used. For example, in some instances, the composition includes one or more antioxidants (e.g., 1, 2, 3, 4, 5, 6, 7, 8, or 9 antioxidants) selected from the group consisting of N-acetyltryptophan (e.g., N-acetyl DL-tryptophan or N-acetyl D-tryptophan), tryptophan, methionine (e.g., L-methionine), cysteine, glutathione, thiosorbitol, ascorbic acid, monothioglycerol, cyclodextrins, Trolox, pyridoxine, polyols (e.g., mannitol), sucrose, a metal chelator (e.g., EDTA), and combinations thereof (e.g., a combination of N-acetyltryptophan and methionine). In some instances, the antioxidant is N-acetyltryptophan (e.g., N-acetyl DL-tryptophan or N-acetyl D-tryptophan). In other instances, the antioxidant is methionine (e.g., L-methionine or D-methionine). In particular instances, the composition includes N-acetyltryptophan (e.g., N-acetyl DL-tryptophan or N-acetyl D-tryptophan) and methionine (e.g., L-methionine or D-methionine). In some instances, the N-acetyltryptophan reduces or prevents oxidation of tryptophan in the antibody. In some instances, the methionine reduces or prevents oxidation of methionine in the antibody.

The pharmaceutical composition may include any suitable concentration of the antioxidant in order to reduce or eliminate oxidation. For example, the concentration of polyols (e.g., mannitol) or sucrose may be about 1% (w/v) to about 25% (w/v), e.g., about 1%, about 2%, about 3%, about 4%, about 5%, about 6%, about 7%, about 8%, about 9%, about 10%, about 11%, about 12%, about 13%, about 15%, about 16%, about 17%, about 18%, about 19%, about 20%, or about 25% (w/v). In particular instances, the concentration of polyols (e.g., mannitol) or sucrose may be about 15% (w/v). In another example, the concentration of metal chelators (e.g., EDTA) may be about 0.01% (w/v) to about 1% (w/v), e.g., about 0.01%, about 0.02%, about 0.03%, about 0.04%, about 0.05%, about 0.06%, about 0.07%, about 0.08%, about 0.09%, about 0.1%, about 0.15%, about 0.2%, about 0.25%, about 0.3%, about 0.4%, about 0.45%, about 0.5%, about 0.6%, about 0.7%, about 0.8%, about 0.9%, or about 1% (w/v). In particular instances, the concentration of a metal chelator (e.g., EDTA) may be about 0.4% (w/v). In yet another example, the concentration of methionine and/or tryptophan may be about 0.1 mg/ml to about 10 mg/ml, e.g., about 0.1 mg/ml, about 0.5 mg/ml, about 1 mg/ml, about 2 mg/ml, about 3 mg/ml, about 4 mg/ml, about 5 mg/ml, about 6 mg/ml, about 7 mg/ml, about 8 mg/ml, about 9 mg/ml, or about 10 mg/ml. In some instances, the concentration of methionine and/or tryptophan is about 2 mg/ml.

For example, in some instances, the invention provides a pharmaceutical composition that includes: (i) an isolated antibody that binds to human tryptase, or an antigen-binding fragment thereof, wherein the antibody comprises the following six hypervariable regions (HVRs): (a) an HVR-H1 comprising the amino acid sequence of DYGMV (SEQ ID NO: 7); (b) an HVR-H2 comprising the amino acid sequence of FISSGSSTVYYADTMKG (SEQ ID NO: 2); (c) an HVR-H3 comprising the amino acid sequence of RNYDDWYFDV (SEQ ID NO: 8); (d) an HVR-L1 comprising the amino acid sequence of SASSSVTYMY (SEQ ID NO: 4); (e) an HVR-L2 comprising the amino acid sequence of RTSDLAS (SEQ ID NO: 5); and (f) an HVR-L3 comprising the amino acid sequence of QHYHSYPLT (SEQ ID NO: 6); (ii) N-acetyltryptophan (e.g., N-acetyl DL-tryptophan or N-acetyl D-tryptophan); and (iii) methionine (e.g., L-methionine or D-methionine).

Any suitable concentration of N-acetyltryptophan (e.g., N-acetyl DL-tryptophan or N-acetyl D-tryptophan) may be used in any of the compositions described herein. In some instances, the concentration of N-acetyltryptophan (e.g., N-acetyl DL-tryptophan or N-acetyl D-tryptophan) is about 0.05 mM to about 20 mM (e.g., about 0.05 mM to about 20 mM, about 0.05 mM to about 19 mM, about 0.05 mM to about 18 mM, about 0.05 mM to about 17 mM, about 0.05 mM to about 16 mM, about 0.05 mM to about 15 mM, about 0.05 mM to about 14 mM, about 0.05 mM to about 13 mM, about 0.05 mM to about 13 mM, about 0.05 mM to about 12 mM, about 0.05 mM to about 11 mM, about 0.05 mM to about 10 mM, about 0.05 mM to about 9 mM, about 0.05 mM to about 8 mM, about 0.05 mM to about 7 mM, about 0.05 mM to about 6 mM, about 0.05 mM to about 5 mM, about 0.05 mM to about 4 mM, about 0.05 mM to about 3 mM, about 0.05 mM to about 2 mM, about 0.05 mM to about 1 mM, about 0.1 mM to about 20 mM, about 0.1 mM to about 19 mM, about 0.1 mM to about 18 mM, about 0.1 mM to about 17 mM, about 0.1 mM to about 16 mM, about 0.1 mM to about 15 mM, about 0.1 mM to about 14 mM, about 0.1 mM to about 13 mM, about 0.1 mM to about 13 mM, about 0.1 mM to about 12 mM, about 0.1 mM to about 11 mM, about 0.1 mM to about 10 mM, about 0.1 mM to about 9 mM, about 0.1 mM to about 8 mM, about 0.1 mM to about 7 mM, about 0.1 mM to about 6 mM, about 0.1 mM to about 5 mM, about 0.1 mM to about 4 mM, about 0.1 mM to about 3 mM, about 0.1 mM to about 2 mM, about 0.1 mM to about 1 mM, about 0.1 mM to about 0.9 mM, about 0.1 to about 0.8 mM, about 0.1 mM to about 0.7 mM, about 0.1 mM to about 0.6 mM, about 0.1 mM to about 0.5 mM, about 0.1 mM to about 0.4 mM, about 0.1 mM to about 0.3 mM, about 0.2 mM to about 20 mM, about 0.2 mM to about 19 mM, about 0.2 mM to about 18 mM, about 0.2 mM to about 17 mM, about 0.2 mM to about 16 mM, about 0.2 mM to about 15 mM, about 0.2 mM to about 14 mM, about 0.2 mM to about 13 mM, about 0.2 mM to about 13 mM, about 0.2 mM to about 12 mM, about 0.2 mM to about 11 mM, about 0.2 mM to about 10 mM, about 0.2 mM to about 9 mM, about 0.2 mM to about 8 mM, about 0.2 mM to about 7 mM, about 0.2 mM to about 6 mM, about 0.2 mM to about 5 mM, about 0.2 mM to about 4 mM, about 0.2 mM to about 3 mM, about 0.2 mM to about 2 mM, about 0.2 mM to about 1 mM, about 0.2 mM to about 0.9 mM, about 0.2 to about 0.8 mM, about 0.2 mM to about 0.7 mM, about 0.2 mM to about 0.6 mM, about 0.2 mM to about 0.5 mM, about 0.2 mM to about 0.4 mM, about 0.2 mM to about 0.3 mM, about 0.3 mM to about 20 mM, about 0.3 mM to about 19 mM, about 0.3 mM to about 18 mM, about 0.3 mM to about 17 mM, about 0.3 mM to about 16 mM, about 0.3 mM to about 15 mM, about 0.3 mM to about 14 mM, about 0.3 mM to about 13 mM, about 0.3 mM to about 13 mM, about 0.3 mM to about 12 mM, about 0.3 mM to about 11 mM, about 0.3 mM to about 10 mM, about 0.3 mM to about 9 mM, about 0.3 mM to about 8 mM, about 0.3 mM to about 7 mM, about 0.3 mM to about 6 mM, about 0.3 mM to about 5 mM, about 0.3 mM to about 4 mM, about 0.3 mM to about 3 mM, about 0.3 mM to about 2 mM, about 0.3 mM to about 1 mM, about 0.3 mM to about 0.9 mM, about 0.3 to about 0.8 mM, about 0.3 mM to about 0.7 mM, about 0.3 mM to about 0.6 mM, about 0.3 mM to about 0.5 mM, or about 0.3 mM to about 0.4 mM). In some instances, the N-acetyltryptophan is at a concentration of about 0.1 mM to about 1 mM (e.g., about 0.1 mM, about 0.2 mM, about 0.3 mM, about 0.4 mM, about 0.5 mM, about 0.6 mM, about 0.7 mM, about 0.8 mM, about 0.9 mM, or about 1 mM). In particular instances, the concentration of N-acetyltryptophan (e.g., N-acetyl DL-tryptophan or N-acetyl D-tryptophan) is about 0.3 mM. In particular instances, the N-acetyltryptophan is or N-acetyl DL-tryptophan.

Any suitable concentration of methionine (e.g., L-methionine or D-methionine) may be used in any of the compositions described herein. For example, in some instances, the concentration of methionine (e.g., L-methionine or D-methionine) is about 0.1 mM to about 30 mM (e.g., about 0.1 mM to about 30 mM, about 0.1 mM to about 25 mM, about 0.1 mM to about 20 mM, about 0.1 mM to about 19 mM, about 0.1 mM to about 18 mM, about 0.1 mM to about 17 mM, about 0.1 mM to about 16 mM, about 0.1 mM to about 15 mM, about 0.1 mM to about 14 mM, about 0.1 mM to about 13 mM, about 0.1 mM to about 13 mM, about 0.1 mM to about 12 mM, about 0.1 mM to about 11 mM, about 0.1 mM to about 10 mM, about 0.1 mM to about 9 mM, about 0.1 mM to about 8 mM, about 0.1 mM to about 7 mM, about 0.1 mM to about 6 mM, about 0.1 mM to about 5 mM, about 0.1 mM to about 4 mM, about 0.1 mM to about 3 mM, about 0.1 mM to about 2 mM, about 0.1 mM to about 1 mM, about 1 mM to about 20 mM, about 1 mM to about 19 mM, about 1 mM to about 18 mM, about 1 mM to about 17 mM, about 1 mM to about 16 mM, about 1 mM to about 15 mM, about 1 mM to about 14 mM, about 1 mM to about 13 mM, about 1 mM to about 13 mM, about 1 mM to about 12 mM, about 1 mM to about 11 mM, about 1 mM to about 10 mM, about 1 mM to about 9 mM, about 1 mM to about 8 mM, about 1 mM to about 7 mM, about 1 mM to about 6 mM, about 1 mM to about 5 mM, about 1 mM to about 4 mM, about 1 mM to about 3 mM, about 1 mM to about 2 mM, about 2 mM to about 20 mM, about 2 mM to about 19 mM, about 2 mM to about 18 mM, about 2 mM to about 17 mM, about 2 mM to about 16 mM, about 2 mM to about 15 mM, about 2 mM to about 14 mM, about 2 mM to about 13 mM, about, 2 mM to about 13 mM, about 2 mM to about 12 mM, about 2 mM to about 11 mM, about 2 mM to about 10 mM, about 2 mM to about 9 mM, about 2 mM to about 8 mM, about 2 mM to about 7 mM, about 2 mM to about 6 mM, about 2 mM to about 5 mM, about 2 mM to about 4 mM, about 2 mM to about 3 mM, about 5 mM to about 20 mM, about 5 mM to about 19 mM, about 5 mM to about 18 mM, about 5 mM to about 17 mM, about 5 mM to about 16 mM, about 5 mM to about 15 mM, about 5 mM to about 14 mM, about 5 mM to about 13 mM, about 5 mM to about 13 mM, about 5 mM to about 12 mM, about 5 mM to about 11 mM, about 5 mM to about 10 mM, about 5 mM to about 9 mM, about 5 mM to about 8 mM, about 5 mM to about 7 mM, or about 5 mM to about 6 mM). In some instances, the methionine (e.g., L-methionine or D-methionine) is at a concentration of about 1 mM to about 10 mM (e.g., about 1 mM, about 2 mM, about 3 mM, about 4 mM, about 5 mM, about 6 mM, about 7 mM, about 8 mM, about 9 mM, or about 10 mM). In particular instances, the concentration of methionine (e.g., L-methionine or D-methionine) is about 5 mM. In other instances, the concentration of methionine is about 10 mM. In particular instances, the methionine is L-methionine.

In some instances, the presence of the antioxidant (e.g., N-acetyltryptophan (e.g., N-acetyl DL-tryptophan) and/or methionine (e.g., L-methionine or D-methionine)) reduces the percent oxidation of the anti-tryptase antibody at a particular residue (e.g., a tryptophan residue or a methionine residue, for example, in an HVR-H3 residue (e.g., W100 of the VH domain of hu31A.v1) or in an Fc residue (e.g., Fc residues M251, M357, and/or M427 (for example, of hu31A.v1)) by about 1%, about 2%, about 5%, about 6%, about 10%, about 15%, about 20%, about 25%, about 28%, about 30%, about 35%, about 40%, about 45%, about 50%, about 55%, about 60%, about 65%, about 70%, about 75%, about 80%, about 85%, about 90%, about 95%, about 96%, about 97%, about 98%, about 99%, or more, for example, relative to the percent oxidation at the residue in the absence of the antioxidant.

In instances where the antibody includes a VH domain W100 residue in HVR-H3 (e.g., hu31A.v11) that is susceptible to oxidation, in some instances, the VH domain W100 residue in HVR-H3 has a percent oxidation of less than about 35% (e.g., less than 35%, less than 34%, less than 33%, less than 32%, less than 31%, less than 30%, less than 29%, less than 28%, less than 27%, less than 26%, less than 25%, less than 24%, less than 23%, less than 22%, less than 21%, less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, less than 1%, or less). For example, in some instances, the W100 residue in HVR-H3 has a percent oxidation of less than about 35%. In other instances, the W100 residue in HVR-H3 has a percent oxidation of less than about 25%. In yet other instances, the W100 residue in HVR-H3 has a percent oxidation of less than about 15%. In still other instances, the W100 residue in HVR-H3 has a percent oxidation of less than about 10%. In other instances, the W100 residue in HVR-H3 has a percent oxidation of less than about 5%. In other instances, the W100 residue in HVR-H3 has a percent oxidation of less than about 4%, about 3%, about 2%, or about 1%.

As an example, in some instances where the antibody includes a VH domain W100 residue in HVR-H3 that is susceptible to oxidation, in some instances, the VH domain W100 residue in HVR-H3 has a percent oxidation of between about 1% to about 50%, between about 1% to about 45%, between about 1% to about 40%, between about 1% to about 35%, between about 1% to about 30%, between about 1% to about 25%, between about 1% to about 20%, between about 1% to about 15%, between about 1% to about 10%, between about 1% to about 5%, between about 1% to about 4%, between about 1% to about 3%, between about 1% to about 2%, between about 5% to about 50%, between about 5% to about 45%, between about 5% to about 50%, between about 5% to about 35%, between about 5% to about 30%, between about 5% to about 25%, between about 5% to about 20%, between about 5% to about 15%, between about 5% to about 10%, between about 10% to about 50%, between about 10% to about 45%, between about 10% to about 40%, between about 10% to about 35%, between about 10% to about 30%, between about 10% to about 25%, between about 10% to about 20%, between about 10% to about 15%, between about 15% to about 50%, between about 15% to about 45%, between about 15% to about 40%, between about 15% to about 35%, between about 15% to about 30%, between about 15% to about 25%, between about 15% to about 20%, between about 25% to about 50%, or between about 30% to about 50%.

Percent oxidation may be determined, for example, within about 1 month, 2 months, 3 months, 4 months, 5 months, 6 months, 7 months, 8 months 9 months, 10 months, 11 months, 12 months, 18 months, two years, or more from the initial production of an antibody or a pharmaceutical composition thereof. In some instances, percent oxidation is determined about 9 months, about 12 months, about 18 months, or two years from the initial production of an antibody or a pharmaceutical composition thereof.

The concentration of an antibody in a composition of the invention may range, for example, from about 1 mg/mL to about 350 mg/mL (e.g., about 1 mg/mL to about 350 mg/mL, about 1 mg/mL to about 325 mg/mL, about 1 mg/mL to about 300 mg/mL, about 1 mg/mL to about 275 mg/mL, about 1 mg/mL to about 250 mg/mL, about 1 mg/mL to about 225 mg/mL, about 1 mg/mL to about 200 mg/mL, about 1 mg/mL to about 175 mg/mL, about 1 mg/mL to about 150 mg/mL, about 1 mg/mL to about 125 mg/mL, about 1 mg/mL to about 100 mg/mL, about 1 mg/mL to about 75 mg/mL, about 1 mg/mL to about 50 mg/mL, about 1 mg/mL to about 25 mg/mL, about 25 mg/mL to about 350 mg/mL, about 25 mg/mL to about 325 mg/mL, about 25 mg/mL to about 300 mg/mL, about 25 mg/mL to about 275 mg/mL, about 25 mg/mL to about 250 mg/mL, about 25 mg/mL to about 225 mg/mL, about 25 mg/mL to about 200 mg/mL, about 25 mg/mL to about 175 mg/mL, about 25 mg/mL to about 150 mg/mL, about 25 mg/mL to about 125 mg/mL, about 25 mg/mL to about 100 mg/mL, about 25 mg/mL to about 75 mg/mL, about 25 mg/mL to about 50 mg/mL, about 50 mg/mL to about 350 mg/mL, about 50 mg/mL to about 325 mg/mL, about 50 mg/mL to about 300 mg/mL, about 50 mg/mL to about 275 mg/mL, about 50 mg/mL to about 250 mg/mL, about 50 mg/mL to about 225 mg/mL, about 50 mg/mL to about 200 mg/mL, about 50 mg/mL to about 175 mg/mL, about 50 mg/mL to about 150 mg/mL, about 50 mg/mL to about 125 mg/mL, about 50 mg/mL to about 100 mg/mL, about 50 mg/mL to about 75 mg/mL, about 75 mg/mL to about 350 mg/mL, about 75 mg/mL to about 325 mg/mL, about 75 mg/mL to about 300 mg/mL, about 75 mg/mL to about 275 mg/mL, about 75 mg/mL to about 250 mg/mL, about 75 mg/mL to about 225 mg/mL, about 75 mg/mL to about 200 mg/mL, about 75 mg/mL to about 175 mg/mL, about 75 mg/mL to about 150 mg/mL, about 75 mg/mL to about 125 mg/mL, about 75 mg/mL to about 100 mg/mL, about 100 mg/mL to about 350 mg/mL, about 100 mg/mL to about 325 mg/mL, about 100 mg/mL to about 300 mg/mL, about 100 mg/mL to about 275 mg/mL, about 100 mg/mL to about 250 mg/mL, about 100 mg/mL to about 225 mg/mL, about 100 mg/mL to about 200 mg/mL, about 100 mg/mL to about 175 mg/mL, about 100 mg/mL to about 150 mg/mL, about 100 mg/mL to about 125 mg/mL, or about 150 mg/mL to about 175 mg/mL. In some instances, the antibody is at a concentration of about 50 mg/mL to about 200 mg/mL (e.g., about 50 mg/mL, about 60 mg/mL, about 70 mg/mL, about 80 mg/mL, about 90 mg/mL, about 100 mg/mL, about 110 mg/mL, about 120 mg/mL, about 130 mg/mL, about 140 mg/mL, about 150 mg/mL, about 160 mg/mL, about 170 mg/mL, about 180 mg/mL, about 190 mg/mL, or about 200 mg/mL. In particular instances, the antibody concentration is about 150 mg/mL.

Any of the compositions described herein may include one or more additional excipients selected from the group consisting of a stabilizer, a buffer, a surfactant, and a tonicity agent. In some instances, the buffer comprises arginine succinate and/or histidine succinate. In some instances, the buffer includes arginine succinate and histidine succinate.

Any suitable concentration of arginine succinate may be used. For example, in some instances, the concentration of arginine succinate is about 10 mM to about 500 mM (e.g., about 10 mM, about 20 mM, about 30 mM, about 40 mM, about 50 mM, about 75 mM, about 100 mM, about 125 mM, about 150 mM, about 175 mM, about 200 mM, about 225 mM, about 250 mM, about 275 mM, about 300 mM, about 325 mM, about 350 mM, about 375 mM, about 400 mM, about 425 mM, about 450 mM, about 475 mM, or about 500 mM). For example, in some instances, the concentration of arginine succinate is about 100 mM to about 300 mM, about 125 mM to about 300 mM, about 150 mM to about 300 mM, about 175 mM to about 300 mM, about 200 mM to about 300 mM, about 225 mM to about 300 mM, about 250 mM to about 300 mM, about 275 mM to about 300 mM, about 100 mM to about 250 mM, about 125 mM to about 250 mM, about 150 mM to about 250 mM, about 175 mM to about 250 mM, about 200 mM to about 250 mM, about 100 mM to about 225 mM, about 125 mM to about 225 mM, about 150 mM to about 225 mM, about 175 mM to about 225 mM, about 200 mM to about 225 mM, about 100 mM to about 200 mM, about 125 mM to about 200 mM, about 150 mM to about 200 mM, or about 175 mM to about 200 mM. In particular instances, the concentration of arginine succinate is about 200 mM.

Any suitable concentration of histidine succinate may be used. For example, in some embodiments, the concentration of histidine succinate is about 1 mM to about 100 mM (e.g., about 1 mM, about 5 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, or about 100 mM). In particular instances, the concentration of histidine succinate is about 20 mM.

Any of the compositions described herein may have a pH of about 4.0 to about 7.0 (e.g., about 4.0, about 4.5, about 5.0, about 5.5, about 6.0, about 6.5, or about 7.0). In some instances, the pH is from about 4.5 to about 7.0 (e.g., about 4.5, about 5.0, about 5.5, about 6.0, about 6.5, or about 7.0). In some instances, the pH is from about 4.5 to about 6.5 (e.g., about 4.5, about 4.6, about 4.7, about 4.8, about 4.9, about 5, about 5.1, about 5.2, about 5.3, about 5.4, about 5.5 about 5.6, about 5.7, about 5.8, about 5.9, about 6, about 6.1, about 6.2, about 6.3, about 6.4, or about 6.5). In some instances, the pH is from about 5.0 to about 6.0 (e.g., about 5.0, about 5.1, about 5.2, about 5.3, about 5.4, about 5.5, about 5.6, about 5.7, about 5.8, about 5.9, or about 6.0). In some instances, the pH is about 5.5.

Any suitable surfactant may be used in the compositions described herein. In some instances, the surfactant is poloxamer 188 or polysorbate 20. Any suitable concentration of poloxamer 188 may be used. For example, the concentration of poloxamer 188 may be about 0.005% to about 0.5%, about 0.005% to about 0.05%, or about 0.02%. In some instances, the concentration of poloxamer 188 is about 0.01%, about 0.02%, about 0.03%, about 0.04%, about 0.05%, about 0.06%, about 0.07%, about 0.08%, about 0.09%, or about 0.1%. In particular embodiments, the concentration of poloxamer 188 is about 0.02%. Any suitable concentration of polysorbate 20 may be used. For example, the concentration of polysorbate 20 may be about 0.005% to about 0.5%, about 0.005% to about 0.05%, or about 0.02%. In some instances, the concentration of polysorbate 20 is about 0.01%, about 0.02%, about 0.03%, about 0.04%, about 0.05%, about 0.06%, about 0.07%, about 0.08%, about 0.09%, or about 0.1%.

In particular instances, the composition includes about 150 mg/mL of an anti-tryptase antibody described herein (e.g., hu31A.v11), about 200 mM arginine succinate, about 20 mM histidine succinate, about 0.3 mM N-acetyl DL-tryptophan), about 5 mM L-methionine, about 0.02% poloxamer 188, and has a pH of about 5.8.

Any of the compositions described herein may be formulated for administration by any suitable route. In particular instances, the composition is formulated for subcutaneous administration or intravenous administration. In some instances, the composition is formulated for subcutaneous administration.

G. Therapeutic Methods and Compositions

Any of the anti-tryptase antibodies or pharmaceutical compositions of the invention may be used in therapeutic methods.

In one aspect, an anti-tryptase antibody, or a pharmaceutical composition thereof, for use as a medicament is provided. In further aspects, an anti-tryptase antibody, or a pharmaceutical composition thereof, for use in treating a disorder is provided. In certain embodiments, an anti-tryptase antibody, or a pharmaceutical composition thereof, for use in a method of treatment is provided. In certain embodiments, the invention provides an anti-tryptase antibody, or a pharmaceutical composition thereof, for use in a method of treating a subject having a disorder that involves administering to the subject an effective amount of the anti-tryptase antibody. In some embodiments, the method further includes administering to the subject an effective amount of at least one additional therapeutic agent, for example, as described below. A "subject" according to any of the above embodiments is preferably a human.

In a further aspect, the invention provides for the use of an anti-tryptase antibody, or a pharmaceutical composition thereof, in the manufacture or preparation of a medicament. In one embodiment, the medicament is for treatment of a disorder. In a further embodiment, the medicament is for use in a method of treating a disorder comprising administering to a subject having the disorder an effective amount of the medicament. In one such embodiment, the method further comprises administering to the subject an effective amount of at least one additional therapeutic agent, e.g., as described below. A "subject" according to any of the above embodiments may be a human.

In a further aspect, the invention provides a method for treating a disorder, including, for example, a pulmonary disorder (e.g., asthma (e.g., Th2-high asthma or Th2-low asthma), airway hyperresponsiveness, or COPD), an autoimmune disorder (e.g., rheumatoid arthritis, psoriasis, eosinophilic esophagitis, IBD, or Crohn's disease), an inflammatory disorder (e.g., chronic idiopathic urticaria (CIU or CSU), anaphylaxis, atopic dermatitis, or allergic rhinitis), a fibrotic disorder (e.g., IPF), a granulocytic (neutrophilic or eosinophilic) disorder, a monocytic disorder, a lymphocytic disorder, a disorder associated with increased numbers or distribution of normal or aberrant tissue resident cells (such as mast cells, macrophages, or lymphocytes) or stromal cells (such as fibroblasts, myofibroblasts, smooth muscle cells, epithelia, or endothelia, and a tryptase-associated disorder or tryptase-mediated disorder. In one embodiment, the method comprises administering to a subject having a disorder an effective amount of an anti-tryptase antibody, or a pharmaceutical composition thereof. In one such embodiment, the method further comprises administering to the subject an effective amount of at least one additional therapeutic agent, as described below. A "subject" according to any of the above embodiments may be a human.

In a further aspect, the invention provides pharmaceutical formulations comprising any of the anti-tryptase antibodies provided herein, e.g., for use in any of the above therapeutic methods. In one embodiment, a pharmaceutical formulation comprises any of the anti-tryptase antibodies provided herein and a pharmaceutically acceptable carrier. In another embodiment, a pharmaceutical formulation comprises any of the anti-tryptase antibodies provided herein and at least one additional therapeutic agent, for example, as described below. Any of the pharmaceutical formulations described in Section F (e.g., those that include an antioxidant such as N-acetyltryptophan and/or methionine) above may be used in any of the uses or methods described herein.

In some embodiments, the disorder is an autoimmune disorder, an inflammatory disorder, a fibrotic disorder, a granulocytic (neutrophilic or eosinophilic) disorder, a monocytic disorder, a lymphocytic disorder, or a disorder associated with increased numbers or distribution of normal or aberrant tissue resident cells (such as mast cells, macrophages, or lymphocytes) or stromal cells (such as fibroblasts, myofibroblasts, smooth muscle cells, epithelia, or endothelia). In some embodiments, the disorder is a pulmonary disorder.

In some embodiments, the pulmonary disorder is associated with granulocytic (eosinophilic and/or neutrophilic) pulmonary inflammation, infection-induced pulmonary conditions (including those associated with viral (e.g., influenza, parainfluenza, rhinovirus, human metapneumovirus, and respiratory syncytial virus), bacterial, or fungal (e.g., *Aspergilius*) triggers. In some embodiments, the disorder is an allergen-induced pulmonary condition, a toxic environmental pollutant-induced pulmonary condition (e.g., asbestosis, silicosis, or berylliosis), a gastric aspiration-induced pulmonary condition, or associated with immune dysregulation or an inflammatory condition with genetic predisposition such as cystic fibrosis. In some embodiments, the disorder is a physical trauma-induced pulmonary condition (e.g., ventilator injury), emphysema, cigarette-induced emphysema, bronchitis, sarcoidosis, histiocytosis, lymphangiomyomatosis, acute lung injury, acute respiratory distress syndrome, chronic lung disease, bronchopulmonary dysplasia, pneumonia (e.g., community-acquired pneumonia, nosocomial pneumonia, ventilator-associated pneumonia, viral pneumonia, bacterial pneumonia, and severe pneumonia), airway exacerbations, and acute respiratory distress syndrome (ARDS)). In some embodiments, the pulmonary disorder is COPD.

In some embodiments of any of the methods, the pulmonary disorder is asthma. In some embodiments, the asthma is persistent chronic severe asthma with acute events of worsening symptoms (exacerbations or flares) that can be life threatening. In some embodiments, the asthma is atopic (also known as allergic) asthma, non-allergic asthma (e.g., often triggered by infection with a respiratory virus (e.g., influenza, parainfluenza, rhinovirus, human metapneumovirus, and respiratory syncytial virus) or inhaled irritant (air pollutants, smog, diesel particles, volatile chemicals and gases indoors or outdoors, or even by cold dry air).

In some embodiments of any of the methods, the asthma is intermittent or exercise-induced, asthma due to acute or chronic primary or second-hand exposure to "smoke" (typically cigarettes, cigars, pipes), inhaling or "vaping" (tobacco, marijuana or other such substances), or asthma triggered by recent ingestion of aspirin or related NSAIDS. In some embodiments, the asthma is mild, or corticosteroid naïve asthma, newly diagnosed and untreated asthma, or not previously requiring chronic use of inhaled topical or systemic steroids to control the symptoms (cough, wheeze, shortness of breath/breathlessness, or chest pain). In some embodiments, the asthma is chronic, corticosteroid resistant asthma, corticosteroid refractory asthma, asthma uncontrolled on corticosteroids or other chronic asthma controller medications.

In some embodiments of any of the methods, the asthma is moderate to severe asthma. In certain embodiments, the asthma is Th2-high asthma. In some embodiments, the asthma is severe asthma. In some embodiments, the asthma is atopic asthma, allergic asthma, non-allergic asthma (e.g., due to infection and/or respiratory syncytial virus (RSV)), exercise-induced asthma, aspirin sensitive/exacerbated asthma, mild asthma, moderate to severe asthma, corticosteroid naïve asthma, chronic asthma, corticosteroid resistant asthma, corticosteroid refractory asthma, newly diagnosed and untreated asthma, asthma due to smoking, asthma uncontrolled on corticosteroids. In some embodiments, the asthma is T helper lymphocyte type 2 (Th2) or type 2 (Th2) high, or Type 2 (T2)-driven asthma. In some embodiments, the asthma is eosinophilic asthma. In some embodiments, the asthma is allergic asthma. In some embodiments, the individual has been determined to be Eosinophilic Inflammation Positive (EIP). See WO2015/061441. In some embodiments, the asthma is periostin-high asthma (e.g., having periostin level at least about any of 20 ng/mL, 25 ng/mL, or 50 ng/mL serum). Methods of determining serum periostin levels are provided, for example, in US2012/0156194. In some embodiments, the asthma is eosinophil-high asthma (e.g., at least about any of 150, 200, 250, 300, 350, 400 eosinophil counts/ml blood). In certain embodiments, the asthma is Th2-low asthma or nonTh2-driven asthma. In some embodiments, the individual has been determined to be Eosinophilic Inflammation Negative (EIN). See WO2015/061441. In some embodiments, the asthma is periostin-low asthma (e.g., having periostin level less than about 20 ng/mL serum). In some embodiments, the asthma is eosinophil-low asthma (e.g., less than about 150 eosinophil counts/µl blood or less than about 100 eosinophil counts/µl blood). In certain embodiments, the individual exhibits elevated level of FeNO (fractional exhaled nitric acid) and/or elevated level of IgE. For example, in some instances, the individual exhibits a FeNO level above about 250 parts per billion (ppb), above about 275 ppb, above about 300 ppb, above about 325 ppb, above about 325 ppb, or above about 350 ppb. In some instances, the individual has an IgE level that is above 50 IU/ml. In some embodiments, the individual has a forced expiratory volume in 1 second (FEV1) of 40% to 80% of predicted.

In other embodiments of any of the methods, the autoimmune disorder, inflammatory disorder, fibrotic disorder, neutrophilic disorder, or eosinophilic disorder is pulmonary fibrosis. In some embodiments, the pulmonary fibrosis is idiopathic pulmonary fibrosis (IPF).

In still further embodiments of any of the methods, the autoimmune disorder, inflammatory disorder, fibrotic disorder, granulocytic (neutrophilic or eosinophilic) disorder, monocytic disorder, or lymphocytic disorder is esophagitis (e.g., eosinophilic esophagitis), allergic rhinitis, non-allergic rhinitis, rhinosinusitis with polyps, nasal polyposis, bronchitis, chronic pneumonia, allergic bronchopulmonary aspergillosis, airway inflammation, allergic rhinitis, bronchiectasis, and/or chronic bronchitis.

In some embodiments of any of the methods, the autoimmune disorder, inflammatory disorder, fibrotic disorder, granulocytic (neutrophilic or eosinophilic) disorder, monocytic disorder, or lymphocytic disorder, is arthritis. In some embodiments, the arthritis is rheumatoid arthritis. In some embodiments, the arthritis is osteoarthritis, rheumatoid arthritis, juvenile arthritis, juvenile rheumatoid arthritis, early arthritis, polyarticular rheumatoid arthritis, systemic-onset rheumatoid arthritis, enteropathic arthritis, reactive arthritis, psoriatic arthritis, and/or arthritis as a result of injury.

In yet other embodiments of any of the methods, the autoimmune disorder, inflammatory disorder, fibrotic disorder, granulocytic (neutrophilic or eosinophilic) disorder, monocytic disorder, or lymphocytic disorder is a gastrointestinal inflammatory condition. In some embodiments, the gastrointestinal inflammatory condition is IBD (inflammatory bowel disease), ulcerative colitis (UC), Crohn's disease (CD), colitis (e.g., colitis caused by environmental insults (e.g., caused by or associated with a therapeutic regimen, such as chemotherapy, radiation therapy, etc.)), infectious colitis, ischemic colitis, collagenous or lymphocytic colitis, necrotizing enterocolitis, colitis in conditions such as chronic granulomatous disease or celiac disease, food allergies, gastritis, gastroenteritis, infectious gastritis or enterocolitis (e.g., *Helicobacter pylori*-infected chronic active gastritis), esophagitis, and other forms of gastrointestinal inflammation caused by an infectious agent, or indeterminate colitis.

In some embodiments of any of the methods, the autoimmune disorder, inflammatory disorder, fibrotic disorder, granulocytic (neutrophilic or eosinophilic) disorder, monocytic disorder, or lymphocytic disorder is a gastrointestinal inflammatory condition. In some embodiments, the gastrointestinal inflammatory condition is IBD (inflammatory bowel disease). In some embodiments the inflammatory bowel disease is ulcerative colitis (UC) or Crohn's disease (CD). In some embodiments, the gastrointestinal inflammatory condition is colitis (e.g., colitis caused by environmental insults (e.g., caused by or associated with a therapeutic regimen, such as chemotherapy, radiation therapy, etc.), infectious colitis, ischemic colitis, collagenous or lymphocytic colitis, necrotizing enterocolitis, colitis in conditions such as chronic granulomatous disease or celiac disease, food allergies, gastritis, gastroenteritis, infectious gastritis or enterocolitis (e.g., *Helicobacter pylori*-infected chronic active gastritis), and other forms of gastrointestinal inflammation caused by an infectious agent, or indeterminate colitis.

In some embodiments of any of the methods, the gastrointestinal inflammatory condition is ulcerative colitis (UC) or Crohn's disease (CD). In some embodiments, the gastrointestinal inflammatory condition is ulcerative colitis (UC). In some embodiments, the ulcerative colitis is mild to moderate distal colitis. In some embodiments, the ulcerative colitis is mild to moderate extensive colitis. In some embodiments, the ulcerative colitis is severe colitis. In some embodiments, the gastrointestinal inflammatory condition is Crohn's disease (CD). In some embodiments, the Crohn's disease is in acute disease stage. In some embodiments, the Crohn's disease is in induced clinical remission stage. In some embodiments, the Crohn's disease is in maintain response/remission stage. In some embodiments, the Crohn's disease is mild to moderate disease. In some embodiments, the Crohn's disease is moderate to severe disease. In some embodiments, the Crohn's disease is severe/fulminant disease. In some embodiments, the Crohn's disease is ileal, ileocolonic, or colonic disease.

In some embodiments of any of the methods, the autoimmune disorder, inflammatory disorder, fibrotic disorder, granulocytic (neutrophilic or eosinophilic) disorder, monocytic disorder, or lymphocytic disorder, or disorder associated with increased numbers or distribution of normal or aberrant tissue resident cells (such as mast cells, macrophages, or lymphocytes) or stromal cells (such as fibroblasts, myofibroblasts, smooth muscle cells, epithelia, or endothelia) is lupus or Systemic Lupus Erythematosus (SLE), or one or more organ-specific manifestations of lupus (e.g., lupus nephritis (LN) affecting the kidney, or extra-renal lupus (ERL) affecting the blood and/or lymphoid organs (lymph nodes, spleen, thymus, and associated lymphatic vessels), and/or joints and/or other organs, but not necessarily the kidney).

In some embodiments of any of the methods, the autoimmune disorder, inflammatory disorder, or fibrotic disorder is related to sepsis and/or trauma, HIV infection, or idiopathic (of unknown etiology) such as ANCA-associated vaculitides (AAV), granulomatosis with polyangiitis (formerly known as Wegener's granulomatosis), Behcet's disease, cardiovascular disease, eosinophilic bronchitis, Reiter's Syndrome, SEA Syndrome (Seronegativity, Enthesopathy, Arthropathy Syndrome), ankylosing spondylitis, dermatomyositis, scleroderma, e.g., systemic scleroderma also called systemic sclerosis, vasculitis (e.g., Giant Cell Arteritis (GCA), also called temporal arteritis, cranial arteritis or Horton disease), myositis, polymyositis, dermatomyositis, polyarteritis nodosa, arteritis, polymyalgia rheumatica, sarcoidosis, primary biliary sclerosis, sclerosing cholangitis, Sjogren's syndrome, psoriasis, plaque psoriasis, guttate psoriasis, inverse psoriasis, pustular psoriasis, erythrodermic psoriasis, dermatitis, atopic dermatitis, pemphigus, e.g., pemphigus vulgaris, atherosclerosis, lupus, Still's disease, myasthenia gravis, celiac disease, multiple sclerosis (MS) of the relapsing-remitting (RRMS) or primary progressive (PPMS) or secondary progressive (SPMS) subtypes, Guillain-Barre disease, Type I diabetes mellitus (T1DM) or insulin-dependent (IDDM) or juvenile onset DM type, thyroiditis (e.g., Graves' disease), coeliac disease, Churg-Strauss syndrome, myalgia syndrome, hypereosinophilic syndrome, oedematous reactions including episodic angioedema, helminth infections, onchocercal dermatitis, eosinophilic esophagitis, eosinophilic enteritis, eosinophilic colitis, obstructive sleep apnea, endomyocardial fibrosis, Addison's disease, Raynaud's disease or phenomenon, autoimmune hepatitis, graft versus host disease (GVHD), or organ transplant rejection.

In some embodiments of any of the methods, the disorder is an inflammatory disorder of the skin. In some embodiments, the disorder is atopic dermatitis or onchocercal dermatitis. In some embodiments, the disorder is chronic idiopathic urticaria (CIU or CSU). In some embodiments of any of the methods, the method further comprises administering an IL-13 antagonist, an IL-33 antagonist, an IgE antagonist, a calcium inhibitor, a leukotrieine inhibitor, or an antihistamine. In some embodiments, the IL-13 antagonist is lebrikizumab. In some embodiments, the IgE antagonist is omalizumab or ligelizumab.

In some embodiments of any of the methods, the autoimmune disorder, inflammatory disorder, fibrotic disorder, neutrophilic disorder, or eosinophilic disorder is a fibrotic disorder. In some embodiments, the fibrotic disorders include lung fibrosis, liver fibrosis (e.g., fibrosis associated with cirrhosis (e.g., alcohol-induced cirrhosis, viral-induced cirrhosis, post-hepatitis C cirrhosis, and primary biliary cirrhosis), schistosomiasis, cholangitis (e.g., sclerosing cholangitis), and autoimmune-induced hepatitis), kidney fibrosis (e.g., tubulointerstitial fibrosis, scleroderma, diabetic nephritis, and glomerular nephritis), dermal fibrosis (e.g., scleroderma, hypertrophic and keloid scarring, nephrogenic fibrosing dermatopathy, and burns), myelofibrosis, neurofibromatosis, fibroma, intestinal fibrosis, and fibrotic adhesions resulting from surgical procedures), heart fibrosis (e.g., fibrosis associated with myocardial infarction), vascular fibrosis (e.g., fibrosis associated with postangioplasty arterial restenosis and atherosclerosis), eye fibrosis (e.g., fibrosis associated with post-cataract surgery, proliferative vitreoretinopathy, and retro-orbital fibrosis), and bone marrow fibrosis (e.g., idiopathic myelofibrosis and drug-induced myelofibrosis). The fibrosis can be organ-specific or systemic (e.g., systemic sclerosis and fibrosis associated with GVHD). In some embodiments, the fibrotic disorder is pulmonary fibrosis. In some embodiments, the pulmonary fibrosis is fibrosing interstitial pneumonia. In some embodiments, the pulmonary fibrosis is idiopathic pulmonary fibrosis (IPF), also known as cryptogenic fibrosing alveolitis. In some embodiments, the IPF is gender, age and physiology (GAP)-stage I. In some embodiments, the IPF is GAP-stage II. In some embodiments, the IPF is GAP-stage III. In some embodiments, the pulmonary fibrosis is sporadic IPF. In some embodiments, the pulmonary fibrosis is familial pulmonary fibrosis. In some embodiments, the pulmonary fibrosis is combined pulmonary fibrosis and emphysema. In some embodiments, the pulmonary fibrosis is associated with one or more of the following: usual interstitial pneumonia; idiopathic interstitial pneumonia; desquamative interstitial pneumonia; respiratory bronchiolitis-interstitial lung disease; acute interstitial pneumonia; nonspecific interstitial pneumonia; sarcoidosis; cryptogenic organizing pneumonia; eosinophilic pneumonia; infection; exposure to occupational or environmental agents; cigarette smoking; interstitial lung disease induced by drugs or radiation; rheumatic disease-associated interstitial lung disease; lymphoid interstitial pneumonia; pleuropulmonary fibroelastosis; pulmonary Langerhans cell histiocytosis; systemic sclerosis-interstitial lung disease; Hermansky-Pudlak syndrome; and telomeropathy.

In some embodiments of any of the methods, the autoimmune disorder, inflammatory disorder, fibrotic disorder, neutrophilic disorder, or eosinophilic disorder is chronic obstructive pulmonary disease (COPD). In some embodiments, the COPD is Global Initiative for Chronic Obstructive Lung Disease (GOLD) category A. In some embodiments, the COPD is GOLD category B. In some embodiments, the COPD is GOLD category C. In some embodiments, the COPD is GOLD category D. In some embodiments, the COPD is chronic bronchitis. In some embodiments, the COPD is emphysema. In some embodiments, the emphysema is proximal acinar, panacinar, or distal acinar emphysema. In some embodiments, the emphysema is cigarette-induced emphysema. In some embodiments, the COPD is associated with exposure to particulate dusts, chemical fumes, and/or air pollution. In some embodiments, the COPD is associated with impaired lung development. In some embodiments, the COPD is chronic obstructive asthma. In some embodiments, the COPD is associated with alpha-1 antitrypsin deficiency. In some embodiments, the COPD is associated with serine protease inhibitor clade E, member 2 (SERPINE2) disruption. In some embodiments, the COPD is COPD with persistent systemic inflammation. In some embodiments, the COPD is eosinophilic or T-helper type 2 ($T_H2$) high COPD. In some embodiments, the COPD is COPD with persistent bacterial colonization. In some embodiments, the COPD is COPD with frequent exacerbations. In some embodiments, the autoimmune disorder, inflammatory disorder, fibrotic disorder, neutrophilic disorder, or eosinophilic disorder is asthma-COPD overlap syndrome (ACOS). In some embodiments, the ACOS is eosinophil-predominant, neutrophil-predominant, mixed-pattern, or no inflammation (paucigranulocytic) ACOS. In some embodiments, the autoimmune disorder, inflammatory disorder, fibrotic disorder, a neutrophilic disorder, or an eosinophilic disorder is COPD-obstructive sleep apnea (OSA) overlap syndrome.

Antibodies of the invention, or pharmaceutical compositions thereof, can be used either alone or in combination with other agents in a therapy. For instance, an antibody of the invention, or a pharmaceutical compositions thereof, may be co-administered with at least one additional therapeutic agent. In certain embodiments, an additional therapeutic agent is an interleukin-13 (IL-13) binding antagonist, an interleukin-17 (IL-17) axis binding antagonist, an interleukin-5 (IL-5) axis binding antagonist, or an IL-33 axis binding antagonist. In some embodiments, the IL-13 axis binding antagonist is an anti-IL-13 antibody, for example, lebrikizumab. In some embodiments, the IL-5 axis binding antagonist is an IL-5 binding antagonist or an IL-5 receptor binding antagonist. In some embodiments, an IL-33 axis binding antagonist is an IL-33 binding antagonist or an ST2 binding antagonist. In some embodiments, the IL-33 binding antagonist is an anti-IL-33 antibody.

In some embodiments, an additional therapeutic agent is an asthma therapy, as described below. Moderate asthma is currently treated with a daily inhaled anti-inflammatory-corticosteroid or mast cell inhibitor such as cromolyn sodium or nedocromil plus an inhaled beta2-agonist as needed (3-4 times per day) to relieve breakthrough symptoms or allergen- or exercise-induced asthma. Exemplary inhaled corticosteroids include QVAR®, PULMICORT®, SYMBICORT®, AEROBID®, FLOVENT®, FLONASE®, ADVAIR®, and AZMACORT®. Additional asthma therapies include long acting bronchial dilators (LABD). In certain embodiments, the LABD is a long-acting beta-2 agonist (LABA), leukotriene receptor antagonist (LTRA), long-acting muscarinic antagonist (LAMA), theophylline, or oral corticosteroids (OCS). Exemplary LABDs include SYMBICORT®, ADVAIR®, BROVANA®, FORADIL®, PERFOROMIST™, and SEREVENT®.

In some embodiments of any of the methods, the method further comprises administering a bronchodilator or asthma symptom controller medication. In some embodiments, the bronchodilator or asthma controller medication is a β2-adrenergic agonist, such as a short-acting 32-agonist (SABA) (such as albuterol), or a long-acting β2-adrenergic agonist (LABA). In some embodiments, the LABA is salmeterol, abediterol, indacaterol, vilanterol, and/or formoterol (formoterol fumarate dehydrate). In some embodiments, the asthma controller medication is a Leukotriene Receptor Antagonist (LTRA). In some embodiments, the LTRA is montelukast, zafirlukast, and/or zileuton. In some embodiments, the bronchodilator or asthma controller medication is a muscarinic antagonist, such as a long-acting muscarinic acetylcholine receptor (cholinergic) antagonist (LAMA). In some embodiments, the LAMA is glycopyrronium. In some embodiments, the bronchodilator or asthma controller medication is an agonist of an ion channel such as a bitter taste receptor (such as TAS2R).

In some embodiments of any of the methods, the method further comprises administering a bronchodilator. In some embodiments, the bronchodilator is an inhaled bronchodilator. In some embodiments, the inhaled bronchodilator is a 32-adrenergic agonist. In some embodiments, the 32-adrenergic agonist is a short-acting 32-adrenergic agonist (SABA). In some embodiments, the SABA is bitolterol, fenoterol, isoproterenol, levalbuterol, metaproterenol, pirbuterol, procaterol, ritodrine, albuterol, and/or terbutaline. In some embodiments, the 32-adrenergic agonist is a long-acting 32-adrenergic agonist (LABA). In some embodiments, the LABA is arformoterol, bambuterol, clenbuterol, formoterol, salmeterol, abediterol, carmoterol, indacaterol, olodaterol, and/or vilanterol. In some embodiments, the inhaled bronchodilator is a muscarinic receptor antagonist. In some embodiments, the muscarinic receptor antagonist is a short-acting muscarinic receptor antagonist (SAMA). In some embodiments, the SAMA is ipratropium bromide. In some embodiments, the muscarinic receptor antagonist is a long-acting muscarinic receptor antagonist (LAMA). In some embodiments, the LAMA is tiotropium bromide, glycopyrronium bromide, umeclidinium bromide, aclidinium bromide, and/or revefenacin. In some embodiments, the inhaled bronchodilator is a SABA/SAMA combination. In some embodiments, SABA/SAMA combination is albuterol/ipratropium. In some embodiments, the inhaled bronchodilator is a LABA/LAMA combination. In some embodiments, the LABA/LAMA combination is formoterol/aclidinium, formoterol/glycopyrronium, formoterol/tiotropium, indacaterol/glycopyrronium, indacaterol/tiotropium, olodaterol/tiotropium, salmeterol/tiotropium, and/or vilanterol/umeclidinium. In some embodiments, the inhaled bronchodilator is a bifunctional bronchodilator. In some embodiments, the bifunctional bronchodilator is a muscarinic antagonist/β2-agonist (MABA). In some embodiments, the MABA is batefenterol, THRX 200495, AZD 2115, LAS 190792, TE13252, PF-3429281 and/or PF-4348235. In some embodiments, the inhaled bronchodilator is an agonist of TAS2R. In some embodiments, the bronchodilator is a nebulized SABA. In some embodiments, the nebulized SABA is albuterol and/or levalbuterol. In some embodiments, the bronchodilator is a nebulized LABA. In some embodiments, the nebulized LABA is arformoterol and/or formoterol. In some embodiments, the bronchodilator is a nebulized SAMA. In some embodiments, the nebulized SAMA is ipratropium. In some embodiments, the bronchodilator is a nebulized LAMA. In some embodiments, the nebulized LAMA is glycopyrronium and/or revefenacin. In some embodiments, the bronchodilator is a nebulized SABA/SAMA combination. In some embodiments, the nebulized SABA/SAMA combination is albuterol/ipratropium. In some embodiments, the bronchodilator is a leukotriene receptor antagonist (LTRA). In some embodiments, the LTRA is montelukast, zafirlukast, and/or zileuton. In some embodiments, the bronchodilator is a methylxanthine. In some embodiments, the methylxanthine is theophylline.

In some embodiments of any of the methods, the method further comprises administering an immunomodulator. In some embodiments, the immunomodulator is an antibody to immunoglobulin type E (IgE) or anti-IgE (an IgE inhibitor). In some embodiments, the anti-IgE is omalizumab and/or ligelizumab. In some embodiments of any of the methods, the method further comprises cromolyn. In some embodiments of any of the methods, the method further comprises methylxanthine. In some embodiments, the methylxanthine is theophylline or caffeine.

In some embodiments of any of the methods, the method further comprises administering one or more corticosteroids, such as an inhaled corticosteroid (ICS) or an oral corticosteroid. Non-limiting exemplary corticosteroids include inhaled corticosteroids, such as beclomethasone dipropionate, budesonide, ciclesonide, flunisolide, fluticasone propionate, fluticasone furoate, mometasone, and/or triamcinolone acetonide and oral corticosteroids, such as methylprednisolone, prednisolone, and prednisone. In some embodiments, the corticosteroid is an ICS. In some embodiments, the ICS is beclomethasone, budesonide, flunisolide, fluticasone furoate, fluticasone propionate, mometasone, ciclesonide, and/or triamcinolone. In some embodiments of any of the methods, the method further comprises administering an ICS/LABA and/or LAMA combination. In some embodiments, the ICS/LABA and/or LAMA combination is fluticasone propionate/salmeterol, budesonide/formoterol, mometasone/formoterol, fluticasone furoate/vilanterol, fluticasone propionate/formoterol, beclomethasone/formoterol, fluticasone furoate/umeclidinium, fluticasone furoate/vilanterol/umeclidinium, fluticasone/salmeterol/tiotropium, beclomethasone/formoterol/glycopyrronium, budesonide/formoterol/glycopyrronium, and/or budesonide/formoterol/tiotropium. In some embodiments of any of the methods, the method further comprises administering a nebulized corticosteroid. In some embodiments, the nebulized corticosteroid is budesonide. In some embodiments of any of the methods, the method further comprises administering an oral or intravenous corticosteroid. In some embodiments, the oral or intravenous corticosteroid is prednisone, prednisolone, methylprednisolone, and/or hydrocortisone In some embodiments of any of the methods, the method further comprises administering a TH2 or T2 pathway inhibitor that inhibits one or more targets selected from ITK, BTK, JAK (JAK1, JAK2 and/or JAK3), IL-9, IL-6, IL-5, IL-13, IL-4, IL-17 (e.g., IL-17A and IL-17F), OX40L, TSLP, IL-25, IL-33, IgE, IL-9 receptor, IL-5 receptor, IL-4 receptor α, IL-13 receptor (e.g., IL-13 receptor α1 and/or α2), OX40, TSLP-R, IL-7 receptor (e.g., IL7Rα), IL-17 receptor (e.g., IL-17Rβ), ST2 (IL-33 receptor), CCR3, CCR4, CRTH2, FcεRI, FcεRII/CD23, Flap, Syk kinase; CCR4, TLR9, CCR3, chemokine receptor antagonist, and GM-CSF. In some embodiments, the method further comprises administering an IL-5 antagonist. In some embodiments, the IL-5 antagonist is benralizumab, mepolizumab, and/or reslizumab. In some embodiments, the method further comprises administering an IL-13 antagonist. In some embodiments, the IL-13 antagonist is lebrikizumab, dectrekumab, or tralokinumab. In some embodiments, the method further comprises administering an IL-4 antagonist (including an IL-4/IL-13 antagonist). In some embodiments, the IL-4 antagonist is dupilumab or QBX-258 (Novartis). In some embodiments, the method further comprises administering a TSLP antagonist. In some embodiments, the TSLP antagonist is AMG-157 (MEDI-9929). In some embodiments, the method further comprises administering an ST2 antagonist. In some embodiments, the method further comprises administering an IL-17 antagonist. In some embodiments, the IL-17 antagonist is secukinumab, ixekizumab or bimekizumab. In some embodiments of any of the methods, the method further comprises administering fevipiprant. In some embodiments of any of the methods, the method further comprises administering masitinib. In some embodiments of any of the methods, the method further comprises administering a phosphodiesterase (PDE) inhibitor or antagonist, such as a PDE3 and/or PDE4 antagonist. In some embodiments, the PDE antagonist is Theo-24, daliresp, or roflumilast.

In some embodiments of any of the methods, the method further comprises administering one or more active ingredients selected from an aminosalicylate; a steroid; a biological; a thiopurine; methotrexate; a calcineurin inhibitor, e.g. cyclosporine or tacrolimus; and an antibiotic. In some embodiments of any of the methods, the method comprises administering the further active ingredient in an oral or topical formulation. Examples of aminosalicylates include 4-aminosalicylic acid, sulfasalazine, balsalazide, olsalazine and mesalazine, in forms like Eudragit-S-coated, pH-dependent mesalamine, ethylcellulose-coated mesalamine, and multimatrix-release mesalamine. Examples of a steroid include corticosteroids or glucocorticosteroids. Examples of a corticosteroid include prednisone and hydrocortisone or methylprednisolone, or a second generation corticosteroid, e.g. budesonide or azathioprine; e.g. in forms like a hydrocortisone enema or a hydrocortisone foam. Examples of biologicais include etanercept; an antibody to tumor necrosis factor alpha, e.g. infliximab, adalimumab or certolizumab; an antibody to IL-12 and IL-23, e.g. ustekinumab; vedolizumab; etrolizumab, and natalizumab. Examples of thiopurines include azathioprine, 6-mercaptopurine and thioguanine. Examples of antibiotics include vancornycin, rifaximin, metronidazole, trimethoprim, sulfamethoxazole, diaminodiphenyl sulfone and ciprofloxacin; and antiviral agents like ganciclovir In some embodiments of any of the methods, the method further comprises administering an antifibrotic agent. In some embodiments, the antifibrotic agent inhibits transforming growth factor beta (TGF-β)-stimulated collagen synthesis, decreases the extracellular matrix, and/or blocks fibroblast proliferation. In some embodiments, the antifibrotic agent is pirfenidone. In some embodiments, the antifibrotic agent is PBI-4050. In some embodiments, the antifibrotic agent is tipelukast.

In some embodiments of any of the methods, the method further comprises administering a tyrosine kinase inhibitor. In some embodiments, the tyrosine kinase inhibitor inhibits a tyrosine kinase that mediates elaboration of one or more fibrogenic growth factors. In some embodiments, the fibrogenic growth factor is platelet-derived growth factor, vascular endothelial growth factor, and/or fibroblast growth factor. In some embodiments, the tyrosine kinase inhibitor is imatinib and/or nintedanib. In some embodiments, the tyrosine kinase inhibitor is nintedanib. In some embodiments of any of the methods, the method further comprises administering an antidiarrheal agent. In some embodiments, the antidiarrheal agent is loperamide.

In some embodiments of any of the methods, the method further comprises administering an antibody. In some embodiments, the antibody is an anti-interleukin (IL)-13 antibody. In some embodiments, the anti-IL-13 antibody is tralokinumab. In some embodiments, the antibody is an anti-IL-4/anti-IL-13 antibody. In some embodiments, the anti-IL-4/anti-IL-13 antibody is SAR 156597. In some embodiments, the antibody is an anti-connective tissue growth factor (CTGF) antibody. In some embodiments, the anti-CTGF antibody is FG-3019. In some embodiments, the antibody is an anti-lysyl oxidase-like 2 (LOXL2) antibody. In some embodiments, the anti-LOXL2 antibody is simtuzumab. In some embodiments, the antibody is an anti-av36 integrin receptor antibody. In some embodiments, the anti-av36 integrin receptor antibody is STX-100. In some embodiments, the antibody is a monoclonal antibody.

In some embodiments of any of the methods, the method further comprises administering a lysophosphatidic acid-1 (LPA1) receptor antagonist. In some embodiments, the LPA1 receptor antagonist is BMS-986020. In some embodiments of any of the methods, the method further comprises administering a galectin 3 inhibitor. In some embodiments, the galectin 3 inhibitor is TD-139.

In some embodiments of any of the methods, the method further comprises administering a palliative therapy. In some embodiments, the palliative therapy comprises one or more of an antibiotic, an anxiolytic, a corticosteroid, and an opioid. In some embodiments, the antibiotic is a broad-spectrum antibiotic. In some embodiments, the antibiotic is penicillin, a p-lactamase inhibitor, and/or a cephalosporin. In some embodiments, the antibiotic is piperacillin/tazobactam, cefixime, ceftriaxone and/or cefdinir. In some embodiments, the anxiolytic is alprazolam, buspirone, chlorpromazine, diazepam, midazolam, lorazepam, and/or promethazine. In some embodiments, the corticosteroid is a glucocorticosteroid. In some embodiments, the glucocorticosteroid is prednisone, prednisolone, methylprednisolone, and/or hydrocortisone. In some embodiments, the opioid is morphine, codeine, dihydrocodeine, and/or diamorphine.

In some embodiments of any of the methods, the method further comprises administering an antibiotic. In some embodiments, the antibiotic is a macrolide. In some embodiments, the macrolide is azithromycin, and/or clarithromycin. In some embodiments, the antibiotic is doxycycline. In some embodiments, the antibiotic is trimethoprim/sulfamethoxazole. In some embodiments, the antibiotic is a cephalosporin. In some embodiments, the cephalosporin is cefepime, cefixime, cefpodoxime, cefprozil, ceftazidime, and/or cefuroxime. In some embodiments, the antibiotic is penicillin. In some embodiments, the antibiotic is amoxicillin, ampicillin, and/or pivampicillin. In some embodiments, the antibiotic is a penicillin/β-lactamase inhibitor combination. In some embodiments, the penicillin/p-lactamase inhibitor combination is amoxicillin/clavulanate and/or piperacillin/tazobactam. In some embodiments, the antibiotic is a fluoroquinolone. In some embodiments, the fluoroquinolone is ciprofloxacin, gemifloxacin, levofloxacin, moxifloxacin, and/or ofloxacin.

In some embodiments of any of the methods, the method further comprises administering a phosphodiesterase inhibitor. In some embodiments, the phosphodiesterase inhibitor is a phosphodiesterase type 5 inhibitor. In some embodiments, the phosphodiesterase inhibitor is avanafil, benzamidenafil, dasantafil, icariin, lodenafil, mirodenafil, sildenafil, tadalafil, udenafil, and/or vardenafil. In some embodiments, the PDE inhibitor is a PDE-4 inhibitor. In some embodiments, the PDE-4 inhibitor is roflumilast, cilomilast, tetomilast, and/or CHF6001. In some embodiments, the PDE inhibitor is a PDE-3/PDE-4 inhibitor. In some embodiments, the PDE-3/PDE-4 inhibitor is RPL-554.

In some embodiments of any of the methods, the method further comprises administering a cytotoxic and/or immunosuppressive agent. In some embodiments, the cytotoxic and/or immunosuppressive agent is azathioprine, colchicine, cyclophosphamide, cyclosporine, methotrexate, penicillamine, and/or thalidomide. In some embodiments of any of the methods, the method further comprises administering an agent that restores depleted glutathione levels in the lung. In some embodiments, the agent that restores depleted glutathione levels in the lung is N-acetylcysteine. In some embodiments of any of the methods, the method further comprises administering an anticoagulant. In some embodiments, the anticoagulant is warfarin, heparin, activated protein C, and/or tissue factor pathway inhibitor.

In some embodiments of any of the methods, the method further comprises administering an endothelin receptor antagonist. In some embodiments, the method endothelin receptor antagonist is bosentan, macitentan, and/or ambrisentan. In some embodiments of any of the methods, the method further comprises administering a TNF-α antagonist. In some embodiments, the TNF-α antagonist comprises one or more of etanercept, adalimumab, infliximab, certolizumab, and golimumab. In some embodiments of any of the methods, the method further comprises administering interferon gamma-1b.

In some embodiments of any of the methods, the method further comprises administering an interleukin (IL) inhibitor. In some embodiments, the IL inhibitor is an IL-5 inhibitor. In some embodiments, the IL-5 inhibitor is mepolizumab and/or benralizumab. In some embodiments, the IL inhibitor is an IL-17A inhibitor. In some embodiments, the IL-17A inhibitor is CNTO-6785.

In some embodiments of any of the methods, the method further comprises administering a p38 mitogen-activated protein kinase (MAPK) inhibitor. In some embodiments, the p38 MAPK inhibitor is losmapimod and/or AZD-7624. In some embodiments of any of the methods, the method further comprises administering a CXCR2 antagonist. In some embodiments, the CXCR2 antagonist is danirixin.

In some embodiments of any of the methods, the method further comprises vaccination. In some embodiments, the vaccination is vaccination against pneumococci and/or influenza. In some embodiments, the vaccination is vaccination against *Streptococcus pneumoniae* and/or influenza. In some embodiments of any of the methods, the method further comprises administering an antiviral therapy. In some embodiments, the antiviral therapy is oseltamivir, peramivir, and/or zanamivir.

In some embodiments of any of the methods, the method further comprises prevention of gastroesophageal reflux and/or recurrent microaspiration.

In some embodiments of any of the methods, the method further comprises ventilatory support. In some embodiments, the ventilatory support is mechanical ventilation. In some embodiments, the ventilatory support is noninvasive ventilation. In some embodiments, the ventilatory support is supplemental oxygen. In some embodiments of any of the methods, the method further comprises pulmonary rehabilitation.

In some embodiments of any of the methods, the method further comprises lung transplantation. In some embodiments, the lung transplantation is single lung transplantation. In some embodiments, the lung transplantation is bilateral lung transplantation.

In some embodiments of any of the methods, the method further comprises a non-pharmacological intervention. In some embodiments, the non-pharmacological intervention is smoking cessation, a healthy diet, and/or regular exercise. In some embodiments of any of the methods, the method further comprises administering a pharmacological aid for smoking cessation. In some embodiments, the pharmacological aid for smoking cessation is nicotine replacement therapy, bupropion, and/or varenicline. In some embodiments, the non-pharmacological intervention is lung therapy. In some embodiments, the lung therapy is pulmonary rehabilitation and/or supplemental oxygen. In some embodiments, the non-pharmacological intervention is lung surgery. In some embodiments, the lung surgery is lung volume reduction surgery, single lung transplantation, bilateral lung transplantation, or bullectomy. In some embodiments, the non-pharmacological intervention is the use of a device. In some embodiments, the device is a lung volume reduction coil, an exhale airway stent, and/or a nasal ventilatory support system.

Such combination therapies noted above encompass combined administration (where two or more therapeutic agents are included in the same or separate formulations), and separate administration, in which case, administration of an anti-tryptase antibody, or a pharmaceutical composition thereof, can occur prior to, simultaneously, and/or following, administration of the additional therapeutic agent(s). In one embodiment, administration of an anti-tryptase antibody, or a pharmaceutical composition thereof, and administration of an additional therapeutic agent occur within about one month; or within about one, two, or three weeks; or within about one, two, three, four, five, or six days; or within about 1, 2, 3, 4, 5, 6, 7, 8, or 9 hours; or within about 1, 5, 10, 20, 30, 40, or 50 minutes, of each other. For embodiments involving sequential administration, the anti-tryptase antibody may be administered prior to or after administration of the additional therapeutic agent(s).

An anti-tryptase antibody of the invention, or a pharmaceutical compositions thereof, (and any additional therapeutic agent) can be administered by any suitable means, including parenteral, intrapulmonary, and intranasal administration. Parenteral infusions include intramuscular, intravenous, intraarterial, intraperitoneal, or subcutaneous administration. In some instances, an anti-tryptase antibody of the invention may be administered intravitreally, intramuscularly, intravenously, intradermally, percutaneously, intraarterially, intraperitoneally, intralesionally, intracranially, intraarticularly, intraprostatically, intrapleurally, intratracheally, intrathecally, intranasally, intravaginally, intrarectally, topically, intratumorally, peritoneally, subcutaneously, subconjunctivally, intravesicularly, mucosally, intrapericardially, intraumbilically, intraocularly, intraorbitally, orally, topically, transdermally, periocularly, conjunctivally, subtenonly, intracamerally, subretinally, retrobulbarly, intracanalicularly, by inhalation, by injection, by implantation, by infusion, by continuous infusion, by localized perfusion bathing target cells directly, by catheter, by lavage, in cremes, or in lipid compositions. In particular instances, the antibody, or a pharmaceutical composition thereof, can be administered by subcutaneous administration. The compositions utilized in the methods described herein can also be administered systemically or locally. Dosing can be by any suitable route, for example, by injections, such as intravenous or subcutaneous injections, depending in part on whether the administration is brief or chronic. Various dosing schedules including but not limited to single or multiple administrations over various timepoints, bolus administration, and pulse infusion are contemplated herein.

Antibodies of the invention, or pharmaceutical compositions thereof, would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody, or pharmaceutical composition thereof, need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g., 0.1 mg/kg to 10 mg/kg) of antibody can be an initial candidate dosage for administration to the patient, whether, for example, by one or more separate administrations, or by continuous infusion. One typical daily dosage might range from about 1 µg/kg to 200 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g., every week, every two weeks, every three weeks, or every four weeks (e.g., such that the patient receives from about two to about twenty, or e.g., about six doses of the antibody). For example, a dose may be administered once per month, (e.g., by subcutaneous injection). An initial higher loading dose, followed by one or more lower doses may be administered. However, other dosage regimens may be useful. The progress of this therapy is easily monitored by conventional techniques and assays. In some instances, a dose of about 50 mg/mL to about 200 mg/mL (e.g., about 50 mg/mL, about 60 mg/mL, about 70 mg/mL, about 80 mg/mL, about 90 mg/mL, about 100 mg/mL, about 110 mg/mL, about 120 mg/mL, about 130 mg/mL, about 140 mg/mL, about 150 mg/mL, about 160 mg/mL, about 170 mg/mL, about 180 mg/mL, about 190 mg/mL, or about 200 mg/mL of an antibody may be administered, e.g., by subcutaneous injection. In some instances, about 150 mg/mL of an antibody may be administered by subcutaneous injection.

It is understood that any of the above formulations or therapeutic methods may be carried out using an immunoconjugate of the invention in place of or in addition to an anti-tryptase antibody.

H. Articles of Manufacture

In another aspect of the invention, an article of manufacture containing materials useful for the treatment, prevention and/or diagnosis of the disorders described above (e.g., tryptase-associated disorders) is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention, or a pharmaceutical composition thereof. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises an additional therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-tryptase antibody.

III. Examples

The following are examples of methods and compositions of the invention. It is understood that various other embodiments may be practiced, given the general description provided above. Unless specifically indicated, human tryptase beta 1 was used in the studies.

Example 1: Generation and Humanization of Anti-Tryptase Antibodies

A. Materials and Methods

Residue numbers are according to Kabat et al. Sequences of proteins of immunological interest, 5$^{th}$ Ed., Public Health Service, National Institutes of Health, Bethesda, MD, 1991.

(i) Recombinant Expression and Purification of Tryptase in Insect Cells and Mammalian Cells The sequence encoding mature wild-type human tryptase beta 1 (Ile16-Pro246 chymotrypsinogen numbering, SEQ ID NO: 97) was cloned into a modified pAcGP67A vector behind the polyhedron promoter and the gp67 secretion signal sequence. Unless noted otherwise, in this section, tryptase refers to human tryptase beta 1 (also referred to as human tryptase b1). The construct contains an N-terminal His6 tag, an enterokinase cleavage site and, for some constructs, a C-terminal FLAG tag. Site-directed mutagenesis was performed using standard QuikChange™ protocols (Stratagene) to generate tryptase mutants. All constructs were confirmed by DNA sequencing. Recombinant baculoviruses were generated using the BaculoGold™ system (BD Biosciences) in Sf9 cells following standard protocols. *Trichoplusia ni* cells were infected for large-scale protein production and harvested 48 h post-infection. The harvested media was supplemented with 1 mM $NiCl_2$, 5 mM $CaCl_2$ and 20 mM Tris pH 8, shaken for 30 min, and then centrifuged for 20 min at 8500×g to remove the cells and precipitate from media. The supernatant media was filtered through a 0.22 μm polyethersulfone (PES) filter prior to loading onto a nickel-nitrilotriacetic acid (Ni-NTA) affinity column. Human tryptase beta 1 was also expressed by transient transfection in the CHO DP12 mammalian cell line. Cell culture media was subjected to the same purification starting with Ni-NTA affinity purification as described below.

Insect cell media or CHO cell media containing secreted His6-tagged recombinant tryptase (wild-type or mutant) was loaded onto a 10 mL Ni-NTA Superflow column (Qiagen) at a volumetric flow rate of 170 cm/h. The column was washed with 10 CV (column volumes) of wash buffer (20 mM Tris pH 8, 10 mM imidazole, 300 mM NaCl) and eluted with 8 CV elution buffer (20 mM Tris pH 8, 300 mM imidazole, 300 mM NaCl). Fractions assayed by sodium dodecyl sulfate polyacrylamide gel electrophoresis (SDS-PAGE) containing tryptase were pooled, concentrated, and loaded onto an S200 size exclusion column (GE Healthcare) for further purification using running buffer (10 mM 3-(N-morpholino) propanesulfonic acid (MOPS) pH 6.8, 2 M NaCl) at flow rates recommended by the manufacturer. Fractions containing the His-tagged recombinant tryptase (monomeric) were pooled and concentrated. Recombinant tryptase was then cleaved overnight at room temperature at a concentration of 2 mg/ml in buffer (10 mM MOPS pH 6.8, 0.2 M NaCl) containing 0.5 mg/ml heparin (Sigma Aldrich) and 0.1 mg/ml enterokinase (New England Biolabs, Inc). This step removes the N-terminal His6-tag and results in tetramerization and proteolytically active tryptase, which has IVGG as the newly formed N-terminal sequence starting at residue 16 (chymotrypsinogen numbering). Tetrameric tryptase was then subjected to size exclusion chromatography using an S200 column (GE Healthcare) in buffer (10 mM MOPS pH 6.8 and 2 M NaCl) to purify tetrameric tryptase by removing enterokinase and any uncleaved recombinant tryptase.

Tryptase mutants Y75C and I99C, as well as the catalytically inactive mutant S195A (chymotrypsinogen numbering, corresponding to Ser224 to Ala subsititution of the full-length tryptase sequence SEQ ID NO: 71) were purified by Ni-affinity chromatography as described above. Disulfide-linked tryptase dimer mutants were then separated from non-disulfide-linked tryptase monomer mutants by S200 size exclusion chromatography. Disulfide-linked dimer mutants were further processed to tetramers as described above for wild-type tryptase.

(ii) Anti-Human Tryptase Rabbit and Mouse Monoclonal Antibody Generation

Two rabbits were immunized with CHO-derived human tryptase beta 1 (tetramer) with Freund's Complete Adjuvant (CFA). The rabbits were boosted with the same protein, with Freund's Incomplete Adjuvant (IFA), once every 2 weeks. Following 4 injections, purified serum samples were evaluated for binding by enzyme-linked immunosorbent assay (ELISA) and inhibition of human tryptase activity using an enzymatic activity assay. B cells from spleen harvested from one of the rabbits, which demonstrated inhibition of human tryptase activity, were then fused with a rabbit fusion partner. After 10-14 days, the supernatants were harvested and screened for protein binding by ELISA.

The ELISA protocol was as follows. 96-well NUNC MAXISORB® ELISA plates were coated overnight with NeutrAvidin® Biotin Binding Protein (Thermo Scientific Catalog No. 31000, stock 10 mg/ml) at 5 µg/ml, 100 µl/well. The wells were washed three times with Wash Buffer (PBS with 0.05% TWEEN®-20) and blotted dry. The wells were then blocked with 200 µl/well of Blocking Buffer (PBS with 0.5% bovine serum albumin (BSA) and 0.05% TWEEN®-20) and incubated for greater than or equal to 30 min at room temperature. Biotinylated human tryptase beta 1 protein (diluted in Assay Buffer; PBS with 0.5% BSA, 0.05% TWEEN®-20, and 0.1 mg/ml heparin) was added to the wells at 1 pg/ml and incubated at room temperature for 1 h±10 min. Heparin was included to ensure that tryptase remained as a tetramer. The wells were washed three times with wash buffer (200 µl/well) and blotted dry. Hybridoma supernatants (samples) or controls (e.g., the positive controls rabbit purified polyclonal antibody YZ4209 (stock 0.25 mg/ml) were added to the wells (diluted in Assay Buffer, 100 µl/well) and incubated at room temperature for 1 h. Next, the wells were washed three times with wash buffer (200 µl/well) and blotted dry. Horseradish peroxidase (HRP) conjugate (goat anti-rabbit IgG (H+L) HRP; Thermo Scientific Catalog No. 31460) was added (diluted 1:10,000 in Assay Buffer, 100 µl/well) and incubated at room temperature for 30 min. The wells were again washed three times with wash buffer (200 µl/well) and blotted dry. The substrate (BioFX TMB Substrate, Product No.: TMBW-1000-01) was added (100 µl/well) and incubated for 5 min at room temperature. The reaction was stopped by addition of 100 µl/well of BioFX stop solution (Product No.: BSTP-0100-01), and the plates were read at $A_{650}$.

All ELISA-positive clones were purified by affinity chromatography using standard methods (MabSelect SuRe™; GE Healthcare) and then screened for inhibition of human tryptase activity in a recombinant tryptase activity assay. Briefly, antibodies were diluted from 0.007 to 100,000 ng/mL (0.046 pM to 667 nM) in PBS, pH 7.4. Recombinant human tryptase beta 1 was diluted to 3 nM in TNH Buffer (200 mM Tris, 150 mM NaCl, 0.1 mg/mL heparin, 0.01% TRITON™ X-100, pH 8.0) and combined 1:1 with anti-tryptase antibodies in black 384-well plates (ViewPlate-384 F, Black, Clear-Bottom, Perkin Elmer, Catalog No. 6007470). Plates were incubated for 1 h at ambient temperature with gentle agitation. Colorimetic substrate S-2288 (Chromogenix, Part No. 82-0852-39) was diluted to 900 pM in TNH Buffer and was added to the plate. Final in-well concentrations were 300 pM S-2288, 1 nM recombinant human tryptase beta 1, and 0.015 pM to 222 nM anti-tryptase antibodies. Plates were incubated for 40 min at ambient temperature with gentle agitation and then were read at $A4_0$. The half-maximal inhibitory concentration (IC50) of the anti-tryptase antibodies were determined from a four-parameter fit of their respective curves. Clones demonstrating the desired inhibition were then subcloned by limiting dilution (single cell/well), retested as described above and further characterized.

Mouse hybridomas were generated and screened and positive clones were analyzed in a similar manner. Three A/J mice (Harlan, Indianapolis, Ind.) were immunized with purified tryptase protein as the antigen (EPC, Inc. # TR913). Enzymatically active tryptase as administed at 20 pg/mouse per immunization subcutaneously and intraperitoneally after mixing and emulsifying 1:1 with Complete Freund's Adjuvant (first immunization) or Incomplete Freund's Adjuvant (second, third, and fourth immunization). The boost (fifth immunization) had no adjuvant. After the fourth immunization, sera from immunized mice were tested by ELISA and the mouse with serum titer higher than $OD_{450}>2.16$ at the dilution of $1:1.28\times10^4$ was selected for hybridoma fusion. $107\times10^6$ isolated spleen cells were mixed with $100\times10^6$ Sp2/0 myeloma cells (ATCC) for fusion in the presence of polyethylene glycol (Sigma-Aldrich, Cat. No. P7777-5G). Twenty-four clones were screened for binding to tryptase and assayed for inhibition of tryptase enzymatic activities. Clone T31a (also referred to herein as "31A" and "mu.31A") was selected for humanization.

(iii) Molecular Cloning and Reformatting of Rabbit Anti-Tryptase Hybridoma Clones Total RNA was extracted from hybridoma cells producing the rabbit anti-tryptase monoclonal antibodies (RNeasy® Mini Kit, Qiagen). Using SMARTer® RACE cDNA Amplification Kit (Clontech), the RNA was first reverse transcribed, then subjected to first strand cDNA synthesis and 5' RACE PCR amplification of variable light (VL) and variable heavy (VH) domains with the following primers:

Light chain (LC) forward primer:
Universal Primer Mix (SMARTer® RACE cDNA Amplification Kit, Clontech, catalog #634858)

Heavy chain (HC) forward primer:
Universal Primer Mix (SMARTer® RACE cDNA Amplification Kit, Clontech, catalog #634858)

```
LC reverse primer:
                                    (SEQ ID NO: 74)
5'-GATGGTGACTGTTCCAGTTGC-3'

HC reverse primer:
                                    (SEQ ID NO: 75)
5'-CATTGGTGAGGGTGCCCGAGTTC-3'
```

The LC and HC reverse primers were designed to anneal to a region in the constant light (CL) and constant heavy domain 1 (CH1).

Amplified PCR products were directly sequenced. The identified VL DNA sequence was then subcloned into pRK mammalian cell expression vector containing the human kappa constant domain. The VH DNA sequence was inserted into pRK vectors encoding the full-length human γ1 constant domain.

(iv) Humanization of the Rabbit Anti-Tryptase Monoclonal Antibody E104

The VL (SEQ ID NO: 53) and VH (SEQ ID NO: 52) domains from the rabbit anti-tryptase monoclonal antibody E104 were aligned with the human VL kappa I ($VL_{KI}$) and human VH subgroup IV ($VH_{IV}$) consensus sequences (SEQ ID NOs: 92 and 93, respectively). See, e.g., Dennis, Ch. 2 CDR Repair: A Novel Approach to Antibody Humanization in Current Trends in Monoclonal Antibody Development and Manufacturing, Eds. Shire et al. Springer, New York, N.Y. The hypervariable regions (HVR) were engineered into the consensus human $VL_{KI}$ and $Vh_{IV}$ acceptor frameworks to generate CDR-graft variants. From the E104 VL domain, positions 24-34 (L1), 50-56 (L2) and 89-97 (L3) were grafted into $VL_{KI}$. From the VH domain, positions 26-35b (H1), 50-65 (H2) and 93-102 (H3) were grafted into $VH_{IV}$. To evaluate framework vernier positions that might be important, selected vernier positions were mutated back to the rabbit sequences. The vernier positions that were mutated back to the rabbit sequences included positions 2, 4, 43, 68, and 87 in VL and 37, 67, 71, 78, and 91 in VH.

The VL and VH domains from the rabbit anti-tryptase monoclonal antibody E104 were also aligned with the human VL kappa I ($VL_{KI}$) and human VH subgroup III ($VH_{III}$) consensus sequences (SEQ ID NOs: 92 and 94, respectively). See Dennis, supra. The hypervariable regions (HVR) were engineered into the consensus human $VL_{KI}$ and $VH_{III}$ acceptor frameworks to generate CDR-graft variants. From the rab.E104 VL domain, positions 24-34 (L1), 50-56 (L2), and 89-97 (L3) were grafted into $VL_{KI}$. From the VH domain, positions 26-35 (H1), 50-65 (H2), and 93-102 (H3) were grafted into $VH_{III}$.

In total, two different versions of humanized VL sequences and six different versions of humanized VH sequences were synthesized and subsequently subcloned into pRK mammalian expression vectors. By combining the different versions of the LC and HC, a total of twelve different humanized E104 variants (v1 to v12) were generated (Table 3). All the humanized anti-tryptase variants were expressed as IgG1 or IgG4 antibodies in mammalian cells. Antibodies were purified by affinity chromatography using standard methods (MabSelect SuRe™; GE Healthcare). All of the IgG4 antibodies used in the Examples section included an S228P mutation (EU numbering) in the heavy chain constant region; however, the invention described herein is not limited to the IgG4 variant with the S228P mutation.

A DNA sequence encoding the VH domain of huE104.v2 is shown in SEQ ID NO: 109. A DNA sequence encoding the VL domain of huE104.v2 is shown in SEQ ID NO: 110. A DNA sequence encoding the heavy chain (IgG1) is shown in SEQ ID NO: 111. A DNA sequence encoding the heavy chain (IgG4.S228P) is shown in SEQ ID NO: 113. A DNA sequence encoding the light chain (IgG1 and IgG4) is shown in SEQ ID NO: 112. The amino acid sequence of the heavy chain (HC) of huE104.v2 IgG1 is shown in SEQ ID NO: 80. The amino acid sequence of the light chain (LC) of huE104.v2 (IgG1 or IgG4) is shown in SEQ ID NO: 81. The amino acid sequence of the HC of huE104.v2 IgG4 S228P is shown in SEQ ID NO: 82.

(v) Humanization of the Mouse Anti-Tryptase Monoclonal Antibody 31A

The VL (SEQ ID NO: 20) and VH (SEQ ID NO: 19) domains from the mouse anti-tryptase monoclonal antibody 31A ("mu.31A") were aligned with the human VL kappa I ($VL_{KI}$) and human VH subgroup III ($VH_{III}$) consensus sequences (SEQ ID NOs: 92 and 93, respectively). The hypervariable regions (HVR) were engineered into the consensus human $VL_{KI}$ and $VH_{III}$ acceptor frameworks to generate CDR-graft variants. From the mu.31A VL domain, positions 24-34 (L1), 50-56 (L2), and 89-97 (L3) were grafted into $VL_{KI}$. From the mu.31A VH domain, positions 26-35 (H1), 50-65 (H2), and 93-102 (H3) were grafted into $VH_{III}$. To evaluate the importance of the framework vernier positions, selected vernier positions were mutated back to the mouse sequences. The vernier positions that were mutated back to the mouse sequences included positions 4, 43, 46, 47, and 71 in VL and position 49 in VH.

In summary, three humanized LC and five humanized HC were synthesized and subsequently subcloned into pRK mammalian expression vectors. By combining the different versions of the LC and HC, a total of fifteen different humanized variants (v1 to v15) of 31A ("hu31A") were generated (Table 4).

All the humanized anti-tryptase variants were expressed as IgG1 or IgG4 antibodies in mammalian cells. Antibodies were purified by affinity chromatography using standard methods (MabSelect SuRe™; GE Healthcare, Piscataway, NJ, USA).

A DNA sequence encoding the VH domain of hu31A.v11 is shown in SEQ ID NO: 104. A DNA sequence encoding the VL domain of hu31A.v11 is shown in SEQ ID NO: 105. A DNA sequence encoding the heavy chain (IgG1) is shown in SEQ ID NO: 106. A DNA sequence encoding the heavy chain (IgG4.S228P) is shown in SEQ ID NO: 108. A DNA sequence encoding the light chain (IgG1 and IgG4) is shown in SEQ ID NO: 107. The amino acid sequence of the HC of hu31A.v11 IgG1 is shown in SEQ ID NO: 76. The amino acid sequence of the LC of hu31A.v11 IgG1 is shown in SEQ ID NO: 77. The amino acid sequence of the HC of hu31A.v11 IgG4 S228P is shown in SEQ ID NO: 78. The amino acid sequence of the LC of hu31A.v11 IgG4 S228P is shown in SEQ ID NO: 79.

(vi) Cloning, Expression, and Purification of Fab Fragments

Fabs were cloned and expressed in *E. coli* as previously described (see Simmons et al. *J. Immunol. Methods* 263: 133-147, 2002; Lombana et al. *Sci. Rep.* 5:17488, 2015). *E. coli* cell paste containing the expressed Fab was harvested from fermentations expressing Fabs and dissolved into PBS buffer containing 25 mM EDTA and 1 mM phenylmethylsulfonyl fluoride (PMSF). The mixture was homogenized and then passed twice through a microfluidizer. The suspension was then centrifuged at 21,500×g for 60 min. The supernatant was then loaded onto a Protein G column equilibrated with PBS at 5 ml/min. The column was washed with PBS buffer to baseline and proteins were then eluted with 0.6% acetic acid. Fractions containing Fabs as assayed by SDS-PAGE were pooled and then loaded onto a 50 mL SP SEPHAROSE® column equilibrated in 20 mM MES (pH 5.5). The column was washed with 20 mM MES buffer (pH 5.5) for 2 column volumes and then eluted with a linear gradient to 0.5M NaCl in 20 mM MES buffer (pH 5.5). For final purification, Fab-containing fractions from the ion exchange chromatography were concentrated and run on a S75 size exclusion column in PBS buffer. The same protocol was used for all Fabs used in the experiments.

(vii) BIAcore® Surface Plasmon Resonance (SPR) Analysis of Humanized Anti-Tryptase Variants In this experiment, all the humanized variants were expressed as IgG by transient transfection of 293 cells. IgG was purified with protein G affinity chromatography. The affinity of each variant for recombinant His-tagged human tryptase beta 1 monomer (SEQ ID NO: 128) was determined by SPR analysis using a BIAcore® T200. BIAcore® Series S CM5 sensor chips were immobilized with monoclonal mouse anti-human IgG (Fc) antibody (Human antibody capture kit from GE Healthcare) and anti-tryptase variants were subsequently captured on each flow cell. Serial 3-fold dilutions of the human tryptase beta 1 monomer were injected at a flow rate of 30 µl/min. Each sample was analyzed with 3 min association and 10 min dissociation. After each injection, the chip was regenerated using 3 M $MgCl_2$. Binding response was corrected by subtracting the response units (RU) from a flow cell capturing an irrelevant IgG at similar density. A 1:1 Languir model of simultaneous fitting of $k_{on}$ and $k_{off}$ was used for kinetics analysis.

(viii) Analysis of Inhibitory Activity of Humanized Anti-Tryptase Variants a. Tryptase Enzymatic Assay The inhibition of human tryptase activity by humanized anti-tryptase antibodies was measured using a recombinant tryptase activity assay. hu31a.v11 IgG4 and hu31a.v11 IgG1 were diluted from 0.05 to 100 µg/ml (0.30 to 667 nM) in PBS, pH 7.4, and huE104.v2 IgG4 and huE104.v2 IgG1 were diluted from 0.02 to 50 µg/ml (0.15 to 333 nM) in PBS pH 7.4. Recombinant human tryptase beta 1 tetramer active enzyme was diluted to 0.75 nM in TNH Buffer (200 mM Tris, 150 mM NaCl, 0.1 mg/mL heparin, 0.01% TRITON™ X-100, pH 8.0), and combined 1:1 with anti-tryptase antibodies in black 384-well plates (ViewPlate-384 F, Black, Clear-Bottom, Perkin Elmer, Catalog No. 6007470). Plates were incubated for 1 h at ambient temperature with gentle agitation. Colorimetric substrate S-2288 (Chromogenix, Part No. 82-0852-39) was diluted to 1200 µM in TNH Buffer and was added to the plate. Final in-well concentrations were 400 µM S-2288, 0.25 nM recombinant human tryptase beta 1 tetramer, 66 µg/mL heparin, and 0.10 to 222 nM anti-tryptase antibodies for hu31A.v11 and 0.05 to 111 nM for huE104.v2. Plates were incubated for 40 min at ambient temperature with gentle agitation and then were read at $A_{405}$. The IC50 of the anti-tryptase antibodies were determined from a four-parameter fit of their respective curves.

b. Bronchial Smooth Muscle Cell Proliferation Assay and Collagen-Based Contraction Assay Human bronchial smooth muscle cells (BSMCs; Catalog No. CC-2576, Lonza Minneapolis, MN) were cultured in a humidified incubator at 37° C. with 5% $CO_2$ in complete culture media SmGM-2 (Catalog No. CC-3182, Lonza). The assay media was SmGm-2 culture media without human serum or supplements added (Catalog No. CC-3181, Lonza). Human wild-type tetramer tryptase or human S195A catalytically-inactive tryptase enzyme (chymotrypsinogen numbering) were used at the specified concentrations. Anti-human tryptase antibodies hu31A.v11 IgG4 and E104.v2 IgG4 were used at the specified concentrations.

For the proliferation assay, 1 day prior to performing the assay, BSMCs were plated at $2 \times 10^5$ cells/ml in a 96 well tissue culture plate (Catalog No. 353072, Falcon BD) in complete culture media. After 24 h, the culture media was replaced with assay media and cells were incubated for an additional 24 h. Anti-human tryptase antibodies were serially diluted 3.3-fold in assay media in a 96 well tissue culture plate (Catalog No. 353072, Falcon BD). 100 µL of diluted hu31A.v11 IgG4 was transferred to a 96 well plate containing 100 µL of 200 nM human tryptase. Active tryptase and anti-human tryptase antibodies were incubated for 30 min at room temperature. At this time, assay media was removed from the plated cells and replaced with 100 µL of the diluted antibodies plus tryptase. The final concentration of antibodies ranged from 2.0 µM to 4 pM. The final concentration of tryptase was 100 nM (without heparin). The final salt concentration was about 130 mM. Wells with tryptase alone were included as stimulation controls. Wells with assay media alone were included as unstimulated controls. Plates were incubated for 24 h at 37° C. before the addition of 1 µCi of $H^3$-thymidine per well. After an additional 6 h of incubation, proliferation was measured by $H^3$-thymidine incorporation. Cell-associated radioactivity was quantified by scintillation counting. Results were expressed as the mean of triplicate samples. Graphs were generated and statistical analysis was performed using KaleidaGraph (Synergy Software).

For the collagen-based contraction assay, 1 day prior to performing the assay, BSMCs were plated in collagen at $9 \times 10^6$ cells/mL in a 24 well plate (Catalog No. 353047, Falcon BD) following the manufacturer's guidelines (Catalog No. CBA-201, Cell BioLabs Inc.). After a 1 h incubation at 37° C., cells were overlayed with 1 mL of assay media. After a 24 h incubation at 37° C., media was replaced with 250 µL of fresh assay media. Tryptase was diluted in 250 µL assay media to 660 nM in the presence or absence of 4 pM of anti-human tryptase antibodies and incubated for 30 min at 37° C. prior to adding to the specified wells containing the cell:collagen matrix. The final concentrations were 330 nM tryptase and 2 µM antibody (without heparin). The final salt concentration was about 130 mM. Cell contraction was initiated by the release of the cell:collagen matrix from the plate wall using a sterile pipette tip. Assay media alone was used as an unstimulated control. At the start of cell contraction (t=0), cell:collagen matrices were visualized, imaged, and recorded using a ProteinSimple AlphaImager®. Cells were incubated at 37° for an additional 3 h and cell:collagen matrices were reimaged and recorded (t=3). Data was analyzed using NIH Image J software. Data were represented as the percent change in cell:collagen matrix diameter from the start of contraction (t=0) until the 3 h time point (t=3). Results were expressed as the mean of triplicate samples.

c. Mast Cell Histamine Release Assay

The human mast cell line LAD2 was used. LAD2 cells were cultured in a humidified incubator at 37° C. with 5% $CO_2$ in serum-free growth medium, StemPro®-34, containing StemPro®-34 nutrient supplement (Catalog No. 10640-019, Gibco/Life Technologies), 1× peniciin-streptomycin-glutarnine (Catalog No. 10378-016, Gibco/Life Technologies) and 100 ng/mL recombinant human stem cell factor (SCF) (Catalog No. 573908, BioLegend). See Kirshenbaum et al. *Leukemia Research* 27:677-682, 2003. Human tryptase wild-type or human tryptase S195A mutant were used at the specified concentrations. Anti-NP human IgE (JW8.5.13; see Jackman et al. *J. Biol Chem.* 285(27):20850-20859, 2010) was obtained from Serotec Inc. NP-BSA (Catalog No. N5050H-10, Biosearch Technologies, Petaluma, CA) was used at the specified concentration for triggering histamine release. Anti-human tryptase antibodies hu31A.v11 IgG4 and E104.v2 IgG4 were used at the specified concentrations. The small molecule inhibitor G02849855 was used at the specified concentration. Cell stimulations were performed using Tyrode's Salt (Catalog No. T-2397, Sigma). Histamine was measured using a histamine ELISA kit (GenWay. Catalog No. 40-371-25010).

For the human IgE triggered histamine release assay, LAD2 cells were plated at $4 \times 10^6$ cells/4 ml in 2 wells of a 6 well dish. Anti-NP IgE (100 ng/ml) was added to one well and the cells were incubated overnight at 37° C. to prime the cells. In the other well, cells were cultured in media only without the addition of anti-NP IgE to serve as a negative control. After the overnight incubation, cells were washed 3 times with cell culture media to remove the unbound IgE. Cells were resuspended in 4 mL Tyrode's salts (cell density $1 \times 10^6$ cells/ml) and aliquoted into Eppendorf® tubes (300,000 cells/tube). Samples were incubated with 100 µg/mL hu31A.v11 IgG4 or 10 µM G02849855, mixed thoroughly, and incubated at room temperature for 1 h. Following this incubation, NP-BSA was added to the samples at a final concentration of 0.1 µg/mL to trigger cell degranulation. Samples were mixed thoroughly and incubated at 37° C. in a $CO_2$ incubator for 1 h. Cells were then centrifuged at 3000 rpm for 5 min at room temperature, and the supernatant was collected for histamine measurement. Histamine in the degranulation supernatant was quantitated using a histamine ELISA kit. Data were represented as the mean of duplicate samples.

For the human tryptase triggered histamine release assay, LAD2 cells were resuspended in Tyrode's salts at a concentration of $10^6$ cells/mL and aliquoted into Eppendorf® tubes (300,000 cells/tube). To promote cell degranulation, cells were treated with 3 µg/mL tryptase (wild-type or S195A mutant) or 3 µg/mL tryptase which had been pre-incubated with 100 µg/mL hu31A.v11 for 45 min at room temperature. PBS was used as a no stimulation control. Samples were mixed thoroughly and incubated at 37° C. in a $CO_2$ incubator for 1 h. The final salt concentration was about 140 mM. Cells were then centrifuged at 3000 rpm for 5 min at room temperature, and the supernatant was collected for histamine measurement. Histamine in the degranulation supernatant was quantitated using a histamine ELISA kit. Data were represented as the mean of duplicate samples.

(ix) Purification of Recombinant Tryptase Monomers and Tetramers

Human tryptase without the endogenous signal peptide (amino acid residues 1-15 of SEQ ID NO:71) and pro-peptide (amino acid residues 16-30 of SEQ ID NO:71) was expressed in mammalian CHO cells as a His-tagged recombinant protein with an engineered enterokinase cleavage site and underwent 5×ultrafiltration followed by a 5×dilution into PBS. Media was then loaded over a Ni-NTA column and eluted with 250 mM imidazole. Eluate was dialyzed into 10 mM MOPS, 0.2M NaCl, pH 6.8 buffer yielding monomeric tryptase. Uncleaved His6-tagged tryptase monomers remain monomeric and do not form tetramers.

To generate tetrameric tryptase, monomeric tryptase containing the His tag was digested using 0.1 mg/ml of enterokinase enzyme and stabilized with dextran sulfate-10 sodium salt at 0.5 mg/ml for 16-20 h at room temperature. Protein was passed over a SUPERDEX™ 200 column into the final buffer of 10 mM MOPS, 2M NaCl, pH 6.8 to separate tetramers from monomers and from any residual contaminating protease. Exemplary purified tetramer is shown in FIG. 3A, peak 1. Pooled tetrameric tryptase was used for immunization and activity assays.

B. Results (i) Hybridoma Cloning

Molecular cloning of five rabbit anti-tryptase antibodies from ELISA-positive hybridoma clones revealed four unique anti-tryptase clones. Of these, clone E104 showed the most robust inhibition activity in the enzymatic assay, and was selected for further engineering. In parallel, a murine anti-tryptase monoclonal antibody clone 31A which showed inhibition activity in the enzymatic assay was also selected for further engineering.

(ii) Generation of Chimeric E104 (chE104) Variants

The light chain of the rabbit anti-tryptase monoclonal antibody E104 is a rabbit kappa light chain, which contains a disulfide bridge between Cys80 in FR3 of the variable domain (VL) and Cys170 in the constant domain (CL). To evaluate the importance of Cys80 in the VL, a chimeric E104 variant with the cysteine at position 80 mutated to alanine (Cys80Ala) was generated. As shown in Table 2, no difference between the two variants in terms of yield or aggregation, as evidenced by the high % monomer in both the Cys80 and the Cys80Ala chimeric variants determined by size exclusion chromatography. Thus, it was determined that the Cys80 residue was not critical and in the humanized version, Cys80 was changed to a proline residue as in the VH4 graft. In addition, chimeric E104 antibodies with the Cys80Ala mutation in the variable domain FR3, either fused to the human IgG1 or IgG4 constant domains, showed similar inhibitory activities as the rabbit monoclonal antibody with cysteine at position 80 (data not shown).

TABLE 2

Effect of Cys80 Residue of Anti-Tryptase Antibody E104 on Yield and Aggregation

| Anti-tryptase clone | Light chain variants (position 80 residue) | Yield (mg) | % monomer |
|---|---|---|---|
| E104 | chE104.C | 3.01 | 95.45 |
|  | chE104.A | 3.14 | 95.2 |

Figure 12B:
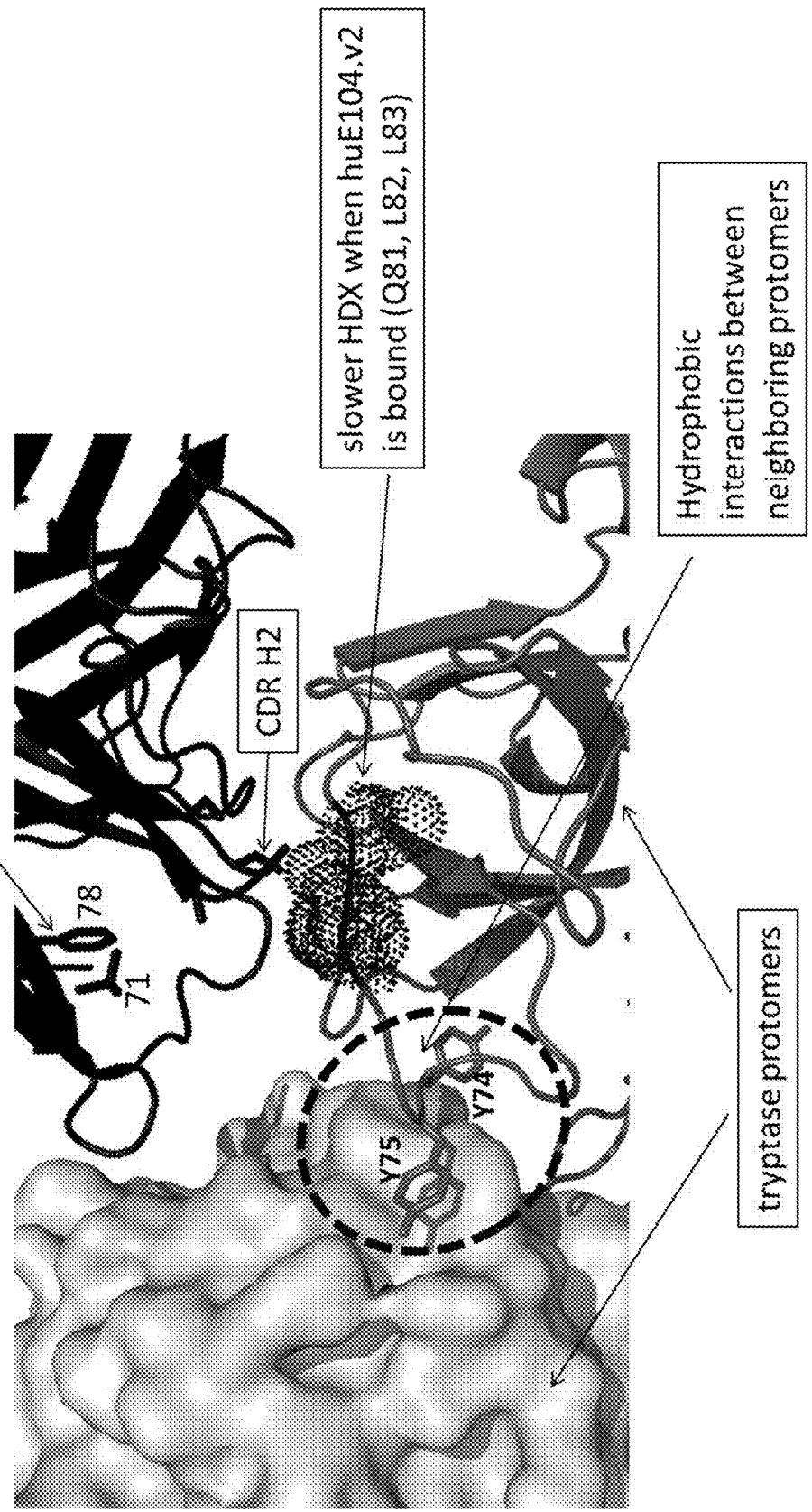
FIG. 12B is a rendering of the effect of huE104.v1 binding on the small interface of the tryptase tetramer as assessed by hydrogen-deuterium exchange (HDX).

(iii) Humanization of the Rabbit Anti-Tryptase Monoclonal Antibody Clone E104 and the Mouse Anti-Tryptase Monoclonal Antibody Clone 31A All of the humanized variants were expressed as IgG and their binding affinities were evaluated in a BIAcore® SPR assay. In general, all of the humanized E104 variants (huE104) showed similar binding affinities towards the human tryptase beta 1 monomer (Table 3). Table 3 lists huE104 variants as well as the binding affinity (in terms of $K_D$) as determined by BIAcore® SPR analysis. Table 3 also provides the SEQ ID NOs of the VH and VL domains for each variant. Each clone in Table 3 was tested in IgG1 format. Consistently, very similar IC50 values were observed for these antibodies in the enzymatic activity assay described above, except that the huE104.v1 and huE104.v5 clones, and to a less extent, huE104.v11 and huE104.v12, showed some "hook effect" (in which an increase of enzymatic activity, i.e., a decrease in antibody inhibitory activity, was observed at high antibody concentrations) in the enzymatic assay. Modifications in the heavy chain FR3 region from V71 of the humanized antibody to the original Arg residue of the rabbit monoclonal antibody (V71R) and F78 of the humanized antibody to the original Val residue of the rabbit monoclonal antibody (F78V) eliminated the hook effect seen in E104.v1, v5, v11 and v12. The E104.v9 chimeric clone contains R71 and V78 as in the parent rabbit monoclonal Ab E104. See Table 3. As shown in FIG. 12B, the arginine (R) residue at position 71 and valine (V) residue at position 78 (both Kabat numbering) may play an important role in conformation of HVR-H2, and thus the binding of the antibody to tryptase. As a result, the V71R and F78V modifications in huE104.v2 may have affected the conformation of the tryptase 80 loop that is important in the association of two protomers that form the small interface. See Example 3 below. Thus, hu104.v2, which has the V71R and F78V reversions, has improved binding and inhibitory activity as compared to v1, which has V at position 71 and F at position 78. All variants except v1, v5, v11, and v12 showed complete inhibition of tryptase activity as measured by the enzymatic assay described above. The humanized clone huE104.v2 was selected for further evaluation. The amino acid sequences of the heavy and light chain variable domains of huE104.v2 are shown in FIG. 1.

TABLE 3

Binding affinities of humanized E104 (huE104) variants (binding affinity to human tryptase b1 monomer in parentheses)

| | | Light Chain | | |
|---|---|---|---|---|
| | | K1 graft (SEQ ID NO: 37) | K1 graft +A2 +L4 +P43 +E68 +F87 (SEQ ID NO: 58) | Chimeric LC (SEQ ID NO: 59) |
| Heavy Chain | VH4 graft (SEQ ID NO: 47) | v1 (0.43 nM) | v5 (0.18 nM) | — |
| | VH4 graft +R71 +V78 (SEQ ID NO: 36) | v2 (0.18 nM) | v6 (0.14 nM) | v10 (0.26 nM) |
| | VH4 graft +V37 +S67 +R71 +V78 +F91 (SEQ ID NO: 48) | v3 (0.21 nM) | v7 (0.25 nM) | — |
| | VH3 graft +I48 +S67 +T73 +V78 (SEQ ID NO: 51) | v4 (0.44 nM) | v8 (0.24 nM) | — |
| | Chimeric HC (SEQ ID NO: 52) | v9 (0.24 nM) | — | — |
| | VH4 graft +V78 (SEQ ID NO: 49) | v11 (0.32 nM) | — | — |
| | VH4 graft +R71 (SEQ ID NO: 50) | v12 (0.12 nM) | — | — |

Table 4 lists hu31A variants as well as the binding affinity (in terms of $K_D$, nanomolar) as measured by BIAcore® SPR analysis. Table 4 also shows the SEQ ID NOs of the $V_H$ and $V_L$ for each antibody. All variants showed complete inhibition of tryptase activity as measured by the enzymatic assay (data not shown). Each clone in Table 4 was tested in IgG1 format. The clone hu3 Å.v11 showed the best affinity and best inhibitory activity in anenzymatic assay and was therefore selected for further evaluation. The amino acid sequences of the heavy and light chain variable domains of hu31AMv11 are shown in FIG. 1.

TABLE 4

Binding affinities of humanized 31A (hu31A) variants (binding affinity to human tryptase b1 monomer in parentheses)

| | | Light Chain | | |
|---|---|---|---|---|
| | | K1 graft (SEQ ID NO: 102) | K1 graft +S43 +P46 +W47 (SEQ ID NO: 10) | K1 graft +L4 +S43 +P46 +W47 +Y71 (SEQ ID NO: 103) |
| Heavy Chain | VH3 graft (SEQ ID NO: 98) | v1 (4.04 nM) | v2 (0.74 nM) | v3 (0.79 nM) |
| | VH3 graft +A49 (SEQ ID NO: 99) | v4 (11.8 nM) | v5 (1.68 nM) | v6 (1.65 nM) |
| | VH3 graft +S31 +F32 +H35 +A49 (SEQ ID NO: 100) | v7 (2.06 nM) | v8 (0.94 nM) | v9 (0.94 nM) |
| | VH3 graft +A49 +T93 +N96 +Y97 +D98 (SEQ ID NO: 9) | v10 (1.19 nM) | v11 (0.40 nM) | v12 (0.43 nM) |
| | VH3 graft +A49 +T93 (SEQ ID NO: 101) | v13 (9.65 nM) | v14 (1.34 nM) | v15 (1.32 nM) |

The inhibitory activity of humanized anti-tryptase antibodies was also determined using the recombinant tryptase enzymatic activity assay described above. Both h31A.v11 and huE104.v2, IgG1 and IgG4, completely inhibited tryptase activity in the enzymatic assay (see FIG. 2A). The IC50 values are shown below (Table 5).

TABLE 5

Inhibitory activity (IC50) of humanized anti-tryptase antibodies

| Antibody | IgG1 | IgG4 |
| --- | --- | --- |
| hu31A.v11 | 1.82 nM ± 0.09 | 3.9 nM ± 0.65 |
| huE104.v2 | 0.91 nM ± 0.35 | 0.59 nM ± 0.11 |

Both hu31Av11 and huE104.v2 bind and inhibit human tryptase beta 2 and beta 3, in addition to tryptase beta 1. Representative data are shown below in Table 6 based on protocols described above for affinity analysis and enzymatic assay using human tryptase beta 1 as the target. Both hu31A.v11 and huE104.v2 also bind and inhibit cyno tryptase D1.

TABLE 6

Affinity and IC50 of humanized anti-tryptase antibodies

| Antibody | Human Tryptase | $K_D$ (nM) | IC50 (nM) |
| --- | --- | --- | --- |
| hu31A.v11 IgG4 | Tryptase beta 1 | 0.27 | 3.16 |
|  | Tryptase beta 2 | 0.12 | 1.46 |
|  | Tryptase beta 3 | 0.10 | 2.47 |
| huE104.v2 IgG4 | Tryptase beta 1 | 0.3 | 0.42 |
|  | Tryptase beta 2 | 0.18 | 0.95 |
|  | Tryptase beta 3 | 0.13 | 2.80 |

The inhibitory activity of hu31A.v1 IgG4 or huE104.v2 IgG4 was further assessed in several ex vivo models of human primary airway smooth muscle cell (SMC) function. Addition of tryptase beta 1 to culture medium results in an increase in proliferation of human primary airway SMCs (FIG. 2B), as well as contraction of the cells (FIG. 2C). Addition of hu31A.v1 or huE104.v2 resulted in a dose-dependent reduction in proliferation, and at 300 µg/ml inhibited proliferation to baseline levels (FIG. 2B). Similarly, addition of hu31A.v11 or huE104.v2 reduced contraction to baseline levels (FIG. 2C). These data demonstrate that the anti-tryptase antibodies hu31A.v1 and huE104.v2 inhibited tryptase function.

Figure 2D:
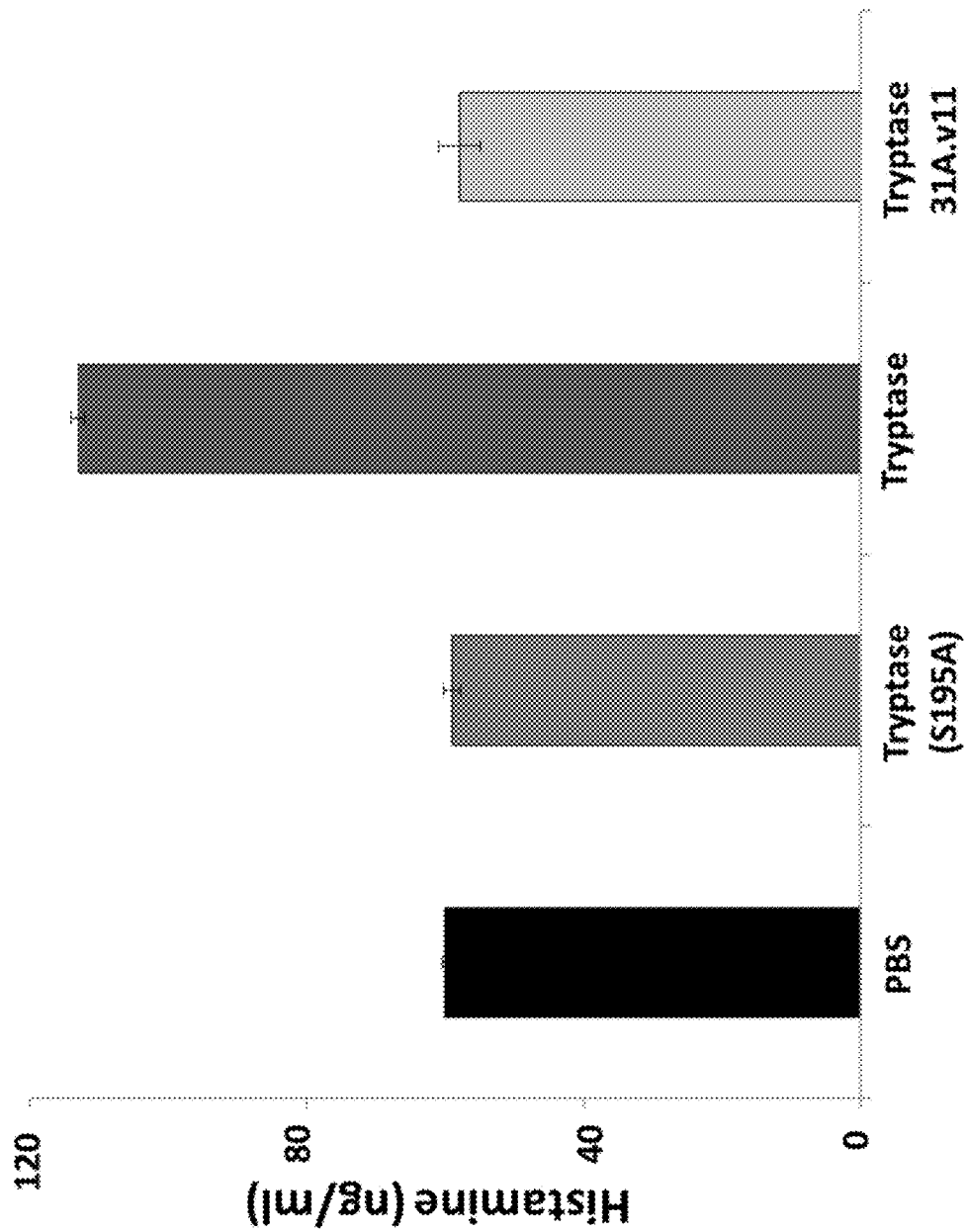
FIGS. 2D and 2E are graphs showing the results of mast cell degranulation assays in which mast cells were stimulated in vitro by addition of tryptase beta or anti-4-hydroxy-3-nitrophenylacetyl (NP) IgE and NP. Addition of tryptase resulted in histamine release, which was blocked by addition of hu31A.v11 (FIG. 2D). A catalytically-inactive mutant tryptase (S195A) served as a control. Addition of IgE and NP also resulted in histamine release, which was inhibited (30-50%) by addition of a tryptase small molecule inhibitor (SMI) or hu31A.v1 (FIG. 2E).
Figure 2E:
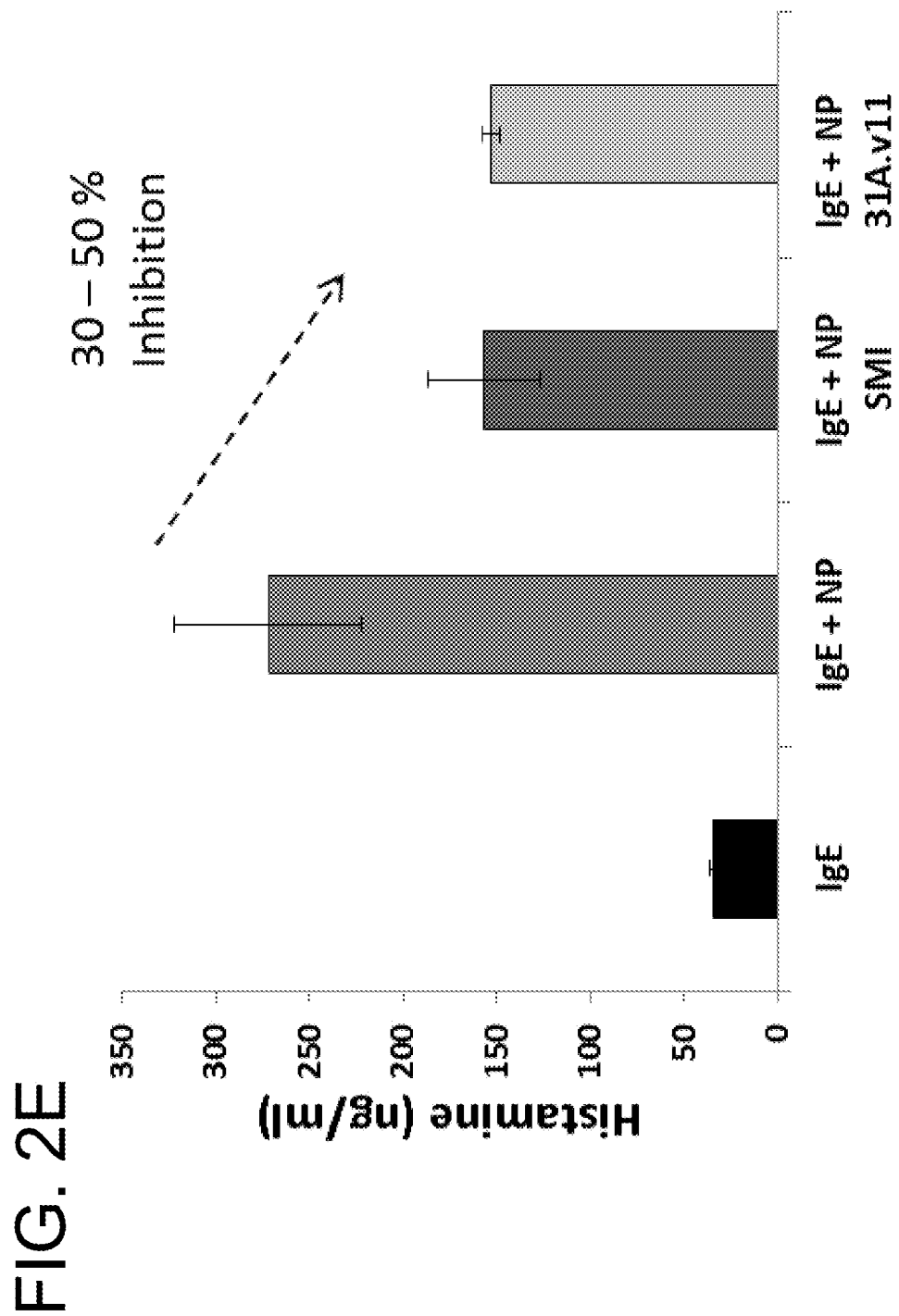

Addition of tryptase or IgE to mast cells results in degranulation and release of histamine (FIGS. 2D-2E). The ability of hu31A.v1 to inhibit histamine release was assessed. Tryptase beta 1 with the S195A substitution is catalytically inactive. Addition of hu31A.v11 blocked the ability of tryptase to promote histimine release (FIGS. 2D-2E). The extent of inhibition (30-50%) was similar to the small molecule inhibitor of tryptase beta 1 activity, G02849855 (FIG. 2E). These results further show that the anti-tryptase antibody hu31A.v1 inhibits tryptase function.

Example 2: hu31A.v1 and huE104.v2 IgG Dissociate Human Tryptase Beta Tetramer

The crystal structure of active tetrameric tryptase shows that the catalytic site of each protomer (represented by S195, H57, and D102 of each protomer, chymotrypsinogen numbering) is located inside the pore of the tetramer, and that access to the active sites is limited such that only peptide substrates and smaller molecules can gain access (Pereira et al. *Nature* 392:306-11, 1999). To date, no mammalian serine protease inhibitors are known to inhibit the proteolytic activity of tryptase. Human serine protease inhibitors of the Kunitz-domain type architecture are too large to access the active sites. There are no known natural inhibitors of tryptase in humans. The only known natural macromolecular inhibitors of tryptase to date are leech-derived tryptase inhibitor (LDTI) (Sommerhoff et al. *Biol. Chem.* 373:685-94, 1997) and tick-derived protease inhibitor (TdPI) (Paesen et al. *J. Mol. Biol.* 368:1172-86, 2007). LDTI (4.7 kDa) and TdPI (11.1 kDa) have the ability to block two or three of the four active sites of the tryptase tetramer, respectively. LDTI and TdPI do not dissociate the tryptase tetramer. Both the IgG and Fab of hu31A.v11 are much larger than LDTI or TdPI, and yet they completely inhibit tryptase.

We determined the stoichiometry of Fab hu31A.v11 binding to tetrameric tryptase in solution. Active tetrameric tryptase beta 1 was mixed with a 2-fold molar excess of Fab hu31A.v11 to each protomer and complex formation was allowed to reach equilibrium. Because the tetramer is assembled non-covalently, the dissociating effect of each antibody on the tetrameric structure was analyzed by size exclusion chromatography (SEC) and the retention times/volumes and the molecular weights of the individual protein peaks were determined. The fractions containing protein were characterized by SDS-PAGE to determine the protein components (FIG. 3A). The retention time of tetrameric tryptase alone was significantly shorter ($t_r$=26 min, run 1, peak 1) than when in complex with Fab hu31A.v1 ($t_r$=28.1 min, run 3, peak 3). An additional SEC analysis in combination with multi-angle light scattering (MALS) was performed to determine the molecular weight of the eluted protein complexes. Tetrameric tryptase had a molecular weight of 120 kDa±0.2% according to MALS, which is consistent with the theoretical molecular weight of 109.537 kDa based on amino acid sequence (excluding glycosylation). The protein peak containing tryptase in complex with Fab hu31A.V11 was measured to be 67.7 kDa±3% by MALS (peak 3), which reflects a complex comprising 1 tryptase monomer bound to 1 Fab. This indicates that the tryptase tetramer dissociates into monomers upon binding to Fab hu31A.v11, which is further corroborated by the crystal structure (see Example 3) and the inhibitory activity of the hu31A.v11 Fab.

When the same tetrameric tryptase/Fab hu31A.v11 complex was analyzed by SEC in enzyme assay buffer that contained a high concentration of heparin, e.g., 100 µg/ml heparin (run 2), the retention time of the tryptase-Fab complex was only slightly decreased from 28.1 min (run 3, peak 3) to 27.6 min (run 2, peak 2), likely due to heparin binding to the protein complex of tryptase monomer and Fab. Heparin from porcine intestinal mucosa is a mixture of polyanion chains having molecular weights ranging from 6 to 30 kDa, with most chains in the range of 17 to 19 kDa. This result indicates that the stabilizing effect of heparin on tetrameric tryptase is also neutralized or disrupted by Fab hu31A.v1; even a high concentration 100 µg/ml of heparin cannot prevent Fab hu31A.v11 from completely dissociating the tetramer. See FIG. 3A.

The binding stoichiometry of the huE104.v1 and huE104.v2 Fabs to tetrameric tryptase in solution was also determined. Active tetrameric tryptase was mixed with a 2-fold molar excess of Fab to each protomer and complex formation was allowed to reach equilibrium. The resulting complex mixture was separated by SEC with tryptase SEC buffer without heparin and the retention times/volumes and the molecular weights of the individual protein peaks were determined). The fractions containing protein were characterized by SDS-PACE to determine the protein components (data not shown). WT tetrameric tryptase had a retention time of $t_r$=26 min (see for example, peak 1 of FIG. 3A) and a molecular weight of 120 kDa±0.2% according to MALS, which is consistent with the theoretical molecular weight of 109.537 kDa based on amino acid sequence (excluding glycosylation).

huE104.v1 Fabs formed a homogeneous complex with WT tetrameric tryptase with a retention time of $t_r$=21.6 mL and a molecular weight of 276.1 kDa, as determined by SEC-MALS (data not shown). This would represent a complex of tryptase tetramer with 4 Fabs bound to it. SDS-PAGE analysis of fractions from this peak confirmed the presence of Fabs and tryptase protomers. Thus, huE104.v1 Fabs formed a stable complex with tetrameric tryptase and did not affect tetramer stability (data not shown).

Monomeric His6-tagged tryptase (FIG. 3B, run 1) or WT tetrameric tryptase (FIG. 3B, run 2) were mixed with 2-fold molar excess of huE104.v2 Fab and each complex mixture analyzed individually by SEC. The first protein peak of each chromatogram had a retention time $t_r$=25.8 min (FIG. 2B, run 1, peak 2) and $t_r$=26 min (FIG. 2B, run 2, peak 3), respectively. SDS-PAGE analysis of fractions from these two first peaks showed that both, tryptase and E104.v2 Fab, were present in this peak. Both protein peaks were also analyzed by MALS and a molecular weight of 68 kDa±3% was determined, which reflects a complex comprising 1 tryptase monomer bound to 1 Fab. The second peak of each run had a retention time of $t_r$=31.6 min min (run 1, peak 6) and $t_r$=31.8 (run 2, peak 7), respectively, and contained only Fab huE104.v2, as determined by SDS-PAGE. The chromatograms of both SEC runs practically superimposed, indicating that huE104.v2 Fab binding dissociates WT tetrameric tryptase into monomers, since the retention times were practically identical, independent of whether tetrameric tryptase or His-tagged monomeric tryptase was used for complex formation.

When tetrameric tryptase was mixed again with excess huE104.v2 Fab in the presence of 100 µg/mL heparin and analyzed by SEC in TNH buffer as running buffer (run 3), 3 protein peaks were observed: the first peak has a much shorter retention time ($t_r$=21 min, FIG. 3B, run 3, peak 1) than WT tetrameric tryptase alone ($t_r$=26 min, e.g., FIG. 3A, peak 1). The second peak has a retention time of $t_r$=27.2 min (FIG. 3B, run 3, peak 4) and the last one has a retention time of $t_r$=31.2 min (FIG. 3B, run 3, peak 5), which is indicative of Fab alone. SDS-PAGE analysis showed that both tryptase and Fab were present in peaks 1 and 4, wherein peak 1 contains the active tetramer bound by huE104.v2 Fabs, and peak 4 contains tryptase monomer bound by huE104.v2 Fab (data not shown). This led us to conclude that in the presence of 100 µg/mL high concentration of heparin, only a fraction of tetrameric tryptase was dissociated by huE104.v2 Fab as in peak 4, while the majority of tryptase remained tetrameric tryptase bound to hu104.v2 Fabs in peak 1. In summary, huE104.v1 Fab showed no detectable inhibitory activity, while huE104.v2 Fab completely dissociated tryptase tetramer. Unlike hu31A.v1 Fab or huE104.v2 IgG, however, the ability of huE104.v2 Fab to dissociate the tetramer was partially neutralized by high concentration of heparin. Thus, based on these data, we conclude that hu31A.v11 Fab is capable of dissociating tryptase tetramer with or without high concentration of heparin, and huE104.v2 Fab is capable of dissociating tryptase tetramer in the absence of high concentration of heparin.

Each tryptase monomer has an identical set of catalytic triad, and the four monomers assemble to form a tetramer with the four catalytic sites facing the middle pore into which the substrate enters. See Pereira et al., supra. Pereira et al. discuss design of small molecule tryptase inhibitors by blocking the active sites. Several small molecule tryptase inhibitors in development had been discontinued due to poor selectivity or poor bioavailability. See, e.g., Cairns, J. A., 2005, Pulmonary Pharmacology & Therapeutics 18:55-66.

Wild-type tetrameric tryptase is not covalently held together and can dissociate into monomers under physiological conditions (Schwartz et al. *J. Biol. Chem.* 261: 7372-7370, 1986; Alter et al. *Biochem. J.* 248:821-827, 1987; Schwartz et al. *J. Immunol.* 144:2304-2311, 1990). It has been reported that mature tryptase demonstrates high enzymatic activity as a tetramer, and is inactive as a monomer under physiologically relevant conditions (Schwartz et al., *J. Biol. Chem.* 261:7372-7379, 1986). The data shown herein demonstrate that both hu31.v11 and huE104.v2 bind to tryptase monomers, dissociate the tetramer to monomers at least at low concentration of heparin, and after dissociation, remain bound to the monomers. It has also been reported that monomeric tryptase may be enzymatically active under certain conditions (Fukuoka et al. *J. Immunol.* 176:3165, 2006; Fajardo et al., 2003, Biochem. J. 369:603-610). The observations raise the question whether a dissociating anti-tryptase antibody will be inferior to an active site blocking inhibitor such as a tetramer-stabilizing, active site blocking antibody, because serum inactive monomer may act as a major sink for the dissociating antibodies that binds to the monomers. And a tetramer-stabilizing, active site blocking antibody may be more advantageous as a therapeutic if monomers can be enzymatically active under certain conditions.

We first investigated the efficacy of a tetrarer-dissociating antibody as compared to a tetramer-stabilizing, neutralizing antibody in an in silico experiments using a pharmacokinetic-pharmacodynamic (PKPD) model. The model was developed in Simbiology® software (Mathworks Inc, Cambridge MA) to simulate tetrameric tryptase generation, dissociation, and clearance in the circulating and in the lung tissue, as well as the PK and binding effects of the anti-tryptase antibodies. Two types of antibodies are considered: (1) a dissociating antibody that dissociates the tetramer rapidly upon binding, but also binds monomer; and (2) a stabilizing tetramer-specific antibody, that binds active tetramer only and neutralizes its activity by blocking the access to its substrates, but also extends half-life of the tetramer. A tetramer-dissociating antibody with a $K_D$ of 0.2 nM was simulated under a hypothetical dose regimen of 300 mg administered subcutaneously every four weeks. We assumed a 10% lung partition coefficient of the antibody. For the baseline scenario, we assumed 4 ng/ml total tryptase in the serum and 10 ng/ml total tryptase in the tissue compartment, and for the high-tryptase scenario, we assumed 10 ng/ml serum tryptase and 40 ng/ml tissue tryptase levels. The relative rate constants for physiologic tetrameric dissociation to monomer and the clearance of each species results in an 8:1 ratio of monomer to tetramer within the total tryptase pools.

Figure 4A:
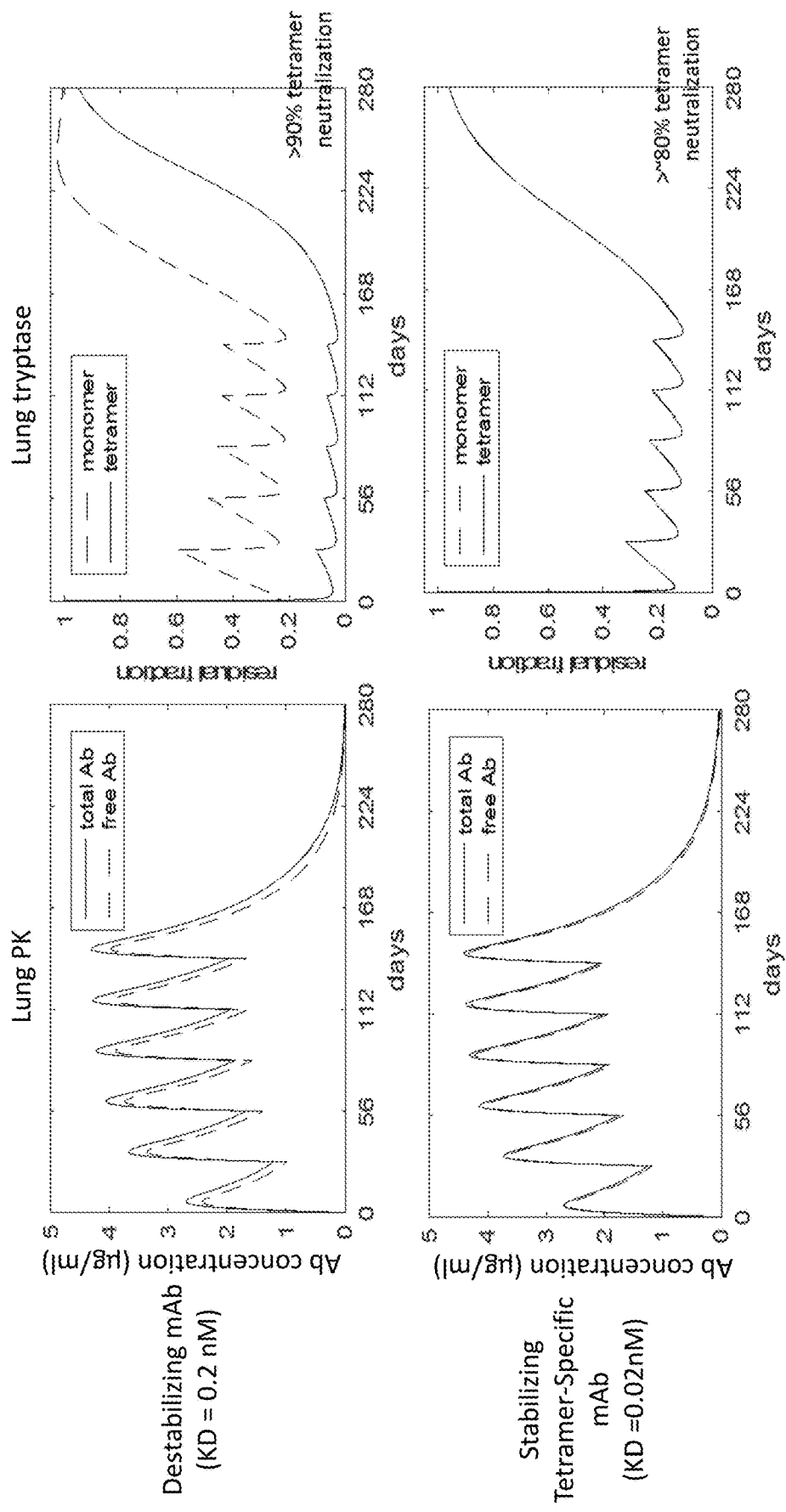
FIGS. 4A and 4B are series of graphs showing the results of a pharmacokinetic (PK) simulation that compares the PK and neutralizing activity of a dissociating anti-tryptase antibody with a tryptase tetramer-specific stabilizing antibody at a baseline tryptase level (4 ng/ml serum, 10 ng/ml lung tissue, FIG. 4A) or a high tryptase level (10 ng/ml serum, 40 ng/ml lung tissue, FIG. 4B).

For the simulated dose regimen of 300 mg sc q4w of either dissociating or stabilizing antibodies, FIG. 4A left panels show the antibody concentration of both total antibody and free/unbound antibody in the lung under the baseline scenario, and right panels show the corresponding lung (free) tryptase levels relative to pre-treatment levels for both monomer and tetramer. Results suggest that for a dissociating antibody with $K_D$=0.2 nM (top panels), most of the lung antibody remains free (top left panel) indicating adequate drug availability despite binding to the monomer and tetramer; results further indicate that the dissociating antibody would achieve a sustained reduction of over 90% in tetrameric (active) tryptase (top right panel). For the stabilizing antibody (bottom panels), nearly all of the antibody is free (bottom left panel); however, reduction in tetramer is only maintained at or above 80%.

Figure 4B:
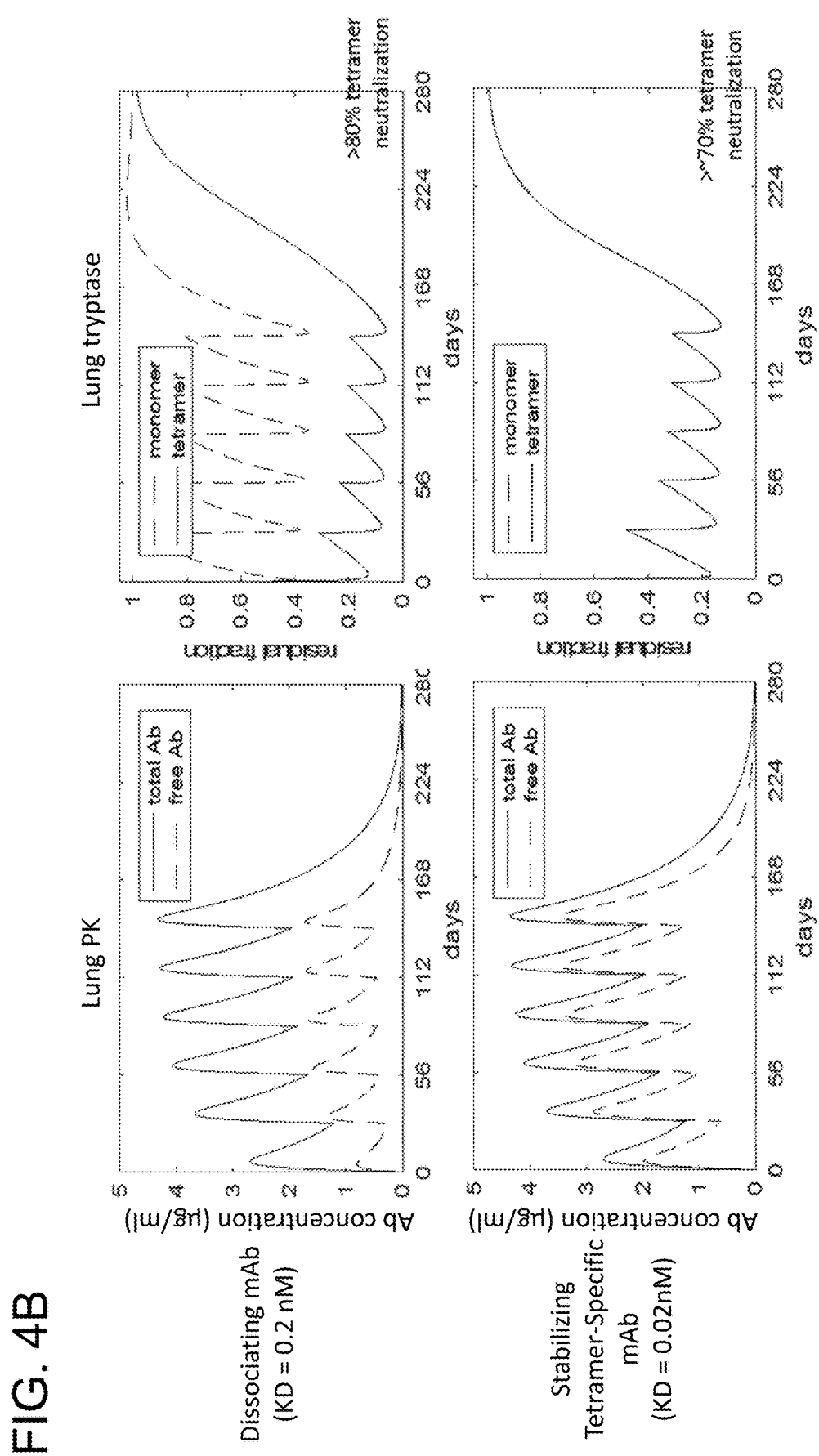

Because the tetramer-specificity of the stabilizing antibody could be considered advantageous under high total tryptase conditions, these simulations were repeated under the higher tryptase scenario (FIG. 4B). Under these conditions, more dissociating antibody is bound by the inactive monomeric tryptase, resulting in lower free antibody (compare top left panel of FIG. 4B with that of FIG. 4A) and leading to a lesser but still good tetramer neutralization (minimum ~80%) by the dissociating antibody (FIG. 4, top right panel). By comparison, for the tetramer-stabilizing antibody, despite greater free antibody due to absence of binding to monomer (FIG. 4B, bottom left panel), the antibody achieves less neutralization (minimum ~70%) as compared with the dissociating antibody under the same conditions, despite a 10-fold higher affinity assumed for the stabilizing antibody ($K_D$=0.02 nM) in the simulations (FIG. 4B, bottom right panel). The lesser neutralization is due to greater stability (half-life) of the bound target which serves as a "reservoir" for tetramer. Thus, our simulations predict that a dissociating antibody is promising and would perform better than tetramer-specific stabilizing antibody under different scenarios tested.

Figure 4C:
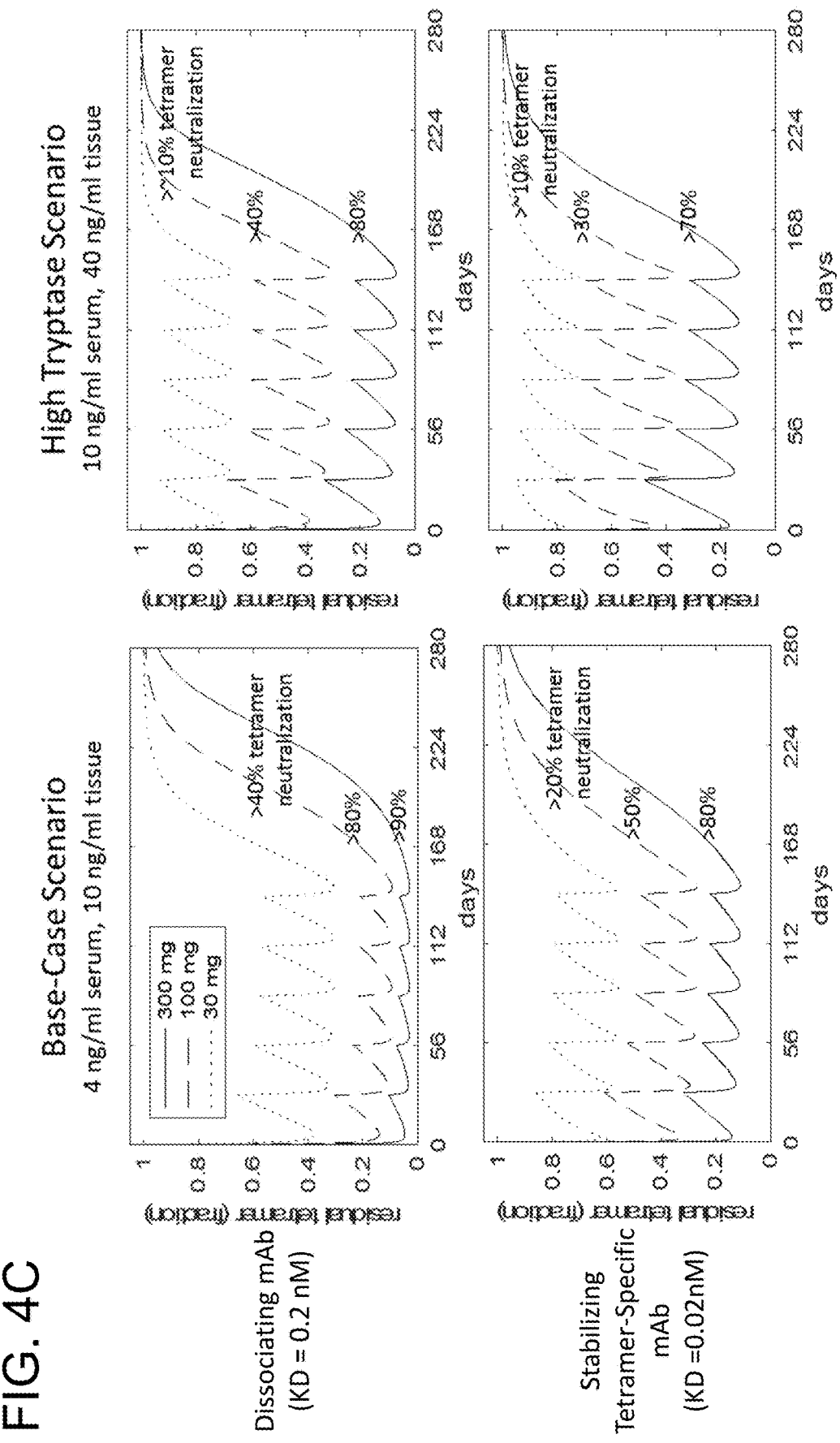
FIG. 4C is a series of graphs showing the results of neutralizing activity simulation comparing a dissociating anti-tryptase antibody and a tryptase tetramer-specific stabilizing antibody at the baseline tryptase level or a high tryptase level.

We next tested how the dissociating antibody compares with the tetramer-specific stabilizing antibody at different antibody doses. FIG. 4C shows the tetramer neutralization for both types of antibodies, at both baseline and high tryptase scenarios, as a function of antibody dose level (30, 100, 300 mg so q4w). In the baseline scenario (FIG. 4C, left panels), the dissociating antibody consistently reduces tetramer activity more than the stabilizing antibody, across all doses considered. In the high tryptase scenario (FIG. 4C, right panels), the dissociating antibody outperforms the stabilizing antibody with respect to tetramer neutralization at all but the lowest dose (30 mg), at which point the two antibodies perform comparably. The generally lesser neutralization achieved using the stabilizing antibody despite a 10× greater affinity ($K_D$=0.02 nM) than the dissociating antibody ($K_D$=0.2 nM), indicates a much higher affinity requirement (>10×) for comparable tetramer neutralization using the stabilizing antibody compared to the dissociating antibody. For both scenarios, the optimal dose for (90%) tetramer neutralization is lower for the dissociating antibody than for the stabilizing antibody (results not shown), despite the 10× greater affinity assumed for the stabilizing antibody. Thus, under the model, the dissociating antibody would outperform or at least match the stabilizing antibody that has 10× higher affinity, across the dose range and serum and lung tryptase concentrations tested. In addition, we demonstrated herein that hu31A.v11 and huE104.v2 IgG completely inhibited all tryptase activity. See FIG. 2A and Table 5.

To our knowledge, there has not been any example of tryptase tetramer dissociating antibody developed for therapeutic uses. It is known that the inflammatory loci of disease tissues including acute asthmatic lung are acidic as compared to control subjects; see, e.g., Hunt et al. *Am. J. Respir. Crit. Care Med.* 161:694-699, 2000; Steen et al. *J. Neuroscience* 15:3982, 1995; Bellocq et al. *J. Biol. Chem.* 273: 5086, 1998; and Lardner *J. Leukocyte Biol.* 69:522, 2001). Published data showed that the murine monoclonal anti-tryptase antibody B12 neutralizes human tryptase beta at neutral pH but is unable to neutralize human tryptase beta activity in an enzymatic assay at acidic pH 6 (see Fukuoka et al. *J. Immunol.* 176:3165, 2006). Therefore, we tested antibodies hu31a.v11 and huE104.v2 for their ability to inhibit the activity of human tryptase beta in cleaving fibrinogen at both neutral pH and at acidic pH.

Briefly, human tryptase beta tetramer (1.0 µg/mL) was preincubated with the tested antibody for 30 min in TNH buffer at pH 6.0 or 7.5 (50 mM Tris, 150 mM NaCl, 0.1 mg/ml heparin) at room temperature. The mixture was then incubated with 5 µg human fibrinogen substrate (Haematologic Technologies, Inc., Cat. No. HIC-0150R) for 2.5 h at 37° C. hu31A.v11 Fab, huE104.v2 Fab, and B12 mIgG1 were each tested at 200 µg/mL. The cleavage products were analyzed by SDS-PAGE and Coomassie Blue staining.

As shown in FIGS. 5A and 5B, human tryptase beta 1 cleaved fibrinogen alpha and beta chains at both pH 6 and 7.5 (compare lane 1, fibrinogen only, with lane 2, fibrinogen plus tryptase beta 1). Antibody hu31A.v11 Fab inhibited human tryptase beta at both pH 6 and pH 7.5 (lane 3), while huE104.v2 Fab, under the assay condition of 0.1 mg/ml of high concentration of heparin, did not (lane 5). Lane 6 was B12 mIgG1 alone. The decrease in fibrinogen alpha chain is indicative of tryptase proteolytic activity. The fibrinogen beta chain is also cleaved, but the beta chain cleavage tends to be obscured on the gel. The intensity of the alpha chain was thus quantified and shown in the bottom panels of FIGS. 5A and 5B. Thus, hu31A.v11 Fab inhibited tryptase activity at pH 6 and 7.5, while huE104.v2 Fab under the assay condition of high heparin concentration, was not inhibitory.

The inhibitory activity of IgG format antibodies (hu31A.v11 IgG4 and huE104.v2 IgG4) was also evaluated using S-2288 peptide as a substrate in an inhibition assay in the presence of 1 nM tryptase and 400 pM chromogenic S-2288 in TNH buffer at pH 6, 7, or 8. The final concentration of heparin in this experiment was about 95 µg/ml. Both hu31A.v11 and huE104.v2 in the IgG format completely inhibited tryptase activity at pH 6, 7, and 8 (data not shown).

Therefore, hu31A.v11 IgG and huE104.v2 IgG both bind to tryptase with high affinity and also efficiently inhibit tryptase activity under physiologically relevant conditions for tryptase-associated disorders such as asthma. Interestingly, in our experimental conditions, murine monoclonal anti-human tryptase antibody B12 IgG1 also showed inhibition of human tryptase beta at pH 6 (FIG. 5A, lane 4), contrary to published results. The discrepancy may be attributed to any residual non-tryptase protease activity present in the material used for the assay in the published data that was activated by acidic pH and resistant to B12 inhibition.

Example 3: Structural Analysis of Anti-Tryptase Antibodies

A. 31A Family Antibodies
(i). X-Ray Crystallography
Wild-type tetrameric tryptase was mixed with 1.5-fold molar excess Fab hu31A.v11 and 2-fold molar excess soybean trypsin inhibitor (STI) (Roche) and incubated for 10 min at room temperature. STI was added to facilitate crystallization. The mixture was then subjected to SEC using an S200 column (GE Healthcare) in 10 mM MOPS (pH 6.8), 0.5 M NaCl. Fractions containing the ternary complex of tryptase, STI, and Fab hu31A.v11 were pooled and concentrated to 40 mg/mL.

Crystals of tryptase/Fab hu31A.v11/STI were grown at 19° C. using the vapor diffusion method in hanging drops. Crystallization buffer containing 0.1 M Tris (pH 7.5), 0.2 M lithium sulfate, and 5% polyethylene glycol (PEG) 4000 was mixed in equal volume with the protein solution. The crystals were dipped in artificial mother liquor containing 25% ethylene glycol and vitrified in liquid nitrogen.

Table 7 shows X-ray data collection and refinement information for the structure of Fab hu31A.v11/tryptase/STI. Diffraction data extending to 2.15 Å were collected in a hexagonal lattice at ALS Beamline 5.0.2. Data reduction and scaling allowed assignment of the Laue class to 6/mmm (Otwinowski, *Methods in Enzymol.* 276, 307-326, 1997; Winn et al. *Acta Crystallogr. Sect. D-Biol. Crystallogr.* 67, 235-242, 2011). Based on unit cell volume and proposed protein content, a single Fab hu31A.v11/tryptase/STI complex was expected in the crystallographic asymmetric unit. The structure was solved using molecular replacement (McCoy et al. *J. Appl. Crystallogr.* 40:658-674, 2007) in space group $P_6 22$. The following search probes were used, each as separate bodies: a previously determined tryptase protomer derived from PDB accession 4A6L (Liang et al. *Bioorg. Med. Chem. Lett.* 22:1049-1054, 2012), STI from PDB 1AVU (Song et al. *J. Mol. Biol.* 275:347-363, 1998), an Fv fragment stripped of CDR loops from PDB 1FVC (Eigenbrot et al. *J. Mol. Biol.* 229:969-995, 1993), and the constant region from PDB 1FVD. After some restrained refinement (Murshudov et al. *Acta Crystallogr. Sect. D-Biol. Crystallogr.* 67:355-367, 2011), electron density maps permitted correction of Fab protein sequence and fitting missing residues and side chains into clear density (Emsley et al. *Acta Crystallogr. Sect. D-Biol. Crystallogr.* 66:486-501, 2010). Waters were added automatically (Adams et al. *Acta Crystallogr. Sect. D-Biol. Crystallogr.* 66:213-221, 2010). More rounds of model adjustments and refinement (BUSTER software; Global Phasing Ltd., 2011) led to the final model. The model is continuous for tryptase residues Ile16-Lys244 (chymotrypsinogen numbering), STI residues Asp1-Asp177, Fab light chain residues Asp1-Cys214 (Kabat numbering) (Kabat, *Sequences of Proteins of Immunological Interest*. Bethesda, MD, U.S. Dept. of Health and Human Services, Public Health Service, National Institutes of Health, 1991). The Fab heavy chain is continuous except for a five amino acid residue gap in the constant domain. The value for the shape complementarity statistic (Sc) (Lawrence et al. *J. Mol. Biol.* 234:946-950, 1993) is 0.73, consistent with other tight-binding Fab/antigen complexes. The largest inter-protein contact area is that between tryptase and STI, as they each lose 1260 Å$^2$ solvent accessible surface (Broger C, xsae, F. Hoffman-La Roche, Basel, Switzerland, 2000) at their interface. In contrast, the Fab/tryptase contact is only 760 Å$^2$ on each side, evenly distributed between light and heavy chains of the Fab. Crystal packing contacts 4 Å or less are well distributed around STI, tryptase, and all four Fab domains, and include numerous hydrogen bonds as well as hydrophobic contacts.

TABLE 7

X-ray Data Collection and Refinement
Fab hu31A.v11/Tryptase/STI

| Data reduction | |
|---|---|
| X-ray source | ALS 5.0.2 |
| Wavelength (Å) | 0.97395 |
| Resolution range (Å) | 31.48-2.15 (2.226-2.149) |
| Space group | $P_6 22$ |
| Unit cell edges (Å) | 128.52 128.52 245.88 |
| Unit cell angles (°) | 90 90 120 |
| Total reflections | 308799 |
| Unique reflections | 65702 (6404) |
| Multiplicity | 4.7 (4.8) |
| Completeness (%) | 99.8 (100) |
| Mean I/sigma(I) | 14.2 (2.3) |
| Wilson B-factor (Å$^2$) | 37.02 |
| R-symm | 0.086 (0.681) |
| Refinement | |
| Refs for R-free | 1996 |
| R-work | 0.190 |
| R-free | 0.233 |
| Number non-H atoms | 7057 |
| macromolecules | 6608 |
| ethylene glycol | 8 |
| water | 441 |
| Protein residues | 850 |
| RMS(bonds) | 0.010 |
| RMS(angles) | 1.1 |
| Rama favored (%) | 97 |
| Ave. B-factor (Å$^2$) | 45.7 |
| macromolecules | 45.6 |
| ethylene glycol | 59.7 |
| solvent | 47.1 |

(ii) Epitope Mapping of Anti-Tryptase Antibodies Analyzed by Hydrogen-Deuterium Exchange (HDX) and Measured by MS Deuterium uptake rates of monomeric tryptase in the presence and absence of antibody were measured to determine structural regions that are modified upon antibody binding. Bound samples contained a 1:1 mixture of tryptase and the respective antibody, prepared and incubated at room temperature for 1 h. Tryptase concentration prior to deuterium labeling was 30 pM in antibody-bound and unbound samples. HDX experiments involved diluting samples 15-fold into deuterium labeling buffer containing 20 mM histidine acetate at pD 7.0. Six labeling times, logarithmically sampled between 30 sec and 1000 min, were taken in triplicate, quenched by lowering the pH to pH 2.5 and adding 2 M guanidinium chloride (GdmCl) and 0.25 M tris(2-carboxyethyl)phosphine (TCEP), and injected into a cold online system, as previously described (Mayne et al., *J. Am. Soc. Mass. Spectrom.* 22:1898-1905, 2011).

Briefly, samples were first passed through an immobilized pepsin column (2.1×30 mm, Applied Biosystems) and loaded onto a trap column (Acquity Vanguard C) for desalting. Peptide fragments were then separated by reversed-phased chromatography using an Acquity UPLC™ BEH $C_{18}$ column (1.7 µm particle size, 1.0×50 mm) and introduced into the mass spectrometer (Thermo Orbitrap Elite™, 120 k Hz resolution at m/z 400) for mass analysis. Chromatographic mobile phases were prepared as previously described to minimize deuterium back exchange (Walters et al., *J. Am. Soc. Mass Spectrom.* 23: 2132-2139, 2012). The ExMS program (Kan et al. *J. Am. Soc. Mass. Spectrom.* 22:1906-1915, 2011) was used to identify deuterated peptides and prepare extracted ion chromatograms, which were then analyzed by in-house python scripts (Walters et al. *Proc. Natl. Acad. Sci. USA* 110:18898-18903, 2013). These scripts combine degenerate charge states, fit isotopic distributions with binomials, and extract the number of deuterium carried, on average, by each peptide.

(iii) Intact Mass by Liquid Chromatography/Mass Spectrometry (LC/MS)

Purified proteins (including tryptase and mutants thereof) were acidified with 0.1% trifluoroacidic acid (TFA) (Thermo, Rockford, IL) and diluted to a final concentration of 10 pM. Samples were analyzed on an Agilent 6520 Accurate-Mass quadrupole time-of-flight (Q-TOF) coupled with an Agilent 1260 Infinity high performance liquid chromatography (HPLC)-Chip Cube Interface (Agilent, Santa Clara, CA). Proteins were separated by reversed phase HPLC on a PLRP-S 150 mm×75 µm column at 40 nL/min flow rate with a 10 min, 5-80% gradient of aqueous solvent A (97% H20, 3% acetonitrile, 0.1% formic acid) to organic solvent B (98% acetonitrile, 0.1% formic acid). Data was collected with a MassHunter® Workstation (Agilent, Santa Clara, CA) and raw mass spectra were deconvoluted to generate intact mass data. Major peaks were observed at 61764.4 Da and 63152.9 Da. The addition of multiple GlcNAc (203 Da) masses were also observed.

(iv) Results

The crystal structure of human tryptase shows that each monomer of the tetramer contacts its neighbors at two different interfaces through six loop segments: the large interface (between protomers A/D and B/C) or the small interface (between protomer A/B and C/D) according to protomer nomenclature described by Pereira et al. *Nature* 392:306-11, 1998, which is incorporated herein by reference in its entirety. The six surface loops of each protomer surround the active site and engage in intermonomer contacts (Pereira, supra). Among which, the 147 loop, the 70-80 loop and the 37 loop engage in the interaction of small interface, and the 173 flap, the 97 loop and the 60 loop are important in large interface interaction. While the small interface involves only hydrophobic interactions, the large interface comprises several polar, charged interactions in addition to hydrophobic interactions. Heparin further stabilizes the small interfaces, which are believed to be the shear points of the tetramer, by binding non-covalently to positively charged residues spanning the two adjacent protomers A/B and C/D. See Pereira supra. Naturally, the small interfaces are the shear points of the tetramer, followed by the dissociation of the dimer held by the large interfaces. The half-life of tryptase is about 2-3 hours in circulation in human blood after development of systemic anaphylaxis (see, e.g., Schwartz et al. *J. Cin Invest.* 83:1551-1555,1989). The normal half-life of the tetramer is about 30 minutes.

We determined whether the small or the large protein interfaces that hold the tryptase tetramer together are destabilized upon hu31A.v11 or huE104.v2 binding to tryptase. Two tryptase mutants were generated which resulted in covalent linkage of two neighboring protomers in the tetramer via an intermolecular disulfide bond in either the large interface (between protomers A/D and B/C) or the small interface (between protomer A/B and C/D) according to protomer nomenclature described by Pereira et al. supra. Thus, when dissociation of the small interface is prevented due to covalent disulfide-linked dimer formation, dissociation of the large interface is still permitted. Conversely, when dissociation of the large interface is prevented due to covalent disulfide-linked dimer formation, dissociation of the small interface is still permitted.

Tyr75 in the small interface and Ile99 in the large interface (chymotrypsinogen numbering, FIG. 7) were individually mutated to cysteine. These sites were selected because they face themselves in these interfaces due to the quasi 2-fold symmetry of the tetramer (Sommerhoff et al. *Proc. Natl. Acad. Sci. USA* 96:10984-91, 1999). Replacement of Tyr75 or Iie99 to cysteine in silico using PyMOL software showed respective distances of 2.4 Å and 3.2 Å between the thiols of each opposing cysteines, which is somewhat greater than a typical disulfide bond length of 2.05 Å. Nonetheless, the two resulting tetramer mutants were expressed and purified and contained a disulfide bond that had formed between the respective interfaces as determined by tryptic peptides MS analysis. Further, both mutants were also enzymatically active, but with about half the catalytic efficiency ($k_{cat}/K_M$) when compared to wild-type tetrameric tryptase (Table 8).

TABLE 8

Enzymatic activity of wild-type and mutant tryptase

| Tryptase | $K_M$ (µM) | $V_{max}$ (nM/sec) | $k_{cat}$ (1/s) | $k_{cat}/K_M$ (1/(M*s)) | Catalytic efficiency (Mutant/WT) |
|---|---|---|---|---|---|
| WT | 554 | 400 | 100 | 180505.42 | 1 |
| Y75C Small interface locked | 320 | 133 | 33.25 | 103906.25 | 0.57 |
| I99C Large interface locked | 798 | 235 | 58.75 | 73621.55 | 0.41 |

The size of these mutants complexed with hu31A.v11 Fab or huE104.v1 Fab was analyzed. Tryptase mutants Y75C and I99C were each mixed with a 2-fold molar excess of Fab hu31A.v11 for complex formation, as described above for wild-type tryptase, and analyzed by size exclusion chromatography. As a reference for comparison, wild-type tetrameric tryptase was complexed with a Fab from the antibody huE104.vi, which binds specifically to tryptase, but does not dissociate the tetramer, and which loses inhibitory activity at high antibody to tetramer ratio. Wild-type tetrameric tryptase complexed with huE104.v1 Fab had a retention time of 21.6 min (FIG. 6A, reference peak). SEC-MALS analysis of this complex determined a molecular weight of 276.1 kDa, indicative of a complex comprising one tryptase tetramer with four bound Fabs.

Figure 6B:
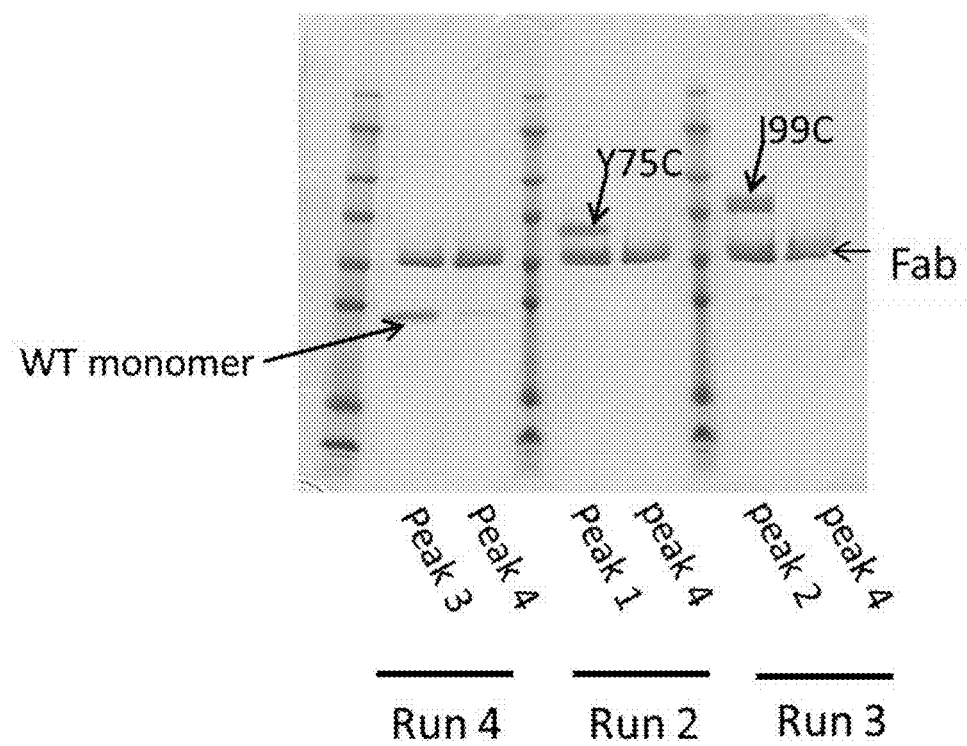
FIG. 6B shows the results of a Coomassie-blue stained SDS-PAGE gel analysis of size exclusion chromatography peaks a FIG. 6A. hu31A.v11 Fab formed complexes with tryptase mutants Y75C and I99C and dissociated the tetramer into covalently linked dimers.

Fab hu31A.v11 formed complexes with tetrameric tryptase mutants Y75C and I99C with retention times of 25.6 min (FIG. 6A, run 2, peak 1) and 23.9 min (FIG. 6A, run 3, peak 2), respectively (FIG. 6A). Both retention times are longer than that of the reference complex, indicating that both tetramer mutants dissociate into their respective covalently linked dimers upon complex formation with Fab hu31A.v1. Samples from each peak were collected and analyzed by SDS-PAGE to confirm the species in each peak (FIG. 6B). SDS-PAGE analysis of these eluted protein peaks show that both Fab hu31A.v1 and respective tryptase dimers were present in the same fraction (FIG. 6B). Peak 3 ($T_r$ of 28.1 min) and peak 4 ($T_r$ of 31.6 min) of run 4 represented WT monomer complexed with Fab hu31A.v11 and excess Fab, respectively. A small amount of peak 3 sample was carried over to peak 4 sample in SDS PAGE. Both tryptase mutants in complex with Fab hu31A.v11 run with a longer retention times than the reference peak, indicating that both the large and the small interface are destabilized upon Fab hu31A.v11 binding. This destabilization results in tetramer dissociation, as observed for wild-type tryptase tetramer, which ultimately inactivates the proteolytic activity of tryptase. B12 Fab also destabilized both mutant tetramers (data not shown).

The binding of the humanized anti-tryptase antibody hu31A.v11 to mature human tryptase beta 1 was studied using X-ray crystallography to determine the structure of the molecular complex between tryptase and the Fab fragment of hu31A.v11 at 2.15 Å resolution. The result was a crystallographic asymmetric unit containing one tryptase/STI (soybean trypsin inhibitor) complex interacting with one hu31A.v11 Fab. STI was included for the purpose of crystallization.

One definition of epitope is the set of tryptase amino acids that are within 4 Å of any atom of the hu31A.v1 Fab. The program PyMOL was used to find epitopes. The amino acid residues in the tryptase polypeptide chains can be numbered according to a convention (chymotrypsinogen numbering) that deviates from sequential numbering to permit comparisons across homologous proteins. A table translating between this tryptase residue numbering scheme and the simple sequential scheme is provided (FIG. 7). Tryptase residues below are named according to the convention, with the gene-sequential numbering scheme in parenthesis.

The epitope of hu31A.v11 on tryptase includes the following residues: H36, 050, V60c, K60d, D60e, L61, A62, A63, R65, P84, V85, S86, R87, E109, E110, P111 (chymotrypsinogen numbering, corresponding to H51, 067, V80, K81, D82, L83, A84, A85, R87, P103, V104, S105, R106, E128, E129, and P130, respectively, of SEQ ID NO: 71). See FIG. 8. Residues of the 60s, 80s, and 100s loops of tryptase are in intimate contact with Fab hu31A.v1, while His36 and Gln50 residues are more on the periphery of the interaction with the Fab. See also Pereira et al. supra. The Fab-tryptase contact excludes 760 Å$^2$ from solvent (each side), with equal contributions from the Fab light chain (Va30, Thr31, Tyr32, Tyr34, Arg50, Tyr90, His92, Ser93, Tyr94) and heavy chain (Phe50, Ser52, Gly53, Ser54, Ser55, Thr56, Tyr58, Arg95, Tyr97, Asp98). It is considered that the epitope residues described above would also apply to other 31A-derived antibodies.

Figure 9:
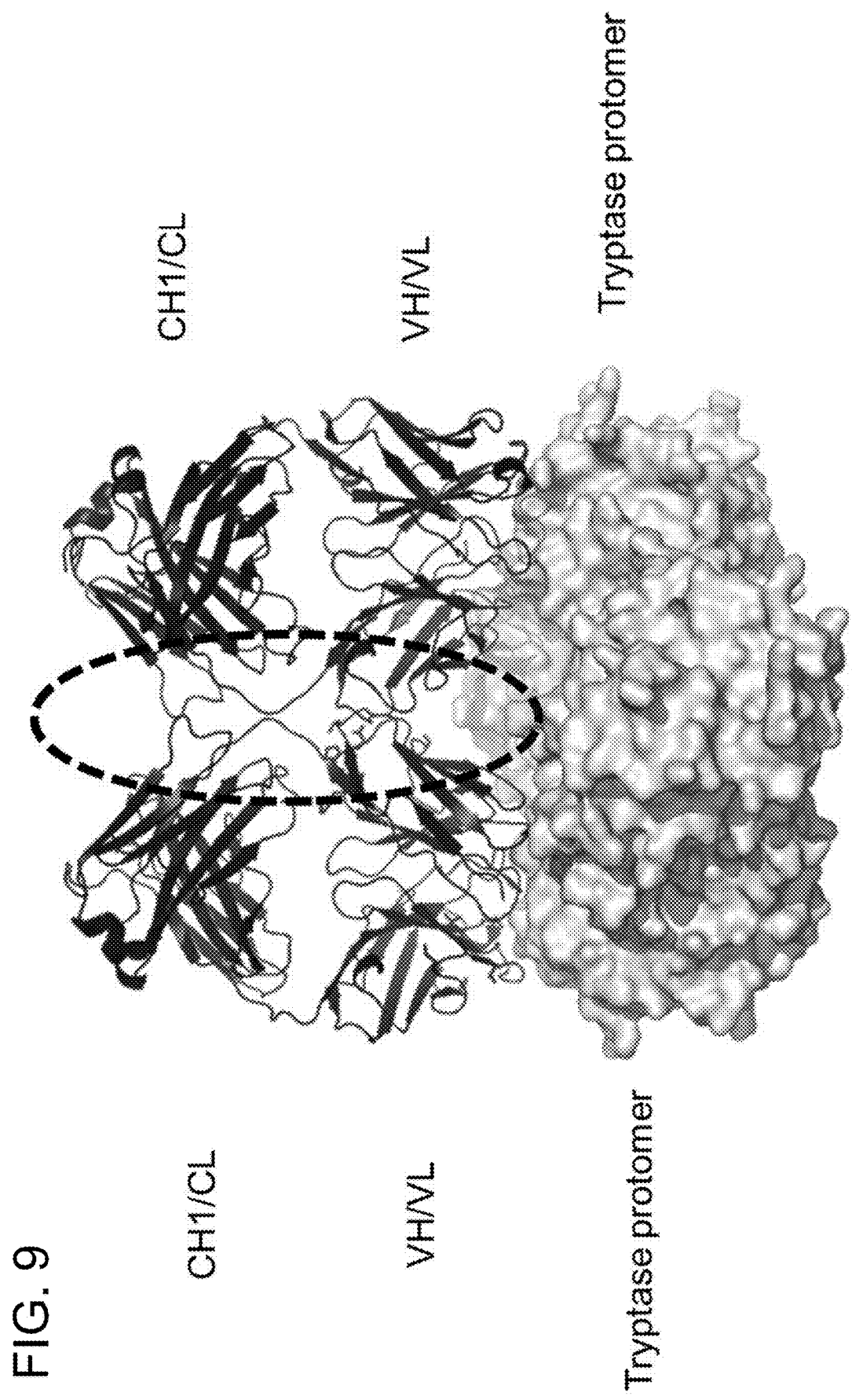
FIG. 9 is a rendering showing modeling of Fab hu31A.v11 onto the tryptase tetramer. The tryptase monomers in complex with Fab hu31A.v11 were aligned to protomers A and C in the tryptase tetramer. Heavy chains and light chains are indicated. Clashes between the light chains of Fab hu31A.v11 on adjacent tryptase protomers in this model are highlighted by a dashed oval.

When the Fab/tryptase dimer from the ternary complex was superposed onto tryptase protomers A and D from the wild-type tetramer (Pereira et al. supra), we found that the two Fabs sit on the same side of the tetramer, almost perpendicular to the tetramer plane (FIG. 9). Repeating this process for protomers B and C places two Fabs on the opposite side of the tetramer. Notably, these results highlight the steric clashes between the Fab light chains, consistent with the fact that the Fab elutes as a 1:1 complex with monomeric tryptase on SEC and not as a complex with tetrameric tryptase (FIG. 9).

Tetrameric tryptase is not covalently held together and can dissociate into monomers under physiological conditions, as monitored by the decay in the enzymatic activity over time and changes in the circular dichroism (CD) spectrum in solution (Schwartz et al. *J. Biol. Chem.* 261: 7372-7379, 1986; Schwartz et al. *J. Immunol.* 144:2304-11, 1990). Binding of hu31A.v11 (Fab or IgG) to each protomer of the tetramer would promote and accelerate the dissociation of the tetramer and prevent any tetramer re-association due to the steric clashes of the Fabs when bound to tryptase. Thus, tryptase dissociates and becomes enzymatically inactive monomer in a more rapid fashion due to allosteric changes on each protomer caused by hu31A.v11 binding. Because of the pseudo-2-fold symmetry in the tetramer, almost all of the interactions that constitute the small and the large interfaces exist twice. This also means that each subtle change in the tryptase structure caused by hu31A.v11 binding occurs twice in each interface, thereby potentiating destabilization.

Figure 10:
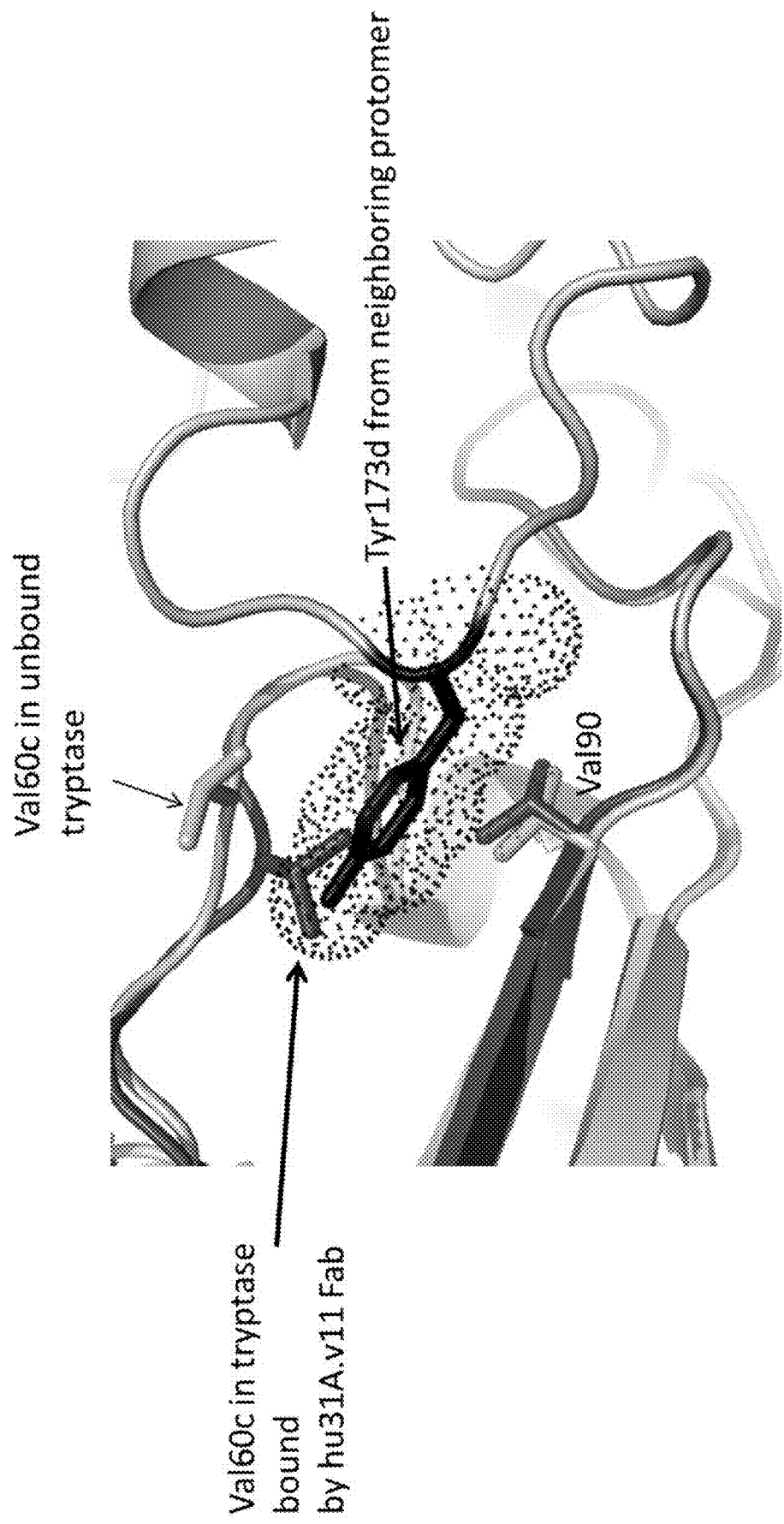
FIG. 10 shows conformational changes in the 60s loop of tryptase detected in the complex structure. Val60c and Val90 (shown in sticks) create a hydrophobic pocket for binding of Tyr173d from the neighboring protomer as part of the protein-protein interaction in the large interface of tetrameric tryptase. Tryptase protomers in the tetramer conformation are indicated. Tryptase bound to Fab hu31A.v11 is superposed to one protomer of the tetramer complex. The conformation of Val60c changes when Fab hu31A.v11 is bound, which creates steric hindrance that is expected to prevent Tyr173d from binding to that pocket (tryptase residues all chymotrypsinogen numbering).

The complex structure of Fab hu31A.v1 with tryptase shows significant changes in the 60s loop, which is in the large interface. In particular, when bound by hu31Av1 Fab, residue Val60c (corresponding to Val80 of SEQ ID NO: 71) has a significant shift in the side chain when compared to its position found in the unbound tryptase structure. In the unbound tryptase tetramer, Tyr173d from the neighboring protomer sits in a hydrophobic pocket created by residues Val60c and Val90 (FIG. 10, both are by chymotrypsinogen numbering, see also FIG. 7). In the antibody complex, the conformational change of Val60c creates steric hindrance that prevents Tyr173d binding to that pocket. Since binding of hu31A.v1 to tryptase involves interactions with parts of the 60s loop and nearby residues, it may be responsible for this conformational change in Val60c. This could lead to destabilization of the large interface and would thus enhance dissociation of tryptase tetramer into inactive monomers.

Figure 11:
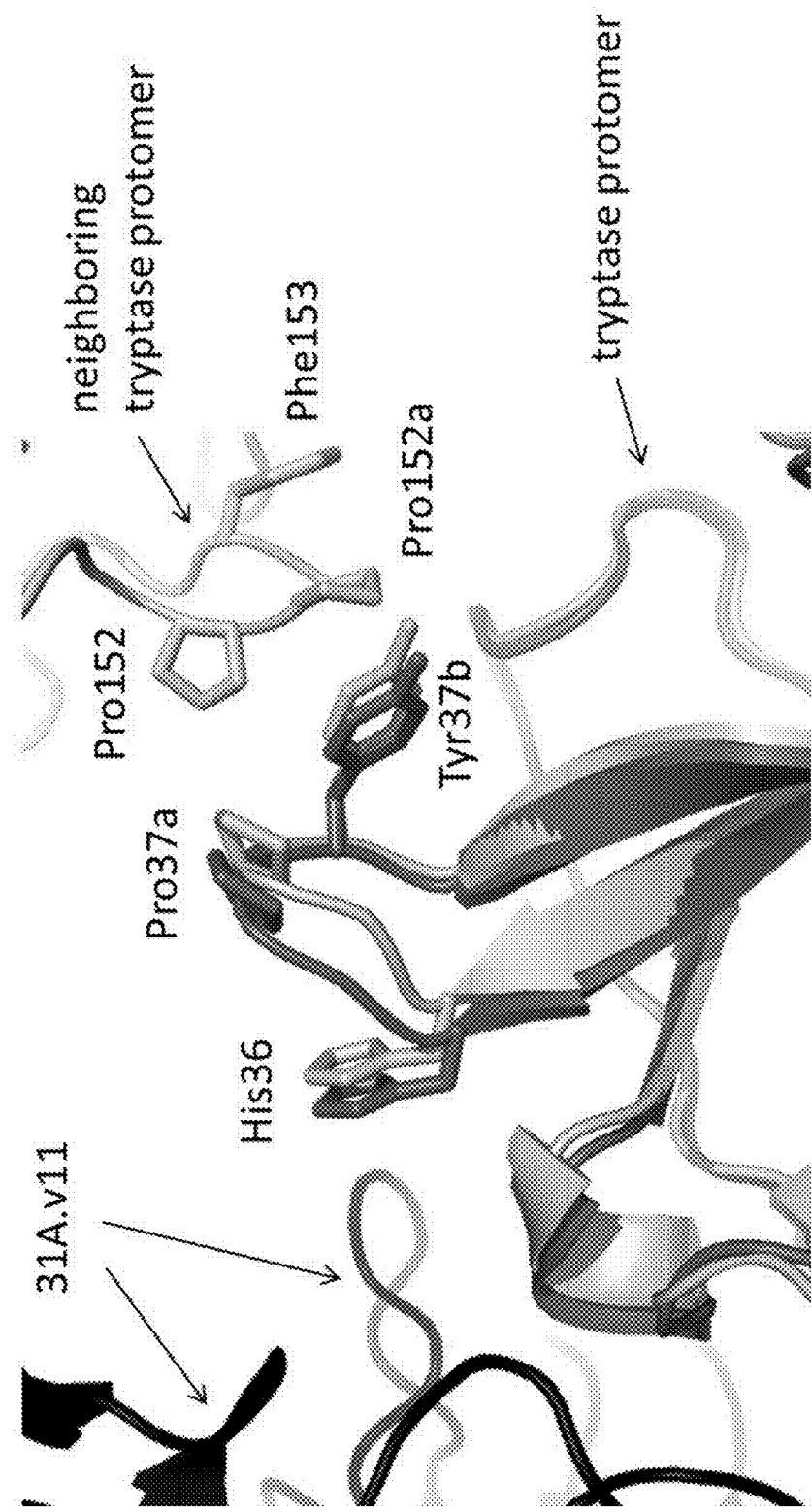
FIG. 11 shows conformational changes in the 30s loop of tryptase located in the small interface detected in the complex structure after binding to hu31A.v11.

The imidazole ring of His36 (chymotrypsinogen numbering; corresponding to His51 of SEQ ID NO: 71) in tryptase makes hydrophobic interactions with Fab hu31A.v1, resulting in changes the Ca trace in the 30s loop of tryptase residues His36, Pro37a, and Tyr37b when compared to tryptase protomers in the unbound tetramer structure. This affects the conformation of the Tyr37b side chain, such that a key hydrophobic interaction with a neighboring protomer comprising Pro152 and Pro152a in the small interface may be weakened (FIG. 11, all are by chymotrypsinogen numbering, see also FIG. 7).

The complex formation studies of the two different disulfide-locked tryptase variants Y75C and I99C with hu31A.v1 Fab show that both the large and the small interface of tetrameric tryptase are destabilized by the antibody. Both the steric clashes of Fabs bound to tetramer and conformational changes to key interacting residues of the large and the small interface are likely important in contributing to tetramer dissociation. These two factors are not mutually exclusive. Steric hindrance stemming from hu31A.v11 Fabs when bound to each protomer of the tetramer demonstrated in silico indicate that two Fabs from a single IgG could typically never bind simultaneously to one tetramer (FIG. 9). This observation is consistent with the finding that both the Fab and the IgG of hu31A.v11 are capable of dissociating the tetramer, thereby inhibiting enzymatic activity. This observation also indicates that dissociated monomers bound by the antibody are unlikely to reassemble to form a tetramer.

Figure 8:
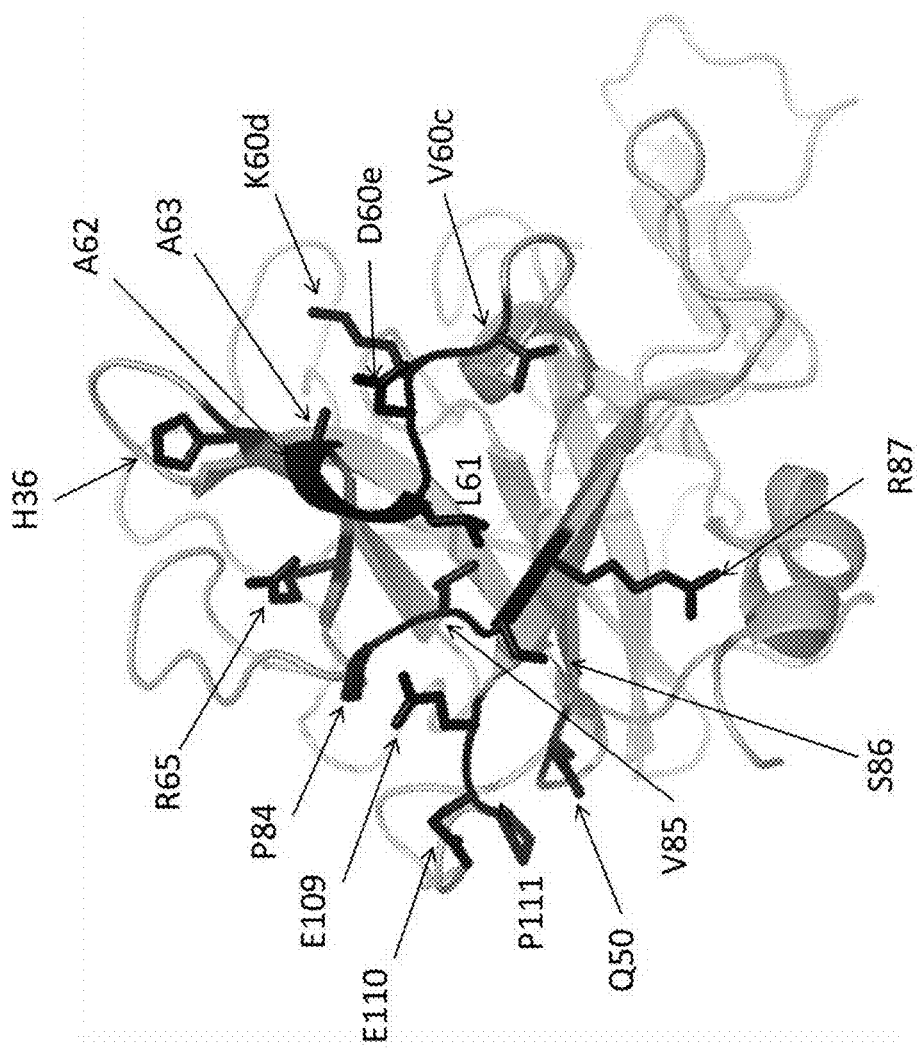
FIG. 8 shows the binding epitope of Fab hu31A.v11 on human tryptase beta 1 (tryptase residues all chymotrypsinogen numbering).

Next, HDX experiments of monomeric tryptase bound to hu31A.v11 Fab were performed to study the binding interactions in solution. The degree of HDX over time was monitored by mass spectrometry. While this method provides information indicative of the binding epitope of hu31 A.v1, it also detects allosteric changes in conformational stability that could occur away from the antibody binding epitope. Amide bonds that showed a slower exchange in tryptase when hu31A.v11 was bound were located in the regions of residues 25-29, 40-41, 57-59, 60-61, 66-67, 83-88, 108-110, and 231-233 (chymotrypsinogen numbering). When comparing these regions with tryptase residues within 4 Å of the Fab hu31A.v11 as seen in the crystal structure, a high degree of overlap between both methods identifying binding epitope residues in the 60s, the 80s and 100s-loop was observed (FIG. 8). Other areas identified by HDX such as positions in the 20s, 40s, 50s, and 230s regions of the primary tryptase sequence are not in direct contact with the antibody according to the crystal structure, but show a reduction in conformational dynamics in the presence of hu31A.v11. Interestingly, residues 57-59 seem to be allosterically affected by hu31A.v11 binding. This short α-helix contains the residue His57 (chymotrypsinogen numbering) that is part of the catalytic triad in serine proteases and essential for catalytic activity. Although residues 40 and 41 identified by HDX are not in direct contact with hu31A.v11, they are in an intriguing structural location as part of an anti-parallel beta-sheet displaying Tyr37b (chymotrypsin numbering) in their hairpin loop, which is an important contact residue for the small interface as discussed above (FIG. 11). Structural alterations to this area could influence the stability of the small interface and potentially lead to tetramer dissociation.

Peptide bonds in the 20s loop (all residues in the unstructured loop) and 230s region (also referred to as 230s helix), which also undergo changes in their structural dynamics according to HDX, are far away from the binding site of hu31A.v11. HDX experiments monitor changes in structural dynamics, and do not distinguish between changes in bulk conformation versus changes in the energetic stability of a particular conformation. Overall, we found a high degree of consistency between the structural information obtained by HDX and X-ray crystallography and identified additional residues that are allosterically affected by hu31A.v11 binding.

B. Structural Analysis of E104-Derived Anti-Tryptase Antibodies (i) Materials and Methods huE104.v1 Fab was used to generate crystal structure with tryptase tetramer because binding of huE104.v1 does not dissociate the tetramer. Tryptase/huE104.v1 crystals were grown at 19° C. using the vapor diffusion method by mixing protein in 1:1 (v/v) with a reservoir solution containing 0.1 M Tris (pH 8.5), 0.2 M calcium chloride, 20% polyethylene glycol (PEG) 4000 and 8% pentaerythritol ethoxylate. The crystals were cryo-protected in artificial mother liquor containing 0.1 M Tris (pH 8.5), 0.2 M calcium chloride, 35% PEG 3350 and flash frozen in liquid nitrogen. Diffraction data were collected at SSRL beamline 12-2 in a monoclinic lattice extending to 3A resolution using a Pilatus 6M pixel array detector and 0.9795 Å wavelength X-rays. Data were reduced (Kabsch, *Acta Crystallogr. D Biol. Crystallogr.* 66:125-132, 2010; Vonrhein et al. *Acta. Crystallogr.* D67: 293-302, 2011) and scaled (Winn et al. *Acta Crystallogr. D Biol. Crystallogr.* 67:235-242, 2011), and the structure solved by molecular replacement (McCoy et al. *J. Appl. Crystallogr.* 40:658-674, 2007) in space group P21 revealing a tryptase tetramer bound by four Fabs. The molecular replacement search probes were a tryptase protomer from PDB accession 4A6L and an antibody Fab fragment derived from PDB accession 1FVD by scanning modified versions with a range of elbow angles using the rotation function only. After limited refinement, one Fab constant region was replaced in a molecular replacement search using just the constant region from 1FVD. Tryptase residue numbering was changed to a chymotrypsinogen scheme and Fab-E104v1 residue numbering to the Kabat scheme. Model and electron density map inspection and adjustments were performed using Coot (Emsley et al. *Acta Crystallogr. D Biol. Crystallogr.* 66:486-501, 2010) and the structure refined using REFMAC5 (Murshudov et al. *Acta Crystallogr. D Biol. Crystallogr.* 67: 355-367, 2011) and Phenix.refine (Adams et al. *Acta Crystallogr. D Biol. Crystallogr.* 66, 213-221, 2010). Data collection and refinement metrics appear in Table 9. HDX experiments were performed as described above.

TABLE 9

Table of X-ray metrics for tryptase beta-huE104.V1 Fab

| Data | |
|---|---|
| X-ray source | SSRL 12-2 |
| Wavelength (Å) | 0.9795 |
| Res. range (Å) | 50 –3.0 (3.112 –3.005) |
| Space group | P21 |
| cell a, b, c (Å) | 89.573 168.811 114.652 |
| cell α, β, γ (°) | 90 109.97 90 |
| Total reflections | 214206 |
| Unique reflections | 62353 |
| Multiplicity | 3.4 (3.5) |
| Completeness (%) | 97.8 (99.7) |
| Mean I/σ(I) | 11.3 (2.1) |
| Wilson B (Å$^2$) | 72.2 |
| R-symm | 0.098 (0.577) |
| Refinement | |
| Reflections for R-free | 1266 |
| R-work | 0.187 (0.278) |
| R-free | 0.232 (0.340) |
| Number non-H atoms | 20794 |
| macromolecules | 20689 |
| ligands | 100 |
| ions | 3 |
| water | 2 |
| Protein residues | 2702 |
| RMS(bonds) (Å) | 0.01 |
| RMS(angles) (°) | 1.2 |
| Ramachandran favored(%) | 94 |
| Ave B-factor (Å$^2$) | 71.5 |
| macromolecule | 71.6 |
| ligands | 48.4 |
| ions, water | 71.6 |

(ii) Results

In order to determine if the small or the large protein interfaces that hold the tryptase tetramer together are destabilized upon huE104.v2 Fab binding, tetrameric tryptase mutant Y75C or I99C (see above) were mixed with a 2-fold molar excess of Fab huE104.v2 for complex formation and analyzed by SEC (FIG. 6C). huE104.v2 Fab formed complexes with tetrameric tryptase mutant Y75C and the chromatogram shows two peaks with retention times of $t_r$=21.6 min (FIG. 6C, run 1, peak 1) and $t_r$=31 min (peak 4) comprising excess Fab. huE104.v2 Fab formed complexes with tetrameric tryptase mutant I99C and the chromatogram shows two peaks with retention times of $t_r$=23.8 min (FIG. 6C, run 2, peak 2) and $t_r$=31 min (run 2, peak 5) comprising excess Fab. SDS-PAGE analysis showed that both huE104.v2 Fab and tryptase dimer mutant were present in peaks 1 and 2 and excess Fab was present in peaks 4 and 5 (data not shown). For comparison, huE104.v2 Fab in complex with WT tryptase tetramer had a retention time of $t_r$=26 min (FIG. 6C, run 3, peak 3), comprising monomer bound by Fab huE104.v, that is smaller than tryptase tetramer mutant I99C in complex with huE104.v2 ($t_r$=23.8 min, run 2, peak 2). The tryptase mutant Y75C (the small interface-locked mutant tetramer) in complex with huE104.v2 Fab had a similar retention time as the stable, intact complex of WT tryptase tetramer bound to four Fabs of huE104.v1 (see FIG. 6A, run 1, ref peak). On the other hand, tryptase mutant I99C (the large interface-locked mutant tetramer) in complex with huE104.v2 had a longer retention time indicative of a smaller complex than the first peak in run 1. The results indicate that huE104.v2 Fab was only able to dissociate the small interface, but not the large interface of the tetramer. Thus, when binding to wild type tryptase tetramer, huE104.v2 Fab binding dissociates the small interface only.

Under the experimental conditions, the dissociated small interface may be quickly restored by heparin present at a high local concentration (e.g., 0.1 mg/ml), which would lead to the reassembly of the tetramer. This heparin concentration is substantially higher than physiological heparin concentration, which has been reported to be about 1.5 μg/ml of serum (see, e.g. Engelberg et al., *Circulation* 23:578-581, 1961 and Davids et al. *S. Afr. Med. J.* 100:307-307, 2010). At low concentration of heparin, huE104.v2 Fab is capable of completely dissociating WT tryptase tetramer and neutralizing tryptase activity, though less potent than huE104.v2 in the IgG format.

To gain further insight into the exact binding epitope of huE104.v2 on tryptase, we attempted to crystallize the Fab huE104.v2/tryptase complex. Since we could not obtain any suitable crystals, the complex of WT tetrameric tryptase bound to four Fabs E104.v1 isolated by size exclusion chromatography was used for crystallization. huE104.v1 and huE104.v2 differ only in two vernier framework positions, while the HVRs are identical. Thus huE104.v1 was a good surrogate to elucidate the binding epitope of huE104.v2. The binding of the humanized anti-tryptase antibody huE104.v1 (see Example 1) to mature human tryptase beta 1 was studied using X-ray crystallography to determine the structure of the molecular complex between tryptase and the Fab fragment of huE104.v1 at 3.0 angstrom (Å) resolution. The result was a crystallographic asymmetric unit containing one tryptase tetramer, stabilized by complexing with EGR-chloromethylketone interacting with four huE104.v1 Fabs in such a way that each Fab interacts almost exclusively with only one of the tryptase protomers (FIG. 12A). The intermolecular crystal packing environment does not include large voids, and has a moderate number of crystal packing contacts of less then 4 Å. For instance, two huE104.v1 Fab VL domains experience a non-crystallographic 2-fold contact at their ABDE β-strands face, involving H-bonds from Thr and Ser chain chains and others. Another smaller region with several intermolecular contacts exists between a heavy chain constant domain (near the peptide link to the same chain's variable domain) and the "bottom" of an adjacent light chain constant domain. There are more residues in packing contacts for the Fabs (average 12) than for the tryptase protomers (average 3.5), despite the tryptase protomers having more residues (243 versus approximately 215). In this sense, the crystals are formed at least in part via Fab-Fab intermolecular contacts.

Three copies of huE104.v1 Fab displayed closely similar elbow angles (the angles between the variable domains (VH and VL) and constant domains (CH and CL) of 140°, 138° and 141°. The fourth copy of huE104.v1 Fab was characterized by a relative poor electron density for its constant region and displayed an elbow angle of 152°. Antibody antigen-binding surface areas (paratopes), calculated as solvent accessible surface area lost (Adams et al. *Acta Crystallogr. D Biol. Crystallogr.* 66:213-221, 2010) to the contact with a tryptase protomer, average 682 Å$^2$ and are dominated by the heavy chain, 71% versus 29% for the light chain. The shape complementarity statistic (Lawrence et al. *J. Mol. Biol.* 234:946-950, 1993), Sc, averaged 0.76, which is on the high end for antibodies with protein antigens. The resolution of our result was too low to discern water structure, but the Sc values suggest there are likely very few interfacial waters. Use of non-crystallographic symmetry (NCS) restraints produced superior refinements according to the value of R-free. The root-mean-squared deviations (RMSDs) for superposition of Cα atoms of Fab domains (VL, CL, VH or CH1) were on the order of a few tenths of an angstrom.

Antibody residues within 4 Å of their partner tryptase were closely similar for the four copies and include: light chain residues Y29, N30, R32 (HVR-L1), R94 (HVR-L3) and heavy chain residues G31, Y32 (HVR-H1), S52, S53, A54, T56, F58 (HVR-H2) and P96, R97, G98, Y99, R100e (HVR-H3).

Each huE104.v1 Fab contacts a closely analogous region of a partner tryptase protomer. This epitope is approximately 90° away from the active site substrate binding cleft, and places each Fab projecting perpendicular from the plane of the roughly square planar tryptase tetramer. Since the tryptase protomers associate in an up/down/up/down manner around the tryptase ring, there are two Fabs projecting "up" from the tetramer and two Fabs projecting "down" (FIG. 12A).

The crystallographic asymmetric unit (asu) includes 4 tryptase protomers organized into an approximately symmetric tetramer. The four tryptase protomers each are covalently modified at the active site (from treatment using Glu-Gly-Arg-chloromethyl ketone) and superpose with pairwise rmsd based on Cα atoms of about 0.1 Å. If each protomer were within 4 Å of only one of the four Fabs in the asu, then it would be possible to define four huE104.v1 epitopes, one for each tryptase protomer, and, lacking strict symmetry, these four epitopes might differ slightly. There are a few tryptase residues that are within 4 Å of a Fab that does not provide the bulk of interactions with it, referred to herein as a "non-partner Fab." Since this is true, it is also possible to define the huE104.v1 epitope for the tryptase tetramer.

The program PyMOL was used to identify the epitope, which in this Example is the set of tryptase amino acids that are within 4 Å of any atom of the huE104.v1 Fab. The amino acid residues in the tryptase polypeptide chains can be numbered according to the chymotrypsinogen numbering scheme, as described above (FIG. 7). Tryptase residues below are named according to the chymotrypsinogen numbering scheme, with the gene-sequential numbering scheme in parenthesis.

There are 4 epitopes defined between a tryptase protomer and its partner Fab. All four contain a very nearly identical set of tryptase amino acid residues. Those residues are: W38, Q50, D60e, L61, A62, R65, Q81, L82, L83, P84, V85, S86, R87, E107, L108, E109, and E110 (chymotrypsinogen numbering, corresponding to residues W55, Q67, D82, L83, A84, R87, Q100, L101, L102, P103, V104, S105, R106, E126, L127, E128, and E129, respectively, using the gene-sequential numbering scheme, with residues corresponding to positions of SEQ ID NO: 71). Residue L61 (L83 of SEQ ID NO: 71) is absent for two of the four, but only barely exceeds the 4 Å criterion. Residue Q81 (Q100 of SEQ ID NO: 71) is absent for one of the four. If this were not the case, then all four would be identical by the defining criterion.

Also, non-partner Fabs make a small number of 4 Å contacts in the tetramer. It is these tryptase residues that distinguish a tetramer epitope from a protomer epitope. The contacted tryptase residues are: Q20 and R187 (Q35 and R216, respectively, of SEQ ID NO: 71).

Thus, the epitope of huE104.v1 on the tryptase tetramer is the sum of: 4 instances of each of the following: W38, Q50, D60e, L61, A62, R65, L82, L83, P84, V85, S86, R87, E107, L108, E109 and E110 (chymotrypsinogen numbering, corresponding to residues W55, Q67, D82, L83, A84, R87, L101, L102, P103, V104, S105, R106, E126, L127, E128, and E129, respectively, of SEQ ID NO: 71), plus three instances of Q81 (Q100 of SEQ ID NO: 71), plus 1 instance of Q20 (Q35 of SEQ ID NO: 71), plus three instances of R187 (R216 of SEQ ID NO: 71). It is considered that the epitope residues described above would also apply to other E104-derived antibodies, including huE104.v2.

Although huE104.v1 and v2 have the same CDR sequences, and would bind to the same epitope, the two variants behave differently in Fab as well as in IgG: huE104.v2 Fab dissociates the tetramer and more specifically at the small interface, while huE104.v1 Fab does not; and in IgG, huE104.v2 dissociates and inactivates the tetramer, while huE104.v1 loses the inhibitory activity at high antibody to tryptase ratio. We hypothesized that although huE104.v1 and huE104.v2 bind to the same contact residues on tryptase, subtle differences exist between how they interact with tryptase. In order to identify differences in the interaction between huE104.v1 and huE104.v2 Fabs with tryptase in solution, HDX experiments were performed with monomeric tryptase alone or bound to either huE104.v1 or huE104.v2, and the degree of hydrogen-deuterium exchange over time was monitored by mass spectrometry. While this method provides information indicative of the binding epitopes of huE104.v1 and huE104.v2, it overall monitors changes in structural dynamics that could occur away from the antibody binding epitope. These measurements do not distinguish between changes in bulk conformation versus changes in the energetic stability of a particular conformation.

Amide bonds that showed a slower exchange in tryptase when either huE104.v1 or huE104.v2 were bound were located to the regions of residues 25-27, 60-61, 66-68, 88 and 108-110 (chymotrypsinogen numbering; Table 10), but amide bonds that showed slower exchange that were specific to only huE104.v1 or huE104.v2 were also found. For example, amide bonds of tryptase residues 47-50, 54-55, 85-87, 119-122, 179, 230-231, and 244-245 (chymotrypsinogen numbering) showed slower exchange only when huE104.v1 was bound. On the other hand, amide bonds of tryptase residues 25, 41-43, 81-81, and 160-162 showed slower exchange only when huE104.v2 was bound (Table 10). The most intriguing differences in slower hydrogen exchange are the amide bonds of residues 81-83 (Q81, L82, and L83 in chymotrypsinogen numbering, corresponding to Q100, L101, and L102 of SEQ ID NO: 71) in tryptase, which only showed slower exchange when huE104.v2 is bound. This area is particularly interesting since it is part of the loop in which two critical contact residues (Y74 and Y75) of the small interface reside. Tryptase residues 81-83 are also in direct contact with HVR-H2 of huE104.v1, as seen in the crystal structure complex with tetrameric tryptase, but according to the HDX results it is considered that this area must make a stronger and presumably different interaction with huE104.v2 than for the interaction of huE104.v1 with tryptase. Conformational changes to the 80s loop Cα-backbone and side chains could affect the conformation of Y74 and Y75, which are key to the hydrophobic small interface between two tryptase protomers in the tetramer complex. Since the interface is symmetric, residues Y74 and Y75 from both interacting protomers are affected when huE104.v2 is bound to each protomer, which would amplify any changes and instability of this interface.

As mentioned above, the differences between huE104.v1 and huE104.v2 are the vernier framework residues V71 R and F78V. It has been previously reported that framework residue changes in position 71 in the heavy chain of antibodies affect the conformation of HVR-H2. Modeling experiments of HVR-H2 in huE104.v1 and huE104.v2 confirm this to be the case (data not shown). Without being bound by theory, changes in both vernier residues could affect the conformation of HVR-H2 such that the interaction with tryptase residues 81 through 83 differs and translates into changes of the small interface of the tetramer. Additionally, tryptase amide bonds of residues R69 and E70 (chymotrypsinogen numbering), which are in close structurally proximity, also show slower HDX only when huE104.v2 is bound. This finding would make changes to the 70s loop, which constitutes a significant part of the small interface, even more likely.

When comparing the regions of slower HDX due to Fab binding with tryptase residues within 4A of the Fab E104.v1 as seen in the crystal structure, a high degree of overlap was observed between both methods, identifying binding epitope residues in the 20s, 40s, 60s, the 80s and 100-loop (Table 10). Other areas identified by HDX, such as positions in the 110s, 160s, 179, 230s and the 245 region of the primary tryptase sequence, are not in direct contact with the antibody according to the crystal structure, but show a reduction in conformational dynamics in the presence of huE104.v1 and huE104.v2.

TABLE 10

Amide bonds of tryptase residues that showed slower HDX when bound to huE104.v1 or huE104.v2

Tryptase Residues Affected (chymotrypsinogen numbering)

| huE104.v1 | huE104.v2 | Contact residues in crystal structure |
|---|---|---|
| 26-27 | 25-27 | 25-29 |
| — | — | 38 |
| — | 41-43 | 40-41 |
| 47-50 | — | 50 |
| 54-55 | — | — |
| — | — | — |
| 60-61 | 60-61 | 60-62 |
| 66-68 | 66-70 | 65 |
| — | 81-83 | 81-87 |
| 85-88 | 88 | — |
| 108-110 | 108-110 | 107-110 |
| 119-122 | — | — |
| — | 160-162 | — |
| 179 | — | — |
| 230-231 | — | — |
| — | — | — |
| 244-245 | — | — |

To summarize these data, huE104.v1 and huE104.v2 have the same HVR sequences and the same contact residues on human tryptase beta 1. Based on the HDX studies, however, subtle differences in the way the two antibodies bind to the target were detected. The V71 and F78 in the heavy chain FR3 region of huE104.v1 are shown in FIG. 12B. As indicated in the figure, the V71R and F78V in the FR3 region of the heavy chain in huE104.v2 may have affected the position of HVR-H2 and the binding of HVR-H2 to tryptase, evidenced by the slower HDX in the Q81, L82, and L83 region (chymotrypsinogen numbering) when huE104.v2 is bound. The Q81, L82 and L83 residues showed slower HDX when huE104.v2 is bound to tryptase as compared to unbound tryptase. As a result, the hydrophobic interaction of Y75 with the neighboring protomer is weakened. huE104.v1 has V at position 71 and F at position 78 (as in the $VH_{IV}$ graft). In this context, the HVR-H2 is presented slightly differently, and the effect of binding of E104.v1 to tryptase, though at the same contact residues, differs slightly in the dissociation of the small interface, as compared to E104.v2.

In summary, hu31A.v11 Fab and IgG both dissociate tryptase tetramer. Both huE104.v2 Fab and IgG also dissociate tryptase tetramer. huE104.v1 IgG, but not Fab, is capable of dissociating tryptase tetramer. However, huE104.v1 IgG at high antibody to tetramer ratio loses inhibitory activity. More than one hu31A.v11 Fab binding to the same tetramer would cause steric clash, while huE104.v2 Fabs binding to the same tetramer do not. Thus, the hinge region of IgG1 or IgG4 may play a role in orienting the two Fabs of the huE104.v1 IgG and creates sufficient tension that results in the dissociation of the tetramer (data not shown). At high antibody to tetramer ratio, however, huE104.v1 IgG more likely binds to tetramer as a monovalent binder, i.e., a Fab, and loses inhibitory activity.

C. hu31A.v11 and huE104.v2 Compete for Binding to Human Tryptase Beta 1

The epitope of hu31A.v11 determined by X-ray crystallography substantially overlaps with the epitope of huE104.v1 and huE104.v2. We next determined whether hu31A.v11 and huE104.v2 compete for binding to human tryptase beta 1 by epitope binning. Epitope binning was done using OCTET® RED384 System (ForteBio, Inc., Menlo Park, CA, USA). Briefly, human tryptase beta 1 monomer protein was biotinylated at Lys residue by reacting with NHS-PEG4-biotin. Biotinylated monomer was diluted to 5 μg/ml in kinetics buffer (ForteBio, Inc., Menlo Park, CA, USA) and immobilized onto streptavidin sensor tips (ForteBio, Inc., Menlo Park, CA, USA). After the immobilization step, human tryptase beta 1-immobilized sensors were saturated with the first antibody, diluted at 10-20 μg/ml, followed by binding with second antibody diluted at 2.5 μg/ml. A binding signal by second antibody implies that the two antibodies can bind antigen simultaneously at distinct, non-overlapping epitopes, whereas no binding signal implies that they share a common epitope. Forte Bio data analysis software 8.1 was used to generate epitope-binning matrix.

The results shown in Table 11 below demonstrate that no additional binding signal was detected either using huE104.v2 as the first antibody and hu31A.v11 as the second antibody or vice versa. Either antibody added after buffer resulted in additional binding. Thus, the two antibodies compete for binding to human tryptase beta 1.

TABLE 11 hu31A.v11 and huE104.v2 compete for binding to human beta tryptase 1

| | 2nd Antibody | |
|---|---|---|
| 1st Antibody | hu31A.v11 IgG4 | huE104.v2 IgG4 |
| huE104.v2 IgG4 | −0.0086 | −0.0083 |
| Hu31A.v11 IgG4 | −0.0205 | 0.011 |
| Buffer | 0.423 | 0.514 |

Example 4: Pharmacokinetic (PK) Analysis of Humanized Anti-Tryptase Antibodies

Figure 13:
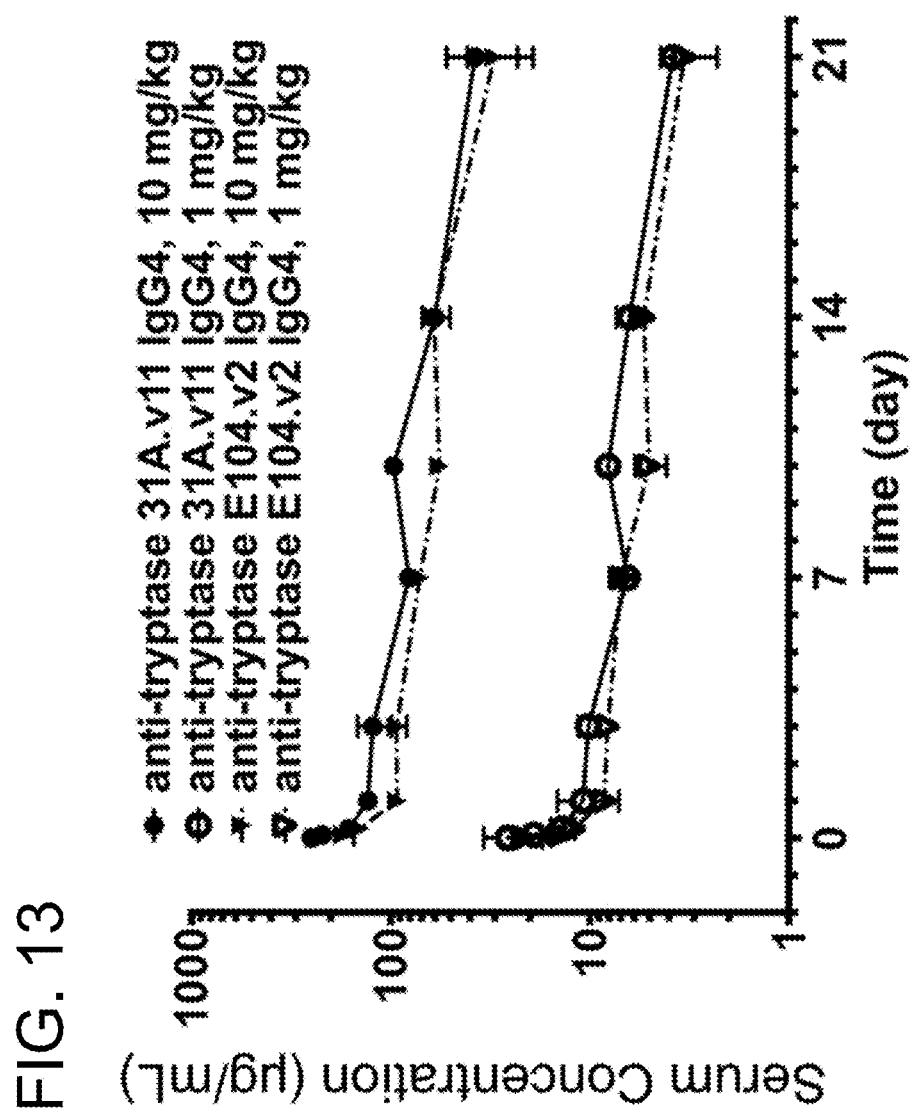
FIG. 13 is a graph showing the results of a pharmacokinetic (PK) analysis of humanized anti-tryptase antibodies huE104.v2 and hu31A.v1, each administered by intravenous (IV) injection at 1 or 10 mg/kg to C57BL/6 mice. The graph shows anti-tryptase antibody concentration (pg/mL) as a function of time (days). The results are from three animals.

To assess the pharmacodynamics (PK) characteristics of humanized anti-tryptase antibodies, huE104.v2 or hu31A.v11 IgG4 antibodies were administered by intravenous (IV) injection at 1 or 10 mg/kg to C57BL/6 mice, n=3. The concentration of anti-gD IgG4, anti-tryptase hu31A.v11 IgG4, or anti-tryptase huE104.v2 IgG4 in C57-BL6 mouse serum was determined with a generic immunoglobulin pharmacokinetic ELISA using sheep-anti-human-IgG (The Binding Site; San Diego, CA) for capture and HRP-conjugated-sheep anti-human-IgG (Bethyl Laboratories, Montgomery, TX), for detection. The assay sensitivity was 15.6 ng/mL in serum. The huE104.v2 and hu31A.v11 IgG4 antibodies exhibited similar PK, characterized by dose-proportional and linear PK across the dose range tested (FIG. 13 and Table 12). In addition, both antibodies had a relatively low clearance (~5 ml/day/kg), suggesting that both antibodies behave well after single dose administration and are well within the accepted range. In other experiments, huE104.v2 IgG1 performed similarly to the huE104.v2 IgG4 and hu31A.v11 IgG4 antibodies (data not shown).

TABLE 12

PK analysis of humanized anti-tryptase antibodies in mice

| Anti-Tryptase IgG4 | Dose | $AUC_{last}$ (day • μg/ml) | Clearance (ml/day/kg) | $C_{max}$ (μg/ml) |
|---|---|---|---|---|
| huE104.v2 | 1 mg/kg | 127 | 5.00 | 21.6 |
| huE104.v2 | 10 mg/kg | 1400 | 5.12 | 242 |
| hu31A.v11 | 1 mg/kg | 155 | 4.74 | 25.8 |
| hu31A.v11 | 10 mg/kg | 1750 | 4.54 | 251 |

Figure 14:
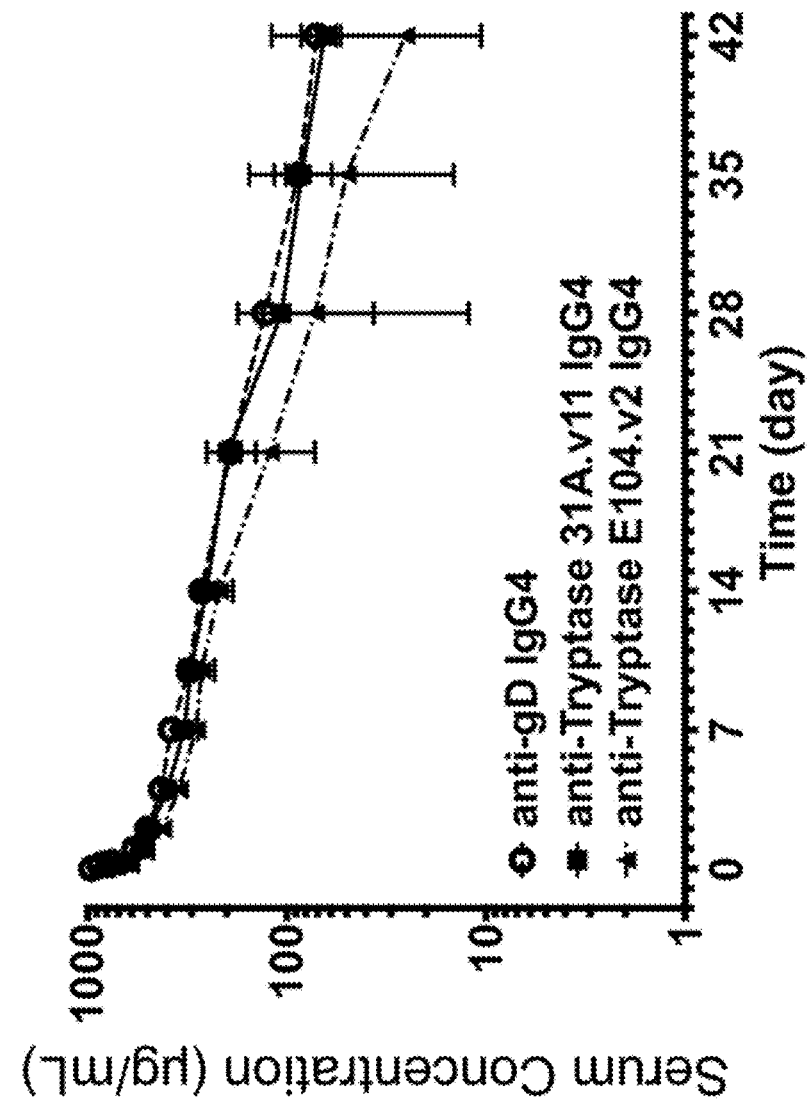
FIG. 14 is a graph showing the results of a PK analysis of humanized anti-tryptase antibodies huE104.v2 and hu31A.v1 compared to a control anti-gD IgG4 antibody. Each antibody was administered by IV injection at 30 mg/kg to cynomolgus (cyno) monkeys. The graph shows anti-tryptase antibody concentration (pg/mL) as a function of time (days).

The PK characteristics of humanized anti-tryptase antibodies were also assessed in male cynomolgus monkeys (cyno), n=3. A control antibody (anti-gD), huE104.v2 IgG4, or hu31A.v11 IgG4 was administered by intravenous (IV) injection at 30 mg/kg (FIG. 14 and Table 13). The concentration of anti-gD IgG4, anti-tryptase hu31A.v11 IgG4, or anti-tryptase huE104.v2 IgG4 in cynomolgus monkey serum was determined with a Gyrolab XP immunoassay consisting of biotin-conjugated goat anti-human IgG (Bethyl Laboratories, Montgomery, TX) capture and Alexa® Fluor 647-conjugated mouse anti-human Fc (R10Z8E9) detection. The assay sensitivity was 41 ng/mL in serum. Table 13 shows the area under the curve (AUC), clearance (CL), $C_{max}$, and half-life ($T_{1/2}$). hu31A.v11 exhibited similar pharmacokinetics to the control anti-gD antibody. A low clearance (CL) of approximately 3 mL/day/kg and $T_{1/2}$ of about 15 days were well within the acceptable range.

TABLE 13

PK analysis of humanized anti-tryptase antibodies in cyno (n = 3)

| Group | AUC (day • μg/mL) | CL (mL/day/kg) | $C_{max}$ (μg/mL) | $T_{1/2}$ (days) |
|---|---|---|---|---|
| Anti-gD | 11100 ± 1220 | 2.73 ± 0.285 | 972 ± 68.8 | 14.1 ± 1.37 |
| hu31A.v11 | 10700 ± 3530 | 2.99 ± 0.855 | 805 ± 72.3 | 14.9 ± 5.95 |
| huE104.v2 | 7910 ± 2270 | 3.98 ± 1.00 | 808 ± 48.9 | 11.5 ± 4.43 |

Example 5: Formulation of Anti-Tryptase Antibody hu31A.v11 to Ameliorate HVR-H3 Trp100 (W100) Oxidation While evaluating both hu31A.v11 and huE104.v2 antibodies, it was unexpectedly discovered that the VH Trp100 residue present in the HVR-H3 region of hu31A.v11 (FIG. 1) is susceptible to oxidation, for example, following exposure to 2,2-azobis(2-amidinopropane) dihydrochloride (AAPH) (also referred to as "AAPH stress") or ambient light ("ambient light stress"). This oxidation can be considered undesirable in the context of a therapeutic antibody. However, the Trp100 residue was found to be important for binding of hu31A.v1 to tryptase, as well as for inhibitory activity. For instance, as described below, mutation of Trp100 to mitigate oxidation resulted in variants with reduced binding affinity and inhibitory activity. Therefore, oxidation of hu31A.v1, particularly at HVR-H3 W100, was mitigated using formulations containing an antioxidant excipient, e.g., N-acetyltryptophan and/or methionine.

The effect of AAPH stress and hu31A.v1 HVR-H3 W100 (i.e., the tryptophan residue at position 100 of the VH domain, see FIG. 1) oxidation on tryptase binding and inhibitory activity was evaluated. Samples were formulated in 1 mM AAPH for 16 h at 40° C. Under these conditions, there was a 75% increase in W100 oxidation (percent oxidation). The stressed antibody was digested with trypsin and the digested peptides were subjected to UHPLC-HRMS (ultra high performance liquid chromatography-high resolution mass spectrometry) to determine percentage of tryptophan oxidation. Briefly, a 250 µg sample of hu31A.v11 was reduced with 20 mM DTT in 6 M guanidine hydrochloride, 360 mM Tris, and 2 mM EDTA at pH 8.6 for 1 hr. The reduced sample was cooled to room temperature and alkylated using 1 M iodoacetic acid (final concentration, 50 mM) for 15 min in the dark. The sample was then buffer-exchanged into digestion buffer (25 mM Tris, 2 mM $CaCl_2$), pH 8.2). The buffer-exchanged sample was digested with trypsin for 4 hr at 37° C. using a 1:40 (w/w) enzyme to antibody ratio. The digestion was stopped by addition of 100% formic acid to a final concentration of 3.0%.

10 µg of the tryptic peptides was injection to a Waters 2.1×150 mm, Acquity UPLC® CSH C18 column with 1.7 µm, 130 Å particles, running at a flow rate of 0.2 mL/min at 77° C. coupled to a Q Exactive mass spectrometer system with the following gradient: 1% B (0.1% formic acid in acetonitrile) at 0-2 min; 13% B at 7 min; 35% B at 42 min; 85% B 44-46 min; 1% B 46.1 min. The Q Exactive was operated in the data dependent mode, collecting a full MS scan from 200-2000 m/z at 35,000 resolution, and an automatic gain control (AGC) target of $1\times10^6$. The 8 most abundant ions per scan were selected for tandem MS at 17,500 resolution and AGC target of $1\times10^5$. Relative quantitation of W100 oxidation was generated as follows: (1) Peak areas were calculated by integrating extracted ion chromatograms of the top three most abundant isotopes from charge states with a relative abundance of 10% and above for the native tryptic peptide and its oxidized counterparts.

(2) The total oxidized peak area was divided by the sum of the oxidized and native peak areas and multiplied by 100 to obtain the percent oxidation.

The results in Table 14 show that AAPH stress reduced binding of hu31A.v1 to tryptase monomer as measured by BIAcore® SPR analysis (Table 14). Reduced binding was also observed for binding to tryptase tetramer. In contrast, the binding of huE104.v2 to tryptase monomer and tetramer was not affected by AAPH stress (Table 14). Additionally, AAPH stress reduced the activity of hu31A.v1 in an in vitro tryptase enzymatic activity assay by about 5-fold, whereas the inhibitory activity of huE104.v2 was not affected (data not shown). In summary, after AAPH stress, hu31A.v11 IgG4, which had 75% oxidation at HVR-H3 W100, showed an approximately 6-fold higher $K_D$ (i.e., reduced affinity) (with 35% Rmax), and a 5-fold increase in IC50 (i.e., decrease in potency). Rmax indicates the maximum response in a BIAcore® SPR experiment, and a decrease in Rmax reflects the fact that less of the AAPH-stressed antibody bound to tryptase. In contrast, AAPH stress had minimal, if any, effect on the binding and potency of huE104.v2 IgG4.

TABLE 14

AAPH stress reduces binding of hu31A.v11 to tryptase

| Sample | Tryptase Beta 1 | $K_{on}$ (1/Ms) | $K_{off}$ (1/s) | $K_D$ (M) |
|---|---|---|---|---|
| hu31A.v11 Control | Monomer | 5.976E5 | 1.328E-4 | 2.222E-10 |
| hu31A.v11 AAPH | Monomer | 6.076E5 | 7.978E-4 | 1.313E-9 |
| huE104.v2 Control | Monomer | 5.846E5 | 1.861E-4 | 3.183E-10 |
| huE104.v2 AAPH | Monomer | 6.795E5 | 1.535E-4 | 2.260E-10 |

In one approach to reduce HVR-H3 oxidation, variant antibodies having substitutions at HVR-H3 W100 were produced, and the binding of these variants to tryptase beta 1 monomers was assessed (Table 15). Residue W100 of hu31A.v11 was mutated to phenylalanine (F), tyrosine (Y), valine (V), leucine (L), or arginine (R). Surprisingly, all of the variants showed reduced binding to tryptase beta 1 monomer. The hu31A.v11 W100F variant had the highest affinity for tryptase beta 1 monomer as compared to the other variants, but exhibited an approximately 100-fold faster off-rate ($K_{off}$) compared to wild-type hu31A.v11, with a similar on-rate ($K_{on}$) (Table 15). Further, these variants were inferior to hu31A.v11 WT in terms of inhibitory activity (Table 15). For some of the variants, the inhibitory activity was essentially lost (e.g., for W100R, W100L, and W100V). The hu31A.v11 W100F and W100Y variants inhibited human tryptase beta 1, but had IC50 values that were approximately 2- to 3-fold increased (i.e., reduced activity) compared to hu31A.v11 WT. In Table 15, "nd" indicates not detectable or above 1 µM.

TABLE 15

Effect of hu31A.v11 W100 variants on binding affinity to tryptase beta 1 monomer and IC50 as compared to hu31A.v11 wild type (as fold increase)

|  | hu31A.v11 (W100) | hu31A.v11 W100F | hu31A.v11 W100Y | hu31A.v11 W100V | huE104.v2 W100L | huE104.v2 W100R |
|---|---|---|---|---|---|---|
| $K_D$ | 1 | 80 | 234 | 821 | 2411 | 54 |
| IC50 | 1 | 2.5 | 3.46 | nd | nd | nd |

As described above, structural studies revealed that HVR-H3 W100 made multiple interactions with tryptase, including interaction with R65 of tryptase (chymotrypsinogen numbering), which was determined to be part of the contact residues of hu31A.v11 (see FIG. 8). The Trp at position 100 is considered to interact with tryptase to a greater extent than the Phe in the W100F mutant, resulting in higher binding affinity and more potent inhibitory activity.

In view of the reduced affinity and inhibitory activity of hu31A.v11 having oxidation at HVR-H3 W100, as well as the importance of W100 in tryptase inhibition, as shown above, an alternative strategy to mitigate oxidation at W100 was pursued. The ability of antioxidant excipients to reduce W100 oxidation was determined. In one example, samples were subjected to 5 mM AAPH for 24 h at 40° C., with or without exemplary anti-oxidant excipients, i.e., 0.3 mM N-acetyltryptophan (NAT) and 5 mM methionine (Met) in formulation containing 0.02% polysorbate 20, 200 mM arginine succinate (pH 5.5), and 150 mg/mL of hu31A.v11 antibody. The oxidation level of CDR H3 W100 and the potency of the antibody were measured based on the chromogenic S-2288 enzymatic assay. The data in Table 16 below show that in this experiment, AAPH stress resulted in 38% oxidation at W100 of hu31A.v11 IgG4, which led to potency loss by 32% as compared to control, non-stressed antibody sample (n=2). Antibody composition in the formulation containing 0.3 mM NAT and 5 mM Met showed reduced oxidation level from 38% to 26%, and reduced potency loss from 32% to 21% (n=2). Thus, formulation containing anti-oxidant excipients such as NAT and Met reduced AAPH-induced oxidation at W100 and restored antibody potency. In a separate example, the sample is subjected to ambient light stress conditions (60 h at 5000 Lux/h, which is a milder stress condition than AAPH) in the same formulation with or without the anti-oxidant excipients. The mild ambient light stress condition resulted in 6% oxidation at W100, and the presence of the excipients further reduced the level of oxidation (Table 16). The oxidation level induced by the ambient light-induced stress process did not affect antibody potency.

TABLE 16

Effect of antioxidant formulation on hu31A.v11 oxidation

| Sample Description | Mean relative potency, (potency loss) (n = 2) | HVR-H3 W100 oxidation |
| --- | --- | --- |
| 5 mM AAPH sample, w/o NAT/MET | 68% (32%) | 38% |
| 5 mM AAPH sample, 0.3 mM NAT/5 mM MET | 79% (21%) | 26% |
| Light stressed sample, w/o NAT/MET | 100% (0%) | 6% |

In summary, these results show that hu31A.v11 HVR-H3 W100 is unexpectedly susceptible to oxidation. Mutagenesis data showed that W100 is important for binding affinity and inhibitory activity of the hu31A.v11 antibody, and none of the tested variants at this residue had comparable affinity or inhibitory activity to wild-type hu31A.v11. Antioxidants such as NAT and Met can be used to mitigate the unexpected oxidation observed at hu31A.v11 HVR-H3 W100, for example, in pharmaceutical antibody formulations for treatment of disorders (e.g., asthma).

Example 6: Anti-Tryptase Antibody hu31A.v11 Inhibits Tryptase Activity In Vivo

A. Materials and Methods
(i) Cyno Active Tryptase ELISA Assay

The concentration of cynomolgus monkey (cyno) active tryptase (tetramer) in biological sample, e.g., bronchoalveolar lavage fluid (BAL), was determined by an ELISA assay. A monoclonal antibody recognizing cyno tryptase D1 was utilized as the capture antibody. Recombinant cyno active tryptase D1 was used as the source material for preparation of assay standards. Assay standards, controls, and diluted samples were incubated with 500 µg/ml soybean trypsin inhibitor (SBTI; Sigma Cat. No. 10109886001) for 10 min and then labeled with the activity-based probe (ABP; G0353816) for 1 h. See Pan et al. *Bioorg. Med. Chem. Lett.* 16:2882-85, 2006. SBTI was used to bind to the active site in the monomer, which reduces any background caused by active monomer, a species that can form in specific in vitro conditions. The SBTI is unable to bind to the active site when the tryptase is in tetrameric conformation. A small molecule tryptase inhibitor (G02849855) was added for 20 min to stop ABP labeling. A tetramer-dissociating antibody (e.g., hu31A.v11 IgG4) was added for 10 min to dissociate both ABP-labeled and unlabeled tetramer. This mixture was added to the ELISA plate with a capture antibody for 1 h, washed with 1×PBST, and incubated with the SA-HRP reagent (streptavidin-conjugated horseradish peroxidase, General Electric (GE) catalog number RPN4401V) for 2 h. A colorimetric signal was generated by applying HRP substrate, tetramethylbenzidine (TMB), and the reaction was stopped by adding phosphoric acid. The plates were read on a SpectraMax® M5 (Molecular Devices; Sunnyvale, CA) plate reader using 450 nm for detection absorbance and 650 nm for reference absorbance. The assay had a reportable range of 20-0.04 ng/mL (in-well), and the assay minimum quantifiable concentration (MQC) was determined to be 0.08 ng/mL in 1:2 dilution of cyno BAL. Each individual cyno sample was screened at a single dilution in duplicate. Samples assayed at minimum dilution that fell below the MQC were reported as less than reportable (LTR).

(ii) Cyno Total Tryptase ELISA Assay

The concentration of cynomolgus monkey (cyno) total tryptase in a biological sample, e.g., BAL, was determined by an ELISA assay. An antibody recognizing cyno tryptase D1 was utilized as the capture antibody. An antibody recognizing cyno tryptase D1 without competing with a tetramer-dissociating antibody for binding to cyno tryptase D1 was utilized as the detection antibody. Recombinant cyno active tryptase D1 was used as the source material for preparation of assay standards. A tetramer-dissociating antibody (e.g., hu31A.v11, IgG4) was added for 10 min to assay standards, controls, and diluted samples in order to dissociate any tetramer present. This mixture was added to the ELISA plate with capture antibody for 2 h and then washed with 1×PBST. The biotinylated detection antibody was added for 1 h. Next, SA-HRP reagent was added for 1 h. A colorimetric signal was generated by TMB, and the reaction was stopped by adding phosphoric acid. The plates were read on a SpectraMax® M5 plate reader using 450 nm for detection absorbance and 650 nm for reference absorbance. The assay had a reportable range of 20-0.02 ng/mL (in-well), and the assay MQC was determined to be 0.08 ng/mL in 1:2 dilution of cyno BAL. Each individual cyno sample was screened at a single dilution in duplicate. Samples assayed at minimum dilution that fell below the MQC were reported as less than reportable (LTR).

(iii) Human Active Tryptase ELISA Assay

The concentration of human active tryptase (tetramer) was determined by an ELISA assay. The mouse monoclonal antibody clone B12 recognizing human tryptase and capable of dissociating the tryptase tetramer was utilized as the capture antibody (Fukuoka et al. supra). Other antibodies that bind human tryptase can also be used. Recombinant human active tryptase beta 1 was purified and used as the source material for preparation of assay standards. Assay standards, controls, and diluted samples were incubated with 500 µg/ml SBTI for 10 min and then labeled with the ABP (G0353816) for 1 h. A small molecule tryptase inhibitor (G02849855) was added for 20 min to stop ABP labeling. This mixture was added to the ELISA plate with capture antibody for 1 h, washed with 1×PBST, and incubated with SA-HRP reagent for 2 h. A colorimetric signal was generated by applying TMB, and the reaction was stopped by adding phosphoric acid. The plates were read on a SpectraMax® M5 plate reader using 450 nm for detection absorbance and 650 nm for reference absorbance.

(iv) Human Total Tryptase ELISA Assay

The concentration of human total tryptase was determined by an ELISA assay. An antibody (clone B12) recognizing human tryptase and capable of dissociating the tryptase tetramer was utilized as the capture antibody. A monoclonal antibody recognizing human tryptase was utilized as the detection antibody. Recombinant human active tryptase beta 1 was purified and used as the source material for preparation of assay standards. Samples were added to the ELISA plate with capture antibody for 2 h and then washed with 1×PBST. The biotinylated detection antibody was added for 1 h. Next, SA-HRP reagent was added for 1 h. A colorimetric signal was generated by applying TMB, and the reaction was stopped by adding phosphoric acid. The plates were read on a SpectraMax® M5 plate reader using 450 nm for detection absorbance and 650 nm for reference absorbance.

B. Results

Figure 15:
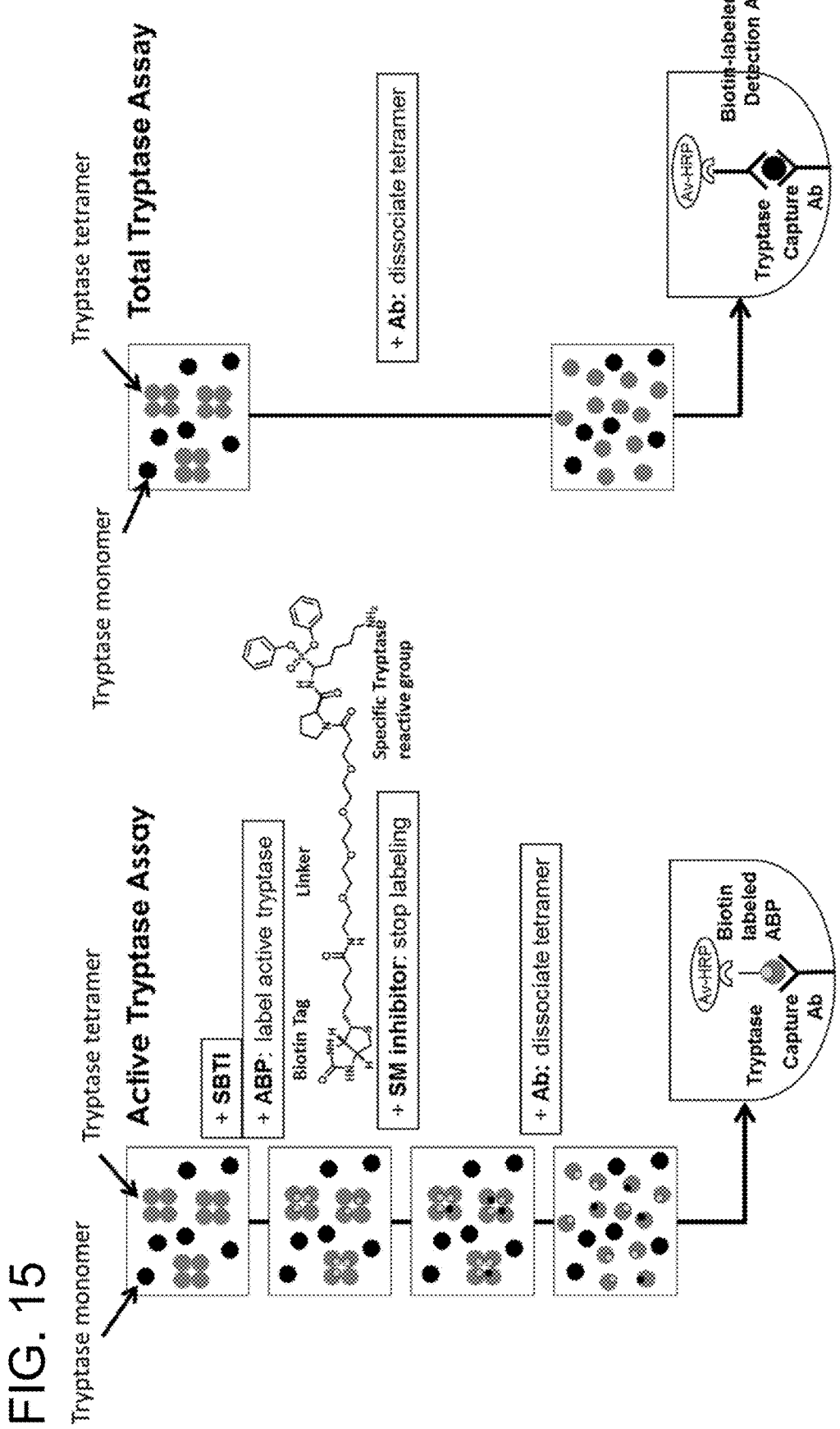
FIG. 15 is a schematic diagram of assays for measuring the amount of active tryptase (left panel) and total tryptase (right panel) in a sample. Tryptase monomers and tetramers are indicated. In the left panel, soy bean trypsin inhibitor (SBTI) is added. Next, an exemplary biotinylated activity-based probe (ABP) was added to a tryptase-containing sample (e.g., broncoalveolar lavage fluid (BAL)) to label active tryptase. Labeling was stopped by addition of an exemplary small molecule inhibitor G02849855 (e.g., BMS-262084, Sutton et al. *Bioorg. Med. Chem. Lett.* 12:3229-33, 2002, Qian et al., *J. Org. Chem.* 2002, 67:3595-3600). The hu31A.v1 antibody was added to dissociate the tryptase tetramers. The labeled tryptase was then detected in an enzyme-linked immunosorbent assay (ELISA) using horseradish peroxidase conjugated to streptavidin. In the total tryptase assay, hu31A.v11 was added to a sample to dissociate tryptase tetramers in the sample. The amount of tryptase was then determined using ELISA.

To assess whether anti-tryptase antibodies such as hu31A.v11 target tryptase in vivo and inhibit active tryptase activity, an assay was developed to measure the amount of active tryptase present in samples such as bronchoalveolar lavage fluid (BAL) (e.g., from cyno) or taken by a less invasive method such as nasosorption. An activity-based probe, which includes a label (e.g., biotin), a linker, and a reactive group that reacts with active tryptase was developed. This probe selectively and covalently binds to active tryptase. See Pan et al. supra. This tool can be used to measure the amount of active tryptase in a sample (FIG. 15). The BAL collection procedure involves instillation of buffer into the airway and the subsequent recovery of that fluid (which can be variable) and therefore a normalization factor is needed to compare samples across timepoints and animals. Because urea is a small molecule with passive diffusion between vascular and airway compartments, the ratio of urea in BAL/urea in serum can be used to normalize across time points and across animals. See Pinheiro de Oliveira et al. 2010, *Critical Care* 14:R39.

Figure 16:
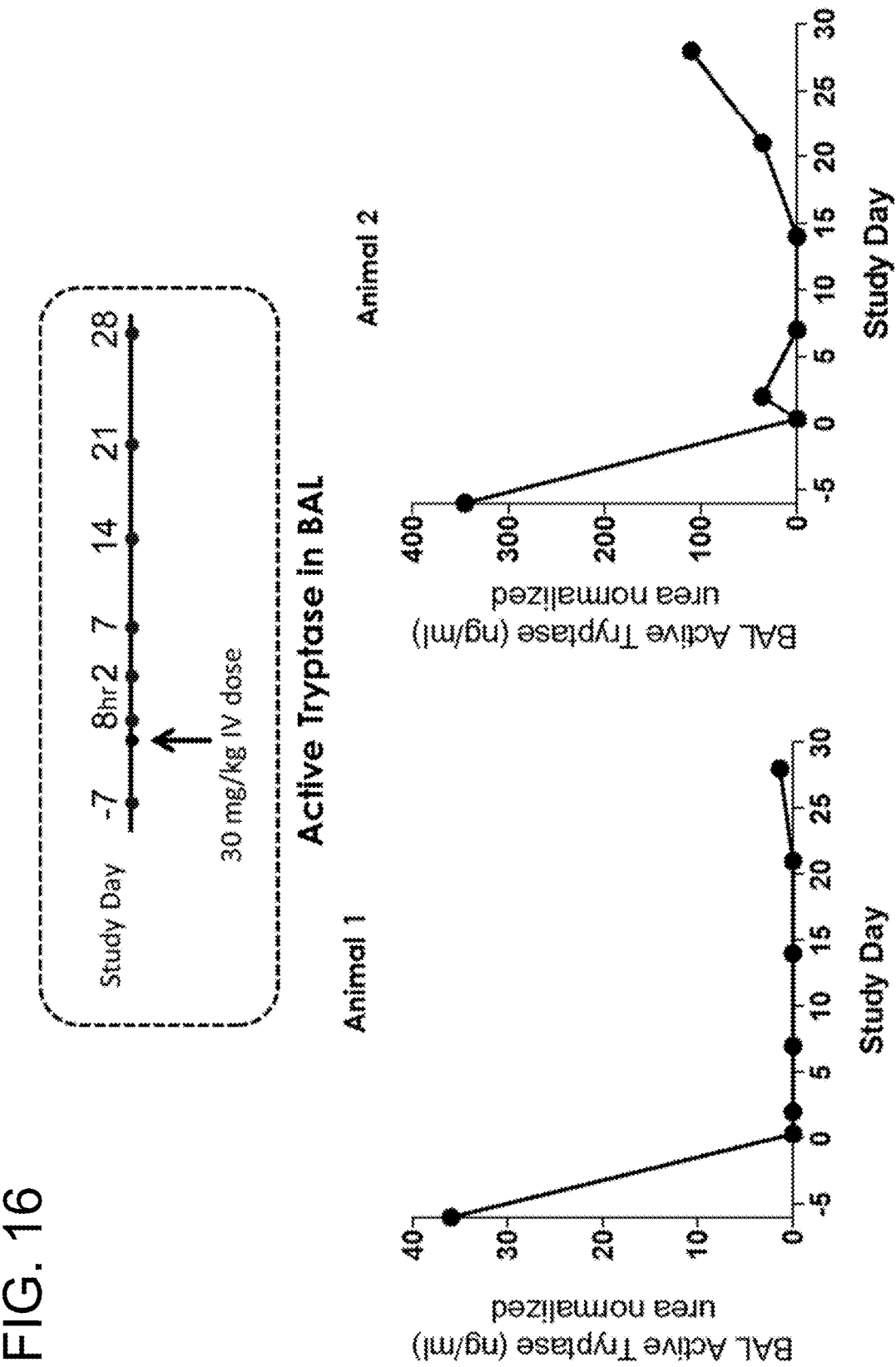
FIG. 16 shows the results of an active tryptase assay performed on BAL samples obtained from cyno monkeys that were administered the anti-tryptase antibody hu31A.v1 by intravenous (IV) administration at 30 mg/kg. The top panel shows a schematic diagram of the experimental protocol.

To determine whether administration of hu31A.v11 targeted tryptase in vivo, a 30 mg/kg dose was administered by intravenous injection to healthy, unchallenged cyno monkeys, and the amount of active tryptase in BAL was determined. At baseline, active tryptase levels were relatively low and variable across animals. A trend of decreased levels of active tryptase was observed in BAL after administration of hu31A.v11 in animals with detectable active tryptase at baseline (FIG. 16).

Figure 17:
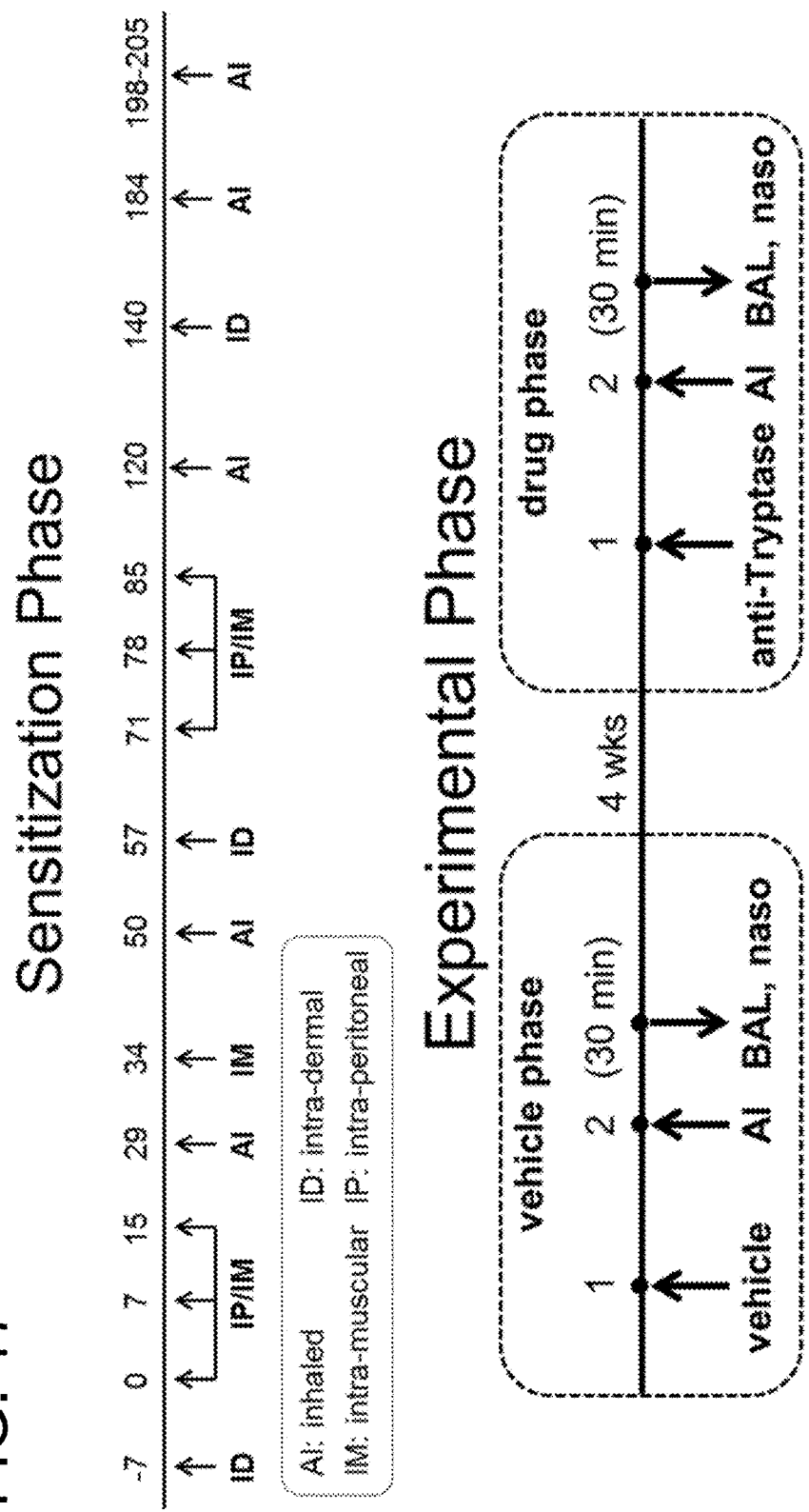
FIG. 17 is a schematic diagram showing the experimental protocol of the cyno Ascaris challenge model described in Example 6.

The effect of hu31A.v11 administration was also assessed in an allergen challenge model in which cyno monkeys are sensitized to the parasitic nematode worm Ascaris by repeated administration by a variety of routes (FIG. 17). The sensitization phase included administration of Ascaris intraperitoneally and intramuscularly on days 0, 7, 15, 71, 78, and 85; by inhalation on days 29, 50, 120, 184, and 198-205; and intramuscularly on day 34 (FIG. 17). Wheal flare was assessed on days −7, 57, and 140 following intradermal administration on those days. Each animal received an optimal dose of Ascaris as determined by ORD (Optimal Response Dose), which was performed to characterize the appropriate dose levels of Ascaris to elicit a desired response in each animal (performed during the sensitization phase). Doses included 4, 400, and 4000 µg/ml. The experimental phase included a vehicle phase, in which vehicle was administered on day 1, followed by administration of Ascaris by inhalation on day 2, followed by sampling of BAL and nasosorption 30 min later to assess the amount of total and active tryptase (FIG. 17). Four weeks later, the drug phase included administration of hu31A.v11 on day 1, followed by administration of Ascaris on day 2, and sampling of BAL and nasosorption 30 min later to assess the amount of total and active tryptase (FIG. 17).

Figure 18A:
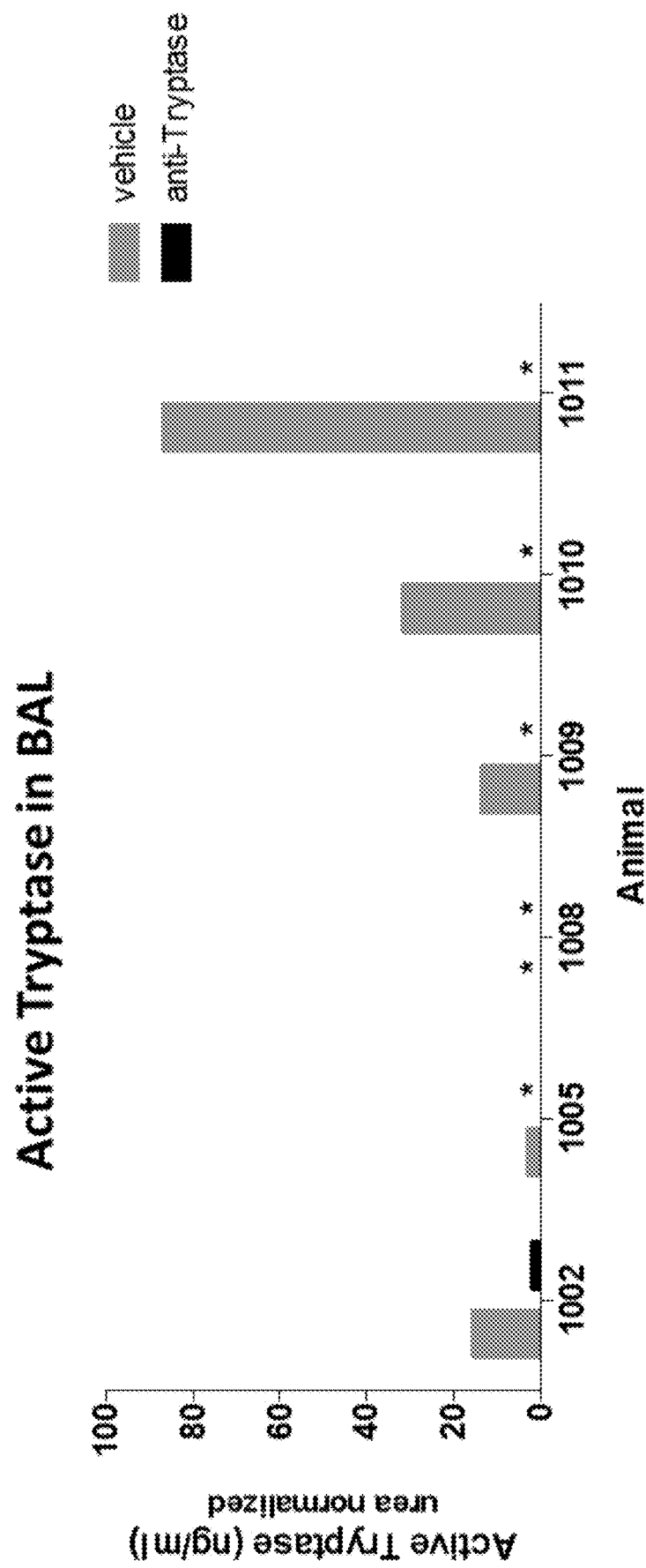
FIGS. 18A and 18B are graphs showing the results of an active tryptase assay (FIG. 18A) and a total tryptase assay (FIG. 18B) performed on BAL obtained from individual animals in the cyno Ascaris challenge experiment described in Example 6.
Figure 18B:
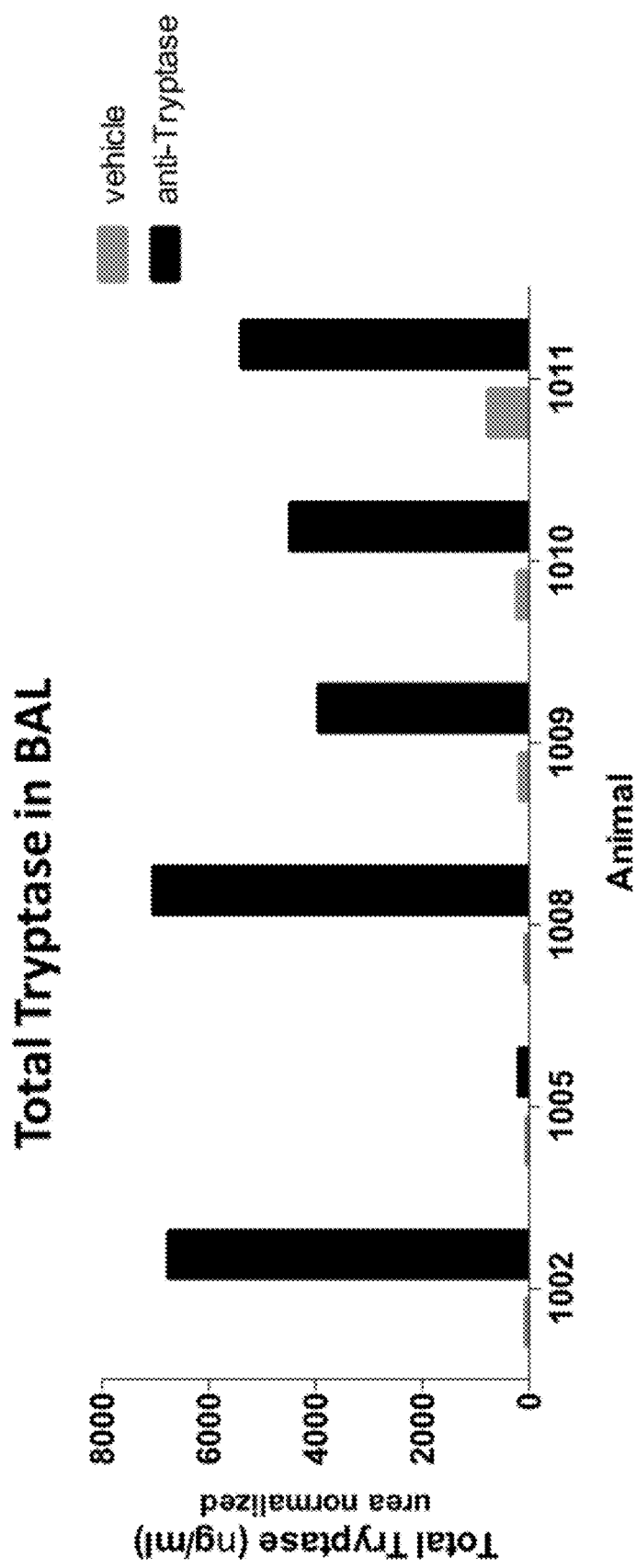
Figure 18C:
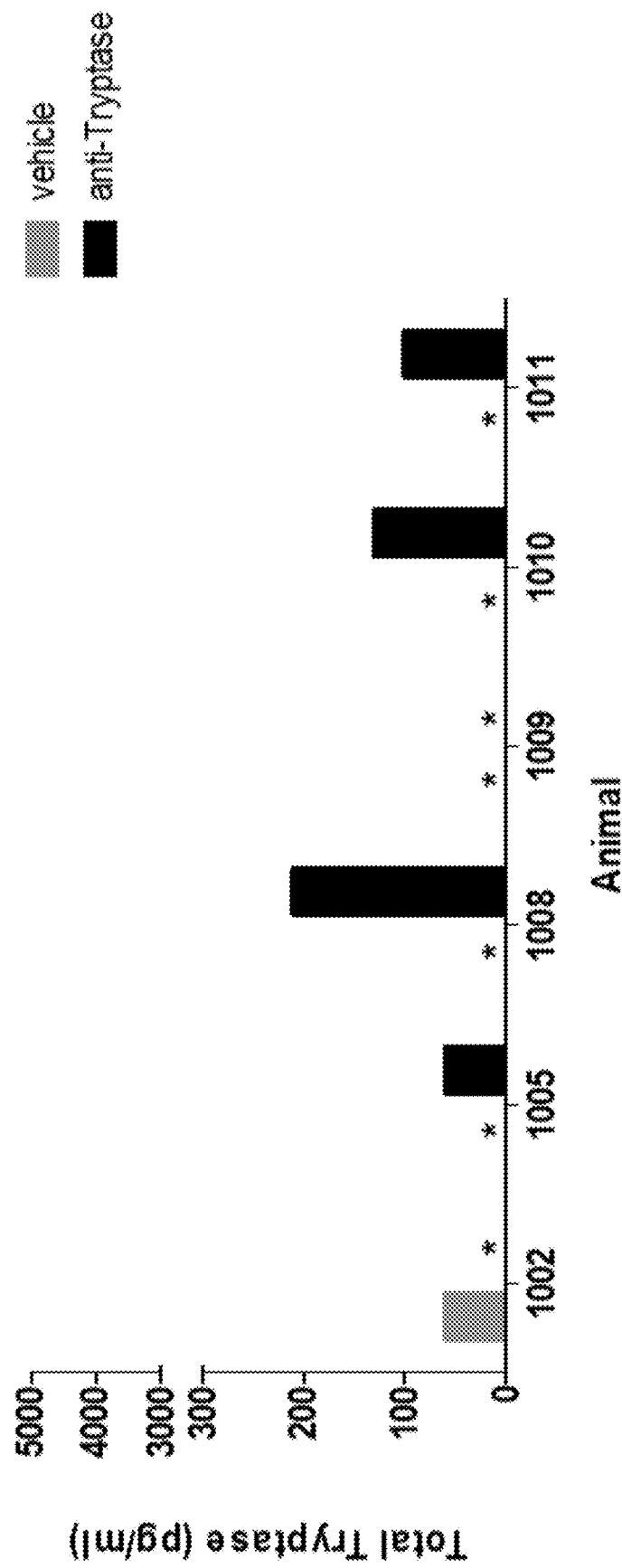
FIG. 18C is a graph showing the results of a total tryptase assay to determine the amount of total tryptase in nasal mucosal lining fluid (MLF) obtained by nasosorption using a synthetic absorptive matrix (SAM) from individual animals in the cyno Ascaris challenge experiment described in Example 6.

In the Ascaris sensitization model, administration of the anti-tryptase antibody hu31A.v11 led to a significant decrease in active tryptase in BAL in 5 animals that had detectable active tryptase levels at baseline (FIG. 18A), indicating that this antibody inhibits tryptase activity in vivo. Additionally, administration of the anti-tryptase antibody also led to an increase in the amount of total tryptase in BAL in all animals (FIG. 18B). Other experiments showed that the level of total tryptase in nasal mucosal lining fluid (MLF) was increased after dosing the anti-tryptase antibody hu31A.v11, as assessed by the level of total tryptase in the nasosorption sample (FIG. 18C). In this experiment, the MLF was collected using a synthetic absorptive matrix (SAM; Hunt Developments (UK), Ltd, West Sussex, England). The increase of total tryptase after dosing is indicative of target engagement. Active tryptase was undetectable in the nasosorption sample before and after dosing. The * in FIGS. 18A and 18C indicate levels below detection.

Next, in vivo proof of activity was also tested in human-engrafted IL2Rgnull-3/GM/SF NOD-SCID mice. A humanized mouse model for human mast cell engraftment and human IgE-dependent allergic responses was previously developed. Briefly, NSG-SGM3 mice (Jackson Laboratory, stock #013062) were developed from the NOD.Cg-Prkdc$^{scid}$ II2rg$^{tm1 Wjl}$/SzJ (NSG) background, and like their NSG parents, NSG-SGM3 mice lack mature T cells, B cells, and functional NK cells, and are deficient in mouse cytokine signaling. These mice contain three co-injected transgenes, each driven by a human cytomegalovirus promoter/enhancer sequence. Triple transgenic NSG-SGM3 mice constitutively produce 2-4 ng/ml serum levels of human SCF, GM-CSF, and IL-3, providing cell proliferation and survival signals (see, e.g., Bryce et al. *J. Allergy Clin Immunol.* 138(3):769-779, 2016). The NSG-SGM3 BLT mice develop human mast cells that populate peripheral lymphoid tissues, mucosal tissues, and the peritoneal cavity. The human mast cells in NSG-SGM3 BLT mice express CD117, tryptase, and IgE-receptor, and can undergo a calcium flux and degranulate in an IgE-dependent antigen-specific manner. Upon challenge, the NSG-SGM3-BLT mice develop a human mast cell dependent, antigen-specific IgE-mediated passive systemic anaphylaxis response that can be analyzed by measuring changes in body temperature.

The experiment was designed to examine the ability of anti-tryptase antibodies in inhibiting IgE-mediated passive systemic anaphylaxis in the engrafted mice. 10-12 weeks old NSG-SGM3 mice (Jackson Laboratory stock #013062) were divided into three groups: Group 1: NSG-SGM3 mice were treated intraperitoneally (i.p.) with isotype antibody (500 µg/mice); Group 2: NSG-SGM3 mice were treated with human anti-tryptase antibody (hu31A.v11 IgG4, 13.3 mg/mL) i.p. (500 µg/mice); and Group 3: NSG-SGM3 mice were treated with tryptase small molecule inhibitor G02849855 (30 mg/kg) i.p. On day −1, all mice were shaved clean of abdominal hair to facilitate body temperature measurement. On day 0, animals were injected with either control isotype antibody or anti-tryptase antibody. Dose volume was formulated in 100 µL. Anti-tryptase antibody was dissolved in 200 µL saline for injection. 15 min after treatment, mice from Groups 1-3 were sensitized intravenously with anti-NP (4-Hydroxy-3-nitrophenylacetyl hapten) IgE JW8.5.13 (Sigma Cat. No. 87080706-1VL; see also US20070253948 and Jackman et al. *J. Biol. Chem.* 285(27): 20850-20859, 2010),1.6 µg in 200 µL of saline. On day 1 (24 h after treatment), body temperature was measured by manually restraining the mice and placing a Braun ThermoScan® Pro 4000 firmly against the shaved abdominal skin just below the sternum. Immediately after baseline body temperature measurement, mice were challenged i.v. with 500 µg of the antigen NP conjugated to a carrier protein BSA (NP-BSA) in 200 µL saline. Every 15 minutes after challenge, body temperature will be measured for at least 60 minutes.

Figure 19:
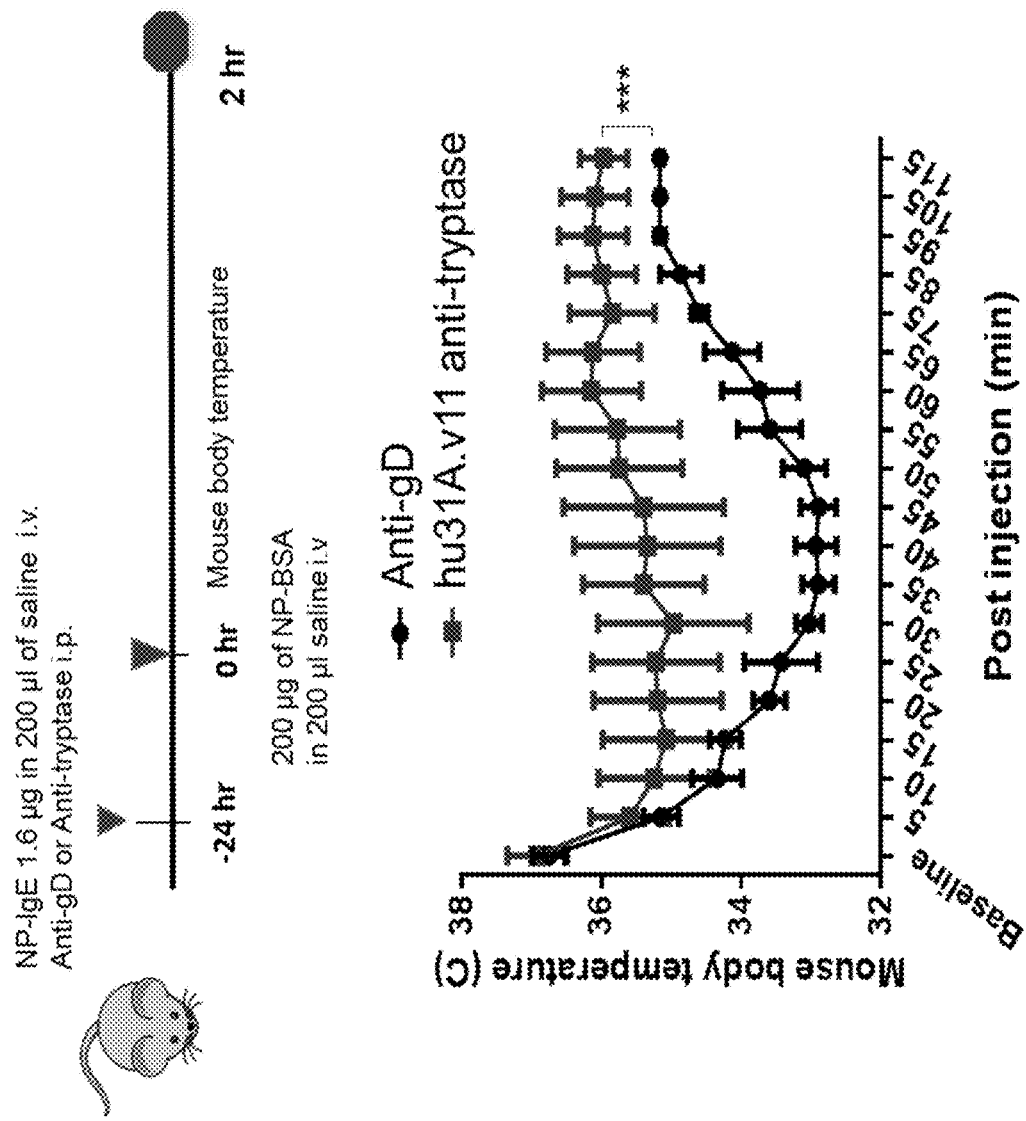
FIG. 19 is a graph showing that administration of the anti-tryptase antibody hu31A.v11 inhibited IgE-mediated passive systemic anaphylaxis in human engrafted mice. Upon IgE challenge, mice treated with the anti-tryptase antibody hu31A.v11 showed an improved body temperature maintenance as compared to mice treated with a control anti-gD antibody. *** P<0.0001 (Paired T test).

As shown in FIG. 19, mice treated with the anti-tryptase antibody hu31A.v11 showed an improved body temperature maintenance as compared to mice treated with a control anti-gD antibody, upon IgE challenge.

These data show that the anti-tryptase antibody hu31A.v11 is active and can bind and inhibit tryptase activity in vivo. These data provide further evidence that anti-tryptase antibodies such as hu31A.v1 can be used as therapeutic agents for treatment of tryptase-associated disorders such as asthma.

Other Embodiments

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

IV. Sequence Listing

Table 17 shows sequences that are used throughout the application.

TABLE 17

Sequence Listing

| SEQ ID NO: | Sequence |
|---|---|
| 1 | $X_1X_2GMX_3$, wherein $X_1$ is Asp or Ser, $X_2$ is Tyr or Phe, and $X_3$ is Val or His |
| 2 | FISSGSSTVYYADTMKG |
| 3 | $RX_1X_2X_3DWYFDV$, wherein $X_1$ is Asn or Asp, $X_2$ is Tyr or Asn, and $X_3$ is Asp or Tyr |
| 4 | SASSSVTYMY |
| 5 | RTSDLAS |
| 6 | QHYHSYPLT |
| 7 | DYGMV |
| 8 | RNYDDWYFDV |
| 9 | EVQLVESGGGLVQPGGSLRLSCAASGFTFSDYGMVWVRQAPGKGLEWVAFISSGSSTVYYADTMKGRFT ISRDNSKNTLYLQMNSLRAEDTAVYYCTRRNYDDWYFDVWGQGTLVTVSS |
| 10 | DIQMTQSPSSLSASVGDRVTITCSASSSVTYMYWYQQKPGKSPKPWIYRTSDLASGVPSRFSGSGSGTD FTLTISSLQPEDFATYYCQHYHSYPLTFGQGTKVEIK |
| 11 | EVQLVESGGGLVQPGGSLRLSCAASGFTFS |
| 12 | WVRQAPGKGLEWVA |
| 13 | RFTISRDNSKNTLYLQMNSLRAEDTAVYYCTR |
| 14 | WGQGTLVTVSS |
| 15 | DIQMTQSPSSLSASVGDRVTITC |
| 16 | WYQQKPGKSPKPWIY |
| 17 | GVPSRFSGSGSGTDFTLTISSLQPEDFATYYC |
| 18 | FGQGTKVEIK |
| 19 | EVKLVESGGGSVQPGGSRKLSCAASGFTFSDYGMVWVRQAPGKGLEWVAFISSGSSTVYYADTMKGRFT ISRDNPKNTLFLQMSSLRSEDTAMYYCARRDNYDWYFDVWGTGTTVTVSS |
| 20 | QIVLTQSPAIMSASPGEKVTISCSASSSVTYMYWYQQKPGSSPKPWIYRTSDLASGVPARFSGSGSGTS YSLTISSMEAEDAATYYCQHYHSYPLTFGAGTKLELK |
| 21 | EVKLVESGGGSVQPGGSRKLSCAASGFTFS |

TABLE 17-continued

Sequence Listing

| SEQ ID NO: | Sequence |
|---|---|
| 22 | WVRQAPGKGLEWVA |
| 23 | RFTISRDNPKNTLFLQMSSLRSEDTAMYYCAR |
| 24 | WGTGTTVTVSS |
| 25 | QIVLTQSPAIMSASPGEKVTISC |
| 26 | WYQQKPGSSPKPWIY |
| 27 | GVPARFSGSGSGTSYSLTISSMEAEDAATYYC |
| 28 | FGAGTKLELK |
| 29 | RDNYDWYFDV |
| 30 | GYAIT |
| 31 | GISSAATTFYSSWAKS |
| 32 | DPRGYGAALDRLDL |
| 33 | QSIKSVYNNRLG |
| 34 | ETSILTS |
| 35 | AGGFDRSGDTT |
| 36 | EVQLVESGPGLVKPSETLSLTCTVSRFSLIGYAITWIRQPPGKGLEWIGGISSAATTFYSSWAKSRVTISRDTSKNQVSLKLSSVTAADTAVYYCARDPRGYGAALDRLDLWGQGTLVTVSS |
| 37 | DIQMTQSPSSLSASVGDRVTITCQSIKSVYNNRLGWYQQKPGKAPKLLIYETSILTSGVPSRFSGSGSGTDFTLTISSLQPEDFATYYCAGGFDRSGDTTFGQGTKVEIK |
| 38 | EVQLVESGPGLVKPSETLSLTCTVSRFSLI |
| 39 | WX$_1$RQPPGKGLEWIG, wherein X$_1$ is Ile or Val |
| 40 | RX$_1$TISX$_2$DTSKNQX$_3$SLKLSSVTAADTAVYX$_4$CAR, wherein X$_1$ is Val or Ser, X$_2$ is Arg or Val, X$_3$ is Val or Phe, and X$_4$ is Tyr or Phe |
| 41 | WGQGTLVTVSS |
| 42 | WIRQPPGKGLEWIG |
| 43 | RVTISRDTSKNQVSLKLSSVTAADTAVYYCAR |
| 44 | EVQLVESGGGLVQPGGSLRLSCAVSRFSLI |
| 45 | WVRQAPGKGLEWIG |
| 46 | RSTISRDTSKNTVYLQMNSLRAEDTAVYFCAR |
| 47 | EVQLVESGPGLVKPSETLSLTCTVSRFSLIGYAITWIRQPPGKGLEWIGGISSAATTFYSSWAKSRVTISVDTSKNQFSLKLSSVTAADTAVYYCARDPRGYGAALDRLDLWGQGTLVTVSS |
| 48 | EVQLVESGPGLVKPSETLSLTCTVSRFSLIGYAITWVRQPPGKGLEWIGGISSAATTFYSSWAKSRSTISRDTSKNQVSLKLSSVTAADTAVYFCARDPRGYGAALDRLDLWGQGTLVTVSS |
| 49 | EVQLVESGPGLVKPSETLSLTCTVSRFSLIGYAITWIRQPPGKGLEWIGGISSAATTFYSSWAKSRVTISVDTSKNQVSLKLSSVTAADTAVYYCARDPRGYGAALDRLDLWGQGTLVTVSS |
| 50 | EVQLVESGPGLVKPSETLSLTCTVSRFSLIGYAITWIRQPPGKGLEWIGGISSAATTFYSSWAKSRVTISRDTSKNQFSLKLSSVTAADTAVYYCARDPRGYGAALDRLDLWGQGTLVTVSS |
| 51 | EVQLVESGGGLVQPGGSLRLSCAVSRFSLIGYAITWVRQAPGKGLEWIGGISSAATTFYSSWAKSRSTISRDTSKNTVYLQMNSLRAEDTAVYFCARDPRGYGAALDRLDLWGQGTLVTVSS |
| 52 | QSLEESGGGLFKPTDTLTLTCTVSRFSLIGYAITWVRQSPENGLEWIGGISSAATTFYSSWAKSRSTITRNTNENTVTLKMTSLTAADTATYFCARDPRGYGAALDRLDLWGQGTLVTVSS |
| 53 | AAVLTQTPASVSAAVGGTVSISCQSIKSVYNNRLGWYQQKPGQPPKLLIYETSILTSGVPSRFKGSGSETQFTLTISDVQCDDAATYFCAGGFDRSGDTTEGGGTEVVVK |

TABLE 17-continued

Sequence Listing

| SEQ ID NO: | Sequence |
|---|---|
| 54 | QSLEESGGGLFKPTDTLTLTCTVSRFSLI |
| 55 | WVRQSPENGLEWIG |
| 56 | RSTITRNTNENTVTLKMTSLTAADTATYFCAR |
| 57 | WGQGTLVTVSS |
| 58 | DAQLTQSPSSLSASVGDRVTITCQSIKSVYNNRLGWYQQKPGKPPKLLIYETSILTSGVPSRFSGSGSE TDFTLTISSLQPEDFATYFCAGGFDRSGDTTFGQGTKVEIK |
| 59 | AAVLTQTPASVSAAVGGTVSISCQSIKSVYNNRLGWYQQKPGQPPKLLIYETSILTSGVPSRFKGSGSE TQFTLTISDVQADDAATYFCAGGFDRSGDTTEGGGTEVVVK |
| 60 | DX$_1$QX$_2$TQSPSSLSASVGDRVTITC, wherein X$_1$ is Ile or Ala, and X$_2$ is Met or Leu |
| 61 | WYQQKPGKX$_1$PKLLIY, wherein X$_1$ is Ala or Pro |
| 62 | GVPSRFSGSGSX$_1$TDFTLTISSLQPEDFATYX$_2$C, wherein X$_1$ is Gly or Glu, and X$_2$ is Tyr or Phe |
| 63 | FGQGTKVEIK |
| 64 | DIQMTQSPSSLSASVGDRVTITC |
| 65 | WYQQKPGKAPKLLIY |
| 66 | GVPSRFSGSGSGTDFTLTISSLQPEDFATYYC |
| 67 | AAVLTQTPASVSAAVGGTVSISC |
| 68 | WYQQKPGQPPKLLIY |
| 69 | GVPSRFKGSGSETQFTLTISDVQX$_1$DDAATYFC, wherein X$_1$ is Cys or Ala |
| 70 | FGGGTEVVVK |
| 71 | MLNLLLLALPVLASRAYAAPAPGQALQRVGIVGGQEAPRSKWPWQVSLRVHGPYWMHFCGGSLIHPQWV LTAAHCVGPDVKDLAALRVQLREQHLYYQDQLLPVSRIIVHPQFYTAQIGADIALLELEEPVNVSSHVH TVTLPPASETFPPGMPCWVTGWGDVDNDERLPPPFPLKQVKVPIMENHICDAKYHLGAYTGDDVRIVRD DMLCAGNTRRDSCQGDSGGPLVCKVNGTWLQAGVVSWGEGCAQPNRPGIYTRVTYYLDWIHHYVPKKP |
| 72 | MLNLLLLALPVLASRAYAAPAPGQALQRVGIVGGQEAPRSKWPWQVSLRVHGPYWMHFCGGSLIHPQWV LTAAHCVGPDVKDLAALRVQLREQHLYYQDQLLPVSRIIVHPQFYTAQIGADIALLELEEPVNVSSHVH TVTLPPASETFPPGMPCWVTGWGDVDNDERLPPPFPLKQVKVPIMENHICDAKYHLGAYTGDDVRIVRD DMLCAGNTRRDSCQGDSGGPLVCKVNGTWLQAGVVSWGEGCAQPNRPGIYTRVTYYLDWIHHYVPKKP |
| 73 | MLNLLLLALPVLASRAYAAPAPGQALQRVGIVGGQEAPRSKWPWQVSLRVRDRYWMHFCGGSLIHPQWV LTAAHCVGPDVKDLAALRVQLREQHLYYQDQLLPVSRIIVHPQFYTAQIGADIALLELEEPVNVSSHVH TVTLPPASETFPPGMPCWVTGWGDVDNDERLPPPFPLKQVKVPIMENHICDAKYHLGAYTGDDVRIVRD DMLCAGNTRRDSCQVATAPHTFPAPS |
| 74 | GATGGTGACTGTTCCAGTTGC |
| 75 | CATTGGTGAGGGTGCCCGAGTTC |
| 76 | EVQLVESGGGLVQPGGSLRLSCAASGFTFSDYGMVWVRQAPGKGLEWVAFISSGSSTVYYADTMKGRFT ISRDNSKNTLYLQMNSLRAEDTAVYYCTRRNYDDWYFDVWGQGTLVTVSSASTKGPSVFPLAPSSKSTS GGTAALGCLVKDYFPEPVTVSWNSGALTSGVHTFPAVLQSSGLYSLSSVVTVPSSSLGTQTYICNVNHK PSNTKVDKKVEPKSCDKTHTCPPCPAPELLGGPSVFLFPPKPKDTLMISRTPEVTCVVVDVSHEDPEVK FNWYVDGVEVHNAKTKPREEQYNSTYRVVSVLTVLHQDWLNGKEYKCKVSNKALPAPIEKTISKAKGQP REPQVYTLPPSREEMTKNQVSLTCLVKGFYPSDIAVEWESNGQPENNYKTTPPVLDSDGSFFLYSKLTV DKSRWQQGNVFSCSVMHEALHNHYTQKSLSLSPG |
| 77 | DIQMTQSPSSLSASVGDRVTITCSASSSVTYMYWYQQKPGKSPKPWIYRTSDLASGVPSRFSGSGSGTD FTLTISSLQPEDFATYYCQHYSYPLTFGQGTKVEIKRTVAAPSVFIFPPSDEQLKSGTASVVCLLNNF YPREAKVQWKVDNALQSGNSQESVTEQDSKDSTYSLSSTLTLSKADYEKHKVYACEVTHQGLSSPVTKS FNRGEC |
| 78 | EVQLVESGGGLVQPGGSLRLSCAASGFTFSDYGMVWVRQAPGKGLEWVAFISSGSSTVYYADTMKGRFT ISRDNSKNTLYLQMNSLRAEDTAVYYCTRRNYDDWYFDVWGQGTLVTVSSASTKGPSVFPLAPCSRSTS ESTAALGCLVKDYFPEPVTVSWNSGALTSGVHTFPAVLQSSGLYSLSSVVTVPSSSLGTKTYTCNVDHK PSNTKVDKRVESKYGPPCPPCPAPEFLGGPSVFLFPPKPKDTLMISRTPEVTCVVVDVSQEDPEVQFNW YVDGVEVHNAKTKPREEQFNSTYRVVSVLTVLHQDWLNGKEYKCKVSNKGLPSSIEKTISKAKGQPREP |

TABLE 17-continued

Sequence Listing

| SEQ ID NO: | Sequence |
|---|---|
|  | QVYTLPPSQEEMTKNQVSLTCLVKGFYPSDIAVEWESNGQPENNYKTTPPVLDSDGSFFLYSRLTVDKS RWQEGNVFSCSVMHEALHNHYTQKSLSLSLG |
| 79 | DIQMTQSPSSLSASVGDRVTITCSASSSVTYMYWYQQKPGKSPKPWIYRTSDLASGVPSRFSGSGSGTD FTLTISSLQPEDFATYYCQHYSYPLTFGQGTKVEIKRTVAAPSVFIFPPSDEQLKSGTASVVCLLNNF YPREAKVQWKVDNALQSGNSQESVTEQDSKDSTYSLSSTLTLSKADYEKHKVYACEVTHQGLSSPVTKS FNRGEC |
| 80 | EVQLVESGPGLVKPSETLSLTCTVSRFSLIGYAITWIRQPPGKGLEWIGGISSAATTFYSSWAKSRVTI SRDTSKNQVSLKLSSVTAADTAVYYCARDPRGYGAALDRLDLWGQGTLVTVSSASTKGPSVFPLAPSSK STSGGTAALGCLVKDYFPEPVTVSWNSGALTSGVHTFPAVLQSSGLYSLSSVVTVPSSSLGTQTYICNV NHKPSNTKVDKKVEPKSCDKTHTCPPCPAPELLGGPSVFLFPPKPKDTLMISRTPEVTCVVVDVSHEDP EVKFNWYVDGVEVHNAKTKPREEQYNSTYRVVSVLTVLHQDWLNGKEYKCKVSNKALPAPIEKTISKAK GQPREPQVYTLPPSREEMTKNQVSLTCLVKGFYPSDIAVEWESNGQPENNYKTTPPVLDSDGSFFLYSK LTVDKSRWQQGNVFSCSVMHEALHNHYTQKSLSLSPG |
| 81 | DIQMTQSPSSLSASVGDRVTITCQSIKSVYNNRLGWYQQKPGKAPKLLIYETSILTSGVPSRFSGSGSG TDFTLTISSLQPEDFATYYCAGGFDRSGDTTFGQGTKVEIKRTVAAPSVFIFPPSDEQLKSGTASVVCL LNNFYPREAKVQWKVDNALQSGNSQESVTEQDSKDSTYSLSSTLTLSKADYEKHKVYACEVTHQGLSSP VTKSFNRGEC |
| 82 | EVQLVESGPGLVKPSETLSLTCTVSRFSLIGYAITWIRQPPGKGLEWIGGISSAATTFYSSWAKSRVTI SRDTSKNQVSLKLSSVTAADTAVYYCARDPRGYGAALDRLDLWGQGTLVTVSSASTKGPSVFPLAPCSR STSESTAALGCLVKDYFPEPVTVSWNSGALTSGVHTFPAVLQSSGLYSLSSVVTVPSSSLGTKTYTCNV DHKPSNTKVDKRVESKYGPPCPPCPAPEFLGGPSVFLFPPKPKDTLMISRTPEVTCVVVDVSQEDPEVQ FNWYVDGVEVHNAKTKPREEQFNSTYRVVSVLTVLHQDWLNGKEYKCKVSNKGLPSSIEKTISKAKGQP REPQVYTLPPSQEEMTKNQVSLTCLVKGFYPSDIAVEWESNGQPENNYKTTPPVLDSDGSFFLYSRLTV DKSRWQEGNVFSCSVMHEALHNHYTQKSLSLSLG |
| 83 | DIQMTQSPSSLSASVGDRVTITCQSIKSVYNNRLGWYQQKPGKAPKLLIYETSILTSGVPSRFSGSGSG TDFTLTISSLQPEDFATYYCAGGFDRSGDTTFGQGTKVEIKRTVAAPSVFIFPPSDEQLKSGTASVVCL LNNFYPREAKVQWKVDNALQSGNSQESVTEQDSKDSTYSLSSTLTLSKADYEKHKVYACEVTHQGLSSP VTKSFNRGEC |
| 84 | AYSVN |
| 85 | MIWGDGKIVYNSALKS |
| 86 | DGYYPYAMDN |
| 87 | RASKSVDSYGNSFMH |
| 88 | LASNLES |
| 89 | QQNNEDPRT |
| 90 | QVTLRESGPALVKPTQTLTLTCTVSGFSLSAYSVNWIRQPPGKALEWLAMIWGDKIVYNSALKSRLTI SKDTSKNQVVLTMTNMDPVDTATYYCAGDGYYPYAMDNWGQGSLVTVSS |
| 91 | DIVMTQSPDSLSVSLGERATINCRASKSVDSYGNSFMHWYQQKPGQPPKLLYLASNLESGVPDRFSGS GSGTDFTLTISSLQAEDVAVYYCQQNNEDPRTFGGGTKVEIK |
| 92 | DIQMTQSPSSLSASVGDRVTITCRASQGISSYLAWYQQKPGKAPKLLIYAASSLQSGVPSRFSGSGSGT DFTLTISSLQPEDFATYYCQQYYSYPFTFGQGTKVEIK |
| 93 | EVQLVESGPGLVKPSETLSLTCTVSGGSISSGGYYWSWIRQPPGKGLEWIGYIYYSGSTYYNPSLKSRV TISVDTSKNQFSLKLSSVTAADTAVYYCARFDYWGQFTLVTVSS |
| 94 | EVQLVESGGGLVQPGGSLRLSCAASGFTFSSYAMSWVRQAPGKGLEWVGAISSSGSSTYYADSVKGRFT ISRDNSKNTLYLQMNSLRAEDTAVYYCARFDYWGQGTLVTVSS |
| 95 | TLTISSLQPEDFATYYCQQYYSYPFTFGQGTKVEIK |
| 96 | TLTISDVQCDDAATYFCAGGFDRSGDTTFGGGTEVVVK |
| 97 | IVGGQEAPRSKWPWQVSLRVHGPYWMHFCGGSLIHPQWVLTAAHCVGPDVKDLAALRVQLREQHLYYQD QLLPVSRIIVHPQFYTAQIGADIALLELEEPVNVSSHVHTVTLPPASETFPPGMPCWVTGWGDVDNDER LPPPFPLKQVKVPIMENHICDAKYHLGAYTGDDVRIVRDDMLCAGNTRRDSCQGDSGGPLVCKVNGTWL QAGVVSWGEGCAQPNRPGIYTRVTYYLDWIHHYVPKKP |
| 98 | EVQLVESGGGLVQPGGSLRLSCAASGFTFSDYGMVWVRQAPGKGLEWVGFISSGSSTVYYADTMKGRFT ISRDNSKNTLYLQMNSLRAEDTAVYYCARRDNYDWYFDVWGQGTLVTVSS |
| 99 | EVQLVESGGGLVQPGGSLRLSCAASGFTFSDYGMVWVRQAPGKGLEWVAFISSGSSTVYYADTMKGRFT ISRDNSKNTLYLQMNSLRAEDTAVYYCARRDNYDWYFDVWGQGTLVTVSS |

TABLE 17-continued

Sequence Listing

| SEQ ID NO: | Sequence |
|---|---|
| 100 | EVQLVESGGGLVQPGGSLRLSCAASGFTFSSFGMHWVRQAPGKGLEWVAFISSGSSTVYYADTMKGRFT<br>ISRDNSKNTLYLQMNSLRAEDTAVVYCARRDNYDWYFDVWGQGTLVTVSS |
| 101 | EVQLVESGGGLVQPGGSLRLSCAASGFTFSDYGMVWVRQAPGKGLEWVAFISSGSSTVYYADTMKGRFT<br>ISRDNSKNTLYLQMNSLRAEDTAVVYCTRRDNYDWYFDVWGQGTLVTVSS |
| 102 | DIQMTQSPSSLSASVGDRVTITCSASSSVTYMYWYQQKPGKAPKLLIYRTSDLASGVPSRFSGSGSGTD<br>FTLTISSLQPEDFATYYCQHYHSYPLTFGQGTKVEIK |
| 103 | DIQLTQSPSSLSASVGDRVTITCSASSSVTYMYWYQQKPGKSPKPWIYRTSDLASGVPSRFSGSGSGTD<br>YTLTISSLQPEDFATYYCQHYHSYPLTFGQGTKVEIK |
| 104 | GAAGTGCAGCTGGTGGAAAGCGGCGGCGGCCTGGTGCAGCCAGGCGGCAGCCTGCGCCTGAGCTGCGCC<br>GCCAGCGGCTTCACCTTCAGCGATTATGGCATGGTGTGGGTGCGCCAGGCCCCAGGCAAAGGCCTGGAA<br>TGGGTGGCCTTCATCAGCAGCGGCAGCAGCACCGTGTATTATGCCGATACCATGAAAGGCCGCTTCACC<br>ATCAGCCGCGATAACAGCAAAAACACCCTGTATCTGCAGATGAACAGCCTGCGCGCCGAAGATACCGCC<br>GTGTATTATTGCACCCGCCGCAACTACGATGATTGGTATTTCGATGTGTGGGGCCAGGGCACCCTGGTG<br>ACCGTCTCGAGT |
| 105 | GATATCCAGATGACCCAGAGCCCAAGCAGCCTGAGCGCCAGCGTGGGCGATCGCGTGACCATCACCTGC<br>AGCGCCAGCAGCAGCGTGACCTATATGTATTGGTATCAGCAGAAACCAGGCAAAAGCCCAAAACCATGG<br>ATCTATCGCACCAGCGATCTGGCCAGCGGCGTGCCAAGCCGCTTCAGCGGCAGCGGCAGCGGCACCGAT<br>TTCACCCTGACCATCAGCAGCCTGCAGCCAGAAGATTTCGCCACCTATTATTGCCAGCACTATCACAGC<br>TATCCACTGACCTTCGGCCAGGGTACCAAGGTGGAGATCAAA |
| 106 | GAAGTGCAGCTGGTGGAAAGCGGCGGCGGCCTGGTGCAGCCAGGCGGCAGCCTGCGCCTGAGCTGCGCC<br>GCCAGCGGCTTCACCTTCAGCGATTATGGCATGGTGTGGGTGCGCCAGGCCCCAGGCAAAGGCCTGGAA<br>TGGGTGGCCTTCATCAGCAGCGGCAGCAGCACCGTGTATTATGCCGATACCATGAAAGGCCGCTTCACC<br>ATCAGCCGCGATAACAGCAAAAACACCCTGTATCTGCAGATGAACAGCCTGCGCGCCGAAGATACCGCC<br>GTGTATTATTGCACCCGCCGCAACTACGATGATTGGTATTTCGATGTGTGGGGCCAGGGCACCCTGGTG<br>ACCGTCTCGAGTGCCTCCACCAAGGGCCCATCGGTCTTCCCCCTGGCACCCTCCTCCAAGAGCACCTCT<br>GGGGGCACAGCGGCCCTGGGCTGCCTGGTCAAGGACTACTTCCCCGAACCGGTGACGGTGTCGTGGAAC<br>TCAGGCGCCCTGACCAGCGGCGTGCACACCTTCCCGGCTGTCCTACAGTCCTCAGGACTCTACTCCCTC<br>AGCAGCGTGGTGACTGTGCCCTCTAGCAGCTTGGGCACCCAGACCTACATCTGCAACGTGAATCACAAG<br>CCCAGCAACACCAAGGTGGACAAGAAAGTTGAGCCCAAATCTTGTGACAAAACTCACACATGCCCACCG<br>TGCCCAGCCACCTGAACTCCTGGGGGGACCGTCAGTCTTCCTCTTCCCCCCAAAACCCAAGGACACCCTC<br>ATGATCTCCCGGACCCCTGAGGTCACATGCGTGGTGGTGGACGTGAGCCACGAAGACCCTGAGGTCAAG<br>TTCAACTGGTACGTGGACGGCGTGGAGGTGCATAATGCCAAGACAAAGCCGCGGGAGGAGCAGTACAAC<br>AGCACGTACCGTGTGGTCAGCGTCCTCACCGTCCTGCACCAGGACTGGCTGAATGGCAAGGAGTACAAG<br>TGCAAGGTCTCCAACAAAGCCCTCCCAGCCCCCATCGAGAAAACCATCTCCAAAGCCAAAGGGCAGCCC<br>CGAGAACCACAGGTGTACACCCTGCCCCCATCCCGGGAAGAGATGACCAAGAACCAGGTCAGCCTGACC<br>TGCCTGGTCAAAGGCTTCTATCCCAGCGACATCGCCGTGGAGTGGGAGAGCAATGGGCAGCCGGAGAAC<br>AACTACAAGACCACGCCTCCCGTGCTGGACTCCGACGGCTCCTTCTTCCTCTACAGCAAGCTCACCGTG<br>GACAAGAGCAGGTGGCAGCAGGGGAACGTCTTCTCATGCTCCGTGATGCATGAGGCTCTGCACAACCAC<br>TACACGCAGAAGAGCCTCTCCCTGTCTCCGGGTAAA |
| 107 | GATATCCAGATGACCCAGAGCCCAAGCAGCCTGAGCGCCAGCGTGGGCGATCGCGTGACCATCACCTGC<br>AGCGCCAGCAGCAGCGTGACCTATATGTATTGGTATCAGCAGAAACCAGGCAAAAGCCCAAAACCATGG<br>ATCTATCGCACCAGCGATCTGGCCAGCGGCGTGCCAAGCCGCTTCAGCGGCAGCGGCAGCGGCACCGAT<br>TTCACCCTGACCATCAGCAGCCTGCAGCCAGAAGATTTCGCCACCTATTATTGCCAGCACTATCACAGC<br>TATCCACTGACCTTCGGCCAGGGTACCAAGGTGGAGATCAAACGAACTGTGGCTGCACCATCTGTCTTC<br>ATCTTCCCGCCATCTGATGAGCAGTTGAAATCTGGAACTGCTTCTGTTGTGTGCCTGCTGAATAACTTC<br>TATCCCAGAGAGGCCAAAGTACAGTGGAAGGTGGATAACGCCCTCCAATCGGGTAACTCCCAGGAGAGT<br>GTCACAGAGCAGGACAGCAAGGACAGCACCTACAGCCTCAGCAGCACCCTGACGCTGAGCAAAGCAGAC<br>TACGAGAAACACAAAGTCTACGCCTGCGAAGTCACCCATCAGGGCCTGAGCTCGCCCGTCACAAAGAGC<br>TTCAACAGGGGAGAGTGT |
| 108 | GAAGTGCAGCTGGTGGAAAGCGGCGGCGGCCTGGTGCAGCCAGGCGGCAGCCTGCGCCTGAGCTGCGCC<br>GCCAGCGGCTTCACCTTCAGCGATTATGGCATGGTGTGGGTGCGCCAGGCCCCAGGCAAAGGCCTGGAA<br>TGGGTGGCCTTCATCAGCAGCGGCAGCAGCACCGTGTATTATGCCGATACCATGAAAGGCCGCTTCACC<br>ATCAGCCGCGATAACAGCAAAAACACCCTGTATCTGCAGATGAACAGCCTGCGCGCCGAAGATACCGCC<br>GTGTATTATTGCACCCGCCGCAACTACGATGATTGGTATTTCGATGTGTGGGGCCAGGGCACCCTGGTG<br>ACCGTCTCGAGTGCCTCCACCAAGGGCCCATCGGTCTTCCCCCTGGCACCCTGCTCCCGCAGTACTTCT<br>GAGTCCACAGCGGCCCTGGGCTGCCTGGTCAAGGACTACTTCCCCGAACCGGTGACGGTGTCGTGGAAC<br>TCAGGCGCCCTGACCAGCGGCGTGCACACCTTCCCGGCTGTCCTACAGTCCTCAGGACTCTACTCCCTC<br>AGCAGCGTGGTGACTGTGCCCTCTAGCAGCTTGGGCACCAAGACCTACACGTGCAACGTGGATCACAAG<br>CCCAGCAACACCAAGGTGGACAAACGCGTTGAGTCCAAATATGGTCCCCCATGCCCACCATGCCCAGCA<br>CCTGAGTTCCTGGGGGGACCATCAGTCTTCCTGTTCCCCCCAAAACCCAAGGACACTCTCATGATCTCC<br>CGGACCCCTGAGGTCACGTGCGTGGTGGTGGACGTGAGCCAGGAAGACCCCGAGGTCCAGTTCAACTGG<br>TACGTGGATGGCGTGGAGGTGCATAATGCCAAGACAAAGCCGCGGGAGGAGCAGTTCAACAGCACGTAC<br>CGTGTGGTCAGCGTCCTCACCGTCCTGCACCAGGACTGGCTGAACGGCAAGGAGTACAAGTGCAAGGTC<br>TCCAACAAAGGCCTCCCGTCCTCCATCGAGAAAACCATCTCCAAAGCCAAAGGGCAGCCCCGAGAGCCA<br>CAGGTGTACACCCTGCCCCCATCCCAGGAGGAGATGACCAAGAACCAGGTCAGCCTGACCTGCCTGGTC<br>AAAGGCTTCTACCCCAGCGACATCGCCGTGGAGTGGGAGAGCAATGGGCAGCCGGAGAACAACTACAAG |

TABLE 17-continued

Sequence Listing

| SEQ ID NO: | Sequence |
|---|---|
| | ACCACGCCTCCCGTGCTGGACTCCGACGGCTCCTTCTTCCTCTACAGCAGGCTAACCGTGGACAAGAGC<br>AGGGTGGCAGGAGGGGAATGTCTTCTCATGCTCCGTGATGCATGAGGCTCTGCACAACCACTACACACAG<br>AAGAGCCTCTCCCTGTCTCTGGGTAAA |
| 109 | GAAGTGCAGCTGGTGGAAAGCGGCCCAGGCCTGGTGAAACCAAGCGAAACCCTGAGCCTGACCTGCACC<br>GTGAGCCGCTTCAGCCTGATCGGCTATGCCATCACCTGGATCCGCCAGCCACCAGGCAAAGGCCTGGAA<br>TGGATCGGCGGCATCAGCAGCGCCGCCACCACCTTCTATAGCAGCTGGGCAAAAGCCGCGTGACCATC<br>AGCCGCGATACCAGCAAAAACCAGGTGAGCCTGAAACTGAGCAGCGTGACCGCCGCCGATACCGCCGTG<br>TATTATTGCGCCCGCGATCCACGCGGCTATGGCGCCGCCCTGGATCGCCTGGATCTGTGGGGCCAGGGC<br>ACCCTGGTGACCGTCTCGAGT |
| 110 | GATATCCAGATGACCCAGAGCCCAAGCAGCCTGAGCGCCAGCGTGGGCGATCGCGTGACCATCACCTGC<br>CAGAGCATCAAAAGCGTGTATAACAACCGCCTGGGCTGGTATCAGCAGAAACCAGGCAAAGCCCCAAAA<br>CTGCTGATCTATGAAACCAGCATCCTGACCAGCGGCGTGCCAAGCCGCTTCAGCGGCAGCGGCAGCGGC<br>ACCGATTTCACCCTGACCATCAGCAGCCTGCAGCCAGAAGATTTCGCCACCTATTATTGCGCCGGCGGC<br>TTCGATCGCAGCGGCGATACCACCTTCGGCCAGGGTACCAAGGTGGAGATCAAA |
| 111 | GAAGTGCAGCTGGTGGAAAGCGGCCCAGGCCTGGTGAAACCAAGCGAAACCCTGAGCCTGACCTGCACC<br>GTGAGCCGCTTCAGCCTGATCGGCTATGCCATCACCTGGATCCGCCAGCCACCAGGCAAAGGCCTGGAA<br>TGGATCGGCGGCATCAGCAGCGCCGCCACCACCTTCTATAGCAGCTGGGCAAAAGCCGCGTGACCATC<br>AGCCGCGATACCAGCAAAAACCAGGTGAGCCTGAAACTGAGCAGCGTGACCGCCGCCGATACCGCCGTG<br>TATTATTGCGCCCGCGATCCACGCGGCTATGGCGCCGCCCTGGATCGCCTGGATCTGTGGGGCCAGGGC<br>ACCCTGGTGACCGTCTCGAGTGCCTCCACCAAGGGCCCATCGGTCTTCCCCCTGGCACCCTCCTCCAAG<br>AGCACCTCTGGGGGCACAGCGGCCCTGGGCTGCCTGGTCAAGGACTACTTCCCCGAACCGGTGACGGTG<br>TCGTGGAACTCAGGCGCCCTGACCAGCGGCGTGCACACCTTCCCGGCTGTCCTACAGTCCTCAGGACTC<br>TACTCCCTCAGCAGCGTGGTGACTGTGCCCTCTAGCAGCTTGGGCACCCAGACCTACATCTGCAACGTG<br>AATCACAAGCCCAGCAACACCAAGGTGGACAAGAAAGTTGAGCCCAAATCTTGTGACAAAACTCACACA<br>TGCCCACCGTGCCCAGCACCTGAACTCCTGGGGGGACCGTCAGTCTTCCTCTTCCCCCCAAAACCCAAG<br>GACACCCTCATGATCTCCCGGACCCCTGAGGTCACATGCGTGGTGGTGGACGTGAGCCACGAAGACCCT<br>GAGGTCAAGTTCAACTGGTACGTGGACGGCGTGGAGGTGCATAATGCCAAGACAAAGCCGCGGGAGGAG<br>CAGTACAACAGCACGTACCGTGTGGTCAGCGTCCTCACCGTCCTGCACCAGGACTGGCTGAATGGCAAG<br>GAGTACAAGTGCAAGGTCTCCAACAAAGCCCTCCCAGCCCCCATCGAGAAAACCATCTCCAAAGCCAAA<br>GGGCAGCCCCGAGAACCACAGGTGTACACCCTGCCCCCATCCCGGGAAGAGATGACCAAGAACCAGGTC<br>AGCCTGACCTGCCTGGTCAAAGGCTTCTATCCCAGCGACATCGCCGTGGAGTGGGAGAGCAATGGGCAG<br>CCGGAGAACAACTACAAGACCACGCCTCCCGTGCTGGACTCCGACGGCTCCTTCTTCCTCTACAGCAAG<br>CTCACCGTGGACAAGAGCAGGTGGCAGCAGGGGAACGTCTTCTCATGCTCCGTGATGCATGAGGCTCTG<br>CACAACCACTACACGCAGAAGAGCCTCTCCCTGTCTCCGGGTAAA |
| 112 | GATATCCAGATGACCCAGAGCCCAAGCAGCCTGAGCGCCAGCGTGGGCGATCGCGTGACCATCACCTGC<br>CAGAGCATCAAAAGCGTGTATAACAACCGCCTGGGCTGGTATCAGCAGAAACCAGGCAAAGCCCCAAAA<br>CTGCTGATCTATGAAACCAGCATCCTGACCAGCGGCGTGCCAAGCCGCTTCAGCGGCAGCGGCAGCGGC<br>ACCGATTTCACCCTGACCATCAGCAGCCTGCAGCCAGAAGATTTCGCCACCTATTATTGCGCCGGCGGC<br>TTCGATCGCAGCGGCGATACCACCTTCGGCCAGGGTACCAAGGTGGAGATCAAACGAACTGTGGCTGCA<br>CCATCTGTCTTCATCTTCCCGCCATCTGATGAGCAGTTGAAATCTGGAACTGCTTCTGTTGTGTGCCTG<br>CTGAATAACTTCTATCCCAGAGAGGCCAAAGTACAGTGGAAGGTGGATAACGCCCTCCAATCGGGTAAC<br>TCCCAGGAGAGTGTCACAGAGCAGGACAGCAAGGACAGCACCTACAGCCTCAGCAGCACCCTGACGCTG<br>AGCAAAGCAGACTACGAGAAACACAAAGTCTACGCCTGCGAAGTCACCCATCAGGGCCTGAGCTCGCCC<br>GTCACAAAGAGCTTCAACAGGGGAGAGTGT |
| 113 | GAAGTGCAGCTGGTGGAAAGCGGCCCAGGCCTGGTGAAACCAAGCGAAACCCTGAGCCTGACCTGCACC<br>GTGAGCCGCTTCAGCCTGATCGGCTATGCCATCACCTGGATCCGCCAGCCACCAGGCAAAGGCCTGGAA<br>TGGATCGGCGGCATCAGCAGCGCCGCCACCACCTTCTATAGCAGCTGGGCAAAAGCCGCGTGACCATC<br>AGCCGCGATACCAGCAAAAACCAGGTGAGCCTGAAACTGAGCAGCGTGACCGCCGCCGATACCGCCGTG<br>TATTATTGCGCCCGCGATCCACGCGGCTATGGCGCCGCCCTGGATCGCCTGGATCTGTGGGGCCAGGGC<br>ACCCTGGTGACCGTCTCGAGTGCCTCCACCAAGGGCCCATCGGTCTTCCCCCTGGCACCCTGCTCCCGC<br>AGTACTTCTGAGTCCACAGCGGCCCTGGGCTGCCTGGTCAAGGACTACTTCCCCGAACCGGTGACGGTG<br>TCGTGGAACTCAGGCGCCCTGACCAGCGGCGTGCACACCTTCCCGGCTGTCCTACAGTCCTCAGGACTC<br>TACTCCCTCAGCAGCGTGGTGACTGTGCCCTCTAGCAGCTTGGGCACCAAGACCTACACGTGCAACGTG<br>GATCACAAGCCCAGCAACACCAAGGTGGACAAACGCGTTGAGTCCAAATATGGTCCCCCATGCCCACCA<br>TGCCCAGCACCTGAGTTCCTGGGGGGACCATCAGTCTTCCTGTTCCCCCCAAAACCCAAGGACACTCTC<br>ATGATCTCCCGGACCCCTGAGGTCACGTGCGTGGTGGTGGACGTGAGCCAGGAAGACCCCGAGGTCCAG<br>TTCAACTGGTACGTGGATGGCGTGGAGGTGCATAATGCCAAGACAAAGCCGCGGGAGGAGCAGTTCAAC<br>AGCACGTACCGTGTGGTCAGCGTCCTCACCGTCCTGCACCAGGACTGGCTGAACGGCAAGGAGTACAAG<br>TGCAAGGTCTCCAACAAAGGCCTCCCGTCCTCATCGAGAAAACCATCTCCAAAGCCAAAGGGCAGCCC<br>CGAGAGCCACAGGTGTACACCCTGCCCCCATCCCAGGAGGAGATGACCAAGAACCAGGTCAGCCTGACC<br>TGCCTGGTCAAAGGCTTCTACCCCAGCGACATCGCCGTGGAGTGGGAGAGCAATGGGCAGCCGGAGAAC<br>AACTACAAGACCACGCCTCCCGTGCTGGACTCCGACGGCTCCTTCTTCCTCTACAGCAGGCTAACCGTG<br>GACAAGAGCAGGTGGCAGGAGGGGAATGTCTTCTCATGCTCCGTGATGCATGAGGCTCTGCACAACCAC<br>TACACACAGAAGAGCCTCTCCCTGTCTCTGGGTAAA |
| 114 | EVTLRESGPALVKPTQTLTLTCTVSGFSLSAYSVNWIRQPPGKALEWLAMIWGDGKIVYNSALKSRLTI<br>SKDTSKNQVVLTMTNMDPVDTATYYCAGDGYYPYAMDNWGQGSLVTVSS |
| 115 | DIVLTQSPDSLSVSLGERATINCRASKSVDSYGNSFMHWYQQKPGQPPKLLIYLASNLESGVPDRFSGS<br>GSGTDFTLTISSLQAEDVAVYYCQQNNEDPRTFGGGTKVEIK |

TABLE 17-continued

Sequence Listing

| SEQ ID NO: | Sequence |
|---|---|
| 116 | IVGGQEAPRSKWPWQVSLRVHGPYWMHFCGGSLIHPQWVLTAAHCVGPDVKDLAALRVQLREQHLYYQD QLLPVSRIIVHPQFYTAQIGADIALLELEEPVKVSSHVHTVTLPPASETFPPGMPCWVTGWGDVDNDER LPPPFPLKQVKVPIMENHICDAKYHLGAYTGDDVRIVRDDMLCAGNTRRDSCQGDSGGPLVCKVNGTWL QAGVVSWGEGCAQPNRPGIYTRVTYYLDWIHHYVPKKPGNSDYKDDDDK |
| 117 | IVGGQEAPRSKWPWQVSLRVRDRYWMHFCGGSLIHPQWVLTAAHCVGPDVKDLAALRVQLREQHLYYQD QLLPVSRIIVHPQFYTAQIGADIALLELEEPVNVSSHVHTVTLPPASETFPPGMPCWVTGWGDVDNDER LPPPFPLKQVKVPIMENHICDAKYHLGAYTGDDVRIVRDDMLCAGNTRRDSCQGDSGGPLVCKVNGTWL QAGVVSWGEGCAQPNRPGIYTRVTYYLDWIHHYVPKKPGNSDYKDDDDK |
| 118 | IVGGQEAPRSKWPWQVSLRVRDRYWMHFCGGSLIHPQWVLTAAHCLGPDVKDLAALRVQLREQHLYYQD QLLPVSRIIVHPQFYIIQTGADIALLELEEPVNISSRVHTVMLPPASETFPPGMPCWVTGWGDVDNDEP LSPPFPLKQVKVPIMENHICDAKYHLGAYTGDDVRIIRDDMLCAGNSQRDSCKGDSGGPLVCKVNGTWL QAGVVSWDEGCAQPNRPGIYTRVTYYLDWIHHYVPKKPGNSDYKDDDDK |
| 119 | ALPVLVSPAHAAPAPGQALQRVGIVGGKEAPRSKWPWQVSLRLHGQYWMHFCGGSLIHPQWVLTAAHCV GPDVKDLADLRVQLREQHLYYQDQLLPVSRIIVHPQFYAVQIGADIALLELEEPVNVSSHVHTVTLPPA LETFPPGTPCWVTGWGDVDNDVRLPPPYPLKEVEVPIVENQLCDAEYHTGLHTGDSFRIVRDDMLCAGS EKHDSCQGDSGGPLVCKVNGTWLQAGVVSWGEGCALPNRPGIYTRVTYYLDWIHRYVPEKP |
| 120 | SFSMS |
| 121 | TISGGKTFTDYVDSVKG |
| 122 | ANYGNWFFEV |
| 123 | RASESVAKYGLSLLN |
| 124 | AASNRGS |
| 125 | QQSKEVPFT |
| 126 | EVQLVESGGGLVQPGGSLRLSCAASGFTFSSFSMSWVRQAPGKGLEWVATISGGKTFTDYVDSVKGRFT ISRDDSKNTLYLQMNSLRAEDTAVYYCTRANYGNWFFEVWGQGTLVTVSS |
| 127 | EIVLTQSPATLSLSPGERATLSCRASESVAKYGLSLLNWFQQKPGQPPRLLIFAASNRGSGIPARFSGS GSGTDFTLTISSLEPEDFAVYYCQQSKEVPFTFGQGTKVEIK |
| 128 | AGSTHHHHHHDDDDKIVGGQEAPRSKWPWQVSLRVHGPYWMHFCGGSLIHPQWVLTAAHCVGPDVKDLA ALRVQLREQHLYYQDQLLPVSRIIVHPQFYTAQIGADIALLELEEPVNVSSHVHTVTLPPASETFPPGM PCWVTGWGDVDNDERLPPPFPLKQVKVPIMENHICDAKYHLGAYTGDDVRIVRDDMLCAGNTRRDSCQG DSGGPLVCKVNGTWLQAGVVSWGEGCAQPNRPGIYTRVTYYLDWIHHYVPKKP |

---

What is claimed is:

1. A method of treating asthma in a human subject in need thereof, the method comprising administering to the subject a therapeutically effective amount of an isolated antibody that binds to human tryptase beta 1, or an antigen-binding fragment thereof, wherein the antibody comprises the following six hypervariable regions (HVRs):
   (a) an HVR-H1 comprising the amino acid sequence of DYGMV (SEQ ID NO: 7);
   (b) an HVR-H2 comprising the amino acid sequence of FISSGSSTVYYADTMKG (SEQ ID NO: 2);
   (c) an HVR-H3 comprising the amino acid sequence of RNYDDWYFDV (SEQ ID NO: 8);
   (d) an HVR-L1 comprising the amino acid sequence of SASSSVTYMY (SEQ ID NO: 4);
   (e) an HVR-L2 comprising the amino acid sequence of RTSDLAS (SEQ ID NO: 5); and
   (f) an HVR-L3 comprising the amino acid sequence of QHYHSYPLT (SEQ ID NO: 6).

2. The method of claim 1, wherein the method further comprises administering an additional therapeutic agent to the subject.

3. The method of claim 1, wherein the antibody is administered subcutaneously, intravenously, intramuscularly, topically, orally, transdermally, intraperitoneally, intraorbitally, by implantation, by inhalation, intrathecally, intraventricularly, or intranasally.

4. The method of claim 1, wherein the antibody comprises (a) a heavy chain variable (VH) domain comprising an amino sequence having at least 90% sequence identity to the amino acid sequence of SEQ ID NO: 9; and (b) a light chain variable (VL) domain comprising an amino acid sequence having at least 90% sequence identity to the amino acid sequence of SEQ ID NO: 10.

5. The method of claim 1, wherein the VH domain comprises the amino acid sequence of SEQ ID NO: 9 and the VL domain comprises the amino acid sequence of SEQ ID NO: 10.

6. The method of claim 1, wherein the antibody comprises (a) a heavy chain comprising the amino acid sequence of SEQ ID NO: 76 or SEQ ID NO:78 and (b) a light chain comprising the amino acid sequence of SEQ ID NO: 77.

7. The method of claim 1, wherein the antibody is capable of inhibiting the enzymatic activity of human tryptase beta 1.

8. The method of claim 7, wherein the antibody binds the tryptase with a $K_D$ of between about 120 pM and about 0.5 nM.

9. The method of claim 8, wherein the antibody binds tryptase with a $K_D$ of about 400 pM.

10. The method of claim 7, wherein the antibody inhibits the activity of tryptase with an IO50 of about 2.5 nM or lower as determined by a human tryptase beta enzymatic assay using a colorimetric synthetic peptide substrate.

11. The method of claim 7, wherein:
   (i) the antibody is capable of inhibiting the enzymatic activity of human tryptase beta 1 at pH 6;
   (ii) the antibody is capable of inhibiting tryptase-mediated stimulation of bronchial smooth muscle cell proliferation and/or collagen-based contraction;
   (iii) the antibody is capable of inhibiting mast cell histamine release;
   (iv) the antibody is capable of inhibiting IgE-triggered histamine release and/or tryptase-triggered histamine release;
   (v) the antibody is capable of inhibiting tryptase activity in cynomolgus monkey bronchoalveolar lavage (BAL) or nasosorption samples;

(vi) the antibody is capable of dissociating tetrameric human tryptase beta 1;
(vii) the antibody is capable of dissociating tetrameric human tryptase beta 1 when in a monovalent format; and/or
(viii) the antibody is capable of dissociating tetrameric human tryptase beta 1 in the presence of heparin.

12. The method of claim 1, wherein the antibody is capable of dissociating both the small interface of tetrameric human tryptase beta 1 and the large interface of tetrameric human tryptase beta 1.

13. The method of claim 1, wherein the antibody is humanized.

14. The method of claim 1, wherein the antibody is an IgG antibody.

15. The method of claim 14, wherein the IgG antibody is an IgG1 antibody or an IgG4 antibody.

16. The method of claim 15, wherein the IgG4 antibody is a human IgG4 antibody, and said antibody comprises an S228P mutation in the heavy chain constant region according to the EU numbering system.

17. The method of claim 1, wherein the antibody is a monospecific antibody.

18. The method of claim 1, wherein the antibody is a multispecific antibody.

19. The method of claim 18, wherein the multispecific antibody is a bispecific antibody.

20. The method of claim 1, wherein the antibody is comprised in a pharmaceutical composition comprising a pharmaceutically acceptable carrier, excipient, or diluent.

21. A method of treating mastocytosis in a subject in need thereof, the method comprising administering to the subject a therapeutically effective amount of an isolated antibody that binds to human tryptase beta 1, or an antigen-binding fragment thereof, wherein the antibody comprises the following six HVRs:
   (a) an HVR-H1 comprising the amino acid sequence of DYGMV (SEQ ID NO: 7);
   (b) an HVR-H2 comprising the amino acid sequence of FISSGSSTVYYADTMKG (SEQ ID NO: 2);
   (c) an HVR-H3 comprising the amino acid sequence of RNYDDWYFDV (SEQ ID NO: 8);
   (d) an HVR-L1 comprising the amino acid sequence of SASSSVTYMY (SEQ ID NO: 4);
   (e) an HVR-L2 comprising the amino acid sequence of RTSDLAS (SEQ ID NO: 5); and
   (f) an HVR-L3 comprising the amino acid sequence of QHYHSYPLT (SEQ ID NO: 6).

22. The method of claim 21, wherein the mastocytosis is nonacute systemic mastocytosis.

23. The method of claim 21, wherein the antibody comprises (a) a heavy chain variable (VH) domain comprising an amino sequence having at least 90% sequence identity to the amino acid sequence of SEQ ID NO: 9; and (b) a light chain variable (VL) domain comprising an amino acid sequence having at least 90% sequence identity to the amino acid sequence of SEQ ID NO: 10.

24. The method of claim 21, wherein the VH domain comprises the amino acid sequence of SEQ ID NO: 9 and the VL domain comprises the amino acid sequence of SEQ ID NO: 10.

25. The method of claim 21, wherein the antibody comprises (a) a heavy chain comprising the amino acid sequence of SEQ ID NO: 76 or SEQ ID NO:78 and (b) a light chain comprising the amino acid sequence of SEQ ID NO: 77.

26. The method of claim 21, wherein the antibody is humanized.

27. The method of claim 21, wherein the antibody is an IgG antibody.

28. The method of claim 27, wherein the IgG antibody is an IgG1 antibody or an IgG4 antibody.

29. The method of claim 28, wherein the IgG4 antibody is a human IgG4 antibody, and said antibody comprises an S228P mutation in the heavy chain constant region according to the EU numbering system.

30. The method of claim 21, wherein the antibody is a monospecific antibody.

31. The method of claim 21, wherein the antibody is a multispecific antibody.

32. The method of claim 31, wherein the multispecific antibody is a bispecific antibody.

33. The method of claim 21, wherein the antibody is comprised in a pharmaceutical composition comprising a pharmaceutically acceptable carrier, excipient, or diluent.

\* \* \* \* \*

SEQUENCE LISTING

<160> NUMBER OF SEQ ID NOS: 128

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: X is Asp or Ser
<220> FEATURE:
<221> NAME/KEY: MOD_RES
<222> LOCATION: (2)..(2)
<223> OTHER INFORMATION: X is Tyr or Phe
<220> FEATURE:
<221> NAME/KEY: MOD_RES
<222> LOCATION: (5)..(5)
<223> OTHER INFORMATION: X is Val or His

<400> SEQUENCE: 1

Xaa Xaa Gly Met Xaa

```
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic Construct

<400> SEQUENCE: 2

Phe Ile Ser Ser Gly Ser Ser Thr Val Tyr Tyr Ala Asp Thr Met Lys
1               5                   10                  15

Gly

<210> SEQ ID NO 3
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: X is Asn or Asp
<220> FEATURE:
<221> NAME/KEY: MOD_RES
<222> LOCATION: (3)..(3)
<223> OTHER INFORMATION: X is Tyr or Asn
<220> FEATURE:
<221> NAME/KEY: MOD_RES
<222> LOCATION: (4)..(4)
<223> OTHER INFORMATION: X is Asp or Tyr

<400> SEQUENCE: 3

Arg Xaa Xaa Xaa Asp Trp Tyr Phe Asp Val
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic Construct

<400> SEQUENCE: 4

Ser Ala Ser Ser Ser Val Thr Tyr Met Tyr
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic Construct

<400> SEQUENCE: 5

Arg Thr Ser Asp Leu Ala Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

Gln His Tyr His Ser Tyr Pro Leu Thr
```

```
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic Construct

<400> SEQUENCE: 7

Asp Tyr Gly Met Val
1               5

<210> SEQ ID NO 8
<211> LENGTH: 10
<212> TYPE: PRT
<213> ORGANISM: Artificial Sequence
<220> FEATURE:
<223> OTHER INFORMATION: Synthetic Construct

<400> SEQUENCE: 8

Arg Asn Tyr Asp Asp Trp Tyr Phe Asp Val
1               5                  10

<210> SEQ ID NO 9
<211> LENGTH: 119
<212> TYPE: PRT
<213> ORGANISM: Artificial Sequence
<220> FEATURE:
<223> OTHER INFORMATION: Synthetic Construct

<400> SEQUENCE: 9

Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Thr Phe Ser Asp Tyr
            20                  25                  30

Gly Met Val Trp Val Arg Gln Ala Pro Gly Lys Gly Leu Glu Trp Val
        35                  40                  45

Ala Phe Ile Ser Ser Gly Ser Ser Thr Val Tyr Tyr Ala Asp Thr Met
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Arg Asn Tyr Asp Asp Trp Tyr Phe Asp Val Trp Gly Gln Gly
            100                 105                 110

Thr Leu Val Thr Val Ser Ser
        115

<210> SEQ ID NO 10
<211> LENGTH: 106
<212> TYPE: PRT
<213> ORGANISM: Artificial Sequence
<220> FEATURE:
<223> OTHER INFORMATION: Synthetic Construct

<400> SEQUENCE: 10

Asp Ile Gln Met Thr Gln Ser Pro Ser Ser Leu Ser Ala Ser Val Gly
1               5                  10                  15

Asp Arg Val Thr Ile Thr Cys Ser Ala Ser Ser Ser Val Thr Tyr Met
            20                  25                  30

Tyr Trp Tyr Gln Gln Lys Pro Gly Lys Ser Pro Lys Pro Trp Ile Tyr
```

```
            35                  40                  45
Arg Thr Ser Asp Leu Ala Ser Gly Val Pro Ser Arg Phe Ser Gly Ser
         50                  55                  60
Gly Ser Gly Thr Asp Phe Thr Leu Thr Ile Ser Ser Leu Gln Pro Glu
 65                  70                  75                  80
Asp Phe Ala Thr Tyr Tyr Cys Gln His Tyr His Ser Tyr Pro Leu Thr
                 85                  90                  95
Phe Gly Gln Gly Thr Lys Val Glu Ile Lys
            100                 105
```

<210> SEQ ID NO 11
<211> LENGTH: 30
<212> TYPE: PRT
<213> ORGANISM: Artificial Sequence
<220> FEATURE:
<223> OTHER INFORMATION: Synthetic Construct

<400> SEQUENCE: 11

```
Glu Val Gln Leu Val Glu Ser Gly Gly Gly Leu Val Gln Pro Gly Gly
 1               5                  10                  15
Ser Leu Arg Leu Ser Cys Ala Ala Ser Gly Phe Thr Phe Ser
            20                  25                  30
```

<210> SEQ ID NO 12
<211> LENGTH: 14
<212> TYPE: PRT
<213> ORGANISM: Artificial Sequence
<220> FEATURE:
<223> OTHER INFORMATION: Synthetic Construct

<400> SEQUENCE: 12

```
Trp Val Arg Gln Ala Pro Gly Lys Gly Leu Glu Trp Val Ala
 1               5                  10
```

<210> SEQ ID NO 13
<211> LENGTH: 32
<212> TYPE: PRT
<213> ORGANISM: Artificial Sequence
<220> FEATURE:
<223> OTHER INFORMATION: Synthetic Construct

<400> SEQUENCE: 13

```
Arg Phe Thr Ile Ser Arg Asp Asn Ser Lys Asn Thr Leu Tyr Leu Gln
 1               5                  10                  15
Met Asn Ser Leu Arg Ala Glu Asp Thr Ala Val Tyr Tyr Cys Thr Arg
            20                  25                  30
```

<210> SEQ ID NO 14
<211> LENGTH: 11
<212> TYPE: PRT
<213> ORGANISM: Artificial Sequence
<220> FEATURE:
<223> OTHER INFORMATION: Synthetic Construct

<400> SEQUENCE: 14

```
Trp Gly Gln Gly Thr Leu Val Thr Val Ser Ser
 1               5                  10
```

<210> SEQ ID NO 15
<211> LENGTH: 23
<212> TYPE: PRT
<213> ORGANISM: Artificial Sequence
<220> FEATURE:
<223> OTHER INFORMATION: Synthetic Construct

```
<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 16
<211> LENGTH: 15
<212> TYPE: PRT
<213> ORGANISM: Artificial Sequence
<220> FEATURE:
<223> OTHER INFORMATION: Synthetic Construct

<400> SEQUENCE: 16

Trp Tyr Gln Gln Lys Pro Gly Lys Ser Pro Lys Pro Trp Ile Tyr
1               5                   10                  15

<210> SEQ ID NO 17
<211> LENGTH: 32
<212> TYPE: PRT
<213> ORGANISM: Artificial Sequence
<220> FEATURE:
<223> OTHER INFORMATION: Synthetic Construct

<400> SEQUENCE: 17

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 18
<211> LENGTH: 10
<212> TYPE: PRT
<213> ORGANISM: Artificial Sequence
<220> FEATURE:
<223> OTHER INFORMATION: Synthetic Construct

<400> SEQUENCE: 18

Phe Gly Gln Gly Thr Lys Val Glu Ile Lys
1               5                   10

<210> SEQ ID NO 19
<211> LENGTH: 119
<212> TYPE: PRT
<213> ORGANISM: Artificial Sequence
<220> FEATURE:
<223> OTHER INFORMATION: Synthetic Construct

<400> SEQUENCE: 19

Glu Val Lys Leu Val Glu Ser Gly Gly Gly Ser Val Gln Pro Gly Gly
1               5                   10                  15

Ser Arg Lys Leu Ser Cys Ala Ala Ser Gly Phe Thr Phe Ser Asp Tyr
            20                  25                  30

Gly Met Val Trp Val Arg Gln Ala Pro Gly Lys Gly Leu Glu Trp Val
        35                  40                  45

Ala Phe Ile Ser Ser Gly Ser Ser Thr Val Tyr Tyr Ala Asp Thr Met
    50                  55                  60

Lys Gly Arg Phe Thr Ile Ser Arg Asp Asn Pro Lys Asn Thr Leu Phe
65                  70                  75                  80

Leu Gln Met Ser Ser Leu Arg Ser Glu Asp Thr Ala Met Tyr Tyr Cys
                85                  90                  95
```

```
Ala Arg Arg Asp Asn Tyr Asp Trp Tyr Phe Asp Val Trp Gly Thr Gly
            100                 105                 110

Thr Thr Val Thr Val Ser Ser
        115

<210> SEQ ID NO 20
<211> LENGTH: 106
<212> TYPE: PRT
<213> ORGANISM: Artificial Sequence
<220> FEATURE:
<223> OTHER INFORMATION: Synthetic Construct

<400> SEQUENCE: 20

Gln Ile Val Leu Thr Gln Ser Pro Ala Ile Met Ser Ala Ser Pro Gly
1               5                   10                  15

Glu Lys Val Thr Ile Ser Cys Ser Ala Ser Ser Val Thr Tyr Met
            20                  25                  30

Tyr Trp Tyr Gln Gln Lys Pro Gly Ser Ser Pro Lys Pro Trp Ile Tyr
        35                  40                  45

Arg Thr Ser Asp Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln His Tyr His Ser Tyr Pro Leu Thr
                85                  90                  95

Phe Gly Ala Gly Thr Lys Leu Glu Leu Lys
            100                 105

<210> SEQ ID NO 21
<211> LENGTH: 30
<212> TYPE: PRT
<213> ORGANISM: Artificial Sequence
<220> FEATURE:
<223> OTHER INFORMATION: Synthetic Construct

<400> SEQUENCE: 21

Glu Val Lys Leu Val Glu Ser Gly Gly Gly Ser Val Gln Pro Gly Gly
1               5                   10                  15

Ser Arg Lys Leu Ser Cys Ala Ala Ser Gly Phe Thr Phe Ser
            20                  25                  30

<210> SEQ ID NO 22
<211> LENGTH: 14
<212> TYPE: PRT
<213> ORGANISM: Artificial Sequence
<220> FEATURE:
<223> OTHER INFORMATION: Synthetic Construct

<400> SEQUENCE: 22

Trp Val Arg Gln Ala Pro Gly Lys Gly Leu Glu Trp Val Ala
1               5                   10

<210> SEQ ID NO 23
<211> LENGTH: 32
<212> TYPE: PRT
<213> ORGANISM: Artificial Sequence
<220> FEATURE:
<223> OTHER INFORMATION: Synthetic Construct

<400> SEQUENCE: 23

Arg Phe Thr Ile Ser Arg Asp Asn Pro Lys Asn Thr Leu Phe Leu Gln
1               5                   10                  15
```

Met Ser Ser Leu Arg Ser Glu Asp Thr Ala Met Tyr Tyr Cys Ala Arg
            20                  25                  30

<210> SEQ ID NO 24
<211> LENGTH: 11
<212> TYPE: PRT
<213> ORGANISM: Artificial Sequence
<220> FEATURE:
<223> OTHER INFORMATION: Synthetic Construct

<400> SEQUENCE: 24

Trp Gly Thr Gly Thr Thr Val Thr Val Ser Ser
1               5                   10

<210> SEQ ID NO 25
<211> LENGTH: 23
<212> TYPE: PRT
<213> ORGANISM: Artificial Sequence
<220> FEATURE:
<223> OTHER INFORMATION: Synthetic Construct

<400> SEQUENCE: 25

Gln Ile Val Leu Thr Gln Ser Pro Ala Ile Met Ser Ala Ser Pro Gly
1               5                   10                  15

Glu Lys Val Thr Ile Ser Cys
            20

<210> SEQ ID NO 26
<211> LENGTH: 15
<212> TYPE: PRT
<213> ORGANISM: Artificial Sequence
<220> FEATURE:
<223> OTHER INFORMATION: Synthetic Construct

<400> SEQUENCE: 26

Trp Tyr Gln Gln Lys Pro Gly Ser Ser Pro Lys Pro Trp Ile Tyr
1               5                   10                  15

<210> SEQ ID NO 27
<211> LENGTH: 32
<212> TYPE: PRT
<213> ORGANISM: Artificial Sequence
<220> FEATURE:
<223> OTHER INFORMATION: Synthetic Construct

<400> SEQUENCE: 27

Gly Val Pro Ala Arg Phe Ser Gly Ser Gly Ser Gly Thr Ser Tyr Ser
1               5                   10                  15

Leu Thr Ile Ser Ser Met Glu Ala Glu Asp Ala Ala Thr Tyr Tyr Cys
            20                  25                  30

<210> SEQ ID NO 28
<211> LENGTH: 10
<212> TYPE: PRT
<213> ORGANISM: Artificial Sequence
<220> FEATURE:
<223> OTHER INFORMATION: Synthetic Construct

<400> SEQUENCE: 28

Phe Gly Ala Gly Thr Lys Leu Glu Leu Lys
1               5                   10

<210> SEQ ID NO 29
<211> LENGTH: 10
<212> TYPE: PRT
<213> ORGANISM: Artificial Sequence

```
<220> FEATURE:
<223> OTHER INFORMATION: Synthetic Construct

<400> SEQUENCE: 29

Arg Asp Asn Tyr Asp Trp Tyr Phe Asp Val
1               5                   10

<210> SEQ ID NO 30
<211> LENGTH: 5
<212> TYPE: PRT
<213> ORGANISM: Artificial Sequence
<220> FEATURE:
<223> OTHER INFORMATION: Synthetic Construct

<400> SEQUENCE: 30

Gly Tyr Ala Ile Thr
1               5

<210> SEQ ID NO 31
<211> LENGTH: 16
<212> TYPE: PRT
<213> ORGANISM: Artificial Sequence
<220> FEATURE:
<223> OTHER INFORMATION: Synthetic Construct

<400> SEQUENCE: 31

Gly Ile Ser Ser Ala Ala Thr Thr Phe Tyr Ser Ser Trp Ala Lys Ser
1               5                   10                  15

<210> SEQ ID NO 32
<211> LENGTH: 14
<212> TYPE: PRT
<213> ORGANISM: Artificial Sequence
<220> FEATURE:
<223> OTHER INFORMATION: Synthetic Construct

<400> SEQUENCE: 32

Asp Pro Arg Gly Tyr Gly Ala Ala Leu Asp Arg Leu Asp Leu
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Synthetic Construct

<400> SEQUENCE: 33

Gln Ser Ile Lys Ser Val Tyr Asn Asn Arg Leu Gly
1               5                   10

<210> SEQ ID NO 34
<211> LENGTH: 7
<212> TYPE: PRT
<213> ORGANISM: Artificial Sequence
<220> FEATURE:
<223> OTHER INFORMATION: Synthetic Construct

<400> SEQUENCE: 34

Glu Thr Ser Ile Leu Thr Ser
1               5

<210> SEQ ID NO 35
<211> LENGTH: 11
<212> TYPE: PRT
<213> ORGANISM: Artificial Sequence
<220> FEATURE:
```

```
<223> OTHER INFORMATION: Synthetic Construct

<400> SEQUENCE: 35

Ala Gly Gly Phe Asp Arg Ser Gly Asp Thr Thr
1               5                   10

<210> SEQ ID NO 36
<211> LENGTH: 122
<212> TYPE: PRT
<213> ORGANISM: Artificial Sequence
<220> FEATURE:
<223> OTHER INFORMATION: Synthetic Construct

<400> SEQUENCE: 36

Glu Val Gln Leu Val Glu Ser Gly Pro Gly Leu Val Lys Pro Ser Glu
1               5                   10                  15

Thr Leu Ser Leu Thr Cys Thr Val Ser Arg Phe Ser Leu Ile Gly Tyr
            20                  25                  30

Ala Ile Thr Trp Ile Arg Gln Pro Pro Gly Lys Gly Leu Glu Trp Ile
        35                  40                  45

Gly Gly Ile Ser Ser Ala Ala Thr Thr Phe Tyr Ser Ser Trp Ala Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asp Pro Arg Gly Tyr Gly Ala Ala Leu Asp Arg Leu Asp Leu Trp
            100                 105                 110

Gly Gln Gly Thr Leu Val Thr Val Ser Ser
        115                 120

<210> SEQ ID NO 37
<211> LENGTH: 110
<212> TYPE: PRT
<213> ORGANISM: Artificial Sequence
<220> FEATURE:
<223> OTHER INFORMATION: Synthetic Construct

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Gln Ser Ile Lys Ser Val Tyr Asn Asn
            20                  25                  30

Arg Leu Gly Trp Tyr Gln Gln Lys Pro Gly Lys Ala Pro Lys Leu Leu
        35                  40                  45

Ile Tyr Glu Thr Ser Ile Leu Thr Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Ala Gly Gly Phe Asp Arg Ser
                85                  90                  95

Gly Asp Thr Thr Phe Gly Gln Gly Thr Lys Val Glu Ile Lys
            100                 105                 110

<210> SEQ ID NO 38
<211> LENGTH: 30
<212> TYPE: PRT
<213> ORGANISM: Artificial Sequence
<220> FEATURE:
<223> OTHER INFORMATION: Synthetic Construct
```

<400> SEQUENCE: 38

Glu Val Gln Leu Val Glu Ser Gly Pro Gly Leu Val Lys Pro Ser Glu
1               5                   10                  15

Thr Leu Ser Leu Thr Cys Thr Val Ser Arg Phe Ser Leu Ile
            20                  25                  30

<210> SEQ ID NO 39
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: X is Ile or Val

<400> SEQUENCE: 39

Trp Xaa Arg Gln Pro Pro Gly Lys Gly Leu Glu Trp Ile Gly
1               5                   10

<210> SEQ ID NO 40
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: X is Val or Ser
<220> FEATURE:
<221> NAME/KEY: MOD_RES
<222> LOCATION: (6)..(6)
<223> OTHER INFORMATION: X is Arg or Val
<220> FEATURE:
<221> NAME/KEY: MOD_RES
<222> LOCATION: (13)..(13)
<223> OTHER INFORMATION: X is Val or Phe
<220> FEATURE:
<221> NAME/KEY: MOD_RES
<222> LOCATION: (29)..(29)
<223> OTHER INFORMATION: X is Tyr or Phe

<400> SEQUENCE: 40

Arg Xaa Thr Ile Ser Xaa Asp Thr Ser Lys Asn Gln Xaa Ser Leu Lys
1               5                   10                  15

Leu Ser Ser Val Thr Ala Ala Asp Thr Ala Val Tyr Xaa Cys Ala Arg
            20                  25                  30

<210> SEQ ID NO 41
<211> LENGTH: 11
<212> TYPE: PRT
<213> ORGANISM: Artificial Sequence
<220> FEATURE:
<223> OTHER INFORMATION: Synthetic Construct

<400> SEQUENCE: 41

Trp Gly Gln Gly Thr Leu Val Thr Val Ser Ser
1               5                   10

<210> SEQ ID NO 42
<211> LENGTH: 14
<212> TYPE: PRT
<213> ORGANISM: Artificial Sequence
<220> FEATURE:
<223> OTHER INFORMATION: Synthetic Construct

```
<400> SEQUENCE: 42

Trp Ile Arg Gln Pro Pro Gly Lys Gly Leu Glu Trp Ile Gly
1               5                   10

<210> SEQ ID NO 43
<211> LENGTH: 32
<212> TYPE: PRT
<213> ORGANISM: Artificial Sequence
<220> FEATURE:
<223> OTHER INFORMATION: Synthetic Construct

<400> SEQUENCE: 43

Arg Val Thr Ile Ser Arg Asp Thr Ser Lys Asn Gln Val Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 44
<211> LENGTH: 30
<212> TYPE: PRT
<213> ORGANISM: Artificial Sequence
<220> FEATURE:
<223> OTHER INFORMATION: Synthetic Construct

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Val Ser Arg Phe Ser Leu Ile
            20                  25                  30

<210> SEQ ID NO 45
<211> LENGTH: 14
<212> TYPE: PRT
<213> ORGANISM: Artificial Sequence
<220> FEATURE:
<223> OTHER INFORMATION: Synthetic Construct

<400> SEQUENCE: 45

Trp Val Arg Gln Ala Pro Gly Lys Gly Leu Glu Trp Ile Gly
1               5                   10

<210> SEQ ID NO 46
<211> LENGTH: 32
<212> TYPE: PRT
<213> ORGANISM: Artificial Sequence
<220> FEATURE:
<223> OTHER INFORMATION: Synthetic Construct

<400> SEQUENCE: 46

Arg Ser Thr Ile Ser Arg Asp Thr Ser Lys Asn Thr Val Tyr Leu Gln
1               5                   10                  15

Met Asn Ser Leu Arg Ala Glu Asp Thr Ala Val Tyr Phe Cys Ala Arg
            20                  25                  30

<210> SEQ ID NO 47
<211> LENGTH: 122
<212> TYPE: PRT
<213> ORGANISM: Artificial Sequence
<220> FEATURE:
<223> OTHER INFORMATION: Synthetic Construct

<400> SEQUENCE: 47

Glu Val Gln Leu Val Glu Ser Gly Pro Gly Leu Val Lys Pro Ser Glu
1               5                   10                  15
```

Thr Leu Ser Leu Thr Cys Thr Val Ser Arg Phe Ser Leu Ile Gly Tyr
            20                  25                  30

Ala Ile Thr Trp Ile Arg Gln Pro Pro Gly Lys Gly Leu Glu Trp Ile
            35                  40                  45

Gly Gly Ile Ser Ser Ala Ala Thr Thr Phe Tyr Ser Ser Trp Ala Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Pro Arg Gly Tyr Gly Ala Ala Leu Asp Arg Leu Asp Leu Trp
            100                 105                 110

Gly Gln Gly Thr Leu Val Thr Val Ser Ser
        115                 120

<210> SEQ ID NO 48
<211> LENGTH: 122
<212> TYPE: PRT
<213> ORGANISM: Artificial Sequence
<220> FEATURE:
<223> OTHER INFORMATION: Synthetic Construct

<400> SEQUENCE: 48

Glu Val Gln Leu Val Glu Ser Gly Pro Gly Leu Val Lys Pro Ser Glu
1               5                   10                  15

Thr Leu Ser Leu Thr Cys Thr Val Ser Arg Phe Ser Leu Ile Gly Tyr
            20                  25                  30

Ala Ile Thr Trp Val Arg Gln Pro Pro Gly Lys Gly Leu Glu Trp Ile
            35                  40                  45

Gly Gly Ile Ser Ser Ala Ala Thr Thr Phe Tyr Ser Ser Trp Ala Lys
        50                  55                  60

Ser Arg Ser Thr Ile Ser Arg Asp Thr Ser Lys Asn Gln Val Ser Leu
65                  70                  75                  80

Lys Leu Ser Ser Val Thr Ala Ala Asp Thr Ala Val Tyr Phe Cys Ala
                85                  90                  95

Arg Asp Pro Arg Gly Tyr Gly Ala Ala Leu Asp Arg Leu Asp Leu Trp
            100                 105                 110

Gly Gln Gly Thr Leu Val Thr Val Ser Ser
        115                 120

<210> SEQ ID NO 49
<211> LENGTH: 122
<212> TYPE: PRT
<213> ORGANISM: Artificial Sequence
<220> FEATURE:
<223> OTHER INFORMATION: Synthetic Construct

<400> SEQUENCE: 49

Glu Val Gln Leu Val Glu Ser Gly Pro Gly Leu Val Lys Pro Ser Glu
1               5                   10                  15

Thr Leu Ser Leu Thr Cys Thr Val Ser Arg Phe Ser Leu Ile Gly Tyr
            20                  25                  30

Ala Ile Thr Trp Ile Arg Gln Pro Pro Gly Lys Gly Leu Glu Trp Ile
            35                  40                  45

Gly Gly Ile Ser Ser Ala Ala Thr Thr Phe Tyr Ser Ser Trp Ala Lys
        50                  55                  60

Ser Arg Val Thr Ile Ser Val Asp Thr Ser Lys Asn Gln Val Ser Leu
65                  70                  75                  80

```
Lys Leu Ser Ser Val Thr Ala Ala Asp Thr Ala Val Tyr Tyr Cys Ala
                85                  90                  95

Arg Asp Pro Arg Gly Tyr Gly Ala Ala Leu Asp Arg Leu Asp Leu Trp
            100                 105                 110

Gly Gln Gly Thr Leu Val Thr Val Ser Ser
        115                 120

<210> SEQ ID NO 50
<211> LENGTH: 122
<212> TYPE: PRT
<213> ORGANISM: Artificial Sequence
<220> FEATURE:
<223> OTHER INFORMATION: Synthetic Construct

<400> SEQUENCE: 50

Glu Val Gln Leu Val Glu Ser Gly Pro Gly Leu Val Lys Pro Ser Glu
1               5                   10                  15

Thr Leu Ser Leu Thr Cys Thr Val Ser Arg Phe Ser Leu Ile Gly Tyr
            20                  25                  30

Ala Ile Thr Trp Ile Arg Gln Pro Pro Gly Lys Gly Leu Glu Trp Ile
        35                  40                  45

Gly Gly Ile Ser Ser Ala Ala Thr Thr Phe Tyr Ser Ser Trp Ala Lys
    50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Pro Arg Gly Tyr Gly Ala Ala Leu Asp Arg Leu Asp Leu Trp
            100                 105                 110

Gly Gln Gly Thr Leu Val Thr Val Ser Ser
        115                 120

<210> SEQ ID NO 51
<211> LENGTH: 122
<212> TYPE: PRT
<213> ORGANISM: Artificial Sequence
<220> FEATURE:
<223> OTHER INFORMATION: Synthetic Construct

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Val Ser Arg Phe Ser Leu Ile Gly Tyr
            20                  25                  30

Ala Ile Thr Trp Val Arg Gln Ala Pro Gly Lys Gly Leu Glu Trp Ile
        35                  40                  45

Gly Gly Ile Ser Ser Ala Ala Thr Thr Phe Tyr Ser Ser Trp Ala Lys
    50                  55                  60

Ser Arg Ser Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Phe Cys Ala
                85                  90                  95

Arg Asp Pro Arg Gly Tyr Gly Ala Ala Leu Asp Arg Leu Asp Leu Trp
            100                 105                 110

Gly Gln Gly Thr Leu Val Thr Val Ser Ser
        115                 120
```

-continued

```
<210> SEQ ID NO 52
<211> LENGTH: 121
<212> TYPE: PRT
<213> ORGANISM: Artificial Sequence
<220> FEATURE:
<223> OTHER INFORMATION: Synthetic Construct

<400> SEQUENCE: 52

Gln Ser Leu Glu Glu Ser Gly Gly Gly Leu Phe Lys Pro Thr Asp Thr
1               5                   10                  15

Leu Thr Leu Thr Cys Thr Val Ser Arg Phe Ser Leu Ile Gly Tyr Ala
            20                  25                  30

Ile Thr Trp Val Arg Gln Ser Pro Glu Asn Gly Leu Glu Trp Ile Gly
        35                  40                  45

Gly Ile Ser Ser Ala Ala Thr Thr Phe Tyr Ser Ser Trp Ala Lys Ser
    50                  55                  60

Arg Ser Thr Ile Thr Arg Asn Thr Asn Glu Asn Thr Val Thr Leu Lys
65                  70                  75                  80

Met Thr Ser Leu Thr Ala Ala Asp Thr Ala Thr Tyr Phe Cys Ala Arg
                85                  90                  95

Asp Pro Arg Gly Tyr Gly Ala Ala Leu Asp Arg Leu Asp Leu Trp Gly
            100                 105                 110

Gln Gly Thr Leu Val Thr Val Ser Ser
        115                 120

<210> SEQ ID NO 53
<211> LENGTH: 110
<212> TYPE: PRT
<213> ORGANISM: Artificial Sequence
<220> FEATURE:
<223> OTHER INFORMATION: Synthetic Construct

<400> SEQUENCE: 53

Ala Ala Val Leu Thr Gln Thr Pro Ala Ser Val Ser Ala Ala Val Gly
1               5                   10                  15

Gly Thr Val Ser Ile Ser Cys Gln Ser Ile Lys Ser Val Tyr Asn Asn
            20                  25                  30

Arg Leu Gly Trp Tyr Gln Gln Lys Pro Gly Gln Pro Pro Lys Leu Leu
        35                  40                  45

Ile Tyr Glu Thr Ser Ile Leu Thr Ser Gly Val Pro Ser Arg Phe Lys
    50                  55                  60

Gly Ser Gly Ser Glu Thr Gln Phe Thr Leu Thr Ile Ser Asp Val Gln
65                  70                  75                  80

Cys Asp Asp Ala Ala Thr Tyr Phe Cys Ala Gly Gly Phe Asp Arg Ser
                85                  90                  95

Gly Asp Thr Thr Phe Gly Gly Gly Thr Glu Val Val Val Lys
            100                 105                 110

<210> SEQ ID NO 54
<211> LENGTH: 29
<212> TYPE: PRT
<213> ORGANISM: Artificial Sequence
<220> FEATURE:
<223> OTHER INFORMATION: Synthetic Construct

<400> SEQUENCE: 54

Gln Ser Leu Glu Glu Ser Gly Gly Gly Leu Phe Lys Pro Thr Asp Thr
1               5                   10                  15

Leu Thr Leu Thr Cys Thr Val Ser Arg Phe Ser Leu Ile
            20                  25
```

-continued

<210> SEQ ID NO 55
<211> LENGTH: 14
<212> TYPE: PRT
<213> ORGANISM: Artificial Sequence
<220> FEATURE:
<223> OTHER INFORMATION: Synthetic Construct

<400> SEQUENCE: 55

Trp Val Arg Gln Ser Pro Glu Asn Gly Leu Glu Trp Ile Gly
1               5                   10

<210> SEQ ID NO 56
<211> LENGTH: 32
<212> TYPE: PRT
<213> ORGANISM: Artificial Sequence
<220> FEATURE:
<223> OTHER INFORMATION: Synthetic Construct

<400> SEQUENCE: 56

Arg Ser Thr Ile Thr Arg Asn Thr Asn Glu Asn Thr Val Thr Leu Lys
1               5                   10                  15

Met Thr Ser Leu Thr Ala Ala Asp Thr Ala Thr Tyr Phe Cys Ala Arg
                20                  25                  30

<210> SEQ ID NO 57
<211> LENGTH: 11
<212> TYPE: PRT
<213> ORGANISM: Artificial Sequence
<220> FEATURE:
<223> OTHER INFORMATION: Synthetic Construct

<400> SEQUENCE: 57

Trp Gly Gln Gly Thr Leu Val Thr Val Ser Ser
1               5                   10

<210> SEQ ID NO 58
<211> LENGTH: 110
<212> TYPE: PRT
<213> ORGANISM: Artificial Sequence
<220> FEATURE:
<223> OTHER INFORMATION: Synthetic Construct

<400> SEQUENCE: 58

Asp Ala Gln Leu Thr Gln Ser Pro Ser Ser Leu Ser Ala Ser Val Gly
1               5                   10                  15

Asp Arg Val Thr Ile Thr Cys Gln Ser Ile Lys Ser Val Tyr Asn Asn
                20                  25                  30

Arg Leu Gly Trp Tyr Gln Gln Lys Pro Gly Lys Pro Lys Leu Leu
            35                  40                  45

Ile Tyr Glu Thr Ser Ile Leu Thr Ser Gly Val Pro Ser Arg Phe Ser
        50                  55                  60

Gly Ser Gly Ser Glu Thr Asp Phe Thr Leu Thr Ile Ser Ser Leu Gln
65                  70                  75                  80

Pro Glu Asp Phe Ala Thr Tyr Phe Cys Ala Gly Gly Phe Asp Arg Ser
                85                  90                  95

Gly Asp Thr Thr Phe Gly Gln Gly Thr Lys Val Glu Ile Lys
                100                 105                 110

<210> SEQ ID NO 59
<211> LENGTH: 110
<212> TYPE: PRT
<213> ORGANISM: Artificial Sequence
<220> FEATURE:
<223> OTHER INFORMATION: Synthetic Construct

<400> SEQUENCE: 59

Ala Ala Val Leu Thr Gln Thr Pro Ala Ser Val Ser Ala Ala Val Gly
1               5                   10                  15

Gly Thr Val Ser Ile Ser Cys Gln Ser Ile Lys Ser Val Tyr Asn Asn
            20                  25                  30

Arg Leu Gly Trp Tyr Gln Gln Lys Pro Gly Gln Pro Pro Lys Leu Leu
        35                  40                  45

Ile Tyr Glu Thr Ser Ile Leu Thr Ser Gly Val Pro Ser Arg Phe Lys
50                  55                  60

Gly Ser Gly Ser Glu Thr Gln Phe Thr Leu Thr Ile Ser Asp Val Gln
65                  70                  75                  80

Ala Asp Asp Ala Ala Thr Tyr Phe Cys Ala Gly Gly Phe Asp Arg Ser
                85                  90                  95

Gly Asp Thr Thr Phe Gly Gly Gly Thr Glu Val Val Val Lys
            100                 105                 110

<210> SEQ ID NO 60
<211> LENGTH: 23
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: X is Ile or Ala
<220> FEATURE:
<221> NAME/KEY: MOD_RES
<222> LOCATION: (4)..(4)
<223> OTHER INFORMATION: X is Met or Leu

<400> SEQUENCE: 60

Asp Xaa Gln Xaa Thr Gln Ser Pro Ser Ser Leu Ser Ala Ser Val Gly
1               5                   10                  15

Asp Arg Val Thr Ile Thr Cys
            20

<210> SEQ ID NO 61
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (9)..(9)
<223> OTHER INFORMATION: X is Ala or Pro

<400> SEQUENCE: 61

Trp Tyr Gln Gln Lys Pro Gly Lys Xaa Pro Lys Leu Leu Ile Tyr
1               5                   10                  15

<210> SEQ ID NO 62
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (12)..(12)
<223> OTHER INFORMATION: X is Gly or Glu
<220> FEATURE:

```
<221> NAME/KEY: MOD_RES
<222> LOCATION: (31)..(31)
<223> OTHER INFORMATION: X is Tyr or Phe

<400> SEQUENCE: 62
```

Gly Val Pro Ser Arg Phe Ser Gly Ser Gly Ser Xaa Thr Asp Phe Thr
1               5                   10                  15

Leu Thr Ile Ser Ser Leu Gln Pro Glu Asp Phe Ala Thr Tyr Xaa Cys
            20                  25                  30

```
<210> SEQ ID NO 63
<211> LENGTH: 10
<212> TYPE: PRT
<213> ORGANISM: Artificial Sequence
<220> FEATURE:
<223> OTHER INFORMATION: Synthetic Construct

<400> SEQUENCE: 63
```

Phe Gly Gln Gly Thr Lys Val Glu Ile Lys
1               5                   10

```
<210> SEQ ID NO 64
<211> LENGTH: 23
<212> TYPE: PRT
<213> ORGANISM: Artificial Sequence
<220> FEATURE:
<223> OTHER INFORMATION: Synthetic Construct

<400> SEQUENCE: 64
```

Asp Ile Gln Met Thr Gln Ser Pro Ser Ser Leu Ser Ala Ser Val Gly
1               5                   10                  15

Asp Arg Val Thr Ile Thr Cys
            20

```
<210> SEQ ID NO 65
<211> LENGTH: 15
<212> TYPE: PRT
<213> ORGANISM: Artificial Sequence
<220> FEATURE:
<223> OTHER INFORMATION: Synthetic Construct

<400> SEQUENCE: 65
```

Trp Tyr Gln Gln Lys Pro Gly Lys Ala Pro Lys Leu Leu Ile Tyr
1               5                   10                  15

```
<210> SEQ ID NO 66
<211> LENGTH: 32
<212> TYPE: PRT
<213> ORGANISM: Artificial Sequence
<220> FEATURE:
<223> OTHER INFORMATION: Synthetic Construct

<400> SEQUENCE: 66
```

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

```
<210> SEQ ID NO 67
<211> LENGTH: 23
<212> TYPE: PRT
<213> ORGANISM: Artificial Sequence
<220> FEATURE:
<223> OTHER INFORMATION: Synthetic Construct

<400> SEQUENCE: 67
```

```
Ala Ala Val Leu Thr Gln Thr Pro Ser Val Ser Ala Ala Val Gly
1               5                   10                  15

Gly Thr Val Ser Ile Ser Cys
            20
```

<210> SEQ ID NO 68
<211> LENGTH: 15
<212> TYPE: PRT
<213> ORGANISM: Artificial Sequence
<220> FEATURE:
<223> OTHER INFORMATION: Synthetic Construct

<400> SEQUENCE: 68

```
Trp Tyr Gln Gln Lys Pro Gly Gln Pro Pro Lys Leu Leu Ile Tyr
1               5                   10                  15
```

<210> SEQ ID NO 69
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (24)..(24)
<223> OTHER INFORMATION: X is Cys or Ala

<400> SEQUENCE: 69

```
Gly Val Pro Ser Arg Phe Lys Gly Ser Gly Ser Glu Thr Gln Phe Thr
1               5                   10                  15

Leu Thr Ile Ser Asp Val Gln Xaa Asp Asp Ala Ala Thr Tyr Phe Cys
            20                  25                  30
```

<210> SEQ ID NO 70
<211> LENGTH: 10
<212> TYPE: PRT
<213> ORGANISM: Artificial Sequence
<220> FEATURE:
<223> OTHER INFORMATION: Synthetic Construct

<400> SEQUENCE: 70

```
Phe Gly Gly Gly Thr Glu Val Val Val Lys
1               5                   10
```

<210> SEQ ID NO 71
<211> LENGTH: 275
<212> TYPE: PRT
<213> ORGANISM: Homo sapiens

<400> SEQUENCE: 71

```
Met Leu Asn Leu Leu Leu Leu Ala Leu Pro Val Leu Ala Ser Arg Ala
1               5                   10                  15

Tyr Ala Ala Pro Ala Pro Gly Gln Ala Leu Gln Arg Val Gly Ile Val
                20                  25                  30

Gly Gly Gln Glu Ala Pro Arg Ser Lys Trp Pro Trp Gln Val Ser Leu
            35                  40                  45

Arg Val His Gly Pro Tyr Trp Met His Phe Cys Gly Gly Ser Leu Ile
        50                  55                  60

His Pro Gln Trp Val Leu Thr Ala Ala His Cys Val Gly Pro Asp Val
65                  70                  75                  80

Lys Asp Leu Ala Ala Leu Arg Val Gln Leu Arg Glu Gln His Leu Tyr
                85                  90                  95
```

Tyr Gln Asp Gln Leu Leu Pro Val Ser Arg Ile Ile Val His Pro Gln
                100                 105                 110

Phe Tyr Thr Ala Gln Ile Gly Ala Asp Ile Ala Leu Leu Glu Leu Glu
            115                 120                 125

Glu Pro Val Asn Val Ser Ser His Val His Thr Val Thr Leu Pro Pro
        130                 135                 140

Ala Ser Glu Thr Phe Pro Pro Gly Met Pro Cys Trp Val Thr Gly Trp
145                 150                 155                 160

Gly Asp Val Asp Asn Asp Glu Arg Leu Pro Pro Phe Pro Leu Lys
                165                 170                 175

Gln Val Lys Val Pro Ile Met Glu Asn His Ile Cys Asp Ala Lys Tyr
            180                 185                 190

His Leu Gly Ala Tyr Thr Gly Asp Asp Val Arg Ile Val Arg Asp Asp
        195                 200                 205

Met Leu Cys Ala Gly Asn Thr Arg Arg Asp Ser Cys Gln Gly Asp Ser
    210                 215                 220

Gly Gly Pro Leu Val Cys Lys Val Asn Gly Thr Trp Leu Gln Ala Gly
225                 230                 235                 240

Val Val Ser Trp Gly Glu Gly Cys Ala Gln Pro Asn Arg Pro Gly Ile
                245                 250                 255

Tyr Thr Arg Val Thr Tyr Tyr Leu Asp Trp Ile His His Tyr Val Pro
            260                 265                 270

Lys Lys Pro
        275

<210> SEQ ID NO 72
<211> LENGTH: 275
<212> TYPE: PRT
<213> ORGANISM: Homo sapiens

<400> SEQUENCE: 72

Met Leu Asn Leu Leu Leu Ala Leu Pro Val Leu Ala Ser Arg Ala
1               5                   10                  15

Tyr Ala Ala Pro Ala Pro Gly Gln Ala Leu Gln Arg Val Gly Ile Val
            20                  25                  30

Gly Gly Gln Glu Ala Pro Arg Ser Lys Trp Pro Trp Gln Val Ser Leu
        35                  40                  45

Arg Val His Gly Pro Tyr Trp Met His Phe Cys Gly Gly Ser Leu Ile
    50                  55                  60

His Pro Gln Trp Val Leu Thr Ala Ala His Cys Val Gly Pro Asp Val
65                  70                  75                  80

Lys Asp Leu Ala Ala Leu Arg Val Gln Leu Arg Glu Gln His Leu Tyr
                85                  90                  95

Tyr Gln Asp Gln Leu Leu Pro Val Ser Arg Ile Ile Val His Pro Gln
                100                 105                 110

Phe Tyr Thr Ala Gln Ile Gly Ala Asp Ile Ala Leu Leu Glu Leu Glu
            115                 120                 125

Glu Pro Val Lys Val Ser Ser His Val His Thr Val Thr Leu Pro Pro
        130                 135                 140

Ala Ser Glu Thr Phe Pro Pro Gly Met Pro Cys Trp Val Thr Gly Trp
145                 150                 155                 160

Gly Asp Val Asp Asn Asp Glu Arg Leu Pro Pro Phe Pro Leu Lys
                165                 170                 175

Gln Val Lys Val Pro Ile Met Glu Asn His Ile Cys Asp Ala Lys Tyr
            180                 185                 190

```
His Leu Gly Ala Tyr Thr Gly Asp Asp Val Arg Ile Val Arg Asp Asp
            195                 200                 205

Met Leu Cys Ala Gly Asn Thr Arg Arg Asp Ser Cys Gln Gly Asp Ser
        210                 215                 220

Gly Gly Pro Leu Val Cys Lys Val Asn Gly Thr Trp Leu Gln Ala Gly
225                 230                 235                 240

Val Val Ser Trp Gly Glu Gly Cys Ala Gln Pro Asn Arg Pro Gly Ile
                245                 250                 255

Tyr Thr Arg Val Thr Tyr Tyr Leu Asp Trp Ile His His Tyr Val Pro
            260                 265                 270

Lys Lys Pro
        275

<210> SEQ ID NO 73
<211> LENGTH: 233
<212> TYPE: PRT
<213> ORGANISM: Homo sapiens

<400> SEQUENCE: 73

Met Leu Asn Leu Leu Leu Ala Leu Pro Val Leu Ala Ser Arg Ala
1               5                   10                  15

Tyr Ala Ala Pro Ala Pro Gly Gln Ala Leu Gln Arg Val Gly Ile Val
            20                  25                  30

Gly Gly Gln Glu Ala Pro Arg Ser Lys Trp Pro Trp Gln Val Ser Leu
        35                  40                  45

Arg Val Arg Asp Arg Tyr Trp Met His Phe Cys Gly Gly Ser Leu Ile
    50                  55                  60

His Pro Gln Trp Val Leu Thr Ala Ala His Cys Val Gly Pro Asp Val
65                  70                  75                  80

Lys Asp Leu Ala Ala Leu Arg Val Gln Leu Arg Glu Gln His Leu Tyr
                85                  90                  95

Tyr Gln Asp Gln Leu Leu Pro Val Ser Arg Ile Ile Val His Pro Gln
            100                 105                 110

Phe Tyr Thr Ala Gln Ile Gly Ala Asp Ile Ala Leu Leu Glu Leu Glu
        115                 120                 125

Glu Pro Val Asn Val Ser Ser His Val His Thr Val Thr Leu Pro Pro
    130                 135                 140

Ala Ser Glu Thr Phe Pro Pro Gly Met Pro Cys Trp Val Thr Gly Trp
145                 150                 155                 160

Gly Asp Val Asp Asn Asp Glu Arg Leu Pro Pro Phe Pro Leu Lys
                165                 170                 175

Gln Val Lys Val Pro Ile Met Glu Asn His Ile Cys Asp Ala Lys Tyr
            180                 185                 190

His Leu Gly Ala Tyr Thr Gly Asp Asp Val Arg Ile Val Arg Asp Asp
        195                 200                 205

Met Leu Cys Ala Gly Asn Thr Arg Arg Asp Ser Cys Gln Val Ala Thr
    210                 215                 220

Ala Pro His Thr Phe Pro Ala Pro Ser
225                 230

<210> SEQ ID NO 74
<211> LENGTH: 21
<212> TYPE: DNA
<213> ORGANISM: Artificial Sequence
<220> FEATURE:
<223> OTHER INFORMATION: Synthetic Construct
```

<400> SEQUENCE: 74
gatggtgact gttccagttg c                                          21

<210> SEQ ID NO 75
<211> LENGTH: 23
<212> TYPE: DNA
<213> ORGANISM: Artificial Sequence
<220> FEATURE:
<223> OTHER INFORMATION: Synthetic Construct

<400> SEQUENCE: 75
cattggtgag ggtgcccgag ttc                                        23

<210> SEQ ID NO 76
<211> LENGTH: 448
<212> TYPE: PRT
<213> ORGANISM: Artificial Sequence
<220> FEATURE:
<223> OTHER INFORMATION: Synthetic Construct

<400> SEQUENCE: 76

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met Val Trp Val Arg Gln Ala Pro Gly Lys Gly Leu Glu Trp Val
        35                  40                  45

Ala Phe Ile Ser Ser Gly Ser Ser Thr Val Tyr Tyr Ala Asp Thr Met
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Arg Asn Tyr Asp Asp Trp Tyr Phe Asp Val Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn

```
                    275                 280                 285
Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

<210> SEQ ID NO 77
<211> LENGTH: 213
<212> TYPE: PRT
<213> ORGANISM: Artificial Sequence
<220> FEATURE:
<223> OTHER INFORMATION: Synthetic Construct

<400> SEQUENCE: 77

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Val Thr Tyr Met
            20                  25                  30

Tyr Trp Tyr Gln Gln Lys Pro Gly Lys Ser Pro Lys Pro Trp Ile Tyr
            35                  40                  45

Arg Thr Ser Asp Leu Ala Ser Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln His Tyr His Ser Tyr Pro Leu Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
```

195                 200                 205

Asn Arg Gly Glu Cys
    210

<210> SEQ ID NO 78
<211> LENGTH: 445
<212> TYPE: PRT
<213> ORGANISM: Artificial Sequence
<220> FEATURE:
<223> OTHER INFORMATION: Synthetic Construct

<400> SEQUENCE: 78

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met Val Trp Val Arg Gln Ala Pro Gly Lys Gly Leu Glu Trp Val
        35                  40                  45

Ala Phe Ile Ser Ser Gly Ser Ser Thr Val Tyr Tyr Ala Asp Thr Met
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Arg Asn Tyr Asp Asp Trp Tyr Phe Asp Val Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro

```
              340                 345                 350
Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly
        435                 440                 445
```

<210> SEQ ID NO 79
<211> LENGTH: 213
<212> TYPE: PRT
<213> ORGANISM: Artificial Sequence
<220> FEATURE:
<223> OTHER INFORMATION: Synthetic Construct

<400> SEQUENCE: 79

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Thr Tyr Met
            20                  25                  30

Tyr Trp Tyr Gln Gln Lys Pro Gly Lys Ser Pro Lys Pro Trp Ile Tyr
        35                  40                  45

Arg Thr Ser Asp Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln His Tyr His Ser Tyr Pro Leu Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 80
<211> LENGTH: 451
<212> TYPE: PRT
<213> ORGANISM: Artificial Sequence
<220> FEATURE:
<223> OTHER INFORMATION: Synthetic Construct

<400> SEQUENCE: 80

```
Glu Val Gln Leu Val Glu Ser Gly Pro Gly Leu Val Lys Pro Ser Glu
1               5                   10                  15
Thr Leu Ser Leu Thr Cys Thr Val Ser Arg Phe Ser Leu Ile Gly Tyr
            20                  25                  30
Ala Ile Thr Trp Ile Arg Gln Pro Pro Gly Lys Gly Leu Glu Trp Ile
        35                  40                  45
Gly Gly Ile Ser Ser Ala Ala Thr Thr Phe Tyr Ser Ser Trp Ala Lys
50                  55                  60
Ser Arg Val Thr Ile Ser Arg Asp Thr Ser Lys Asn Gln Val Ser Leu
65                  70                  75                  80
Lys Leu Ser Ser Val Thr Ala Ala Asp Thr Ala Val Tyr Tyr Cys Ala
                85                  90                  95
Arg Asp Pro Arg Gly Tyr Gly Ala Ala Leu Asp Arg Leu Asp Leu Trp
            100                 105                 110
Gly Gln Gly Thr Leu Val Thr Val Ser Ser Ala Ser Thr Lys Gly Pro
        115                 120                 125
Ser Val Phe Pro Leu Ala Pro Ser Ser Lys Ser Thr Ser Gly Gly Thr
130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Ser Leu Gly Thr Gln Thr Tyr Ile Cys Asn Val Asn
        195                 200                 205
His Lys Pro Ser Asn Thr Lys Val Asp Lys Lys Val Glu Pro Lys Ser
210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
His Glu Asp Pro Glu Val Lys Phe Asn Trp Tyr Val Asp Gly Val Glu
        275                 280                 285
Val His Asn Ala Lys Thr Lys Pro Arg Glu Glu Gln Tyr Asn Ser Thr
290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Arg Glu Glu Met Thr Lys Asn Gln Val
        355                 360                 365
Ser Leu Thr Cys Leu Val Lys Gly Phe Tyr Pro Ser Asp Ile Ala Val
370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
```

405                 410                 415
Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 81
<211> LENGTH: 217
<212> TYPE: PRT
<213> ORGANISM: Artificial Sequence
<220> FEATURE:
<223> OTHER INFORMATION: Synthetic Construct

<400> SEQUENCE: 81

Asp Ile Gln Met Thr Gln Ser Pro Ser Ser Leu Ser Ala Ser Val Gly
1               5                   10                  15

Asp Arg Val Thr Ile Thr Cys Gln Ser Ile Lys Ser Val Tyr Asn Asn
            20                  25                  30

Arg Leu Gly Trp Tyr Gln Gln Lys Pro Gly Lys Ala Pro Lys Leu Leu
        35                  40                  45

Ile Tyr Glu Thr Ser Ile Leu Thr Ser Gly Val Pro Ser Arg Phe Ser
50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Ala Gly Gly Phe Asp Arg Ser
                85                  90                  95

Gly Asp Thr Thr Phe Gly Gln Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 82
<211> LENGTH: 448
<212> TYPE: PRT
<213> ORGANISM: Artificial Sequence
<220> FEATURE:
<223> OTHER INFORMATION: Synthetic Construct

<400> SEQUENCE: 82

Glu Val Gln Leu Val Glu Ser Gly Pro Gly Leu Val Lys Pro Ser Glu
1               5                   10                  15

Thr Leu Ser Leu Thr Cys Thr Val Ser Arg Phe Ser Leu Ile Gly Tyr
            20                  25                  30

-continued

```
Ala Ile Thr Trp Ile Arg Gln Pro Gly Lys Gly Leu Glu Trp Ile
         35                  40                  45
Gly Gly Ile Ser Ser Ala Thr Thr Phe Tyr Ser Ser Trp Ala Lys
 50                  55                  60
Ser Arg Val Thr Ile Ser Arg Asp Thr Ser Lys Asn Gln Val Ser Leu
 65                  70                  75                  80
Lys Leu Ser Ser Val Thr Ala Ala Asp Thr Ala Val Tyr Tyr Cys Ala
                 85                  90                  95
Arg Asp Pro Arg Gly Tyr Gly Ala Ala Leu Asp Arg Leu Asp Leu Trp
             100                 105                 110
Gly Gln Gly Thr Leu Val Thr Val Ser Ser Ala Ser Thr Lys Gly Pro
         115                 120                 125
Ser Val Phe Pro Leu Ala Pro Cys Ser Arg Ser Thr Ser Glu Ser Thr
    130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Ser Leu Gly Thr Lys Thr Tyr Thr Cys Asn Val Asp
        195                 200                 205
His Lys Pro Ser Asn Thr Lys Val Asp Lys Arg Val Glu Ser Lys Tyr
    210                 215                 220
Gly Pro Pro Cys Pro Pro Cys Pro Ala Pro Glu Phe Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser Gln Glu Asp
            260                 265                 270
Pro Glu Val Gln Phe Asn Trp Tyr Val Asp Gly Val Glu Val His Asn
        275                 280                 285
Ala Lys Thr Lys Pro Arg Glu Glu Gln Phe Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Gly Leu Pro Ser Ser Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Gln Glu Glu Met Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Arg Leu Thr Val Asp Lys
                405                 410                 415
Ser Arg Trp Gln Glu Gly Asn Val Phe Ser Cys Ser Val Met His Glu
            420                 425                 430
Ala Leu His Asn His Tyr Thr Gln Lys Ser Leu Ser Leu Ser Leu Gly
        435                 440                 445
```

```
<210> SEQ ID NO 83
<211> LENGTH: 217
<212> TYPE: PRT
<213> ORGANISM: Artificial Sequence
<220> FEATURE:
<223> OTHER INFORMATION: Synthetic Construct

<400> SEQUENCE: 83

Asp Ile Gln Met Thr Gln Ser Pro Ser Ser Leu Ser Ala Ser Val Gly
1               5                   10                  15

Asp Arg Val Thr Ile Thr Cys Gln Ser Ile Lys Ser Val Tyr Asn Asn
            20                  25                  30

Arg Leu Gly Trp Tyr Gln Gln Lys Pro Gly Lys Ala Pro Lys Leu Leu
        35                  40                  45

Ile Tyr Glu Thr Ser Ile Leu Thr Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Ala Gly Gly Phe Asp Arg Ser
                85                  90                  95

Gly Asp Thr Thr Phe Gly Gln Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 84
<211> LENGTH: 5
<212> TYPE: PRT
<213> ORGANISM: Artificial Sequence
<220> FEATURE:
<223> OTHER INFORMATION: Synthetic Construct

<400> SEQUENCE: 84

Ala Tyr Ser Val Asn
1               5

<210> SEQ ID NO 85
<211> LENGTH: 16
<212> TYPE: PRT
<213> ORGANISM: Artificial Sequence
<220> FEATURE:
<223> OTHER INFORMATION: Synthetic Construct

<400> SEQUENCE: 85

Met Ile Trp Gly Asp Gly Lys Ile Val Tyr Asn Ser Ala Leu Lys Ser
1               5                   10                  15

<210> SEQ ID NO 86
```

```
<211> LENGTH: 10
<212> TYPE: PRT
<213> ORGANISM: Artificial Sequence
<220> FEATURE:
<223> OTHER INFORMATION: Synthetic Construct

<400> SEQUENCE: 86

Asp Gly Tyr Tyr Pro Tyr Ala Met Asp Asn
1               5                   10

<210> SEQ ID NO 87
<211> LENGTH: 15
<212> TYPE: PRT
<213> ORGANISM: Artificial Sequence
<220> FEATURE:
<223> OTHER INFORMATION: Synthetic Construct

<400> SEQUENCE: 87

Arg Ala Ser Lys Ser Val Asp Ser Tyr Gly Asn Ser Phe Met His
1               5                   10                  15

<210> SEQ ID NO 88
<211> LENGTH: 7
<212> TYPE: PRT
<213> ORGANISM: Artificial Sequence
<220> FEATURE:
<223> OTHER INFORMATION: Synthetic Construct

<400> SEQUENCE: 88

Leu Ala Ser Asn Leu Glu Ser
1               5

<210> SEQ ID NO 89
<211> LENGTH: 9
<212> TYPE: PRT
<213> ORGANISM: Artificial Sequence
<220> FEATURE:
<223> OTHER INFORMATION: Synthetic Construct

<400> SEQUENCE: 89

Gln Gln Asn Asn Glu Asp Pro Arg Thr
1               5

<210> SEQ ID NO 90
<211> LENGTH: 118
<212> TYPE: PRT
<213> ORGANISM: Artificial Sequence
<220> FEATURE:
<223> OTHER INFORMATION: Synthetic Construct

<400> SEQUENCE: 90

Gln Val Thr Leu Arg Glu Ser Gly Pro Ala Leu Val Lys Pro Thr Gln
1               5                   10                  15

Thr Leu Thr Leu Thr Cys Thr Val Ser Gly Phe Ser Leu Ser Ala Tyr
            20                  25                  30

Ser Val Asn Trp Ile Arg Gln Pro Pro Gly Lys Ala Leu Glu Trp Leu
        35                  40                  45

Ala Met Ile Trp Gly Asp Gly Lys Ile Val Tyr Asn Ser Ala Leu Lys
    50                  55                  60

Ser Arg Leu Thr Ile Ser Lys Asp Thr Ser Lys Asn Gln Val Val Leu
65                  70                  75                  80

Thr Met Thr Asn Met Asp Pro Val Asp Thr Ala Thr Tyr Tyr Cys Ala
                85                  90                  95

Gly Asp Gly Tyr Tyr Pro Tyr Ala Met Asp Asn Trp Gly Gln Gly Ser
```

```
                    100                 105                 110

Leu Val Thr Val Ser Ser
            115

<210> SEQ ID NO 91
<211> LENGTH: 111
<212> TYPE: PRT
<213> ORGANISM: Artificial Sequence
<220> FEATURE:
<223> OTHER INFORMATION: Synthetic Construct

<400> SEQUENCE: 91

Asp Ile Val Met Thr Gln Ser Pro Asp Ser Leu Ser Val Ser Leu Gly
1               5                   10                  15

Glu Arg Ala Thr Ile Asn Cys Arg Ala Ser Lys Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Asn
                85                  90                  95

Glu Asp Pro Arg Thr Phe Gly Gly Gly Thr Lys Val Glu Ile Lys
            100                 105                 110

<210> SEQ ID NO 92
<211> LENGTH: 107
<212> TYPE: PRT
<213> ORGANISM: Artificial Sequence
<220> FEATURE:
<223> OTHER INFORMATION: Synthetic Construct

<400> SEQUENCE: 92

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Tyr Pro Phe
                85                  90                  95

Thr Phe Gly Gln Gly Thr Lys Val Glu Ile Lys
            100                 105

<210> SEQ ID NO 93
<211> LENGTH: 113
<212> TYPE: PRT
<213> ORGANISM: Artificial Sequence
<220> FEATURE:
<223> OTHER INFORMATION: Synthethic Construct

<400> SEQUENCE: 93

Glu Val Gln Leu Val Glu Ser Gly Pro Gly Leu Val Lys Pro Ser Glu
1               5                   10                  15
```

Thr Leu Ser Leu Thr Cys Thr Val Ser Gly Gly Ser Ile Ser Ser Gly
            20                  25                  30

Gly Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                85                  90                  95

Cys Ala Arg Phe Asp Tyr Trp Gly Gln Phe Thr Leu Val Thr Val Ser
            100                 105                 110

Ser

<210> SEQ ID NO 94
<211> LENGTH: 112
<212> TYPE: PRT
<213> ORGANISM: Artificial Sequence
<220> FEATURE:
<223> OTHER INFORMATION: Synthetic Construct

<400> SEQUENCE: 94

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Gly Ala Ile Ser Ser Ser Gly Ser Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Phe Asp Tyr Trp Gly Gln Gly Thr Leu Val Thr Val Ser Ser
            100                 105                 110

<210> SEQ ID NO 95
<211> LENGTH: 36
<212> TYPE: PRT
<213> ORGANISM: Artificial Sequence
<220> FEATURE:
<223> OTHER INFORMATION: Synthetic Construct

<400> SEQUENCE: 95

Thr Leu Thr Ile Ser Ser Leu Gln Pro Glu Asp Phe Ala Thr Tyr Tyr
 1               5                  10                  15

Cys Gln Gln Tyr Tyr Ser Tyr Pro Phe Thr Phe Gly Gln Gly Thr Lys
            20                  25                  30

Val Glu Ile Lys
        35

<210> SEQ ID NO 96
<211> LENGTH: 38
<212> TYPE: PRT
<213> ORGANISM: Artificial Sequence
<220> FEATURE:
<223> OTHER INFORMATION: Synthetic Construct

<400> SEQUENCE: 96

Thr Leu Thr Ile Ser Asp Val Gln Cys Asp Asp Ala Ala Thr Tyr Phe
1               5                   10                  15

Cys Ala Gly Gly Phe Asp Arg Ser Gly Asp Thr Thr Phe Gly Gly Gly
                20                  25                  30

Thr Glu Val Val Val Lys
            35

<210> SEQ ID NO 97
<211> LENGTH: 245
<212> TYPE: PRT
<213> ORGANISM: Homo sapiens

<400> SEQUENCE: 97

Ile Val Gly Gly Gln Glu Ala Pro Arg Ser Lys Trp Pro Trp Gln Val
1               5                   10                  15

Ser Leu Arg Val His Gly Pro Tyr Trp Met His Phe Cys Gly Gly Ser
                20                  25                  30

Leu Ile His Pro Gln Trp Val Leu Thr Ala Ala His Cys Val Gly Pro
                35                  40                  45

Asp Val Lys Asp Leu Ala Ala Leu Arg Val Gln Leu Arg Glu Gln His
            50                  55                  60

Leu Tyr Tyr Gln Asp Gln Leu Leu Pro Val Ser Arg Ile Ile Val His
65              70                  75                  80

Pro Gln Phe Tyr Thr Ala Gln Ile Gly Ala Asp Ile Ala Leu Leu Glu
                85                  90                  95

Leu Glu Glu Pro Val Asn Val Ser Ser His Val His Thr Val Thr Leu
                100                 105                 110

Pro Pro Ala Ser Glu Thr Phe Pro Pro Gly Met Pro Cys Trp Val Thr
            115                 120                 125

Gly Trp Gly Asp Val Asp Asn Asp Glu Arg Leu Pro Pro Pro Phe Pro
130                 135                 140

Leu Lys Gln Val Lys Val Pro Ile Met Glu Asn His Ile Cys Asp Ala
145                 150                 155                 160

Lys Tyr His Leu Gly Ala Tyr Thr Gly Asp Asp Val Arg Ile Val Arg
                165                 170                 175

Asp Asp Met Leu Cys Ala Gly Asn Thr Arg Arg Asp Ser Cys Gln Gly
            180                 185                 190

Asp Ser Gly Gly Pro Leu Val Cys Lys Val Asn Gly Thr Trp Leu Gln
        195                 200                 205

Ala Gly Val Val Ser Trp Gly Glu Gly Cys Ala Gln Pro Asn Arg Pro
    210                 215                 220

Gly Ile Tyr Thr Arg Val Thr Tyr Tyr Leu Asp Trp Ile His His Tyr
225                 230                 235                 240

Val Pro Lys Lys Pro
                245

<210> SEQ ID NO 98
<211> LENGTH: 119
<212> TYPE: PRT
<213> ORGANISM: Artificial Sequence
<220> FEATURE:
<223> OTHER INFORMATION: Synthetic Construct

<400> SEQUENCE: 98

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
         20                  25                  30

Gly Met Val Trp Val Arg Gln Ala Pro Gly Lys Gly Leu Glu Trp Val
         35                  40                  45

Gly Phe Ile Ser Ser Gly Ser Ser Thr Val Tyr Tyr Ala Asp Thr Met
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Val Tyr Cys
             85                  90                  95

Ala Arg Arg Asp Asn Tyr Asp Trp Tyr Phe Asp Val Trp Gly Gln Gly
             100                 105                 110

Thr Leu Val Thr Val Ser Ser
        115

<210> SEQ ID NO 99
<211> LENGTH: 119
<212> TYPE: PRT
<213> ORGANISM: Artificial Sequence
<220> FEATURE:
<223> OTHER INFORMATION: Synthetic Construct

<400> SEQUENCE: 99

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
         20                  25                  30

Gly Met Val Trp Val Arg Gln Ala Pro Gly Lys Gly Leu Glu Trp Val
         35                  40                  45

Ala Phe Ile Ser Ser Gly Ser Ser Thr Val Tyr Tyr Ala Asp Thr Met
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Val Tyr Cys
             85                  90                  95

Ala Arg Arg Asp Asn Tyr Asp Trp Tyr Phe Asp Val Trp Gly Gln Gly
             100                 105                 110

Thr Leu Val Thr Val Ser Ser
        115

<210> SEQ ID NO 100
<211> LENGTH: 119
<212> TYPE: PRT
<213> ORGANISM: Artificial Sequence
<220> FEATURE:
<223> OTHER INFORMATION: Synthetic Construct

<400> SEQUENCE: 100

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
         20                  25                  30

Gly Met His Trp Val Arg Gln Ala Pro Gly Lys Gly Leu Glu Trp Val
         35                  40                  45

Ala Phe Ile Ser Ser Gly Ser Ser Thr Val Tyr Tyr Ala Asp Thr Met
 50                  55                  60

Lys Gly Arg Phe Thr Ile Ser Arg Asp Asn Ser Lys Asn Thr Leu Tyr

```
                65                  70                  75                  80
Leu Gln Met Asn Ser Leu Arg Ala Glu Asp Thr Ala Val Val Tyr Cys
                    85                  90                  95

Ala Arg Arg Asp Asn Tyr Asp Trp Tyr Phe Asp Val Trp Gly Gln Gly
                100                 105                 110

Thr Leu Val Thr Val Ser Ser
        115

<210> SEQ ID NO 101
<211> LENGTH: 119
<212> TYPE: PRT
<213> ORGANISM: Artificial Sequence
<220> FEATURE:
<223> OTHER INFORMATION: Synthetic Construct

<400> SEQUENCE: 101

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
                20                  25                  30

Gly Met Val Trp Val Arg Gln Ala Pro Gly Lys Gly Leu Glu Trp Val
            35                  40                  45

Ala Phe Ile Ser Ser Gly Ser Ser Thr Val Tyr Tyr Ala Asp Thr Met
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Val Tyr Cys
                85                  90                  95

Thr Arg Arg Asp Asn Tyr Asp Trp Tyr Phe Asp Val Trp Gly Gln Gly
                100                 105                 110

Thr Leu Val Thr Val Ser Ser
        115

<210> SEQ ID NO 102
<211> LENGTH: 106
<212> TYPE: PRT
<213> ORGANISM: Artificial Sequence
<220> FEATURE:
<223> OTHER INFORMATION: Synthetic Construct

<400> SEQUENCE: 102

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Thr Tyr Met
                20                  25                  30

Tyr Trp Tyr Gln Gln Lys Pro Gly Lys Ala Pro Lys Leu Leu Ile Tyr
            35                  40                  45

Arg Thr Ser Asp Leu Ala Ser Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln His Tyr His Ser Tyr Pro Leu Thr
                85                  90                  95

Phe Gly Gln Gly Thr Lys Val Glu Ile Lys
                100                 105

<210> SEQ ID NO 103
<211> LENGTH: 106
```

```
<212> TYPE: PRT
<213> ORGANISM: Artificial Sequence
<220> FEATURE:
<223> OTHER INFORMATION: Synthetic Construct

<400> SEQUENCE: 103

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Thr Tyr Met
            20                  25                  30

Tyr Trp Tyr Gln Gln Lys Pro Gly Lys Ser Pro Lys Pro Trp Ile Tyr
        35                  40                  45

Arg Thr Ser Asp Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln His Tyr His Ser Tyr Pro Leu Thr
                85                  90                  95

Phe Gly Gln Gly Thr Lys Val Glu Ile Lys
            100                 105

<210> SEQ ID NO 104
<211> LENGTH: 357
<212> TYPE: DNA
<213> ORGANISM: Artificial Sequence
<220> FEATURE:
<223> OTHER INFORMATION: Synthetic Construct

<400> SEQUENCE: 104
gaagtgcagc tggtggaaag cggcggcggc ctggtgcagc caggcggcag cctgcgcctg      60
agctgcgccg ccagcggctt caccttcagc gattatggca tggtgtgggt gcgccaggcc     120
ccaggcaaag cctggaatg gtggccttc atcagcagcg gcagcagcac cgtgtattat      180
gccgatacca tgaaaggccg cttcaccatc agccgcgata acagcaaaaa caccctgtat     240
ctgcagatga acagcctgcg cgccgaagat accgccgtgt attattgcac cgccgcaac     300 tacgatgatt ggtatttcga tgtgtggggc cagggcaccc tggtgaccgt ctcgagt       357

<210> SEQ ID NO 105
<211> LENGTH: 318
<212> TYPE: DNA
<213> ORGANISM: Artificial Sequence
<220> FEATURE:
<223> OTHER INFORMATION: Synthetic Construct

<400> SEQUENCE: 105
gatatccaga tgacccagag cccaagcagc ctgagcgcca gcgtgggcga tcgcgtgacc      60
atcacctgca gcgccagcag cagcgtgacc tatatgtatt ggtatcagca gaaaccaggc     120
aaaagcccaa aaccatggat ctatcgcacc agcgatctgg ccagcggcgt gccaagccgc     180
ttcagcggca gcggcagcgg caccgatttc accctgacca tcagcagcct gcagccagaa     240
gatttcgcca cctattattg ccagcactat cacagctatc cactgacctt cggccagggt     300
accaaggtgg agatcaaa                                                   318

<210> SEQ ID NO 106
<211> LENGTH: 1347
<212> TYPE: DNA
<213> ORGANISM: Artificial Sequence
<220> FEATURE:
<223> OTHER INFORMATION: Synthetic Construct
```

<400> SEQUENCE: 106

```
gaagtgcagc tggtggaaag cggcggcggc ctggtgcagc aggcggcag cctgcgcctg      60
agctgcgccg ccagcggctt caccttcagc gattatggca tggtgtgggt gcgccaggcc    120
ccaggcaaag gcctggaatg ggtggccttc atcagcagcg gcagcagcac cgtgtattat    180
gccgatacca tgaaaggccg cttcaccatc agccgcgata cagcaaaaa caccctgtat    240
ctgcagatga cagcctgcg cgccgaagat accgccgtgt attattgcac cgccgcaac    300
tacgatgatt ggtatttcga tgtgtgggc cagggcaccc tggtgaccgt ctcgagtgcc    360
tccaccaagg gcccatcggt cttccccctg gcacctcct ccaagagcac ctctgggggc    420
acagcggccc tgggctgcct ggtcaaggac tacttccccg aaccggtgac ggtgtcgtgg    480
aactcaggcg ccctgaccag cggcgtgcac accttcccgg ctgtcctaca gtcctcagga    540
ctctactccc tcagcagcgt ggtgactgtg ccctctagca gcttgggcac ccagacctac    600
atctgcaacg tgaatcacaa gcccagcaac accaaggtgg acaagaaagt tgagcccaaa    660
tcttgtgaca aaactcacac atgcccaccg tgcccagcac ctgaactcct ggggggaccg    720
tcagtcttcc tcttccccccc aaaacccaag gacaccctca tgatctcccg gacccctgag    780
gtcacatgcg tggtggtgga cgtgagccac gaagaccctg aggtcaagtt caactggtac    840
gtggacggcg tggaggtgca taatgccaag acaaagccgc gggaggagca gtacaacagc    900
acgtaccgtg tggtcagcgt cctcaccgtc ctgcaccagg actggctgaa tggcaaggag    960
tacaagtgca aggtctccaa caaagccctc ccagccccca tcgagaaaac catctccaaa   1020
gccaaagggc agccccgaga accacaggtg tacaccctgc cccatcccg ggaagagatg   1080
accaagaacc aggtcagcct gacctgcctg gtcaaaggct tctatcccag cgacatcgcc   1140
gtggagtggg agagcaatgg gcagccggag aacaactaca agaccacgcc tcccgtgctg   1200
gactccgacg gctccttctt cctctacagc aagctcaccg tggacaagag caggtggcag   1260
caggggaacg tcttctcatg ctccgtgatg catgaggctc tgcacaacca ctacacgcag   1320
aagagcctct ccctgtctcc gggtaaa                                        1347
```

<210> SEQ ID NO 107
<211> LENGTH: 639
<212> TYPE: DNA
<213> ORGANISM: Artificial Sequence
<220> FEATURE:
<223> OTHER INFORMATION: Synthetic Construct

<400> SEQUENCE: 107

```
gatatccaga tgacccagag cccaagcagc ctgagcgcca gcgtgggcga tcgcgtgacc     60
atcacctgca gcgccagcag cagcgtgacc tatatgtatt ggtatcagca gaaaccaggc   120
aaaagcccaa accatggat ctatcgcacc agcgatctgg ccagcggcgt gccaagccgc   180
ttcagcggca gcggcagcgg caccgatttc accctgacca tcagcagcct gcagccagaa   240
gatttcgcca cctattattg ccagcactat acagctatc cactgaccct cggccagggt   300
accaaggtgg agatcaaacg aactgtggct gcaccatctg tcttcatctt cccgccatct   360
gatgagcagt tgaaatctgg aactgcttct gttgtgtgcc tgctgaataa cttctatccc   420
agagaggcca aagtacagtg gaaggtggat aacgccctcc aatcgggtaa ctcccaggag   480
agtgtcacag agcaggacag caaggacagc acctacagcc tcagcagcac cctgacgctg   540
agcaaagcag actacgagaa acacaaagtc tacgcctgcg aagtcaccca tcagggcctg   600
```
agctcgcccg tcacaaagag cttcaacagg ggagagtgt           639

<210> SEQ ID NO 108
<211> LENGTH: 1338
<212> TYPE: DNA
<213> ORGANISM: Artificial Sequence
<220> FEATURE:
<223> OTHER INFORMATION: Synthetic Construct

<400> SEQUENCE: 108
gaagtgcagc tggtggaaag cggcggcggc ctggtgcagc aggcggcag cctgcgcctg      60
agctgcgccg ccagcggctt caccttcagc gattatggca tggtgtgggt gcgccaggcc     120
ccaggcaaag gcctggaatg ggtggccttc atcagcagcg gcagcagcac cgtgtattat     180
gccgatacca tgaaaggccg cttcaccatc agccgcgata acagcaaaaa caccctgtat     240
ctgcagatga acagcctgcg cgccgaagat accgccgtgt attattgcac ccgccgcaac     300
tacgatgatt ggtatttcga tgtgtggggc cagggcaccc tggtgaccgt ctcgagtgcc     360
tccaccaagg gcccatcggt cttccccctg gcacctgct cccgcagtac ttctgagtcc      420
acagcggccc tgggctgcct ggtcaaggac tacttcccg aaccggtgac ggtgtcgtgg      480
aactcaggcg ccctgaccag cggcgtgcac accttcccgg ctgtcctaca gtcctcagga     540
ctctactccc tcagcagcgt ggtgactgtg ccctctagca gcttgggcac caagacctac     600
acgtgcaacg tggatcacaa gcccagcaac accaaggtgg acaaacgcgt tgagtccaaa     660
tatggtcccc catgcccacc atgcccagca cctgagttcc tggggggacc atcagtcttc     720
ctgttccccc caaaacccaa ggacactctc atgatctccc ggacccctga ggtcacgtgc     780
gtggtggtgg acgtgagcca ggaagacccc gaggtccagt tcaactggta cgtggatggc     840
gtggaggtgc ataatgccaa gacaaagccg cgggaggagc agttcaacag cacgtaccgt     900
gtggtcagcg tcctcaccgt cctgcaccag gactggctga acggcaagga gtacaagtgc     960
aaggtctcca acaaaggcct cccgtcctcc atcgagaaaa ccatctccaa agccaaaggg    1020
cagccccgag agccacaggt gtacaccctg cccccatccc aggaggagat gaccaagaac    1080
caggtcagcc tgacctgcct ggtcaaaggc ttctacccca gcgacatcgc cgtggagtgg    1140
gagagcaatg ggcagccgga gaacaactac aagaccacgc ctcccgtgct ggactccgac    1200
ggctccttct tcctctacag caggctaacc gtggacaaga gcaggtggca ggaggggaat    1260
gtcttctcat gctccgtgat gcatgaggct ctgcacaacc actacacaca gaagagcctc    1320
tccctgtctc tgggtaaa                                                  1338

<210> SEQ ID NO 109
<211> LENGTH: 366
<212> TYPE: DNA
<213> ORGANISM: Artificial Sequence
<220> FEATURE:
<223> OTHER INFORMATION: Synthetic Construct

<400> SEQUENCE: 109
gaagtgcagc tggtggaaag cggcccaggc ctggtgaaac caagcgaaac cctgagcctg      60
acctgcaccg tgagccgctt cagcctgatc ggctatgcca tcacctggat ccgcagcca      120
ccaggcaaag gcctggaatg gatcggcggc atcagcagcg ccgccaccac cttctatagc     180
agctgggcca aaagccgcgt gaccatcagc cgcgatacca gcaaaaacca ggtgagcctg     240
aaactgagca gcgtgaccgc cgccgatacc gccgtgtatt attgcgcccg cgatccacgc     300
ggctatggcg ccgccctgga tcgcctggat ctgtggggcc agggcaccct ggtgaccgtc     360

-continued

| | |
|---|---|
| tcgagt | 366 |

<210> SEQ ID NO 110
<211> LENGTH: 330
<212> TYPE: DNA
<213> ORGANISM: Artificial Sequence
<220> FEATURE:
<223> OTHER INFORMATION: Synthetic Construct

<400> SEQUENCE: 110

| | |
|---|---|
| gatatccaga tgacccagag cccaagcagc ctgagcgcca gcgtgggcga tcgcgtgacc | 60 |
| atcacctgcc agagcatcaa aagcgtgtat aacaaccgcc tgggctggta tcagcagaaa | 120 |
| ccaggcaaag ccccaaaact gctgatctat gaaaccagca tcctgaccag cggcgtgcca | 180 |
| agccgcttca gcggcagcgg cagcggcacc gatttcaccc tgaccatcag cagcctgcag | 240 |
| ccagaagatt tcgccaccta ttattgcgcc ggcggcttcg atcgcagcgg cgataccacc | 300 |
| ttcggccagg gtaccaaggt ggagatcaaa | 330 |

<210> SEQ ID NO 111
<211> LENGTH: 1356
<212> TYPE: DNA
<213> ORGANISM: Artificial Sequence
<220> FEATURE:
<223> OTHER INFORMATION: Synthetic Construct

<400> SEQUENCE: 111

| | |
|---|---|
| gaagtgcagc tggtggaaag cggcccaggc ctggtgaaac caagcgaaac cctgagcctg | 60 |
| acctgcaccg tgagccgctt cagcctgatc ggctatgcca tcacctggat ccgccagcca | 120 |
| ccaggcaaag gcctggaatg gatcggcggc atcagcagcg ccgccaccac cttctatagc | 180 |
| agctgggcca aaagccgcgt gaccatcagc cgcgatacca gcaaaaacca ggtgagcctg | 240 |
| aaactgagca gcgtgaccgc cgccgatacc gccgtgtatt attgcgcccg cgatccacgc | 300 |
| ggctatggcg ccgccctgga tcgcctggat ctgtggggcc agggcaccct ggtgaccgtc | 360 |
| tcgagtgcct ccaccaaggg cccatcggtc ttccccctgg cacccteete aagagcacc | 420 |
| tctgggggca gcggccct gggctgcctg gtcaaggact acttccccga accggtgacg | 480 |
| gtgtcgtgga actcaggcgc cctgaccagc ggcgtgcaca ccttcccggc tgtcctacag | 540 |
| tcctcaggac tctactccct cagcagcgtg gtgactgtgc cctctagcag cttgggcacc | 600 |
| cagacctaca tctgcaacgt gaatcacaag cccagcaaca ccaaggtgga caagaaagtt | 660 |
| gagcccaaat cttgtgacaa aactcacaca tgcccaccgt gcccagcacc tgaactcctg | 720 |
| gggggaccgt cagtcttcct cttccccca aaacccaagg acaccctcat gatctcccgg | 780 |
| accecctgagg tcacatgcgt ggtggtggac gtgagccacg aagaccctga ggtcaagttc | 840 |
| aactggtacg tggacggcgt ggaggtgcat aatgccaaga caaagccgcg ggaggagcag | 900 |
| tacaacagca cgtaccgtgt ggtcagcgtc ctcaccgtcc tgcaccagga ctggctgaat | 960 |
| ggcaaggagt acaagtgcaa ggtctccaac aaagccctcc cagcccccat cgagaaaacc | 1020 |
| atctccaaag ccaaagggca gccccgagaa ccacaggtgt acaccctgcc cccatcccgg | 1080 |
| gaagagatga ccaagaacca ggtcagcctg acctgcctgg tcaaaggctt ctatcccagc | 1140 |
| gacatcgccg tggagtggga gagcaatggg cagccggaga caactacaa gaccacgcct | 1200 |
| cccgtgctgg actccgacgg ctccttcttc ctctacagca agctcaccgt ggacaagagc | 1260 |
| aggtggcagc aggggaacgt cttctcatgc tccgtgatgc atgaggctct gcacaaccac | 1320 |

```
tacacgcaga agagcctctc cctgtctccg ggtaaa                            1356

<210> SEQ ID NO 112
<211> LENGTH: 651
<212> TYPE: DNA
<213> ORGANISM: Artificial Sequence
<220> FEATURE:
<223> OTHER INFORMATION: Synthetic Construct

<400> SEQUENCE: 112
gatatccaga tgacccagag cccaagcagc ctgagcgcca gcgtgggcga tcgcgtgacc     60
atcacctgcc agagcatcaa aagcgtgtat aacaaccgcc tgggctggta tcagcagaaa    120
ccaggcaaag ccccaaaaact gctgatctat gaaaccagca tcctgaccag cggcgtgcca   180
agccgcttca gcggcagcgg cagcggcacc gatttcaccc tgaccatcag cagcctgcag    240
ccagaagatt tcgccaccta ttattgcgcc ggcggcttcg atcgcagcgg cgataccacc    300
ttcggccagg gtaccaaggt ggagatcaaa cgaactgtgg ctgcaccatc tgtcttcatc    360
ttcccgccat ctgatgagca gttgaaatct ggaactgctt ctgttgtgtg cctgctgaat    420
aacttctatc ccagagaggc caaagtacag tggaaggtgg ataacgccct ccaatcgggt    480
aactcccagg agagtgtcac agagcaggac agcaaggaca gcacctacag cctcagcagc    540
accctgacgc tgagcaaagc agactacgag aaacacaaag tctacgcctg cgaagtcacc    600
catcagggcc tgagctcgcc cgtcacaaag agcttcaaca ggggagagtg t             651

<210> SEQ ID NO 113
<211> LENGTH: 1347
<212> TYPE: DNA
<213> ORGANISM: Artificial Sequence
<220> FEATURE:
<223> OTHER INFORMATION: Synthetic Construct

<400> SEQUENCE: 113
gaagtgcagc tggtggaaag cggcccaggc ctggtgaaac caagcgaaac cctgagcctg     60
acctgcaccg tgagccgctt cagcctgatc ggctatgcca tcacctggat ccgccagcca    120
ccaggcaaag gcctggaatg gatcggcggc atcagcagcg ccgccaccac cttctatagc    180
agctgggcca aaagccgcgt gaccatcagc cgcgatacca gcaaaaacca ggtgagcctg    240
aaactgagca gcgtgaccgc cgccgatacc gccgtgtatt attgcgcccg cgatccacgc    300
ggctatggcg ccgcccctgga tcgcctggat ctgtggggcc agggcaccct ggtgaccgtc    360
tcgagtgcct ccaccaaggg cccatcggtc ttccccctgg cacccctgct ccgcagtact    420
tctgagtcca cagcggccct gggctgcctg gtcaaggact acttccccga accggtgacg    480
gtgtcgtgga actcaggcgc cctgaccagc ggcgtgcaca ccttcccggc tgtcctacag    540
tcctcaggac tctactccct cagcagcgtg gtgactgtgc cctctagcag cttgggcacc    600
aagacctaca cgtgcaacgt ggatcacaag cccagcaaca ccaaggtgga caaacgcgtt    660
gagtccaaat atggtccccc atgcccacca tgcccagcac ctgagttcct ggggggacca    720
tcagtcttcc tgttcccccc aaaacccaag gacactctca tgatctcccg gacccctgag    780
gtcacgtgcg tggtggtgga cgtgagccag gaagaccccg aggtccagtt caactggtac    840
gtggatggcg tggaggtgca taatgccaag acaaagccgc gggaggagca gttcaacagc    900
acgtaccgtg tggtcagcgt cctcaccgtc ctgcaccagg actggctgaa cggcaaggag    960
tacaagtgca aggtctccaa caaaggcctc ccgtcctcca tcgagaaaac catctccaaa   1020
gccaaagggc agccccgaga gccacaggtg tacaccctgc ccccatccca ggaggagatg   1080
```

```
accaagaacc aggtcagcct gacctgcctg gtcaaaggct tctacccag cgacatcgcc   1140 gtggagtggg agagcaatgg gcagccggag aacaactaca agaccacgcc tcccgtgctg   1200
gactccgacg gctccttctt cctctacagc aggctaaccg tggacaagag caggtggcag   1260 gagggggaatg tcttctcatg ctccgtgatg catgaggctc tgcacaacca ctacacacag   1320
aagagcctct ccctgtctct gggtaaa                                        1347
```

<210> SEQ ID NO 114
<211> LENGTH: 118
<212> TYPE: PRT
<213> ORGANISM: Artificial Sequence
<220> FEATURE:
<223> OTHER INFORMATION: Synthetic Construct

<400> SEQUENCE: 114

```
Glu Val Thr Leu Arg Glu Ser Gly Pro Ala Leu Val Lys Pro Thr Gln
1               5                   10                  15

Thr Leu Thr Leu Thr Cys Thr Val Ser Gly Phe Ser Leu Ser Ala Tyr
            20                  25                  30

Ser Val Asn Trp Ile Arg Gln Pro Pro Gly Lys Ala Leu Glu Trp Leu
        35                  40                  45

Ala Met Ile Trp Gly Asp Gly Lys Ile Val Tyr Asn Ser Ala Leu Lys
    50                  55                  60

Ser Arg Leu Thr Ile Ser Lys Asp Thr Ser Lys Asn Gln Val Val Leu
65                  70                  75                  80

Thr Met Thr Asn Met Asp Pro Val Asp Thr Ala Thr Tyr Tyr Cys Ala
                85                  90                  95

Gly Asp Gly Tyr Tyr Pro Tyr Ala Met Asp Asn Trp Gly Gln Gly Ser
            100                 105                 110

Leu Val Thr Val Ser Ser
        115
```

<210> SEQ ID NO 115
<211> LENGTH: 111
<212> TYPE: PRT
<213> ORGANISM: Artificial Sequence
<220> FEATURE:
<223> OTHER INFORMATION: Synthetic Construct

<400> SEQUENCE: 115

```
Asp Ile Val Leu Thr Gln Ser Pro Asp Ser Leu Ser Val Ser Leu Gly
1               5                   10                  15

Glu Arg Ala Thr Ile Asn Cys Arg Ala Ser Lys Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Asn
                85                  90                  95

Glu Asp Pro Arg Thr Phe Gly Gly Gly Thr Lys Val Glu Ile Lys
            100                 105                 110
```

<210> SEQ ID NO 116
<211> LENGTH: 256

```
<212> TYPE: PRT
<213> ORGANISM: Homo sapiens

<400> SEQUENCE: 116

Ile Val Gly Gly Gln Glu Ala Pro Arg Ser Lys Trp Pro Trp Gln Val
1               5                   10                  15

Ser Leu Arg Val His Gly Pro Tyr Trp Met His Phe Cys Gly Gly Ser
                20                  25                  30

Leu Ile His Pro Gln Trp Val Leu Thr Ala Ala His Cys Val Gly Pro
            35                  40                  45

Asp Val Lys Asp Leu Ala Ala Leu Arg Val Gln Leu Arg Glu Gln His
        50                  55                  60

Leu Tyr Tyr Gln Asp Gln Leu Leu Pro Val Ser Arg Ile Ile Val His
65                  70                  75                  80

Pro Gln Phe Tyr Thr Ala Gln Ile Gly Ala Asp Ile Ala Leu Leu Glu
                85                  90                  95

Leu Glu Glu Pro Val Lys Val Ser Ser His Val His Thr Val Thr Leu
            100                 105                 110

Pro Pro Ala Ser Glu Thr Phe Pro Pro Gly Met Pro Cys Trp Val Thr
        115                 120                 125

Gly Trp Gly Asp Val Asp Asn Asp Glu Arg Leu Pro Pro Pro Phe Pro
130                 135                 140

Leu Lys Gln Val Lys Val Pro Ile Met Glu Asn His Ile Cys Asp Ala
145                 150                 155                 160

Lys Tyr His Leu Gly Ala Tyr Thr Gly Asp Asp Val Arg Ile Val Arg
                165                 170                 175

Asp Asp Met Leu Cys Ala Gly Asn Thr Arg Arg Asp Ser Cys Gln Gly
            180                 185                 190

Asp Ser Gly Gly Pro Leu Val Cys Lys Val Asn Gly Thr Trp Leu Gln
        195                 200                 205

Ala Gly Val Val Ser Trp Gly Glu Gly Cys Ala Gln Pro Asn Arg Pro
210                 215                 220

Gly Ile Tyr Thr Arg Val Thr Tyr Tyr Leu Asp Trp Ile His His Tyr
225                 230                 235                 240

Val Pro Lys Lys Pro Gly Asn Ser Asp Tyr Lys Asp Asp Asp Asp Lys
                245                 250                 255

<210> SEQ ID NO 117
<211> LENGTH: 256
<212> TYPE: PRT
<213> ORGANISM: Homo sapiens

<400> SEQUENCE: 117

Ile Val Gly Gly Gln Glu Ala Pro Arg Ser Lys Trp Pro Trp Gln Val
1               5                   10                  15

Ser Leu Arg Val Arg Asp Arg Tyr Trp Met His Phe Cys Gly Gly Ser
                20                  25                  30

Leu Ile His Pro Gln Trp Val Leu Thr Ala Ala His Cys Val Gly Pro
            35                  40                  45

Asp Val Lys Asp Leu Ala Ala Leu Arg Val Gln Leu Arg Glu Gln His
        50                  55                  60

Leu Tyr Tyr Gln Asp Gln Leu Leu Pro Val Ser Arg Ile Ile Val His
65                  70                  75                  80

Pro Gln Phe Tyr Thr Ala Gln Ile Gly Ala Asp Ile Ala Leu Leu Glu
                85                  90                  95
```

```
Leu Glu Glu Pro Val Asn Val Ser Ser His Val His Thr Val Thr Leu
                100                 105                 110

Pro Pro Ala Ser Glu Thr Phe Pro Pro Gly Met Pro Cys Trp Val Thr
            115                 120                 125

Gly Trp Gly Asp Val Asp Asn Asp Glu Arg Leu Pro Pro Phe Pro
130                 135                 140

Leu Lys Gln Val Lys Val Pro Ile Met Glu Asn His Ile Cys Asp Ala
145                 150                 155                 160

Lys Tyr His Leu Gly Ala Tyr Thr Gly Asp Asp Val Arg Ile Val Arg
                165                 170                 175

Asp Asp Met Leu Cys Ala Gly Asn Thr Arg Arg Asp Ser Cys Gln Gly
            180                 185                 190

Asp Ser Gly Gly Pro Leu Val Cys Lys Val Asn Gly Thr Trp Leu Gln
        195                 200                 205

Ala Gly Val Val Ser Trp Gly Glu Gly Cys Ala Gln Pro Asn Arg Pro
210                 215                 220

Gly Ile Tyr Thr Arg Val Thr Tyr Tyr Leu Asp Trp Ile His His Tyr
225                 230                 235                 240

Val Pro Lys Lys Pro Gly Asn Ser Asp Tyr Lys Asp Asp Asp Lys
                245                 250                 255

<210> SEQ ID NO 118
<211> LENGTH: 256
<212> TYPE: PRT
<213> ORGANISM: Homo sapiens

<400> SEQUENCE: 118

Ile Val Gly Gly Gln Glu Ala Pro Arg Ser Lys Trp Pro Trp Gln Val
1               5                   10                  15

Ser Leu Arg Val Arg Asp Arg Tyr Trp Met His Phe Cys Gly Gly Ser
            20                  25                  30

Leu Ile His Pro Gln Trp Val Leu Thr Ala Ala His Cys Leu Gly Pro
        35                  40                  45

Asp Val Lys Asp Leu Ala Ala Leu Arg Val Gln Leu Arg Glu Gln His
    50                  55                  60

Leu Tyr Tyr Gln Asp Gln Leu Leu Pro Val Ser Arg Ile Ile Val His
65                  70                  75                  80

Pro Gln Phe Tyr Ile Ile Gln Thr Gly Ala Asp Ile Ala Leu Leu Glu
                85                  90                  95

Leu Glu Glu Pro Val Asn Ile Ser Ser Arg Val His Thr Val Met Leu
            100                 105                 110

Pro Pro Ala Ser Glu Thr Phe Pro Pro Gly Met Pro Cys Trp Val Thr
        115                 120                 125

Gly Trp Gly Asp Val Asp Asn Asp Glu Pro Leu Ser Pro Pro Phe Pro
130                 135                 140

Leu Lys Gln Val Lys Val Pro Ile Met Glu Asn His Ile Cys Asp Ala
145                 150                 155                 160

Lys Tyr His Leu Gly Ala Tyr Thr Gly Asp Asp Val Arg Ile Ile Arg
                165                 170                 175

Asp Asp Met Leu Cys Ala Gly Asn Ser Gln Arg Asp Ser Cys Lys Gly
            180                 185                 190

Asp Ser Gly Gly Pro Leu Val Cys Lys Val Asn Gly Thr Trp Leu Gln
        195                 200                 205

Ala Gly Val Val Ser Trp Asp Glu Gly Cys Ala Gln Pro Asn Arg Pro
210                 215                 220
```

```
Gly Ile Tyr Thr Arg Val Thr Tyr Leu Asp Trp Ile His His Tyr
225                 230                 235                 240

Val Pro Lys Lys Pro Gly Asn Ser Asp Tyr Lys Asp Asp Asp Lys
                245                 250                 255
```

<210> SEQ ID NO 119
<211> LENGTH: 268
<212> TYPE: PRT
<213> ORGANISM: Macaca fascicularis

<400> SEQUENCE: 119

```
Ala Leu Pro Val Leu Val Ser Pro Ala His Ala Ala Pro Ala Pro Gly
1               5                   10                  15

Gln Ala Leu Gln Arg Val Gly Ile Val Gly Gly Lys Glu Ala Pro Arg
            20                  25                  30

Ser Lys Trp Pro Trp Gln Val Ser Leu Arg Leu His Gly Gln Tyr Trp
        35                  40                  45

Met His Phe Cys Gly Gly Ser Leu Ile His Pro Gln Trp Val Leu Thr
    50                  55                  60

Ala Ala His Cys Val Gly Pro Asp Val Lys Asp Leu Ala Asp Leu Arg
65                  70                  75                  80

Val Gln Leu Arg Glu Gln His Leu Tyr Tyr Gln Asp Gln Leu Leu Pro
                85                  90                  95

Val Ser Arg Ile Ile Val His Pro Gln Phe Tyr Ala Val Gln Ile Gly
            100                 105                 110

Ala Asp Ile Ala Leu Leu Glu Leu Glu Glu Pro Val Asn Val Ser Ser
        115                 120                 125

His Val His Thr Val Thr Leu Pro Pro Ala Leu Glu Thr Phe Pro Pro
    130                 135                 140

Gly Thr Pro Cys Trp Val Thr Gly Trp Gly Asp Val Asp Asn Asp Val
145                 150                 155                 160

Arg Leu Pro Pro Pro Tyr Pro Leu Lys Glu Val Glu Val Pro Ile Val
                165                 170                 175

Glu Asn Gln Leu Cys Asp Ala Glu Tyr His Thr Gly Leu His Thr Gly
            180                 185                 190

Asp Ser Phe Arg Ile Val Arg Asp Asp Met Leu Cys Ala Gly Ser Glu
        195                 200                 205

Lys His Asp Ser Cys Gln Gly Asp Ser Gly Gly Pro Leu Val Cys Lys
    210                 215                 220

Val Asn Gly Thr Trp Leu Gln Ala Gly Val Val Ser Trp Gly Glu Gly
225                 230                 235                 240

Cys Ala Leu Pro Asn Arg Pro Gly Ile Tyr Thr Arg Val Thr Tyr Tyr
                245                 250                 255

Leu Asp Trp Ile His Arg Tyr Val Pro Glu Lys Pro
            260                 265
```

<210> SEQ ID NO 120
<211> LENGTH: 5
<212> TYPE: PRT
<213> ORGANISM: Artificial Sequence
<220> FEATURE:
<223> OTHER INFORMATION: Synthetic Construct

<400> SEQUENCE: 120

```
Ser Phe Ser Met Ser
1               5
```

```
<210> SEQ ID NO 121
<211> LENGTH: 17
<212> TYPE: PRT
<213> ORGANISM: Artificial Sequence
<220> FEATURE:
<223> OTHER INFORMATION: Synthetic Construct

<400> SEQUENCE: 121

Thr Ile Ser Gly Gly Lys Thr Phe Thr Asp Tyr Val Asp Ser Val Lys
1               5                   10                  15

Gly

<210> SEQ ID NO 122
<211> LENGTH: 10
<212> TYPE: PRT
<213> ORGANISM: Artificial Sequence
<220> FEATURE:
<223> OTHER INFORMATION: Synthetic Construct

<400> SEQUENCE: 122

Ala Asn Tyr Gly Asn Trp Phe Phe Glu Val
1               5                   10

<210> SEQ ID NO 123
<211> LENGTH: 15
<212> TYPE: PRT
<213> ORGANISM: Artificial Sequence
<220> FEATURE:
<223> OTHER INFORMATION: Synthetic Construct

<400> SEQUENCE: 123

Arg Ala Ser Glu Ser Val Ala Lys Tyr Gly Leu Ser Leu Leu Asn
1               5                   10                  15

<210> SEQ ID NO 124
<211> LENGTH: 7
<212> TYPE: PRT
<213> ORGANISM: Artificial Sequence
<220> FEATURE:
<223> OTHER INFORMATION: Synthetic Construct

<400> SEQUENCE: 124

Ala Ala Ser Asn Arg Gly Ser
1               5

<210> SEQ ID NO 125
<211> LENGTH: 9
<212> TYPE: PRT
<213> ORGANISM: Artificial Sequence
<220> FEATURE:
<223> OTHER INFORMATION: Synthetic Construct

<400> SEQUENCE: 125

Gln Gln Ser Lys Glu Val Pro Phe Thr
1               5

<210> SEQ ID NO 126
<211> LENGTH: 119
<212> TYPE: PRT
<213> ORGANISM: Artificial Sequence
<220> FEATURE:
<223> OTHER INFORMATION: Synthetic Construct

<400> SEQUENCE: 126

Glu Val Gln Leu Val Glu Ser Gly Gly Gly Leu Val Gln Pro Gly Gly
1               5                   10                  15
```

-continued

```
Ser Leu Arg Leu Ser Cys Ala Ala Ser Gly Phe Thr Phe Ser Ser Phe
         20                  25                  30

Ser Met Ser Trp Val Arg Gln Ala Pro Gly Lys Gly Leu Glu Trp Val
     35                  40                  45

Ala Thr Ile Ser Gly Gly Lys Thr Phe Thr Asp Tyr Val Asp Ser Val
 50                  55                  60

Lys Gly Arg Phe Thr Ile Ser Arg Asp Asp Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Arg Ala Asn Tyr Gly Asn Trp Phe Phe Glu Val Trp Gly Gln Gly
             100                 105                 110

Thr Leu Val Thr Val Ser Ser
            115
```

<210> SEQ ID NO 127
<211> LENGTH: 111
<212> TYPE: PRT
<213> ORGANISM: Artificial Sequence
<220> FEATURE:
<223> OTHER INFORMATION: Synthetic Construct

<400> SEQUENCE: 127

```
Glu Ile Val Leu Thr Gln Ser Pro Ala Thr Leu Ser Leu Ser Pro Gly
1                5                  10                  15

Glu Arg Ala Thr Leu Ser Cys Arg Ala Ser Glu Ser Val Ala Lys Tyr
             20                  25                  30

Gly Leu Ser Leu Leu Asn Trp Phe Gln Gln Lys Pro Gly Gln Pro Pro
         35                  40                  45

Arg Leu Leu Ile Phe Ala Ala Ser Asn Arg Gly Ser Gly Ile Pro Ala
 50                  55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln Gln Ser Lys
                 85                  90                  95

Glu Val Pro Phe Thr Phe Gly Gln Gly Thr Lys Val Glu Ile Lys
             100                 105                 110
```

<210> SEQ ID NO 128
<211> LENGTH: 260
<212> TYPE: PRT
<213> ORGANISM: Artificial Sequence
<220> FEATURE:
<223> OTHER INFORMATION: Synthetic Construct

<400> SEQUENCE: 128

```
Ala Gly Ser Thr His His His His His His Asp Asp Asp Lys Ile
1                5                  10                  15

Val Gly Gly Gln Glu Ala Pro Arg Ser Lys Trp Pro Trp Gln Val Ser
             20                  25                  30

Leu Arg Val His Gly Pro Tyr Trp Met His Phe Cys Gly Gly Ser Leu
         35                  40                  45

Ile His Pro Gln Trp Val Leu Thr Ala Ala His Cys Val Gly Pro Asp
 50                  55                  60

Val Lys Asp Leu Ala Ala Leu Arg Val Gln Leu Arg Glu Gln His Leu
 65                  70                  75                  80

Tyr Tyr Gln Asp Gln Leu Leu Pro Val Ser Arg Ile Ile Val His Pro
```

-continued

```
                    85                      90                       95
Gln Phe Tyr Thr Ala Gln Ile Gly Ala Asp Ile Ala Leu Leu Glu Leu
            100                     105                 110

Glu Glu Pro Val Asn Val Ser Ser His Val His Thr Val Thr Leu Pro
        115                     120                 125

Pro Ala Ser Glu Thr Phe Pro Pro Gly Met Pro Cys Trp Val Thr Gly
    130                     135                 140

Trp Gly Asp Val Asp Asn Asp Glu Arg Leu Pro Pro Pro Phe Pro Leu
145                     150                 155                 160

Lys Gln Val Lys Val Pro Ile Met Glu Asn His Ile Cys Asp Ala Lys
                165                     170                 175

Tyr His Leu Gly Ala Tyr Thr Gly Asp Asp Val Arg Ile Val Arg Asp
                180                     185                 190

Asp Met Leu Cys Ala Gly Asn Thr Arg Arg Asp Ser Cys Gln Gly Asp
            195                     200                 205

Ser Gly Gly Pro Leu Val Cys Lys Val Asn Gly Thr Trp Leu Gln Ala
        210                     215                 220

Gly Val Val Ser Trp Gly Glu Gly Cys Ala Gln Pro Asn Arg Pro Gly
225                     230                     235                 240

Ile Tyr Thr Arg Val Thr Tyr Tyr Leu Asp Trp Ile His His Tyr Val
                245                     250                 255

Pro Lys Lys Pro
            260
```